United States Patent
Priestley et al.

(10) Patent No.: US 7,592,331 B2
(45) Date of Patent: Sep. 22, 2009

(54) MACROCYCLIC FACTOR VIIA INHIBITORS USEFUL AS ANTICOAGULANTS

(75) Inventors: Eldon Scott Priestley, Yardley, PA (US); Daniel L. Cheney, Ringoes, NJ (US); Nicholas Ronald Wurtz, Pennington, NJ (US); Peter W. Glunz, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 340 days.

(21) Appl. No.: 11/614,131

(22) Filed: Dec. 21, 2006

(65) Prior Publication Data

US 2007/0208054 A1    Sep. 6, 2007

Related U.S. Application Data

(60) Provisional application No. 60/753,786, filed on Dec. 23, 2005, provisional application No. 60/865,475, filed on Nov. 13, 2006.

(51) Int. Cl.
*C07D 267/22* (2006.01)
*C07D 513/00* (2006.01)
*A61K 31/33* (2006.01)
*A61K 31/47* (2006.01)
*A61P 7/02* (2006.01)

(52) U.S. Cl. .................. 514/183; 514/307; 540/456; 540/460

(58) Field of Classification Search ................ 514/183, 514/307; 540/456, 460
See application file for complete search history.

(56) References Cited

U.S. PATENT DOCUMENTS

| | | | |
|---|---|---|---|
| 5,843,442 A | 12/1998 | Soule et al. |
| 5,866,542 A | 2/1999 | Vlasuk et al. |
| 6,642,252 B2 | 11/2003 | Bisacchi et al. |
| 7,122,559 B2 | 10/2006 | Glunz et al. |
| 7,144,895 B2 | 12/2006 | Bisacchi et al. |
| 2006/0166997 A1 | 7/2006 | Zhang et al. |
| 2007/0003539 A1 | 1/2007 | Zhang et al. |

FOREIGN PATENT DOCUMENTS

WO    WO03/011222 A    2/2003

OTHER PUBLICATIONS

Morrissey et al., *Quantitation of Activated Factor VII Levels in Plasma Using a Tissue Factor Mutant Selectively Deficient in Promoting Factor VII Activation*, Blood, vol. 81, No. 3 (Feb. 1), 1993, pp. 734-744.
Carson et al., *The role of tissue factor in production of thrombin*, Blood Coagulation and Fibrinolysis, vol. 4, 1993, pp. 281-292.
Hoffman et al., *A cell-based model of coagulation and the role of factor VIIa*, Blood Reviews (2003) 17, pp. S1-S5.
Giesen et al., *Blood-borne tissue factor: Another view of thrombosis*, PNAS, vol. 96, pp. 2311-2315, Mar. 1999.
Himber et al., *Inhibition of tissue factor limits the growth of venous thrombus in the rabbit*, J. Thrombosis and Haemostasis, 1: 889-895, (2002).
Morrissey et al, *Tissue factor: in at the start . . . and the finish?*, J. of Thrombosis and Haemostasis, 1: 878-880, 2003.
Hirsh et al., *New anticoagulants*, Blood, Jan. 15, 2005, vol. 105, No. 2, pp. 453-463.
Girard et al., *The role of tissue factor/factor VIIa in the pathophysiology of acute thrombotic formation*, Curr. Opin. Pharmacol. 2001, 1, 159-163.
Lazarus et al., *Inhibitors of Tissue Factor-Factor VIIa for Anticoagulant Therapy*, Curr. Med. Chem. 2004, 11, 2275-2290.
Frederick et al., *Modulators of the Coagulation Cascade: Focus and Recent Advances in Inhibitors of Tissue Factor, Factor VIIa and their Complex*, Curr. Med. Chem, 2005, 12, pp. 397-417.
Szalony et al., *Administration of a small molecule tissue factor/Factor VIIa inhibitor in a non-human primate thrombosis model of venous thrombosis: effects on thrombus formation and bleeding time*, Thrombosis Research 112 (2003) 167-174.
Suleymanov et al, *Pharmacological Interrruption of Acute Thrombus Formation with Minimal Hemorrhagic Complications by a Small Molecule Tissue Factor/Factor VIIa Inhibitor: Comparison to Factor Xa and Thrombin Inhibition in a Nonhuman Primate Thrombosis Model*, JPET 2003, vol. 306, No. 3, 1115-1121.
Olivero et al., *A Selective Slow Binding Inhibitor fo Factor Viia Binds to a Nonstandard Active Site Conformation and Attenuates Thrombus Formation in Vivo*, J. Biological Chemistry, vol. 280, No. 10, pp. 9169-9169 (2005).

(Continued)

*Primary Examiner*—Bruck Kifle
(74) *Attorney, Agent, or Firm*—Jing G. Sun

(57) ABSTRACT

The present invention relates generally to novel macrocycles of Formula (I):

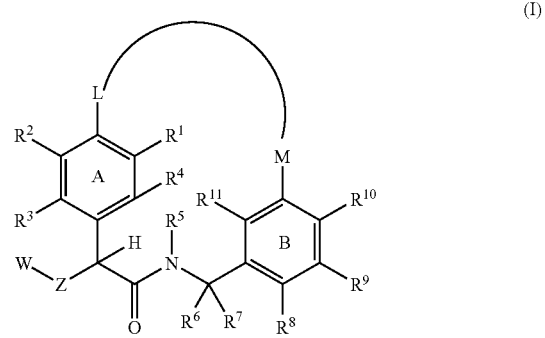

or stereoisomers, tautomers, pharmaceutically acceptable salts, solvates, or prodrugs thereof, wherein the variables A, B, L, M, W, Z, $R^1$, $R^2$, $R^3$, $R^4$, $R^5$, $R^6$, $R^7$, $R^8$, $R^9$, and $R^{10}$ are as defined herein. These compounds are selective inhibitors of the serine protease coagulation factor VIIa which can be used as medicaments.

25 Claims, No Drawings

OTHER PUBLICATIONS

Zbinden et al., *Dose-dependent antithrombotic activity of an orally active tissue factor/factor VIIa inhibitor without concomitant enhancement of bleeding propensity*, Bioorganic & Medicinal Chemistry 14 (2006) 5357-5369.

Szalony et al., *Pharmacological Intervention at Disparate Sites in the Coagulation Cascade: Comparison of Anti-thrombosis*, Thrombosis Research 14(2), 113-121 (2002).

Arnold et al., "The antithrombotic and anti-inflammatory effects of BCX-3607, a small molecule tissue factor/factor VIIa inhibitor", Thrombosis Research (2006) 117, 343-349.

Lee et al., *Dose-Response Study of Recombinant Factor VIIa/Tissue Factor Inhibitor RRecombinant Nematode Anticoagulation Protein c2 in Prevention of Postoperative Venous Thromboembolism in Patients Undergoing Total Knee Replacement*, Circulation 2001; 104; 74-78.

Moons M.D. et al., *Recombinant Nematode Anticoagulant Protein c2, an Inhibitor of Tissue Factor/Factor VIIa Complex, in Patients Undergoing Elective Coronary Angioplasty*, J. Amer. Coll. Of Cardiology, vol. 41, No. 12 (2003).

Young et al., *Factor VIIa Inhibitors: Chemical optimization, preclinical pharmacokinetics, pharmacodynamics, and efficacy in an arterial baboon thrombosis model*, Biorganic & Medicinal Chemistry Letters 2006, 16, 2037-2041.

Giugliano et al. World Congress of Cardiology 2006, Barcelona, Poster #3897.

Goodnight et al., Screening Tests of Hemostasis, *Disorders of Thrombosis and Hemostasis: a clinical guide*, 2001, pp. 41-51.

MACROCYCLIC FACTOR VIIA INHIBITORS USEFUL AS ANTICOAGULANTS

CROSS-REFERENCE TO RELATED APPLICATIONS

The present application claims priority benefit of U.S. provisional application Ser. No. 60/753,786, filed Dec. 23, 2005; and Ser. No. 60/865,475, filed Nov. 13, 2006, each of which is incorporated by reference herein.

FIELD OF THE INVENTION

The present invention provides novel macrocycles, and analogues thereof, which are selective inhibitors of the serine protease coagulation factor VIIa. This invention also relates to pharmaceutical compositions comprising these compounds and methods of using the same.

BACKGROUND OF THE INVENTION

Factor VII is a plasma serine protease involved in the initiation of the coagulation cascade. It is present in human blood at a concentration of approximately 500 ng/mL, with about 1% of the total amount in the proteolytically active form factor VIIa (Morrissey, J. H. et al. *Blood* 1993, 81, 734-744). Factor VIIa binds with high affinity to its cofactor, tissue factor, in the presence of calcium ions to form a complex with enhanced proteolytic activity (Carson, S. D. and Brozna, J. P. *Blood Coag. Fibrinol.* 1993, 4, 281-292). Tissue factor is normally expressed in cells surrounding the vasculature, and is exposed to factor VIIa in blood by vessel injury or atherosclerotic plaque rupture. Once formed, the tissue factor/factor VIIa complex initiates blood coagulation by proteolytic cleavage of factor X to factor Xa, factor IX to factor IXa and autoactivation of additional factor VII to VIIa. Factor Xa, generated either directly by tissue factor/factor VIIa or indirectly through action of factor IXa, catalyzes the conversion of prothrombin to thrombin. Thrombin converts fibrinogen to fibrin, which polymerizes to form the structural framework of a blood clot, and activates platelets, which are a key cellular component of coagulation (Hoffman, M. *Blood Reviews* 2003, 17, S1-S5). In addition, there is evidence that tissue factor is present in blood, likely in an encrypted form that is de-encrypted during clot formation. (Giesen, P. L. A. et al. *Proc. Natl. Acad. Sci.* 1999, 96, 2311-2315; Himber, J. et al. *J. Thromb. Haemost.* 2003, 1, 889-895). The tissue factor/factor VIIa complex derived from blood borne tissue factor may play an important role in propagation of the coagulation cascade (clot growth) and in thrombus formation in the absence of vessel wall injury (i.e., stasis induced deep vein thrombosis or sepsis). The source of blood borne tissue factor is an area of active research (Morrissey, J. H. *J. Thromb. Haemost.* 2003, 1, 878-880).

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thrombotic or thromboembolic disorders and include acute coronary syndrome, unstable angina, myocardial infarction, ischemic stroke, deep vein thrombosis, peripheral occlusive arterial disease, transient ischemic attack, and pulmonary embolism. In addition, thrombosis occurs on artificial surfaces in contact with blood, including catheters and artificial heart valves. Therefore, drugs that inhibit blood coagulation, or anticoagulants, are "pivotal agents for prevention and treatment of thromboembolic disorders" (Hirsh, J. et al. *Blood* 2005, 105, 453-463).

Because of its key role in the coagulation cascade, researchers have postulated that inhibition of factor VIIa could be used to treat or prevent thrombotic or thromboembolic disease. (Girard, T. J.; Nicholson, N. S. *Curr. Opin. Pharmacol.* 2001, 1, 159-163; Lazarus, R. A., et al. *Curr. Med. Chem.* 2004, 11, 2275-2290; Frederick, R. et al. *Curr. Med. Chem.* 2005, 12, 397-417.) Several studies have confirmed that various biological and small molecule inhibitors of factor VIIa have in vivo antithrombotic efficacy with a low bleeding liability. For instance, it has been demonstrated that a biological factor VIIa inhibitor XK1, comprising a hybrid of Factor X light chain and tissue factor pathway inhibitor first kunitz domain, prevents thrombus formation in a rat model of arterial thrombosis, with no change in bleeding time or total blood loss (Szalony, J. A. et al. *J. Thrombosis and Thrombolysis* 2002, 14, 113-121). In addition, small molecule active site directed factor VIIa inhibitors have demonstrated antithrombotic efficacy in animal models of arterial thrombosis (Suleymanov, O., et al. *J Pharmacology and Experimental Therapeutics* 2003, 306, 1115-1121; Olivero, A. G. et al. *J. Biol. Chem.* 2005, 280, 9160-9169; Young, W. B., et al. *Bioorg. Med. Chem. Lett.* 2006, 16, 2037-2041; Zbinden, K. G. et al. *Bioorg. Med. Chem.* 2006, 14, 5357-5369) and venous thrombosis (Szalony, J. A., et al. *Thrombosis Research* 2003, 112, 167-174; Arnold, C. S., et al. *Thrombosis Research* 2006, 117, 343-349), with little impact on bleeding time or blood loss. Moreover, the biological factor VIIa inhibitor recombinant nematode anticoagulant protein c2 (rNAPc2) is currently under clinical investigation for treatment of acute coronary syndromes. Results of initial clinical trials demonstrate that rNAPc2 prevents deep vein thrombosis in patients undergoing total knee replacement (Lee, A., et al. *Circulation* 2001, 104, 74-78), reduces systemic thrombin generation in patients undergoing coronary angioplasty (Moons, A. H. M. *J. Am. Coll. Cardiol.* 2003, 41, 2147-2153), and reduces magnitude and duration of ischemic events in patients with acute coronary syndromes (Giugliano, R. P. et al. World Congress of Cardiology 2006, Barcelona, Poster #3897).

Work has accordingly been performed to identify and optimize factor VIIa inhibitors. For example, U.S. Pat. No. 5,866,542 describes recombinant nematode anticoagulant proteins which inhibit factor VIIa. U.S. Pat. No. 5,843,442 discloses monoclonal antibodies or antibody fragments possessing factor VIIa inhibitory activity, and U.S. Pat. No. 5,023,236 presents tripeptides and tripeptide derivatives that inhibit factor VIIa.

While a number of factor VIIa inhibitors have been discussed in the art, improved inhibitors, especially non-peptide inhibitors, of serine proteases for the treatment of thromboembolic disorders are always desirable. The present invention discloses novel macrocyclic derivatives and analogues thereof, as inhibitors of coagulation Factor VIIa and, as such, their utility in the treatment of thromboembolic disorders.

In addition, it is also desirable to find new compounds with improved pharmacological characteristics compared with known serine protease inhibitors. For example, it is preferred to find new compounds with improved factor VIIa inhibitory activity and selectivity for factor VIIa versus other serine proteases. Also, it is preferred to find new compounds with improved activity in in vitro clotting assays, such as the prothrombin time (PT) assay. (for a description of the PT assay see, Goodnight, S. H.; Hathaway, W. E. Screening Tests of Hemostasis. *Disorders of Thrombosis and Hemostasis: a clinical guide*, $2^{nd}$ edition, McGraw-Hill: New York, 2001 pp. 41-51). It is also desirable and preferable to find compounds with advantageous and improved characteristics in one or more of the following categories, which are given as examples and are not intended to be limiting: (a) pharmacokinetic properties, including oral bioavailability, half life, and clearance; (b) pharmaceutical properties; (c) dosage requirements; (d) factors which decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) factors that improve manufacturing costs or feasibility.

SUMMARY OF THE INVENTION

The present invention provides novel macrocycles, and analogues thereof, which are useful as selective inhibitors of serine protease enzymes, especially factor VIIa, including stereoisomers, tautomers, pharmaceutically acceptable salts, solvates, or prodrugs thereof.

The present invention also provides processes and intermediates for making the compounds of the present invention or stereoisomers, tautomers, pharmaceutically acceptable salt, solvates, or prodrugs thereof.

The present invention also provides pharmaceutical compositions comprising a pharmaceutically acceptable carrier and at least one of the compounds of the present invention or a stereoisomer, tautomer, pharmaceutically acceptable salt, solvate, or prodrug thereof.

The present invention also provides a method for modulation of the coagulation cascade comprising administering to a host in need of such treatment a therapeutically effective amount of at least one of the compounds of the present invention or a stereoisomer, tautomer, pharmaceutically acceptable salt, solvate, or prodrug thereof.

The present invention also provides a method for treating thrombotic or thromboembolic disorders comprising administering to a host in need of such treatment a therapeutically effective amount of at least one of the compounds of the present invention or a stereoisomer, tautomer, pharmaceutically acceptable salt, solvate, or prodrug thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of a thromboembolic disorder.

These and other features of the invention will be set forth in expanded form as the disclosure continues.

DETAILED DESCRIPTION OF THE INVENTION

In a first aspect, the present invention provides, inter alia, a compound of Formula (I):

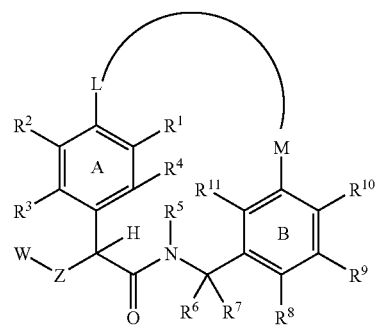

(I)

or stereoisomers, tautomers, pharmaceutically acceptable salts, solvates, or prodrugs thereof, wherein:

ring A is phenyl or a pyridyl isomer defined by replacing one of $CR^1$, $CR^2$, $CR^3$, or $CR^4$ in ring A of formula (I) with N;

ring B is phenyl or a pyridyl isomer defined by replacing one of $CR^8$, $CR^9$, $CR^{10}$, or $CR^{11}$ in ring B of formula (I) with N;

for the definitions of M and L, as they are written from left to right, the atom connectivity is in the order (ring A)-L-M-(ring B);

M is —CONH—, —SO$_2$NH—, —NHCO—, or —NHSO$_2$—;

when M is —CONH—, L is selected from —C($R^{12}R^{13}$)C($R^{12}R^{13}$)—, —XC($R^{12}R^{13}$)—, —C($R^{12}R^{13}$)Y—, —C($R^{12}R^{13}$)C($R^{12}R^{13}$)C($R^{12}R^{13}$)—, —XC($R^{12}R^{13}$)C($R^{12}R^{13}$)—, —C($R^{12}R^{13}$)XC($R^{12}R^{13}$)—, —C($R^{12}R^{13}$)C($R^{12}R^{13}$)Y—, —XC($R^{12}R^{13}$)Y—, —C($R^{12}R^{13}$)C($R^{12}R^{13}$)C($R^{12}R^{13}$)C($R^{12}R^{13}$)—, —XC($R^{12}R^{13}$)C($R^{12}R^{13}$)C($R^{12}R^{13}$)—, —C($R^{12}R^{13}$)XC($R^{12}R^{13}$)C($R^{12}R^{13}$)—, —C($R^{12}R^{13}$)C($R^{12}R^{13}$)XC($R^{12}R^{13}$)—, —C($R^{12}R^{13}$)C($R^{12}R^{13}$)C($R^{12}R^{13}$)Y—, —XC($R^{12}R^{13}$)C($R^{12}R^{13}$)Y—, —XC($R^{12}R^{13}$)XC($R^{12}R^{13}$)—, and —C($R^{12}R^{13}$)XC($R^{12}R^{13}$)Y—;

when M is —SO$_2$NH—, L is selected from —C($R^{12}R^{13}$)C($R^{12}R^{13}$)—, —C($R^{12}R^{13}$)C($R^{12}R^{13}$)C($R^{12}R^{13}$)—, —XC($R^{12}R^{13}$)C($R^{12}R^{13}$)—, —C($R^{12}R^{13}$)C($R^{12}R^{13}$)C($R^{12}R^{13}$)C($R^{12}R^{13}$)—, —XC($R^{12}R^{13}$)C($R^{12}R^{13}$)C($R^{12}R^{13}$)—, —C($R^{12}R^{13}$)XC($R^{12}R^{13}$)C($R^{12}R^{13}$)—, —C($R^{12}R^{13}$)XC($R^{12}R^{13}$)—, —C($R^{12}R^{13}$)C($R^{12}R^{13}$)Y—, —C($R^{12}R^{13}$)C($R^{12}R^{13}$)XC($R^{12}R^{13}$)—, —C($R^{12}R^{13}$)C($R^{12}R^{13}$)C($R^{12}R^{13}$)Y—, —XC($R^{12}R^{13}$)C($R^{12}R^{13}$)Y——XC($R^{12}R^{13}$)XC($R^{12}R^{13}$)—, and —C($R^{12}R^{13}$)XC($R^{12}R^{13}$)Y—;

when M is —NHCO—, L is selected from —C($R^{12}R^{13}$)C($R^{12}R^{13}$)—, —C($R^{12}R^{13}$)C($R^{12}R^{13}$)C($R^{12}R^{13}$)—, —XC($R^{12}R^{13}$)C($R^{12}R^{13}$)—, —C($R^{12}R^{13}$)C($R^{12}R^{13}$)C($R^{12}R^{13}$)C($R^{12}R^{13}$)—, —XC($R^{12}R^{13}$)C($R^{12}R^{13}$)C($R^{12}R^{13}$)—, and —C($R^{12}R^{13}$)XC($R^{12}R^{13}$)C($R^{12}R^{13}$)—;

when M is —NHSO$_2$—, L is selected from —C($R^{12}R^{13}$)C($R^{12}R^{13}$)—, —C($R^{12}R^{13}$)C($R^{12}R^{13}$)C($R^{12}R^{13}$)—, —XC($R^{12}R^{13}$)C($R^{12}R^{13}$)—, —C($R^{12}R^{13}$)C($R^{12}R^{13}$)C($R^{12}R^{13}$)C($R^{12}R^{13}$)—, —XC($R^{12}R^{13}$)C($R^{12}R^{13}$)C($R^{12}R^{13}$)—, and —C($R^{12}R^{13}$)XC($R^{12}R^{13}$)C($R^{12}R^{13}$)—;

W is substituted with 0-2 $R^{14}$ and is selected from:

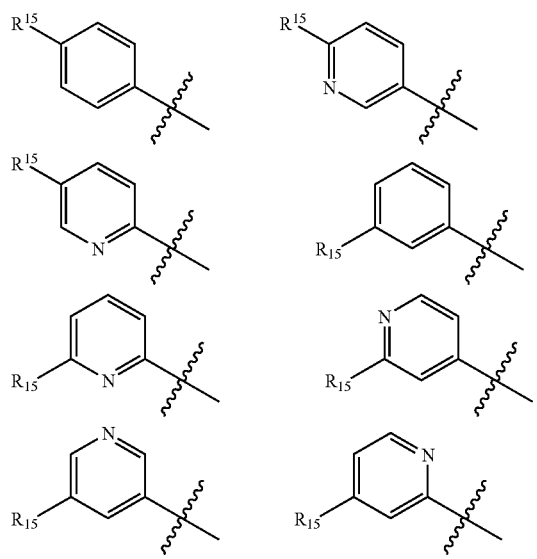

-continued

[Chemical structures shown: various aminoheterocyclic groups including aminoisoquinoline, aminophthalazine, aminoquinazoline, aminonaphthyridine, and aminobenzimidazole variants]

X is O, S(O)$_p$, or NR$^{16}$;
Y is O or NR$^{16a}$;
Z is NH, O or S;
R$^1$ is H, F, Cl, Br, I, C$_{1-4}$ alkyl substituted with 0-1 OH, C$_{1-4}$ fluoroalkyl, C$_{2-4}$ alkenyl, C$_{2-4}$ alkynyl, C$_{1-4}$ alkoxy, C$_{1-4}$ alkylthio, or C$_{3-6}$ cycloalkyl;
R$^2$ is H, F, Cl, Br, I, —(CH$_2$)$_s$OR$^a$, —(CH$_2$)$_s$SR$^b$, —(CH$_2$)$_s$CF$_3$, —(CH$_2$)$_s$OCF$_3$, —(CH$_2$)$_s$OCHF$_2$, —(CH$_2$)$_s$OCH$_2$F, —(CH$_2$)$_s$CN, —(CH$_2$)$_s$NO$_2$, —(CH$_2$)$_s$NR$^c$R$^d$, —(CH$_2$)$_s$C(O)R$^a$, —(CH$_2$)$_s$CO$_2$R$^a$, —(CH$_2$)$_s$NR$^c$C(O)R$^a$, —(CH$_2$)$_s$C(O)NR$^c$R$^d$, —(CH$_2$)$_s$NR$^c$C(O)OR$^b$, —(CH$_2$)$_s$OC(O)OR$^b$, —(CH$_2$)$_s$NR$^c$C(O)NR$^c$R$^d$, —(CH$_2$)$_s$OC(O)NR$_c$R$^d$, —(CH$_2$)$_s$SO$_2$NR$^c$R$^d$, —(CH$_2$)$_s$NR$^c$SO$_2$NR$^c$R$^d$, —(CH$_2$)$_s$NR$^c$SO$_2$R$^b$, —(CH$_2$)$_s$NR$^c$SO$_2$CF$_3$, —(CH$_2$)$_s$SO$_2$CF$_3$, —(CH$_2$)$_s$S(O)$_2$R$^b$, C$_{1-6}$ alkyl substituted with 0-2 R$^e$, C$_{1-4}$ fluoroalkyl, C$_{2-4}$ alkenyl substituted with 0-2 R$^e$, C$_{2-4}$ alkynyl substituted with 0-2 R$^e$, —(CH$_2$)$_s$C$_{3-6}$ carbocycle substituted with 0-2 R$^f$, —(CH$_2$)$_s$-(5- to 6-membered heterocycle), —(CH$_2$)$_s$NR$^c$-(5 to 6-membered heterocycle), or —(CH$_2$)$_s$—O-(5- to 6-membered heterocycle); wherein said heterocycle comprises carbon atoms and 1-3 heteroatoms selected from N, NR$^c$, O, and S(O)$_p$ and is substituted with 0-2 R$^g$;
R$^3$ is H, F, Cl, Br, I, —(CH$_2$)$_s$OR$^a$, —(CH$_2$)$_s$SR$^b$, —(CH$_2$)$_s$CF$_3$, —(CH$_2$)$_s$OCF$_3$, —(CH$_2$)$_s$OCHF$_2$, —(CH$_2$)$_s$OCH$_2$F, —(CH$_2$)$_s$CN, —(CH$_2$)$_s$NO$_2$, —(CH$_2$)$_s$NR$^c$R$^d$, —(CH$_2$)$_s$C(O)R$^a$, —(CH$_2$)$_s$CO$_2$R$^a$, —(CH$_2$)$_s$NR$^c$C(O)R$^a$, —(CH$_2$)$_s$C(O)NR$^c$R$^d$, —(CH$_2$)$_s$NR$^c$C(O)OR$^b$, —(CH$_2$)$_s$OC(O)OR$^b$, —(CH$_2$)$_s$NR$^c$C(O)NR$^c$R$^d$, —(CH$_2$)$_s$OC(O)NR$_c$R$^d$, —(CH$_2$)$_s$SO$_2$NR$^c$R$^d$, —(CH$_2$)$_s$NR$^c$SO$_2$NR$^c$R$^d$, —(CH$_2$)$_s$NR$^c$SO$_2$R$^b$, —(CH$_2$)$_s$NR$^c$SO$_2$CF$_3$, —(CH$_2$)$_s$SO$_2$CF$_3$, —(CH$_2$)$_s$S(O)$_2$R$^b$, —O(CH$_2$)$_n$CO$_2$R$^a$, —(CH$_2$)$_s$SO$_2$NHCOR$^b$, —(CH$_2$)$_s$CONHSO$_2$R$^b$, C$_{1-6}$ alkyl substituted with 0-2 R$^e$, C$_{1-4}$ fluoroalkyl, C$_{2-4}$ alkenyl substituted with 0-2 R$^e$, C$_{2-4}$ alkynyl substituted with 0-2 R$^e$, —O(benzyl substituted with CO$_2$R$^a$), —(CH$_2$)$_s$tetrazolyl, —(CH$_2$)$_s$—C$_{3-6}$ carbocycle substituted with 0-2 R$^{f1}$, —(CH$_2$)$_s$-(5- to 6-membered heterocycle), —(CH$_2$)$_s$—NR$^c$-(5 to 6-membered heterocycle), or —(CH$_2$)$_s$—O-(5- to 6-membered heterocycle); wherein said heterocycle comprises carbon atoms and 1-3 heteroatoms selected from N, NR$^c$, O, and S(O)$_p$ and is substituted with 0-2 R$^{g1}$;
alternatively, R$^2$ and R$^3$ may combine to form a 5- to 7-membered carbocycle or heterocycle comprising: carbon atoms and 0-2 heteroatoms selected from N, NR$^c$, O, and S(O)$_p$; wherein said carbocycle and heterocycle are substituted with 0-3 R$^{g1}$;
R$^4$ is H, F, Cl, Br, I, or C$_{1-4}$ alkyl;
R$^5$ is H, —(CH$_2$)$_q$OR$^a$, —(CH$_2$)$_q$SR$^b$, —(CH$_2$)$_r$CF$_3$, —(CH$_2$)$_q$OCF$_3$, —(CH$_2$)$_q$OCHF$_2$, —(CH$_2$)$_q$OCH$_2$F, —(CH$_2$)$_q$CN, —(CH$_2$)$_q$NO$_2$, —(CH$_2$)$_q$NR$^c$R$^d$, —(CH$_2$)$_s$C(O)R$^a$, —(CH$_2$)$_s$CO$_2$R$^a$, —(CH$_2$)$_q$NR$^c$C(O)R$^a$, —(CH$_2$)$_s$C(O)NR$^c$R$^d$, —(CH$_2$)$_q$NR$^c$C(O)OR$^b$, —(CH$_2$)$_q$OC(O)OR$^b$, —(CH$_2$)$_q$NR$^c$C(O)NR$^c$R$^d$, —(CH$_2$)$_q$OC(O)NR$_c$R$^d$, —(CH$_2$)$_q$SO$_2$NR$^c$R$^d$, —(CH$_2$)$_q$NR$^c$SO$_2$NR$^c$R$^d$, —(CH$_2$)$_q$NR$^c$SO$_2$R$^b$, —(CH$_2$)$_q$NR$^c$SO$_2$CF$_3$, —(CH$_2$)$_q$SO$_2$CF$_3$, —(CH$_2$)$_q$S(O)$_2$R$^b$, —(CH$_2$)$_q$SO$_2$NHCOR$^b$, —(CH$_2$)$_s$CONHSO$_2$R$^b$, —O(benzyl substituted with CO$_2$R$^a$), —(CH$_2$)$_s$tetrazolyl, C$_{1-6}$ alkyl substituted with 0-2 R$^e$, C$_{2-4}$ alkenyl substituted with 0-2 R$^e$, C$_{2-4}$ alkynyl substituted with 0-2 R$^e$, —(CH$_2$)$_s$—C$_{3-6}$ carbocycle substituted with 0-2 R$^{f1}$, or —(CH$_2$)$_s$-5- to 6-membered heterocycle; wherein said heterocycle comprises carbon atoms and 1-3 heteroatoms selected from N, NR$^c$, O, and S(O)$_p$ and is substituted with 0-2 R$^{g1}$;
R$^6$ is H, —(CH$_2$)$_r$OR$^a$, —(CH$_2$)$_r$SR$^b$, —(CH$_2$)$_s$CF$_3$, —(CH$_2$)$_r$OCF$_3$, —(CH$_2$)$_r$OCHF$_2$, —(CH$_2$)$_r$OCH$_2$F, —(CH$_2$)$_s$CN, —(CH$_2$)$_s$NO$_2$, —(CH$_2$)$_r$NR$^c$R$^d$, —(CH$_2$)$_s$C(O)R$^a$, —(CH$_2$)$_s$CO$_2$R$^a$, —(CH$_2$)$_r$NR$^c$C(O)R$^a$, —(CH$_2$)$_s$C(O)NR$^c$R$^d$, —(CH$_2$)$_r$NR$^c$C(O)OR$^b$, —(CH$_2$)$_r$OC(O)OR$^b$, —(CH$_2$)$_r$NR$^c$C(O)NR$^c$R$^d$, —(CH$_2$)$_r$OC(O)NR$_c$R$^d$, —(CH$_2$)$_r$SO$_2$NR$^c$R$^d$, —(CH$_2$)$_r$NR$^c$SO$_2$NR$^c$R$^d$, —(CH$_2$)$_r$NR$^c$SO$_2$R$^b$, —(CH$_2$)$_r$NR$^c$SO$_2$CF$_3$, —(CH$_2$)$_r$SO$_2$CF$_3$, —(CH$_2$)$_r$S(O)$_2$R$^b$, —(CH$_2$)$_r$SO$_2$NHCOR$^b$, —(CH$_2$)$_s$CONHSO$_2$R$^b$, C$_{1-6}$ alkyl substituted with 0-2 R$^e$, C$_{2-4}$ alkenyl substituted with 0-2 R$^e$, C$_{2-4}$ alkynyl substituted with 0-2 R$^e$, —(CH$_2$)$_s$—C$_{3-6}$ carbocycle substituted with 0-2 R$^{f1}$, or —(CH$_2$)$_s$-5- to 6-membered heterocycle; wherein said heterocycle comprises carbon atoms and 1-3 heteroatoms selected from N, NR$^c$, O, and S(O)$_p$ and is substituted with 0-2 R$^{g1}$;
alternatively, R$^5$ and R$^6$ can be joined to form a 2 to 5-membered alkylene chain, which may be substituted with 0-1 R$^{f1}$;
R$^7$ is H or C$_{1-6}$ alkyl;
alternatively, R$^6$ and R$^7$ can be joined to form a 3-7 membered carbocycle or heterocycle; wherein said carbocycle may be substituted with 0-2 R$^{f1}$; and said heterocycle comprises carbon atoms and 1-3 heteroatoms selected from N, NR$^c$, O, and S(O)$_p$ and is substituted with 0-2 R$^{g1}$;
R$^8$ is H, F, Cl, Br, CN, CH$_2$F, CHF$_2$, —(CH$_2$)$_s$CF$_3$, —(CH$_2$)$_s$OCF$_3$, —(CH$_2$)$_s$SCF$_3$, —(CH$_2$)$_s$OCHF$_2$, —(CH$_2$)$_s$OCH$_2$F, —(CH$_2$)$_s$CN, —(CH$_2$)$_s$NO$_2$, C$_{1-6}$ alkyl, C$_{2-6}$ alkenyl, C$_{2-6}$ alkynyl, —(CH$_2$)$_n$—OR$^a$, —(CH$_2$)$_n$—SR$^b$, —(CH$_2$)$_n$—NR$^c$R$^d$, —(CH$_2$)$_s$C(O)R$^a$, —(CH$_2$)$_s$CO$_2$R$^a$, —(CH$_2$)$_s$NR$^c$C(O)R$^a$, —(CH$_2$)$_s$CONR$^c$R$^d$, —(CH$_2$)$_s$SO$_2$R$^b$, —(CH$_2$)$_s$SO$_2$NR$^c$R$^d$, —(CH$_2$)$_s$NR$^c$C(O)OR$^b$, —(CH$_2$)$_s$OC(O)OR$^b$, —(CH$_2$)$_s$NR$^c$C(O)NR$^c$R$^d$, —(CH$_2$)$_s$ OC(O)NR$^c$R$^d$, —(CH$_2$)$_s$NR$^c$SO$_2$NR$^c$R$^d$, —(CH$_2$)$_s$NR$^c$SO$_2$R$^b$, —(CH$_2$)$_s$NR$^c$SO$_2$CF$_3$, —(CH$_2$)$_s$SO$_2$CF$_3$, —O(CH$_2$)$_n$CO$_2$R$^a$, —(CH$_2$)$_s$SO$_2$NHCOR$^b$, —(CH$_2$)$_s$CONHSO$_2$R$^b$, —O(benzyl substituted with CO$_2$R$^a$), —(CH$_2$)$_s$tetrazolyl, C$_{1-6}$ alkyl substituted with 0-2 R$^e$, C$_{1-4}$ fluoroalkyl, C$_{2-4}$ alkenyl substituted with 0-2 R$^e$, C$_{2-4}$ alkynyl substituted with 0-2 R$^e$, —(CH$_2$)$_s$—C$_{3-6}$ carbocycle substituted with 0-2 R$^{f1}$, or —(CH$_2$)$_n$-5- to 10-membered heterocycle comprising: carbon atoms and 1-4 heteroatoms selected from N, NR$^c$, O, and S(O)$_p$, wherein said phenyl and heterocycle are substituted with 0-3 R$^{g1}$;

R$^9$, R$^{10}$, and R$^{11}$ are, independently at each occurrence, H, F, Cl, Br, I, C$_{1-4}$ alkyl, or C$_{1-4}$ alkoxy;

R$^{12}$ and R$^{13}$ are, independently at each occurrence, H, F, Cl, OR$^a$, SR$^b$, CF$_3$, OCF$_3$, OCHF$_2$, OCH$_2$F, CN, NO$_2$, —NR$^c$R$^d$, —C(O)R$^a$, —CO$_2$R$^a$, —NR$^c$C(O)R$^a$, —C(O)NR$^c$R$^d$, —NR$^c$C(O)OR$^b$, —NR$^c$C(O)NR$^c$R$^d$, —OC(O)NR$^c$R$^d$, —OC(O)OR$^a$, —SO$_2$NR$^c$R$^d$, —NR$^c$SO$_2$NR$^c$R$^d$, —NR$^c$SO$_2$R$^b$, —NR$^c$SO$_2$CF$_3$, —SO$_2$CF$_3$, —S(O)$_2$R$^b$, C$_{1-6}$ alkyl substituted with 0-2 R$^e$, C$_{2-4}$ alkenyl substituted with 0-2 R$^e$, C$_{2-4}$ alkynyl substituted with 0-2 R$^e$, —(CH$_2$)$_s$—C$_{3-6}$ carbocycle substituted with 0-2 R$^{f1}$, —(CH$_2$)$_s$-(5- to 6-membered heterocycle), —NR$^c$-(5- to 6-membered heterocycle), or —O-(5- to 6-membered heterocycle); wherein said heterocycle comprises carbon atoms and 1-3 heteroatoms selected from N, NR$^c$, O, and S(O)$_p$ and is substituted with 0-2 R$^{g1}$;

alternatively, any two R$^{12}$ or R$^{13}$ attached to either the same carbon or to two adjacent carbons may combine to form a 3- to 7-membered carbocycle or heterocycle comprising: carbon atoms and 0-3 heteroatoms selected from N, NR$^c$, O, and S(O)$_p$, wherein said carbocycle or heterocycle is substituted with 0-3 R$^g$;

alternately, two R$^{12}$ or R$^{13}$ on the same carbon atom can be replaced with oxo;

optionally, two R$^{12}$ or R$^{13}$ on adjacent carbon atoms in L may be replaced with a double or triple bond between the two carbon atoms;

R$^{14}$ is, independently at each occurrence, CN, F, Cl, Br, I, OH, N(R$^{17}$R$^{17}$), C$_{1-3}$ alkyl, or C$_{1-3}$ alkoxy;

R$^{15}$ is, independently at each occurrence, H, —C(=NH) NH$_2$, N(R$^{17}$R$^{17}$), —C(R$^{17}$R$^{17}$)N(R$^{17}$R$^{17}$), —CON(R$^{17}$R$^{17}$), CN, F, Cl, Br, I, OH, C$_{1-3}$ alkyl, or C$_{1-3}$ alkoxy;

R$^{16}$ is, independently at each occurrence, H, C$_{1-6}$ alkyl, C$_{3-6}$ cycloalkyl, phenyl, benzyl, —C(O)R$^a$, —C(O)NR$^c$R$^d$, —C(O)OR$^b$, —SO$_2$NR$^c$R$^d$, —SO$_2$CF$_3$, —S(O)$_2$R$^b$, or —(CH$_2$)$_s$-(5- to 6-membered heterocycle); wherein said alkyl or cycloalkyl are optionally substituted with 0-2 R$^e$, said phenyl and benzyl are optionally substituted with 0-2 R$^f$, and said heterocycle comprises carbon atoms and 1-3 heteroatoms selected from N, NR$^c$, O, and S(O)$_p$ and is substituted with 0-2 R$^g$;

R$^{16a}$ is, independently at each occurrence, H, C$_{1-6}$ alkyl, C$_{3-6}$ cycloalkyl, phenyl, benzyl, —C(O)R$^a$, —C(O)NR$^c$R$^d$, —C(O)OR$^b$, —SO$_2$NR$^c$R$^d$, —SO$_2$CF$_3$, —S(O)$_2$R$^b$, or 5- to 6-membered heterocycle; wherein said alkyl or cycloalkyl are optionally substituted with 0-2 R$^e$, said phenyl and benzyl are optionally substituted with 0-2 R$^f$, and said heterocycle comprises carbon atoms and 1-3 heteroatoms selected from N, NR$^c$, O, and S(O)$_p$ and is substituted with 0-2 R$^g$;

R$^{17}$ is, independently at each occurrence, H or Me;

R$^a$ is, independently at each occurrence, H, C$_{1-4}$ alkyl, C$_{3-6}$ cycloalkyl, phenyl, or benzyl; wherein said alkyl and cycloalkyl are optionally substituted with 0-2 R$^e$, and said phenyl and benzyl are optionally substituted with 0-2 R$^f$;

R$^b$ is, independently at each occurrence, C$_{1-4}$ alkyl, C$_{3-6}$ cycloalkyl, phenyl, or benzyl; wherein said alkyl and cycloalkyl are optionally substituted with 0-2 R$^e$, and said phenyl and benzyl are optionally substituted with 0-2 R$^f$;

R$^c$ and R$^d$ are, independently at each occurrence, H, C$_{1-4}$ alkyl, C$_{3-6}$ cycloalkyl, phenyl, or benzyl;

alternatively, R$^c$ and R$^d$, when attached to the same nitrogen atom, combine to form a 4- to 7-membered heterocycle comprising: carbon atoms and 0-2 additional heteroatoms selected from N, O, and S(O)$_p$; wherein said heterocycle is substituted with 0-2 R$^g$;

R$^e$ is, independently at each occurrence, F, CF$_3$, OH, or C$_{1-3}$ alkoxy;

R$^f$ is, independently at each occurrence, F, Cl, Br, CF$_3$, OH, C$_{1-3}$ alkyl, or C$_{1-3}$ alkoxy;

R$^{f1}$ is, independently at each occurrence, R$^f$, —CO$_2$R$^a$, —C(O)NR$^c$R$^d$, —CONHSO$_2$R$^b$, or —CH$_2$CONHSO$_2$R$^b$;

R$^g$ is, independently at each occurrence, =O, F, Cl, Br, CF$_3$, OH, C$_{1-3}$ alkyl, or C$_{1-3}$ alkoxy;

R$^{g1}$ is, independently at each occurrence, R$^g$, —CO$_2$R$^a$, —C(O)NR$^c$R$^d$, —CONHSO$_2$R$^b$, or —CH$_2$CONHSO$_2$R$^b$;

n, at each occurrence, is selected from 0, 1, 2, 3, and 4;
p, at each occurrence, is selected from 0, 1, and 2;
q, at each occurrence is selected from 2 or 3;
r, at each occurrence is selected from 1, 2, or 3; and
s, at each occurrence, is selected from 0, 1, and 2.

In a second aspect, the present invention includes the compounds of Formula (I), or stereoisomers, tautomers, pharmaceutically acceptable salts, solvates, or prodrugs thereof, within the scope of the first aspect wherein:

M is —CONH—, —SO$_2$NH—, —NHCO—, or —NHSO$_2$—;

when M is —CONH—, L is selected from —C(R$^{12}$R$^{13}$)C(R$^{12}$R$^{13}$)—, —XC(R$^{12}$R$^{13}$)—, —C(R$^{12}$R$^{13}$)Y—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)XC(R$^{12}$R$^{13}$)—, —C(R$^{12}$R$^{13}$)C(R$^{12}$R$^{13}$)Y—, —XC(R$^{12}$R$^{13}$)Y—, —C(R$^{12}$R$^{13}$)C(R$^{12}$R$^{13}$)C(R$^{12}$R$^{13}$)C(R$^{12}$R$^{13}$)—, —XC(R$^{12}$R$^{13}$)C(R$^{12}$R$^{13}$)C(R$^{12}$R$^{13}$)—, —C(R$^{12}$R$^{13}$)XC(R$^{12}$R$^{13}$)C(R$^{12}$R$^{13}$)—, —C(R$^{12}$R$^{13}$)C(R$^{12}$R$^{13}$)XC(R$^{12}$R$^{13}$)—, —C(R$^{12}$R$^{13}$)C(R$^{12}$R$^{13}$)C(R$^{12}$R$^{13}$)Y—, and —XC(R$^{12}$R$^{13}$)C(R$^{12}$R$^{13}$)Y—;

when M is —SO$_2$NH—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)C(R$^{12}$R$^{13}$)C(R$^{12}$R$^{13}$)C(R$^{12}$R$^{13}$)—, —XC(R$^{12}$R$^{13}$)C(R$^{12}$R$^{13}$)C(R$^{12}$R$^{13}$)—, and —C(R$^{12}$R$^{13}$)XC(R$^{12}$R$^{13}$)C(R$^{12}$R$^{13}$)—;

when M is —NHCO—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)C(R$^{12}$R$^{13}$)C(R$^{12}$R$^{13}$)C(R$^{12}$R$^{13}$)—, —XC(R$^{12}$R$^{13}$)C(R$^{12}$R$^{13}$)C(R$^{12}$R$^{13}$)—, and —C(R$^{12}$R$^{13}$)XC(R$^{12}$R$^{13}$)C(R$^{12}$R$^{13}$)—;

when M is —NHSO$_2$—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)C(R$^{12}$R$^{13}$)C(R$^{12}$R$^{13}$)C(R$^{12}$R$^{13}$)—, —XC(R$^{12}$R$^{13}$)C(R$^{12}$R$^{13}$)C(R$^{12}$R$^{13}$)—, and —C(R$^{12}$R$^{13}$)XC(R$^{12}$R$^{13}$)C(R$^{12}$R$^{13}$)—;

X is O, S, or NR$^{16}$;

Z is NH or O;

R$^2$ is H, F, Cl, Br, I, OR$^a$, SR$^b$, CF$_3$, OCF$_3$, OCHF$_2$, OCH$_2$F, CN, NO$_2$, —NR$^c$R$^d$, —C(O)R$^a$, —CO$_2$R$^a$, —NR$^c$C(O)R$^a$, —C(O)NR$^c$R$^d$, —NR$^c$C(O)OR$^b$, —NR$^c$C(O)NR$^c$R$^d$, —OC(O)NR$^c$R$^d$, —SO$_2$NR$^c$R$^d$, —NR$^c$SO$_2$NR$^c$R$^d$, —NR$^c$SO$_2$R$^b$, —NR$^c$SO$_2$CF$_3$, —SO$_2$CF$_3$, —S(O)$_2$R$^b$, C$_{1-6}$ alkyl substituted with 0-2 R$^e$, C$_{2-4}$ alkenyl substituted with 0-2 R$^e$, C$_{2-4}$ alkynyl substituted with 0-2 R$^e$, C$_{3-6}$ carbocycle substituted with 0-2 R$^f$, —(CH$_2$)$_s$-(5- to 6-membered heterocycle), —NR$^c$-(5- to 6-membered heterocycle), or —O-(5- to 6-membered heterocycle); wherein said heterocycle comprises carbon atoms and 1-3 heteroatoms selected from N, NR$^c$, O, and S(O)$_p$ and is substituted with 0-2 R$^g$;

R$^3$ is H, F, Cl, Br, I, OR$^a$, SR$^b$, CF$_3$, OCF$_3$, OCHF$_2$, OCH$_2$F, CN, NO$_2$, —NR$^c$R$^d$, —C(O)R$^a$, —CO$_2$R$^a$, —NR$^c$C(O)R$^a$, —C(O)NR$^c$R$^d$, —NR$^c$C(O)OR$^b$, —NR$^c$C(O)NR$^c$R$^d$, —OC(O)NR$^c$R$^d$, —SO$_2$NR$^c$R$^d$, —NR$^c$SO$_2$NR$^c$R$^d$, —NR$^c$SO$_2$R$^b$, —NR$^c$SO$_2$CF$_3$, —SO$_2$CF$_3$, —S(O)$_2$R$^b$, —O(CH$_2$)$_n$CO$_2$R$^a$, —SO$_2$NHCOR$^b$, —CONHSO$_2$R$^b$, C$_{1-6}$ alkyl substituted with 0-2 R$^e$, C$_{2-4}$ alkenyl substituted with 0-2 R$^e$, C$_{2-4}$ alkynyl substituted with 0-2 R$^e$, —O(benzyl substituted with CO$_2$R$^a$), or tetrazolyl;

alternatively, R$^2$ and R$^3$ may combine to form a 5- to 7-membered carbocycle or heterocycle comprising: carbon atoms and 0-2 heteroatoms selected from N, NR$^c$, O, and S(O)$_p$; wherein said carbocycle and heterocycle are substituted with 0-3 R$^g$;

R$^5$ is H, —CH$_2$CO$_2$R$^a$, —CH$_2$C(O)NR$^c$R$^d$, —CH$_2$CH$_2$CO$_2$R$^a$, —CH$_2$CH$_2$C(O)NR$^c$R$^d$, —CH$_2$CH$_2$OR$^a$, —CH$_2$CH$_2$CH$_2$OR$^a$, —CH$_2$CONHSO$_2$R$^b$, —CH$_2$CH$_2$CONHSO$_2$R$^b$, C$_{1-6}$ alkyl substituted with 0-2 R$^e$, —(CH$_2$)$_s$—C$_{3-6}$ carbocycle substituted with 0-2 R$^f$, or —(CH$_2$)$_s$-5- to 6-membered heterocycle; wherein said heterocycle comprises carbon atoms and 1-3 heteroatoms selected from N, NR$^c$, O, and S(O)$_p$ and is substituted with 0-2 R$^g$;

R$^6$ is H, —CH$_2$OR$^a$, —CH$_2$CH$_2$OR$^a$, CN, —CO$_2$R$^a$, —C(O)NR$^c$R$^d$, —CH$_2$CO$_2$R$^a$, —CH$_2$C(O)NR$^c$R$^d$, —CONHSO$_2$R$^b$, —CH$_2$CONHSO$_2$R$^b$, C$_{1-6}$ alkyl substituted with 0-2 R$^e$, —(CH$_2$)$_s$—C$_{3-6}$ carbocycle substituted with 0-2 R$^f$, or —(CH$_2$)$_s$-5- to 6-membered heterocycle; wherein said heterocycle comprises carbon atoms and 1-3 heteroatoms selected from N, NR$^c$, O, and S(O)$_p$ and is substituted with 0-2 R$^g$;

alternatively, R$^5$ and R$^6$ can be joined to form a 2 to 5-membered alkylene chain, which may be substituted with 0-1 R$^{f1}$;

R$^7$ is H or C$_{1-6}$ alkyl;

alternatively, R$^6$ and R$^7$ can be joined to form a 3-7 membered carbocycle or heterocycle; wherein said carbocycle may be substituted with 0-2 R$^{f1}$; and said heterocycle comprises carbon atoms and 1-3 heteroatoms selected from N, NR$^c$, O, and S(O)$_p$ and is substituted with 0-2 R$^{g1}$;

R$^8$ is, H, F, Cl, Br, CN, CH$_2$F, CHF$_2$, CF$_3$, OCF$_3$, SCF$_3$, NO$_2$, C$_{1-6}$ alkyl, C$_{2-6}$ alkenyl, C$_{2-6}$ alkynyl, —(CH$_2$)$_n$—OR$^a$, —(CH$_2$)$_n$—SR$^b$, —(CH$_2$)$_n$—NR$^c$R$^d$, —CONR$^c$R$^d$, —SO$_2$R$^b$, —SO$_2$NR$^c$R$^d$, —(CH$_2$)$_n$-phenyl, or —(CH$_2$)$_n$-5- to 10-membered heterocycle comprising: carbon atoms and 1-4 heteroatoms selected from N, O, and S(O)$_p$, wherein said phenyl and heterocycle are substituted with 0-3 R$^g$;

R$^9$ is H, F, Cl, Br, I, C$_{1-4}$ alkyl, or C$_{1-4}$ alkoxy; and

R$^{10}$ and R$^{11}$ are, independently at each occurrence, H, F, Cl, Br, I, or C$_{1-4}$ alkyl.

In a third aspect, the present invention includes the compounds of Formula (I), or stereoisomers, tautomers, pharmaceutically acceptable salts, solvates, or prodrugs thereof, within the scope of the first or second aspect wherein:

ring A is phenyl or a pyridyl isomer defined by replacing one of CR$^1$, CR$^2$, CR$^3$, or CR$^4$ in ring A of formula (I) with N;

ring B is phenyl or a pyridyl isomer defined by replacing one of CR$^8$, CR$^9$, CR$^{10}$, or CR$^{11}$ in ring B of formula (I) with N;

with the proviso that when ring A is pyridyl, then ring B is not pyridyl;

M is —CONH—, —SO$_2$NH—, —NHCO—, or —NHSO$_2$—;

when M is —CONH—, L is selected from —C(R$^{12}$R$^{13}$)C(R$^{12}$R$^{13}$)—, —XC(R$^{12}$R$^{13}$)—, —C(R$^{12}$R$^{13}$)Y—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)XC(R$^{12}$R$^{13}$)—, XC(R$^{12}$R$^{13}$)Y—, and —C(R$^{12}$R$^{13}$)C(R$^{12}$R$^{13}$)Y—;

when M is —SO$_2$NH—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)C(R$^{12}$R$^{13}$)C(R$^{12}$R$^{13}$)C(R$^{12}$R$^{13}$)—, —XC(R$^{12}$R$^{13}$)C(R$^{12}$R$^{13}$)C(R$^{12}$R$^{13}$)—, and —C(R$^{12}$R$^{13}$)XC(R$^{12}$R$^{13}$)C(R$^{12}$R$^{13}$)—;

when M is —NHCO—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)C(R$^{12}$R$^{13}$)C(R$^{12}$R$^{13}$)C(R$^{12}$R$^{13}$)—, —XC(R$^{12}$R$^{13}$)C(R$^{12}$R$^{13}$)C(R$^{12}$R$^{13}$)—, and —C(R$^{12}$R$^{13}$)XC(R$^{12}$R$^{13}$)C(R$^{12}$R$^{13}$)—;

when M is —NHSO$_2$—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)C(R$^{12}$R$^{13}$)C(R$^{12}$R$^{13}$)C(R$^{12}$R$^{13}$)—, —XC(R$^{12}$R$^{13}$)C(R$^{12}$R$^{13}$)C(R$^{12}$R$^{13}$)—, and —C(R$^{12}$R$^{13}$)XC(R$^{12}$R$^{13}$)C(R$^{12}$R$^{13}$)—;

Z is NH or O;

R$^4$ is H or F;

R$^{10}$ and R$^{11}$ are H; and

R$^{15}$ is, independently at each occurrence, —C(=NH)NH$_2$, N(R$^{17}$R$^{17}$), —C(R$^{17}$R$^{17}$)N(R$^{17}$R$^{17}$), —CON(R$^{17}$R$^{17}$), or OH.

In a fourth aspect, the present invention includes the compounds of Formula (I), or stereoisomers, tautomers, pharmaceutically acceptable salts, solvates, or prodrugs thereof, within the scope of the first, second, or third aspect wherein:

ring A is phenyl;

ring B is phenyl;

M is —CONH— or —NHSO$_2$—;

when M is —CONH—, L is selected from —C(R$^{12}$R$^{13}$)C(R$^{12}$R$^{13}$)—, —XC(R$^{12}$R$^{13}$)—, —C(R$^{12}$R$^{13}$)Y—, —C(R$^{12}$R$^{13}$)C(R$^{12}$R$^{13}$)C(R$^{12}$R$^{13}$)—, —C(R$^{12}$R$^{13}$)XC(R$^{12}$R$^{13}$)—, and —C(R$^{12}$R$^{13}$)C(R$^{12}$R$^{13}$)Y—;

when M is —NHSO$_2$—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, and —XC(R$^{12}$R$^{13}$)C(R$^{12}$R$^{13}$)—;

W is substituted with 0-2 R$^{14}$ and is selected from:

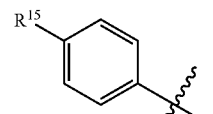

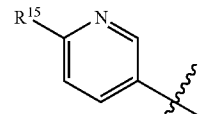

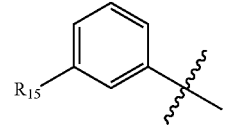

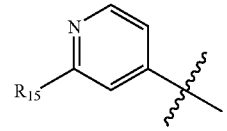

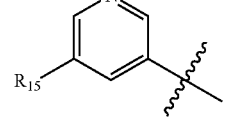

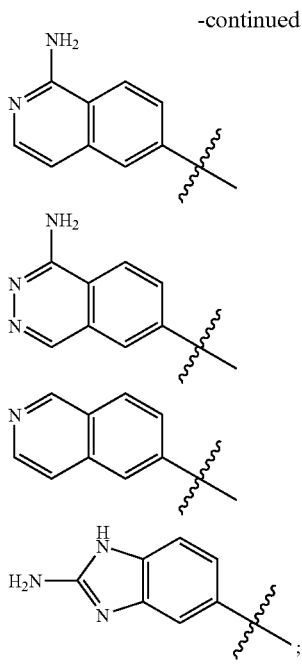

Z is NH;

R¹ is H, Cl, Br, methyl, ethyl, 1-hydroxyethyl, propyl, isopropyl, vinyl, allyl, 2-propenyl, ethynyl, 1-propynyl, methoxy, ethoxy, cyclopropyl, cyclobutyl, or cyclopentyl;

R⁴ is H;

R⁵ is H, $C_{1-4}$ alkyl, —$CH_2CO_2R^a$, —$CH_2C(O)NR^cR^d$, —$CH_2CH_2CO_2R^a$, —$CH_2CH_2C(O)NR^cR^d$, —$CH_2CH_2OR^a$, or —$CH_2CH_2CH_2OR^a$;

R⁶ is H, —$CH_2OR^a$, —$CH_2CH_2OR^a$, CN, $C_{1-4}$ alkyl, —$CO_2R^a$, —$C(O)NR^cR^d$, —$CH_2CO_2R^a$, or —$CH_2C(O)NR^cR^d$;

R⁷ is H;

R¹⁰ and R¹¹ are H; and

R¹⁵ is, independently at each occurrence, —C(=NH)NH₂, N(R¹⁷R¹⁷), —C(R¹⁷R¹⁷)N(R¹⁷R¹⁷), or —CONH₂.

In a fifth aspect, the present invention includes the compounds of Formula (I), or stereoisomers, tautomers, pharmaceutically acceptable salts, solvates, or prodrugs thereof, within the scope of the first, second, third or fourth aspect wherein:

ring A is phenyl;
ring B is phenyl;
M is —CONH—;
L is selected from —C(R¹²R¹³)C(R¹²R¹³)—, —XC(R¹²R¹³)—, —C(R¹²R¹³)Y—, —C(R¹²R¹³)C(R¹²R¹³)C(R¹²R¹³)—, —C(R¹²R¹³)XC(R¹²R¹³)—, and —C(R¹²R¹³)C(R¹²R¹³)Y—;
W is substituted with 0-2 R¹⁴ and is selected from:

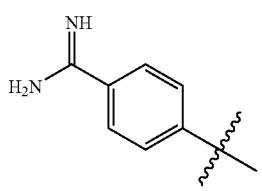

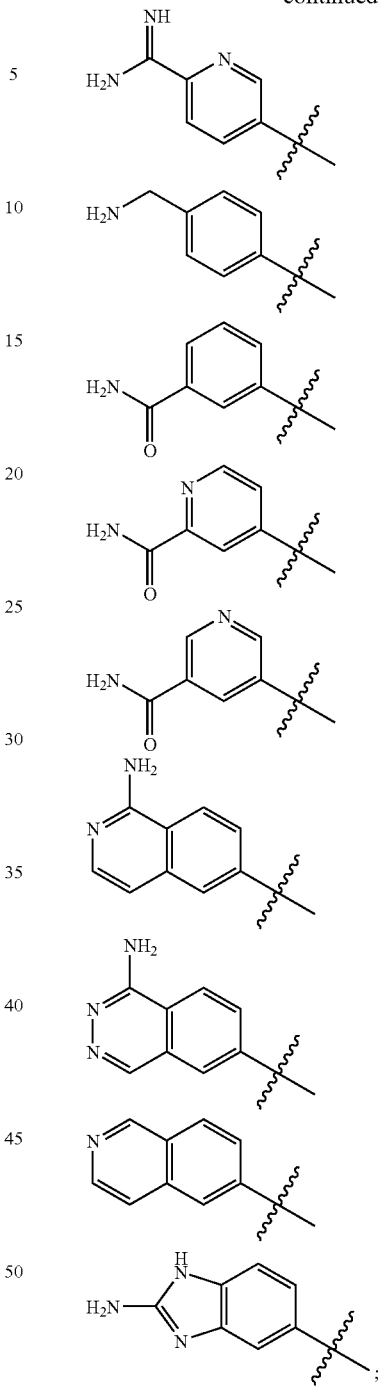

Z is NH;

R¹ is H, Cl, Br, methyl, ethyl, vinyl, 2-propenyl, allyl, ethynyl, 1-propynyl, methoxy, ethoxy, or cyclopropyl;

R⁴ is H;

R⁵ is H, $C_{1-4}$ alkyl, —$CH_2CO_2R^a$, —$CH_2C(O)NR^cR^d$, —$CH_2CH_2CO_2R^a$, —$CH_2CH_2C(O)NR^cR^d$, —$CH_2CH_2OR^a$, or —$CH_2CH_2CH_2OR^a$;

R⁶ is H, —$CH_2OR^a$, —$CH_2CH_2OR^a$, CN, $C_{1-4}$ alkyl, —$CO_2R^a$, —$C(O)NR^cR^d$, —$CH_2CO_2R^a$, or —$CH_2C(O)NR^cR^d$;

US 7,592,331 B2

$R^7$ is H;

$R^8$ is H, $C_{1-6}$ alkyl, $OR^a$, —$CONR^cR^d$, —$SO_2R^b$, —$SO_2NR^cR^d$, phenyl, or 5- to 6-membered heterocycle comprising: carbon atoms and 1-3 heteroatoms selected from N, O, and $S(O)_p$, wherein said phenyl and heterocycle are substituted with 0-3 $R^g$;

$R^9$, $R^{10}$, and $R^{11}$ are H; and $R^{14}$ is, independently at each occurrence, F, Cl, methyl, ethyl, hydroxyl, or methoxy.

In a sixth aspect, the present invention includes the compounds of Formula (I), or a stereoisomer, tautomer, pharmaceutically acceptable salt, solvate, or prodrug form thereof, within the scope of the first aspect wherein:

ring A is phenyl;

ring B is phenyl;

M is —CONH—;

L is selected from —$C(R^{12}R^{13})C(R^{12}R^{13})C(R^{12}R^{13})$—, —$C(R^{12}R^{13})NR^{16}C(R^{12}R^{13})$—, —$C(R^{12}R^{13})C(R^{12}R^{13})Y$—, —$C(R^{12}R^{13})C(R^{12}R^{13})$—, —$OC(R^{12}R^{13})$—, or —$C(R^{12}R^{13})Y$—;

W is selected from:

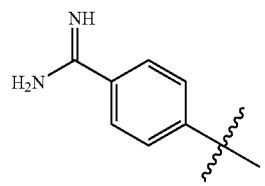

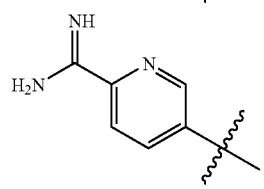

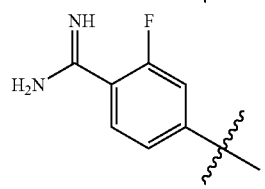

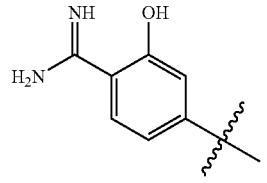

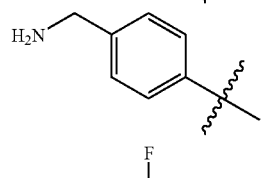

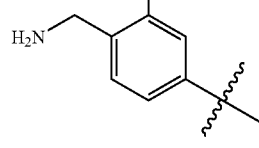

-continued

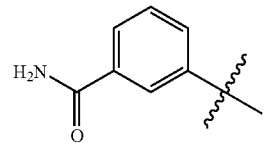

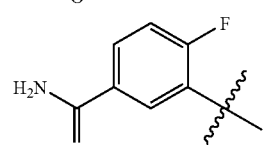

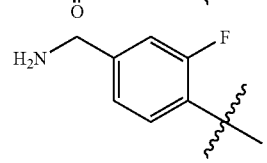

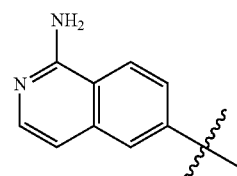

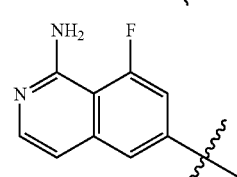

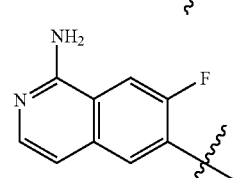

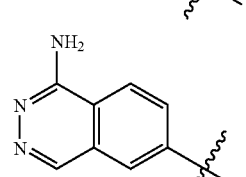

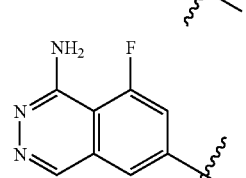

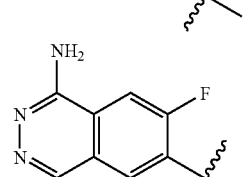

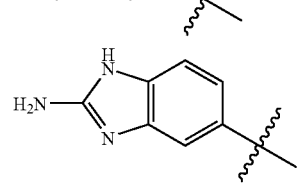 and

-continued

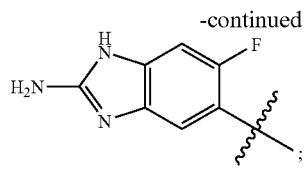

Y is O or NMe,

Z is NH;

R$^1$ is H, Cl, Br, methyl, ethyl, vinyl, 2-propenyl, ethynyl, methoxy, or ethoxy;

R$^2$ is H, F, Cl, Br, —OR$^a$, —SR$^b$, —CF$_3$, —OCF$_3$, —OCHF$_2$, —OCH$_2$F, CN, NO$_2$, —NR$^c$R$^d$, —C(O)R$^a$, —CO$_2$R$^a$, —NR$^c$C(O)R$^a$, —C(O)NR$^c$R$^d$, —NR$^c$C(O)OR$^b$, —OC(O)OR$^b$, —NR$^c$C(O)NR$^c$R$^d$, —OC(O)NR$^c$R$^d$, —SO$_2$NR$^c$R$^d$, —NR$^c$SO$_2$NR$^c$R$^d$, —NR$^c$SO$_2$R$^b$, —S(O)$_2$R$^b$, C$_{1-6}$ alkyl substituted with 0-2 R$^e$, C$_{1-4}$ fluoroalkyl, C$_{2-4}$ alkenyl substituted with 0-2 R$^e$, C$_{2-4}$ alkynyl substituted with 0-2 R$^e$, —C$_{3-6}$ carbocycle substituted with 0-2 R$^f$, -(5- to 6-membered heterocycle), —NR$^c$-(5- to 6-membered heterocycle), or —O-(5- to 6-membered heterocycle); wherein said heterocycle comprises carbon atoms and 1-3 heteroatoms selected from N, NR$^c$, O, and S(O)$_p$ and is substituted with 0-2 R$^g$;

R$^3$ is H, F, Cl, Me, OCH$_2$CO$_2$H;

R$^4$ is H;

R$^5$ is H, C$_{1-4}$ alkyl, —CH$_2$CO$_2$R$^a$, or —CH$_2$C(O)NR$^c$R$^d$;

R$^6$ is H, C$_{1-4}$ alkyl, —CO$_2$R$^a$, —C(O)NR$^c$R$^d$, —CH$_2$CO$_2$R$^a$, or —CH$_2$C(O)NR$^c$R$^d$;

R$^7$ is H;

R$^8$ is —CONR$^c$R$^d$, —SO$_2$R$^b$, —SO$_2$NR$^c$R$^d$, or 4-morpholino;

R$^9$, R$^{10}$, and R$^{11}$ are H;

R$^{12}$ and R$^{13}$ are, independently at each occurrence, H, methyl, ethyl, propyl, isopropyl, cyclopropyl, t-butyl, methoxy, ethoxy, propoxy, isopropoxy, or cyclopropoxy, with the proviso that no more than two of R$^{12}$ and R$^{13}$ in L are other than H; and R$^{16}$ is H, C$_{1-4}$ alkyl, —C(O)R$^a$, —C(O)NR$^c$R$^d$, —C(O)OR$^b$, or —S(O)$_2$R$^b$.

In a seventh aspect, the present invention includes the compounds of Formula (I), or a stereoisomer, tautomer, pharmaceutically acceptable salt, solvate, or prodrug form thereof, within the scope of any of the above aspects wherein:

M is —CONH—;

L is selected from —C(R$^{12}$R$^{13}$)C(R$^{12}$R$^{13}$)CH$_2$—, —C(R$^{12}$R$^{13}$)C(R$^{12}$R$^{13}$)O—, —C(R$^{12}$R$^{13}$)C(R$^{12}$R$^{13}$)NMe-, —C(R$^{12}$R$^{13}$)N(C=OCH$_3$)CH$_2$—, —C(R$^{12}$R$^{13}$)NHCH$_2$—, —C(R$^{12}$R$^{13}$)CH$_2$—, and —OCH$_2$—;

W is selected from:

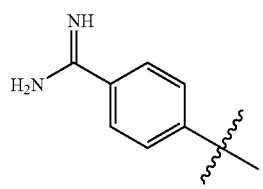

-continued

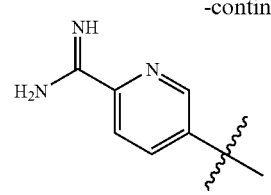

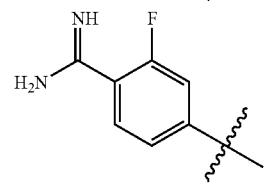

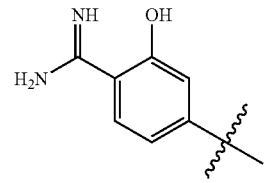

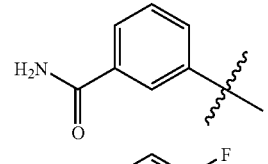

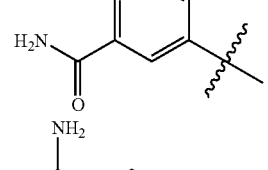

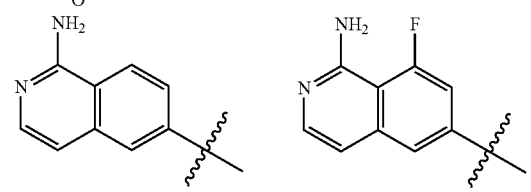

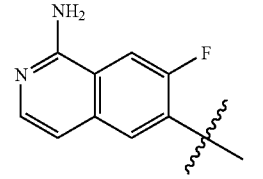

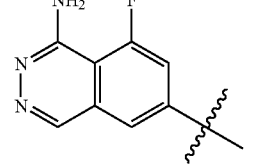

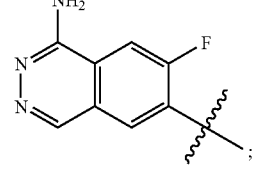

and ;

R$^1$ is H, Cl, Br, methyl, ethyl, methoxy, or ethoxy;
R$^2$ is H, Cl, Br, methyl, ethyl, methoxy, or ethoxy;
R$^3$ is H;
R$^4$ is H;

$R^5$ is H, methyl, ethyl, or —CH$_2$CO$_2$H;

$R^6$ is H, methyl, ethyl, —CO$_2$H or —CH$_2$CO$_2$H;

$R^7$ is H; and $R^8$ is —CONR$^c$R$^d$ or —SO$_2$R$^b$.

In an eighth aspect, the present invention includes the compounds of Formula (I), or a stereoisomer, tautomer, pharmaceutically acceptable salt, solvate, or prodrug form thereof, within the scope of the first aspect wherein:

when M is —CONH—; L is selected from —(CH$_2$)$_2$—, —(CH$_2$)$_3$—, —(CH$_2$)$_4$—, —O(CH$_2$)—, —O(CH$_2$)$_2$—, —O(CH$_2$)$_3$—, —(CH$_2$)$_2$O—, —CH(Me)CH$_2$O—, —C(Me)$_2$CH$_2$O—, —CH$_2$CH(Me)O—, —CH(Et)CH$_2$O—, —CH$_2$CH(Et)O—, —CH$_2$OCH$_2$—, —(CH$_2$)$_2$NMe-, —(CH$_2$)$_3$NMe-, —CH$_2$NHCH$_2$—, and —CH$_2$N(Ac)CH$_2$—;

when M is —NHSO$_2$—, L is selected from —(CH$_2$)$_2$— and —(CH$_2$)$_3$—;

W is selected from:

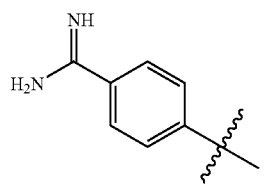

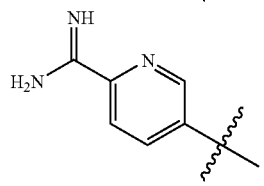

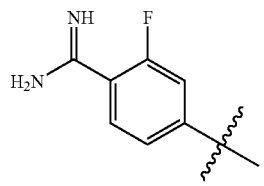

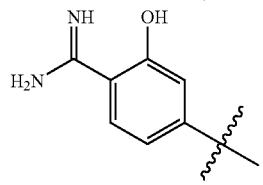

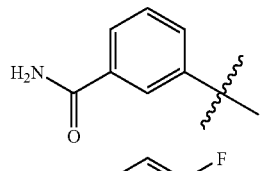

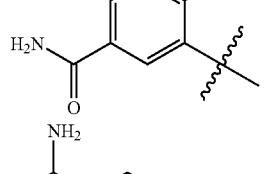

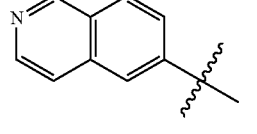

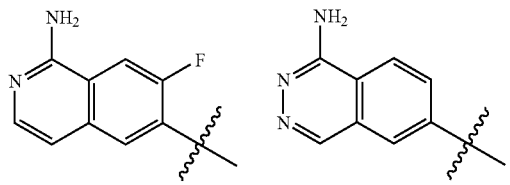

-continued

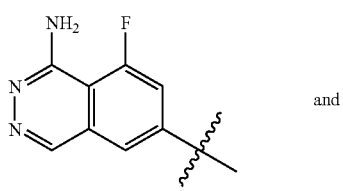

and

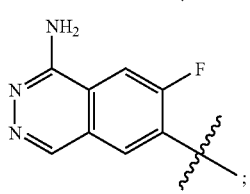

;

Z is NH;

$R^1$ is H, Cl, Br, C$_{1-4}$ alkyl, or C$_{1-4}$ alkoxy;

$R^2$ is H, Cl, Br, C$_{1-4}$ alkyl, or C$_{1-4}$ alkoxy;

$R^3$ is H;

$R^4$ is H;

$R^5$ is H, C$_{1-4}$ alkyl, —CH$_2$CO$_2$H, or —CH$_2$CO$_2$Et;

$R^6$ is H, C$_{1-4}$ alkyl, —CO$_2$H, —CH$_2$CO$_2$H, or —CH$_2$CO$_2$Et;

$R^7$ is H;

$R^8$ is H, —SO$_2$(C$_{1-4}$ alkyl), or —S(C$_{1-4}$ alkyl);

$R^9$ is H; and $R^{10}$ is H.

In a ninth aspect, the present invention includes the compounds of Formula (I), or a stereoisomer, tautomer, pharmaceutically acceptable salt, solvate, or prodrug form thereof, within the scope of the eighth aspect wherein:

W is selected from:

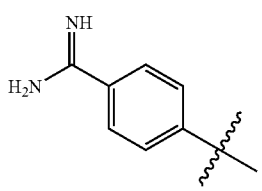

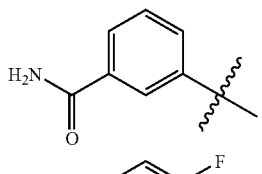

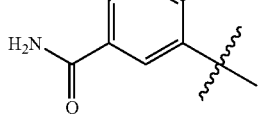

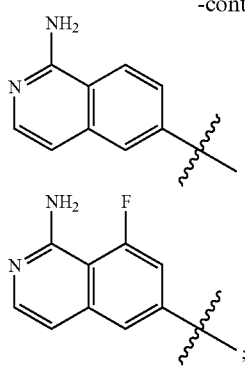

$R^1$ is H, Cl, Br, methyl, ethyl, methoxy, or ethoxy;
$R^2$ is H, Cl, Br, methyl, ethyl, methoxy, or ethoxy;
$R^5$ is H, methyl, ethyl, or —$CH_2CO_2H$;
$R^6$ is H, methyl, ethyl, —$CO_2H$, —$CH_2CO_2H$, or —$CH_2CO_2Et$; and
$R^8$ is H, —$SO_2Et$, —$SO_2$(i-Pr), —$SO_2$(t-Bu), or —S(i-Pr).

In a tenth aspect, the present invention provides a compound selected from the exemplified examples or a stereoisomer, tautomer, pharmaceutically acceptable salt, solvate, or prodrug thereof.

In another embodiment the present invention provides compounds wherein: ring A is phenyl; and ring B is phenyl or a pyridyl isomer defined by replacing one of $CR^8$, $CR^9$, $CR^{10}$, or $CR^{11}$ in ring B of formula (I) with N.

In another embodiment the present invention provides compounds wherein: ring A is phenyl or a pyridyl isomer defined by replacing one of $CR^1$, $CR^2$, $CR^3$, or $CR^4$ in ring A of formula (I) with N; and ring B is phenyl.

In another embodiment the present invention provides compounds wherein: ring A is phenyl; and ring B is phenyl.

In another embodiment the present invention provides compounds wherein: M is —CONH—, —$SO_2NH$—, —NHCO—, or —$NHSO_2$—;
when M is —CONH—, L is selected from —$C(R^{12}R^{13})C(R^{12}R^{13})$—, —$XC(R^{12}R^{13})$—, —$C(R^{12}R^{13})Y$—, —$C(R^{12}R^{13})C(R^{12}R^{13})C(R^{12}R^{13})$—, —$XC(R^{12}R^{13})C(R^{12}R^{13})$—, —$C(R^{12}R^{13})XC(R^{12}R^{13})$—, $XC(R^{12}R^{13})Y$—, and —$C(R^{12}R^{13})C(R^{12}R^{13})Y$—;
when M is —$SO_2NH$—, L is selected from —$C(R^{12}R^{13})C(R^{12}R^{13})$—, —$C(R^{12}R^{13})C(R^{12}R^{13})C(R^{12}R^{13})$—, —$XC(R^{12}R^{13})C(R^{12}R^{13})$—, —$C(R^{12}R^{13})C(R^{12}R^{13})C(R^{12}R^{13})C(R^{12}R^{13})$—, —$XC(R^{12}R^{13})C(R^{12}R^{13})C(R^{12}R^{13})$—, and —$C(R^{12}R^{13})XC(R^{12}R^{13})C(R^{12}R^{13})$—;
when M is —NHCO—, L is selected from —$C(R^{12}R^{13})C(R^{12}R^{13})$—, —$C(R^{12}R^{13})C(R^{12}R^{13})C(R^{12}R^{13})$—, —$XC(R^{12}R^{13})C(R^{12}R^{13})$—, —$C(R^{12}R^{13})C(R^{12}R^{13})C(R^{12}R^{13})C(R^{12}R^{13})$—, —$XC(R^{12}R^{13})C(R^{12}R^{13})C(R^{12}R^{13})$—, and —$C(R^{12}R^{13})XC(R^{12}R^{13})C(R^{12}R^{13})$—;
when M is —$NHSO_2$—, L is selected from —$C(R^{12}R^{13})C(R^{12}R^{13})$—, —$C(R^{12}R^{13})C(R^{12}R^{13})C(R^{12}R^{13})$—, —$XC(R^{12}R^{13})C(R^{12}R^{13})$—, —$C(R^{12}R^{13})C(R^{12}R^{13})C(R^{12}R^{13})C(R^{12}R^{13})$—, —$XC(R^{12}R^{13})C(R^{12}R^{13})C(R^{12}R^{13})$—, and —$C(R^{12}R^{13})XC(R^{12}R^{13})C(R^{12}R^{13})$—.

In another embodiment the present invention provides compounds wherein: M is —CONH— or —$NHSO_2$—;
when M is —CONH—, L is selected from —$C(R^{12}R^{13})C(R^{12}R^{13})$—, —$XC(R^{12}R^{13})$—, —$C(R^{12}R^{13})Y$—, —$C(R^{12}R^{13})C(R^{12}R^{13})C(R^{12}R^{13})$—, —$C(R^{12}R^{13})XC(R^{12}R^{13})$—, and —$C(R^{12}R^{13})C(R^{12}R^{13})Y$—;
when M is —$NHSO_2$—, L is selected from —$C(R^{12}R^{13})C(R^{12}R^{13})$—, —$C(R^{12}R^{13})C(R^{12}R^{13})C(R^{12}R^{13})$—, and —$XC(R^{12}R^{13})C(R^{12}R^{13})$—.

In another embodiment the present invention provides compounds wherein: M is —CONH—; and L is selected from —$C(R^{12}R^{13})C(R^{12}R^{13})$—, —$XC(R^{12}R^{13})$—, —$C(R^{12}R^{13})Y$—, —$C(R^{12}R^{13})C(R^{12}R^{13})C(R^{12}R^{13})$—, —$XC(R^{12}R^{13})C(R^{12}R^{13})$—, —$C(R^{12}R^{13})XC(R^{12}R^{13})$—, —$C(R^{12}R^{13})C(R^{12}R^{13})Y$—, —$XC(R^{12}R^{13})Y$—, —$C(R^{12}R^{13})C(R^{12}R^{13})C(R^{12}R^{13})C(R^{12}R^{13})$—, —$XC(R^{12}R^{13})C(R^{12}R^{13})C(R^{12}R^{13})$—, —$C(R^{12}R^{13})XC(R^{12}R^{13})C(R^{12}R^{13})$—, —$C(R^{12}R^{13})C(R^{12}R^{13})XC(R^{12}R^{13})$—, —$C(R^{12}R^{13})C(R^{12}R^{13})C(R^{12}R^{13})Y$—, and —$XC(R^{12}R^{13})C(R^{12}R^{13})Y$—.

In another embodiment the present invention provides compounds wherein: M is —CONH—; and L is selected from —$C(R^{12}R^{13})C(R^{12}R^{13})$—, —$XC(R^{12}R^{13})$—, —$C(R^{12}R^{13})Y$—, —$C(R^{12}R^{13})C(R^{12}R^{13})C(R^{12}R^{13})$—, —$C(R^{12}R^{13})XC(R^{12}R^{13})$—, and —$C(R^{12}R^{13})C(R^{12}R^{13})Y$—.

In another embodiment the present invention provides compounds wherein: M is —$SO_2NH$—; and L is selected from —$C(R^{12}R^{13})C(R^{12}R^{13})$—, —$C(R^{12}R^{13})C(R^{12}R^{13})C(R^{12}R^{13})$—, —$XC(R^{12}R^{13})C(R^{12}R^{13})$—, —$C(R^{12}R^{13})C(R^{12}R^{13})C(R^{12}R^{13})C(R^{12}R^{13})$—, —$XC(R^{12}R^{13})C(R^{12}R^{13})C(R^{12}R^{13})$—, and —$C(R^{12}R^{13})XC(R^{12}R^{13})C(R^{12}R^{13})$—.

In another embodiment the present invention provides compounds wherein: M is —$NHSO_2$—; and L is selected from —$C(R^{12}R^{13})C(R^{12}R^{13})$—, —$C(R^{12}R^{13})C(R^{12}R^{13})C(R^{12}R^{13})$—, and —$XC(R^{12}R^{13})C(R^{12}R^{13})$—.

In another embodiment the present invention provides compounds wherein: M is —NHCO—; and L is selected from —$C(R^{12}R^{13})C(R^{12}R^{13})$—, —$C(R^{12}R^{13})C(R^{12}R^{13})C(R^{12}R^{13})$—, —$XC(R^{12}R^{13})C(R^{12}R^{13})$—, —$C(R^{12}R^{13})C(R^{12}R^{13})C(R^{12}R^{13})C(R^{12}R^{13})$—, —$XC(R^{12}R^{13})C(R^{12}R^{13})C(R^{12}R^{13})$—, and —$C(R^{12}R^{13})XC(R^{12}R^{13})C(R^{12}R^{13})$—.

In another embodiment the present invention provides compounds wherein: M is —$NHSO_2$—; and L is selected from —$C(R^{12}R^{13})C(R^{12}R^{13})$—, —$C(R^{12}R^{13})C(R^{12}R^{13})C(R^{12}R^{13})$—, —$XC(R^{12}R^{13})C(R^{12}R^{13})$—, —$C(R^{12}R^{13})C(R^{12}R^{13})C(R^{12}R^{13})C(R^{12}R^{13})$—, —$XC(R^{12}R^{13})C(R^{12}R^{13})C(R^{12}R^{13})$—, and —$C(R^{12}R^{13})XC(R^{12}R^{13})C(R^{12}R^{13})$—, In another embodiment the present invention provides compounds wherein: W is substituted with 0-2 $R^{14}$ and is selected from:

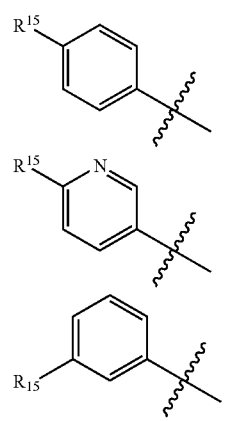

-continued

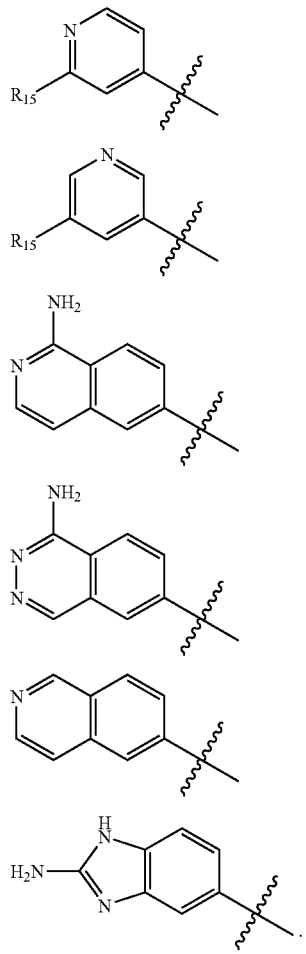

In another embodiment the present invention provides compounds wherein: W is substituted with 0-2 $R^{14}$ and is selected from:

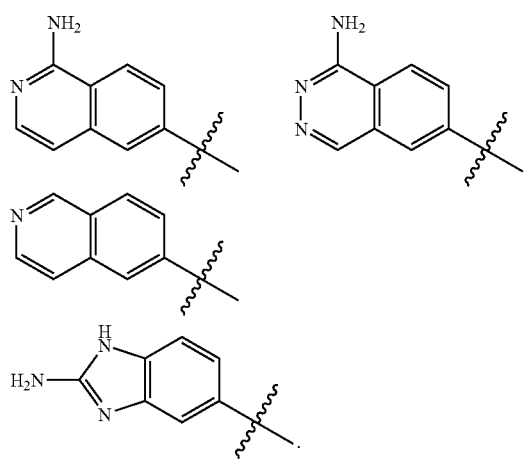

In another embodiment the present invention provides compounds wherein: W is substituted with 0-2 $R^{14}$ and is selected from:

In another embodiment the present invention provides compounds wherein: W is substituted with 0-2 $R^{14}$ and is selected from:

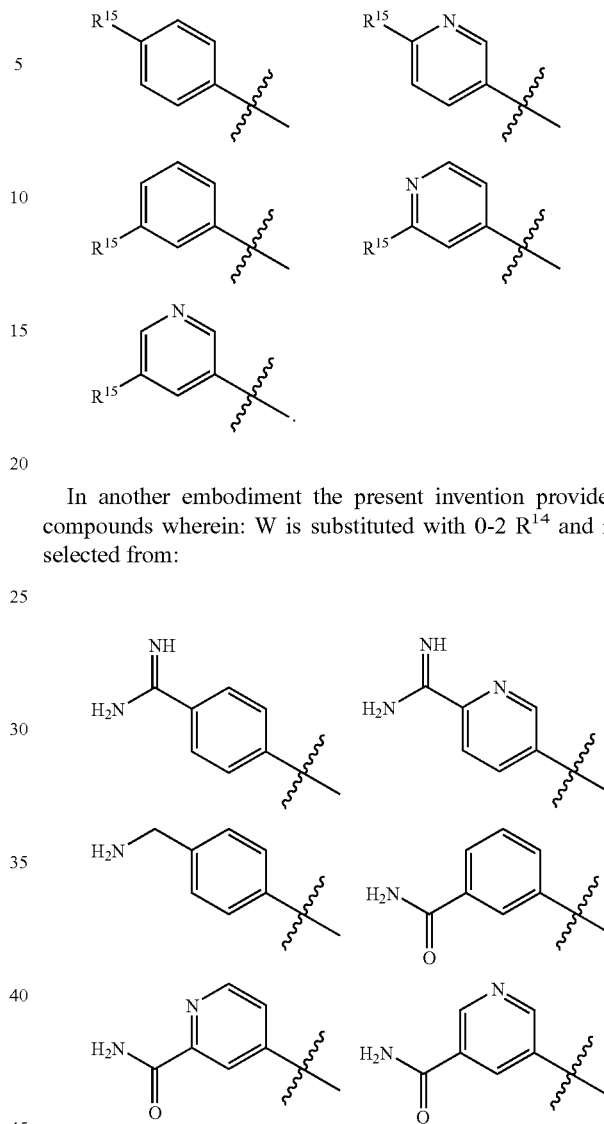

In another embodiment the present invention provides compounds wherein: W is selected from:

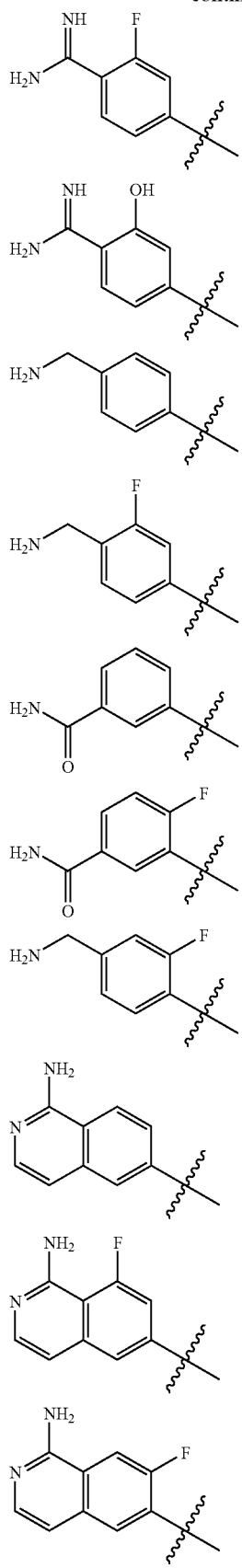
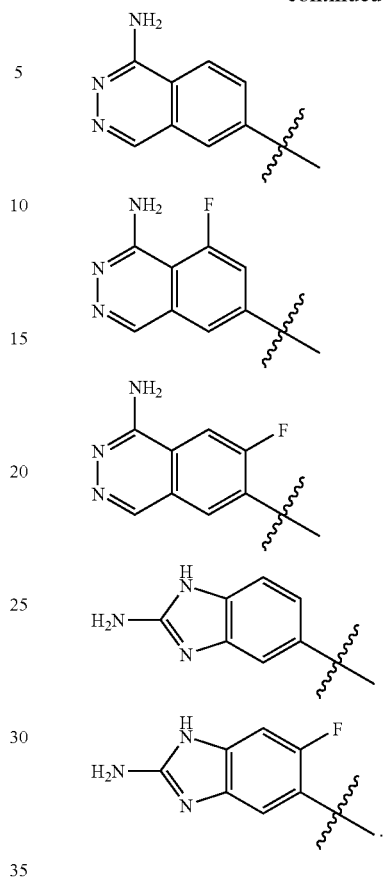
In another embodiment the present invention provides compounds wherein: W is selected from:
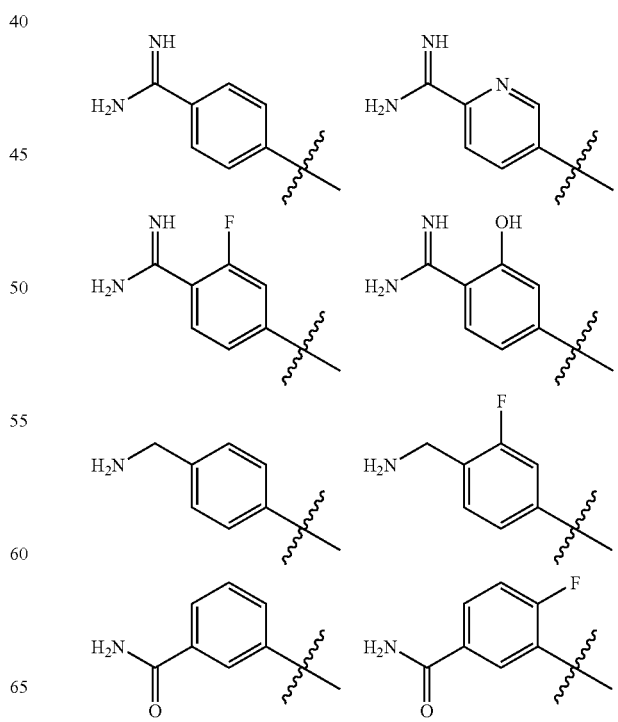

-continued

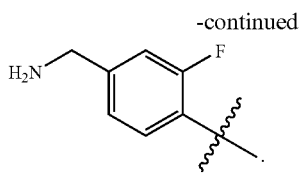

In another embodiment the present invention provides compounds wherein: W is selected from:

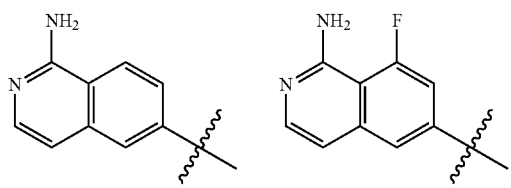

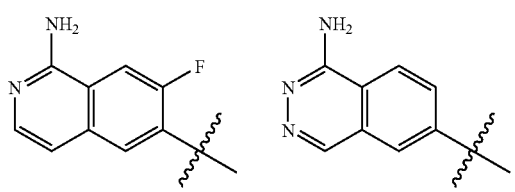

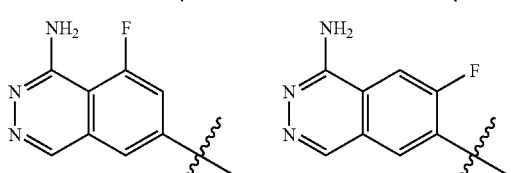

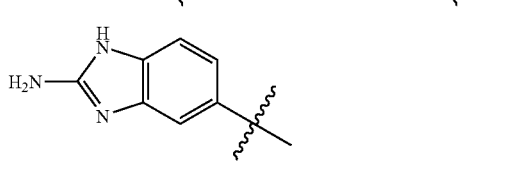

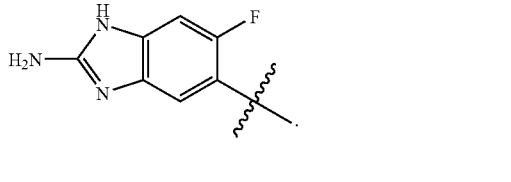

In another embodiment the present invention provides compounds wherein: W is selected from:

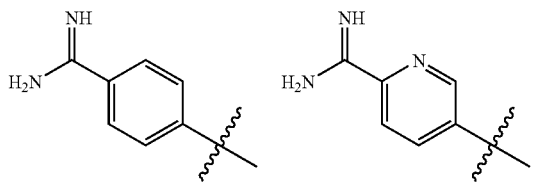

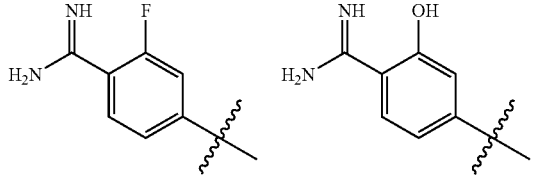

-continued

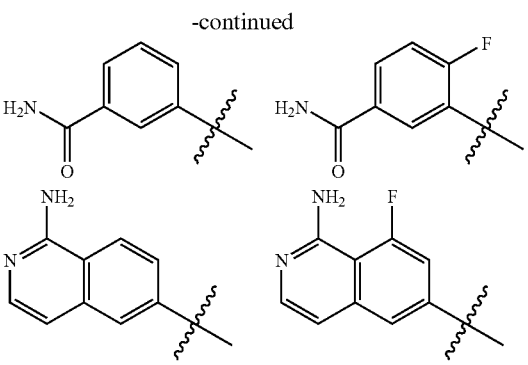

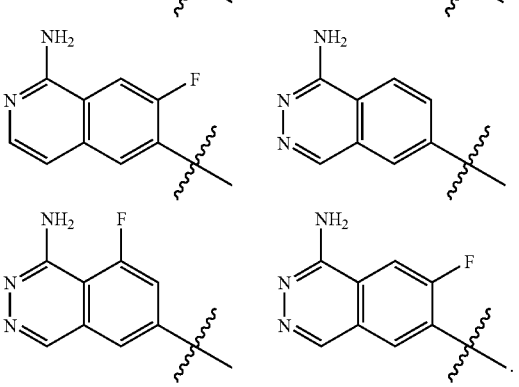

In another embodiment the present invention provides compounds wherein: W is selected from:

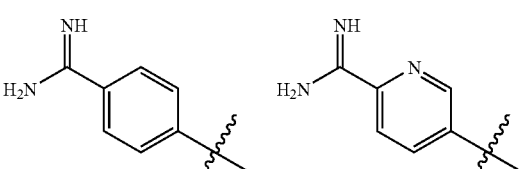

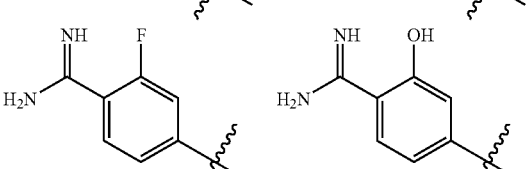

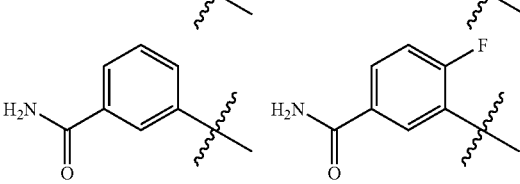

In another embodiment the present invention provides compounds wherein: W is selected from:

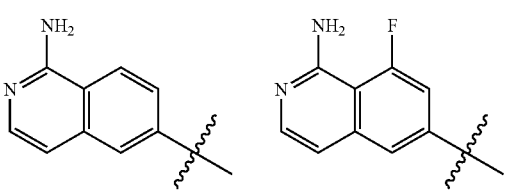

-continued

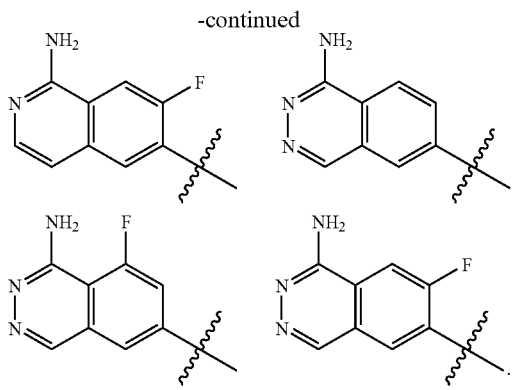

In another embodiment the present invention provides compounds wherein: X is O, S, or NH.

In another embodiment the present invention provides compounds wherein: X is O.

In another embodiment the present invention provides compounds wherein: X is S.

In another embodiment the present invention provides compounds wherein: X is $NR^{16}$.

In another embodiment the present invention provides compounds wherein: X is NH.

In another embodiment the present invention provides compounds wherein: Y is O, S, NMe, or NH.

In another embodiment the present invention provides compounds wherein: Y is O or $NR^{16a}$.

In another embodiment the present invention provides compounds wherein: Y is O or NMe.

In another embodiment the present invention provides compounds wherein: Y is O.

In another embodiment the present invention provides compounds wherein: Y is S.

In another embodiment the present invention provides compounds wherein: Y is $NR^{16a}$.

In another embodiment the present invention provides compounds wherein: Y is NMe.

In another embodiment the present invention provides compounds wherein: Y is NH.

In another embodiment the present invention provides compounds wherein: Z is NH or O.

In another embodiment the present invention provides compounds wherein: Z is NH.

In another embodiment the present invention provides compounds wherein: $R^1$ is H, Cl, Br, methyl, ethyl, 1-hydroxyethyl, propyl, isopropyl, vinyl, allyl, 2-propenyl, ethynyl, 1-propynyl, methoxy, ethoxy, cyclopropyl, cyclobutyl, or cyclopentyl.

In another embodiment the present invention provides compounds wherein: $R^1$ is H, Cl, Br, methyl, ethyl, vinyl, 2-propenyl, allyl, ethynyl, 1-propynyl, methoxy, ethoxy, or cyclopropyl.

In another embodiment the present invention provides compounds wherein: $R^1$ is H, Cl, Br, methyl, ethyl, vinyl, 2-propenyl, ethynyl, methoxy, or ethoxy.

In another embodiment the present invention provides compounds wherein: $R^1$ is H, Cl, Br, methyl, ethyl, methoxy, or ethoxy;

In another embodiment the present invention provides compounds wherein: $R^2$ is H, F, Cl, Br, I, $OR^a$, $SR^b$, $CF_3$, $OCF_3$, $OCHF_2$, $OCH_2F$, CN, $NO_2$, —$NR^cR^d$, —$C(O)R^a$, —$CO_2R^a$, —$NR^cC(O)R^a$, —$C(O)NR^cR^d$, —$NR^cC(O)OR^b$, —$NR^cC(O)NR^cR^d$, —$OC(O)NR^cR^d$, —$SO_2NR^cR^d$, —$NR^cSO_2NR^cR^d$, —$NR^cSO_2R^b$, —$NR^cSO_2CF_3$, —$SO_2CF_3$, —$S(O)_2R^b$, $C_{1-6}$ alkyl substituted with 0-2 $R^e$, $C_{2-4}$ alkenyl substituted with 0-2 $R^e$, $C_{2-4}$ alkynyl substituted with 0-2 $R^e$, $C_{3-6}$ carbocycle substituted with 0-2 $R^f$, —$(CH_2)_s$-(5- to 6-membered heterocycle), —$NR^c$-(5- to 6-membered heterocycle), or —O-(5- to 6-membered heterocycle); wherein said heterocycle comprises carbon atoms and 1-3 heteroatoms selected from N, $NR^c$, O, and $S(O)_p$ and is substituted with 0-2 $R^g$;

$R^3$ is H, F, Cl, Br, I, $OR^a$, $SR^b$, $CF_3$, $OCF_3$, $OCHF_2$, $OCH_2F$, CN, $NO_2$, —$NR^cR^d$, —$C(O)R^a$, —$CO_2R^a$, —$NR^cC(O)R^a$, —$C(O)NR^cR^d$, —$NR^cC(O)OR^b$, —$NR^cC(O)NR^cR^d$, —$OC(O)NR^cR^d$, —$SO_2NR^cR^d$, —$NR^cSO_2NR^cR^d$, —$NR^cSO_2R^b$, —$NR^cSO_2CF_3$, —$SO_2CF_3$, —$S(O)_2R^b$, —$O(CH_2)_nCO_2R^a$, —$SO_2NHCOR^b$, —$CONHSO_2R^b$, $C_{1-6}$ alkyl substituted with 0-2 $R^e$, $C_{2-4}$ alkenyl substituted with 0-2 $R^e$, $C_{2-4}$ alkynyl substituted with 0-2 $R^e$, —O(benzyl substituted with $CO_2R^a$), or tetrazolyl;

alternatively, $R^2$ and $R^3$ may combine to form a 5- to 7-membered carbocycle or heterocycle comprising: carbon atoms and 0-2 heteroatoms selected from N, $NR^c$, O, and $S(O)_p$; wherein said carbocycle and heterocycle are substituted with 0-3 $R^g$.

In another embodiment the present invention provides compounds wherein: $R^2$ is H, F, Cl, Br, I, $OR^a$, $SR^b$, $CF_3$, $OCF_3$, $OCHF_2$, $OCH_2F$, CN, $NO_2$, —$NR^cR^d$, —$C(O)R^a$, —$CO_2R^a$, —$NR^cC(O)R^a$, —$C(O)NR^cR^d$, —$NR^cC(O)OR^b$, —$NR^cC(O)NR^cR^d$, —$OC(O)NR^cR^d$, —$SO_2NR^cR^d$, —$NR^cSO_2NR^cR^d$, —$NR^cSO_2R^b$, —$NR^cSO_2CF_3$, —$SO_2CF_3$, —$S(O)_2R^b$, $C_{1-6}$ alkyl substituted with 0-2 $R^e$, $C_{2-4}$ alkenyl substituted with 0-2 $R^e$, $C_{2-4}$ alkynyl substituted with 0-2 $R^f$, $C_{3-6}$ carbocycle substituted with 0-2 $R^f$, —$(CH_2)_s$-(5- to 6-membered heterocycle), —$NR^c$-(5- to 6-membered heterocycle), or —O-(5- to 6-membered heterocycle); wherein said heterocycle comprises carbon atoms and 1-3 heteroatoms selected from N, $NR^c$, O, and $S(O)_p$ and is substituted with 0-2 $R^g$.

In another embodiment the present invention provides compounds wherein: $R^2$ is H, Cl, Br, methyl, ethyl, vinyl, 2-propenyl, ethynyl, methoxy, or ethoxy.

In another embodiment the present invention provides compounds wherein: $R^2$ is H, Cl, Br, methyl, ethyl, methoxy, or ethoxy.

In another embodiment the present invention provides compounds wherein: $R^3$ is H, F, Cl, Me, $OCH_2CO_2H$.

In another embodiment the present invention provides compounds wherein: $R^3$ is H.

In another embodiment the present invention provides compounds wherein: $R^4$ is H or F.

In another embodiment the present invention provides compounds wherein: $R^5$ is H, $C_{1-4}$ alkyl, —$CH_2CO_2R^a$, —$CH_2C(O)NR^cR^d$, —$CH_2CH_2CO_2R^a$, —$CH_2CH_2C(O)NR^cR^d$, —$CH_2CH_2OR^a$, or —$CH_2CH_2CH_2OR^a$.

In another embodiment the present invention provides compounds wherein: $R^5$ is H, $C_{1-4}$ alkyl, —$CH_2CO_2R^a$, or —$CH_2C(O)NR^cR^d$.

In another embodiment the present invention provides compounds wherein: $R^5$ is H, methyl, ethyl, or —$CH_2CO_2H$.

In another embodiment the present invention provides compounds wherein: $R^6$ is H, —$CH_2OR^a$, —$CH_2CH_2OR^a$, CN, $C_{1-4}$ alkyl, —$CO_2R^a$, —$C(O)NR^cR^d$, —$CH_2CO_2R^a$, or —$CH_2C(O)NR^cR^d$.

In another embodiment the present invention provides compounds wherein: $R^6$ is H, $C_{1-4}$ alkyl, —$CO_2R^a$, —$C(O)NR^cR^d$, —$CH_2CO_2R^a$, or —$CH_2C(O)NR^cR^d$.

In another embodiment the present invention provides compounds wherein: $R^6$ is H, methyl, ethyl, —$CO_2H$ or —$CH_2CO_2H$.

In another embodiment the present invention provides compounds wherein: $R^7$ is H.

In another embodiment the present invention provides compounds wherein: $R^8$ is, F, Cl, Br, CN, $CH_2F$, $CHF_2$, $CF_3$, $OCF_3$, $SCF_3$, $NO_2$, $C_{1-6}$ alkyl, $C_{2-6}$ alkenyl, $C_{2-6}$ alkynyl, —$(CH_2)_n$—$OR^a$, —$(CH_2)_n$—$SR^b$, —$(CH_2)_n$—$NR^cR^d$, —$CONR^cR^d$, —$SO_2R^b$, —$SO_2NR^cR^d$, —$(CH_2)_n$-phenyl, or —$(CH_2)_n$-5- to 10-membered heterocycle comprising: carbon atoms and 1-4 heteroatoms selected from N, O, and $S(O)_p$, wherein said phenyl and heterocycle are substituted with 0-3 $R^g$.

In another embodiment the present invention provides compounds wherein: $R^8$ is $C_{1-6}$ alkyl, $OR^a$, —$CONR^cR^d$, —$SO_2R^b$, —$SO_2NR^cR^d$, phenyl, or 5- to 6-membered heterocycle comprising: carbon atoms and 1-3 heteroatoms selected from N, O, and $S(O)_p$, wherein said phenyl and heterocycle are substituted with 0-3 $R^g$.

In another embodiment the present invention provides compounds wherein: $R^8$ is —$CONR^cR^d$, —$SO_2R^b$, —$SO_2NR^cR^d$, or 4-morpholino.

In another embodiment the present invention provides compounds wherein: $R^8$ is —$CONR^cR^d$ or —$SO_2R^b$.

In another embodiment the present invention provides compounds wherein: $R^9$ is H, F, Cl, Br, I, $C_{1-4}$ alkyl, or $C_{1-4}$ alkoxy.

In another embodiment the present invention provides compounds wherein: $R^9$ is H.

In another embodiment the present invention provides compounds wherein: $R^{10}$ and $R^{11}$ are, independently at each occurrence, H, F, Cl, Br, I, or $C_{1-4}$ alkyl.

In another embodiment the present invention provides compounds wherein: $R^{10}$ and $R^{11}$ are H.

In another embodiment the present invention provides compounds wherein: $R^{14}$ is, independently at each occurrence, F, Cl, methyl, ethyl, hydroxyl, or methoxy.

In another embodiment the present invention provides compounds wherein: $R^{15}$ is, independently at each occurrence, —$C(=NH)NH_2$, $N(R^{17}R^{17})$, —$C(R^{17}R^{17})N(R^{17}R^{17})$, —$CON(R^{17}R^{17})$, or OH.

In another embodiment the present invention provides compounds wherein: $R^{15}$ is, independently at each occurrence, —$C(=NH)NH_2$, $N(R^{17}R^{17})$, —$C(R^{17}R^{17})N(R^{17}R^{17})$, or —$CONH_2$.

In another embodiment the present invention provides compounds wherein: $R^{16}$ is H, $C_{1-4}$ alkyl, —$C(O)R^a$, —$C(O)NR^cR^d$, —$C(O)OR^b$, or —$S(O)_2R^b$.

In another embodiment the present invention provides compounds wherein: $R^{16}$ is, independently at each occurrence, H or $C_{1-6}$ alkyl.

In another embodiment the present invention provides compounds wherein: $R^{16}$ is H.

In another embodiment the present invention provides compounds wherein: $R^{16}$ is $C_{1-6}$ alkyl.

In another embodiment the present invention provides compounds wherein: $R^{16a}$ is, independently at each occurrence, H or $C_{1-6}$ alkyl.

In another embodiment the present invention provides compounds wherein: $R^{16a}$ is, independently at each occurrence, H or $C_{1-6}$ alkyl.

In another embodiment the present invention provides compounds wherein: $R^{16a}$ is H.

In another embodiment the present invention provides compounds herein: $R^{16a}$ is $C_{1-6}$ alkyl.

In another embodiment the present invention provides a pharmaceutical composition comprising a pharmaceutically acceptable carrier and at least one of the compounds of the present invention or a stereoisomer, tautomer, pharmaceutically acceptable salt, solvate, or prodrug thereof.

In another embodiment the present invention provides a pharmaceutical composition comprising a pharmaceutically acceptable carrier and a therapeutically effective amount of at least one of the compounds of the present invention or a stereoisomer, tautomer, pharmaceutically acceptable salt, solvate, or prodrug thereof.

In another embodiment, the present invention provides a novel process for making one of the compounds of the present invention or a stereoisomer, tautomer, pharmaceutically acceptable salt, solvate or prodrug thereof.

In another embodiment, the present invention provides a novel intermediate for making one of the compounds of the present invention or a stereoisomer, tautomer, pharmaceutically acceptable salt, solvate or prodrug thereof.

In another embodiment the present invention provides a method for modulation of the coagulation cascade comprising administering to a host in need of such treatment a therapeutically effective amount of at least one of the compounds of the present invention or a stereoisomer, tautomer, pharmaceutically acceptable salt, solvate, or prodrug form thereof.

In another embodiment the present invention provides a method for treating thrombotic or thromboembolic disorders comprising: administering to a host in need of such treatment a therapeutically effective amount of at least one of the compounds of the present invention or a stereoisomer, tautomer, pharmaceutically acceptable salt, solvate, or prodrug form thereof.

In another embodiment, the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

In another embodiment, the thromboembolic disorder is selected unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a novel method of treating a patient in need of thromboembolic disorder treatment, comprising: administering a compound of the present invention or a stereoisomer, tautomer, pharmaceutically acceptable salt, solvate, or prodrug form thereof in an amount effective to treat a thromboembolic disorder.

In another embodiment, the present invention provides a method, comprising: administering a compound of the present invention or a stereoisomer, tautomer, pharmaceutically acceptable salt, solvate, or prodrug form thereof in an amount effective to treat a thromboembolic disorder.

In another embodiment, the present invention provides a pharmaceutical composition further comprising at least one additional therapeutic agent selected from one or more of potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In a preferred embodiment, the present invention provides a pharmaceutical composition wherein the additional therapeutic agent(s) is an antihypertensive agent selected from ACE inhibitors, AT-1 receptor antagonists, beta-adrenergic receptor antagonists, ETA receptor antagonists, dual ETA/AT-1 receptor antagonists, and vasopeptidase inhibitors, an antiarrythmic agent selected from IKur inhibitors, an anticoagulant agent selected from thrombin inhibitors, antithrombin-III activators, heparin co-factor II activators, other factor VIIa inhibitors, other plasma kallikrein inhibitors, plasminogen activator inhibitor (PAI-1) antagonists, thrombin activatable fibrinolysis inhibitor (TAFI) inhibitors, factor IXa inhibitors, factor Xa inhibitors, and factor XIa inhibitors, or an antiplatelet agent selected from GPIIb/IIIa blockers, protease activated receptor (PAR-1) antagonists, phosphodiesterase-III inhibitors, $P2Y_1$ receptor antagonists, $P2Y_{12}$ receptor antagonists, thromboxane receptor antagonists, cyclooxygense-1 inhibitors, and aspirin, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In a preferred embodiment, the present invention provides a pharmaceutical composition, wherein the additional therapeutic agent(s) are an anti-platelet agent or a combination thereof.

In a preferred embodiment, the present invention provides a pharmaceutical composition, wherein the additional therapeutic agent is the anti-platelet agent selected from clopidogrel and aspirin, or a combination thereof.

In a preferred embodiment, the present invention provides a pharmaceutical composition, wherein the additional therapeutic agent is the anti-platelet agent clopidogrel.

In another embodiment, the present invention provides a compound of the present invention for use in therapy.

In another embodiment, the present invention also provides the use of a compound of the present invention for the manufacture of a medicament for the treatment of a thrombotic or thromboembolic disorder.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment of a thrombotic or thromboembolic disorder.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used for the treatment of a thrombotic or thromboembolic disorder.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used in combination with a second therapeutic agent to treat a thrombotic or thromboembolic disorder.

In another preferred embodiment, the present invention provides a novel article of manufacture, further comprising: (d) a second container; wherein components (a) and (b) are located within the second container and component (c) is located within or outside of the second container.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis using optically active starting materials or optically active catalysts. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral (enantiomeric and diastereomeric), racemic forms and all geometric isomeric forms of a structure are intended, unless the specific stereochemistry or isomeric form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention. The inventive compounds may be in the free or hydrate form.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 700 grams per mole. Even more preferably, the molecular weight is less than about 600 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. When a ring system (e.g., carbocyclic or heterocyclic) is said to be substituted with a carbonyl group or a double bond, it is intended that the carbon atom of the carbonyl group or one carbon atom of the double bond be part of (i.e., within) the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative. In cases wherein there are quarternary carbon atoms on compounds of the present invention, these can be replaced by silicon atoms, provided they do not form Si—N or Si—O bond.

When any variable occurs more than one time in any constituent or formula for a compound, its definition at each occurrence is independent of its definition at every other occurrence. Thus, for example, if a group is shown to be substituted with 0-3 $R^e$, then said group may optionally be substituted with up to three $R^e$ groups and $R^e$ at each occurrence is selected independently from the definition of $R^e$.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_{1-6}$ alkyl" denotes alkyl having 1 to 6 carbon atoms. Alkyl groups can be unsubstituted or substituted so that one or more of its hydrogens are replaced by another chemical group. Examples of alkyl include, but are not limited to, methyl (Me), ethyl (Et), n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, 4-methylpentyl, and the like.

"Alkenyl" or "alkenylene" is intended to include hydrocarbon chains of either a straight or branched configuration having the specified number of carbon atoms and one or more unsaturated carbon-carbon bonds which may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. Branched cycloalkyl groups such as 1-methylcyclopropyl and 2-methylcyclopropyl are included in the definition of "cycloalkyl".

"Alkoxy" or "alkyloxy" represents an alkyl group as defined above with the indicated number of carbon atoms attached through an oxygen bridge. For example, "$C_{1-6}$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, ethyl-S—, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$-$C_6$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle" is intended to mean any stable 3, 4, 5, 6, 7, or 8-membered monocyclic or bicyclic or 7, 8, 9, 10, 11, 12, or 13-membered bicyclic or tricyclic ring system consisting of carbon atoms, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred carbocycles, unless otherwise specified, are cyclopropyl, cyclobutyl, cyclopentyl, cyclohexyl, phenyl, and indanyl.

As used herein, the term "bicyclic carbocycle" or "bicyclic carbocyclic group" is intended to mean a stable 9 or 10-membered carbocyclic ring system which contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl. When the term "carbocycle" is used, it is intended to include "aryl".

"Aryl" groups refer to monocyclic or polycyclic aromatic hydrocarbons, including, for example, phenyl, naphthyl, phenanthranyl, and the like. Aryl moieties are well known and described, for example, in *Hawley's Condensed Chemical Dictionary* (13 ed.), R. J. Lewis, ed., J. Wiley & Sons, Inc., New York (1997). Aryl groups can be substituted or unsubstituted.

As used herein, the term "heterocycle" or "heterocyclic group" is intended to mean a stable 5, 6, or 7-membered monocyclic or polycyclic or 7, 8, 9, 10, 11, 12, 13, or 14-membered polycyclic heterocyclic ring which is saturated, partially unsaturated or fully unsaturated, and which consists of carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized to —NO—, —SO—, or —$SO_2$—. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include "heteroaryl".

Examples of heterocycles include, but are not limited to, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9 or 10-membered heterocyclic ring system which contains two fused rings and consists of carbon atoms and 1, 2, 3, or 4 heteroatoms independently selected from the group consisting of N, O and S. Of the two fused rings, one ring is a 5 or 6-membered monocyclic aromatic ring comprising a 5 membered heteroaryl ring, a 6-membered heteroaryl ring or a benzo ring, each fused to a second ring. The second ring is a 5 or 6 membered monocyclic ring which is saturated, partially unsaturated, or unsaturated, and comprises a 5 membered heterocycle, a 6 membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinoline, 2,3-dihydrobenzofuranyl, chromanyl, 1,2,3,4-tetrahydro-quinoxaline, and 1,2,3,4-tetrahydro-quinazoline.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Preferred heteroaryl groups are stable 5, 6, or 7-membered monocyclic or 7, 8, 9, or 10-membered bicyclic heterocyclic aromatic rings which consists of carbon atoms and 1, 2, 3, or 4 heteroatoms independently selected from the group consisting of N, NH, O and S. It is to be noted that total number of S and O atoms in the aromatic heterocycle is not more than 1. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, oxadiazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-5-oxide, 2,3-dihydrobenzothienyl-5-dioxide, benzoxazolin-2-on-yl, indolinyl, benzodioxolanyl, benzodioxane, and the like. Heteroaryl groups can be substituted or unsubstituted.

Also included are fused ring and spiro compounds containing, for example, the above carbocycles or heterocycles.

Bridged rings are also included in the definition of carbocycle or heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

When a dotted ring is used within a ring structure, this indicates that the ring structure may be saturated, partially saturated or unsaturated.

The term "counterion" is used to represent a small, negatively charged species such as chloride, bromide, hydroxide, acetate, and sulfate.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylactic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, the disclosure of which is hereby incorporated by reference.

Isotopically labeled compounds of the present invention, i.e., wherein one or more of the atoms described are replaced by an isotope of that atom (e.g., C replaced by $^{13}$C or by $^{14}$C; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs,* edited by H. Bundgaard, (Elsevier, 1985), and *Methods in Enzymology,* Vol. 42, at pp. 309-396, edited by K. Widder, et. al. (Academic Press, 1985);

b) *A Textbook of Drug Design and Development,* edited by Krosgaard-Larsen and H. Bundgaard, Chapter 5, "Design and Application of prodrugs," by H. Bundgaard, at pp. 113-191 (1991);

c) H. Bundgaard, *Advanced Drug Delivery Reviews,* Vol. 8, p. 1-38 (1992);

d) H. Bundgaard, et al., *Journal of Pharmaceutical Sciences*, Vol. 77, p. 285 (1988); and e) N. Kakeya, et. al., *Chem Phar Bull.*, Vol. 32, p. 692 (1984).

Preparation of Prodrugs is Well Known in the Art and Described in, for example, *Medicinal Chemistry: Principles and Practice*, ed. F. D. King, The Royal Society of Chemistry, Cambridge, UK, 1994, which is incorporated herein by reference in its entirety.

Compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$ alkyl, $C_{1-6}$alkylbenzyl, 4-methoxybenzyl, indanyl, phthalyl, methoxymethyl, $C_{1-6}$ alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates and the like. Methods of solvation are generally known in the art.

As used herein, the term "patient" or "host" encompasses all mammalian species.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination with other active ingredients to inhibit factor VIIa or to treat the disorders listed herein. When applied to a combination, the term refers to combined amounts of the active ingredients that result in the therapeutic effect, whether administered in combination, serially or simultaneously. The combination of compounds is preferably a synergistic combination. Synergy, as described, for example, by Chou and Talalay, *Adv. Enzyme Regul.* 1984, 22:27-55, occurs when the effect (in this case, anticoagulant effect) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

The term "pharmaceutical composition" means a composition comprising a compound of the invention in combination with at least one additional pharmaceutical carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., 1990, which is incorporated herein by reference in its entirety.

Abbreviations used in the Examples are defined as follows: "1×" for once, "2×" for twice, "3×" for thrice, "C" for degrees Celsius, "eq" for equivalent or equivalents, "g" for gram or grams, "mg" for milligram or milligrams, "L" for liter or liters, "mL" for milliliter or milliliters, "µL" for microliter or microliters, "M" for molar, "mmol" for millimole or millimoles, "min" for minute or minutes, "h" for hour or hours, "rt" for room temperature, "atm" for atmosphere, "psi" for pounds per square inch, "RT" for retention time, "sat" or "sat'd" for saturated, "MW" for molecular weight, "MS" for mass spectrometry, "ESI" for electrospray ionization mass spectroscopy, "HR" for high resolution, "LC-MS" for liquid chromatography mass spectrometry, "HPLC" for high pressure liquid chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, "tlc" or "TLC" for thin layer chromatography, and "α", "β", "R", "S", "E", and "Z" are stereochemical designations familiar to one skilled in the art.

ACN is acetonitrile,

AcOH or HOAc is acetic acid,

AIBN is azo-bis-isobutyrlnitrile,

9-BBN is 9-borabicyclo[3.3.1]nonane,

BINAP is 2,2'-bis(diphenylphosphino)-1,1'-binaphthalene,

Bn is benzyl,

Boc is tert-butyl oxycarbonyl,

BOM is benzyloxymethyl,

BOP is benzotriazol-1-yloxy-tris(dimethylamino)phosphonium hexafluorophosphate,

Bu is butyl, iBu or i-Bu is isobutyl, t-Bu is tert-butyl,

Cbz is carbonylbenzyloxy,

DCE is 1,2-dichloroethane,
DCM or CH$_2$Cl$_2$ is dichloromethane,
DIBAH is diisobutylaluminum hydride,
DIC is 1,3-diisopropylcarbodiimide,
DIEA is diethylpropyl amine,
DMAP is dimethylaminopyridine,
DME is dimethyl ether,
DMF is dimethylformamide,
DMPU is 1,3-dimethyl-3,4,5,6-tetrahydro-2(1H)-pyrimidinone,
DMSO is dimethyl sulfoxide,
DPPA is diphenylphosphoryl azide,
EDCI is 1-(3-dimethylaminopropyl)-3-ethylcarbodiimide hydrochloride,
Et is ethyl,
EtOH is ethanol,
EtOAc is ethyl acetate,
Et$_2$O is diethyl ether HEPES is 4-(2-hydroxyethyl)piperaxine-1-ethanesulfonic acid,
HOAt or HOAT is 1-hydroxy-7-azabenzotriazole,
HOBt is 1-hydroxybenzotriaole hydrate
LAH is lithium aluminum hydride
LDA is lithium diisopropylamide,
LiHMDS is bis(trimethylsilyl)amide,
mCPBA or MCPBA is meta-chloroperbenzoic acid,
Me is methyl,
MeOH is methanol,
MsCl is methanesulfonyl chloride,
NaHMDS is sodium hexamethyldisilazane,
NaOAc is sodium acetate,
NBS is N-bromosuccinimide,
OAc is acetate,
Pd$_2$(dba)$_3$ is tris(dibenzylideneacetone)dipalladium(0),
Pd(PPh$_3$)$_4$ is tetrakis(triphenylphosphine)palladium,
Ph is phenyl,
PMDTA is N,N,N',N',N''-pentamethyldiethylenetriamine,
Pr is propyl,
PyBOP is benzotriazol-1-yl-oxytripyrrolidinophosphonium hexafluorophosphate,
iPr or i-Pr is isopropyl,
i-PrOH or IPA is isopropanol,
TBAF is tetrabutylammoniumfluoride,
TBAI is tetrabutylammonium iodide,
TBS is tert-butyldimethylsilyl,
TBSCl is tert-butyldimethylsilyl chloride,
TEA is triethylamine,
TFA is trifluoroacetic acid,
TFAA is trifluoroacetic anhydride,
THF is tetrahydrofuran,
TrCl is trityl chloride,
TRIS is tris(hydroxymethyl)aminomethane,
Tr is trityl,
Xantphos is 4,5-bis(diphenylphosphino)-9,9-dimethylxanthene.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C. *Comprehensive Organic Transformations*, VCH: New York, 1989. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley-Interscience, 3nd Edition, 1999). All references cited herein are hereby incorporated in their entirety herein by reference.

Compounds having the general Formula (I) can be prepared according to the general methods shown in the schemes below. Compounds of formula (I) where Z=NH can be prepared using the general method shown in Scheme 1. Using the Petasis boronic acid Mannich reaction (Petasis, N. A., Zavialov, I. A. *J. Am. Chem. Soc.* 1997, 119, 445-446; Petasis, N. A., Goodman, A., Zavialov, I. A. *Tetrahedron* 1997, 53, 16463-16470.), amines 1 are reacted with glyoxylic acid and phenyl boronic acids 2 to afford arylglycines 3. This reaction is typically conducted in a solvent such as, but not limited to, toluene, dichloromethane, 1,2-dichloroethane, methanol, ethanol, dimethylformamide, or acetonitrile, or appropriate mixtures thereof. In some cases, mixtures of acetonitrile and dimethylformamide are preferred. Fluorinated alcohols such as hexafluoroisopropanol are useful additives that may improve the rate and or yield of the reaction. If necessary, the reaction is heated conventionally or in a microwave reactor to achieve a practical reaction rate.

The preparation of amines 1 is described below in Scheme 7 and in the experimental procedures for Intermediate 1. Additionally, preparation of primary amines is well known in the art of organic synthesis and many primary amines are commercially available. Preparation of phenylboronic acids 2, which contain a protected benzylamine (PG=protecting group) is described in the synthesis of Examples 6, 8, 9, 10, and 11 and in Schemes 8 and 9. Additionally, preparation of phenylboronic acids 2 can be achieved through methods known to one skilled in the art of organic synthesis. The protecting group PG in 2 may be, for instance, a carbamate such as Boc or Cbz, or as in Examples 6, 8, 9, 10, and 11, the entire PGNR$^5$CR$^6$R$^7$ group may be a nitrile, which may be deprotected by catalytic hydrogenation to an unsubstituted benzylamine. The protecting group is removed under appropriate conditions from arylglycines 3 to provide amino acids 4. Amino acids 4 can be cyclized to macrocycles 5 under conditions suitable for forming an amide bond between the acid and the amine. Coupling reagents and conditions can be found in Bodanszky, "Principles of Peptide Synthesis, Second Edition" Springer Verlag Ed, Berlin (1993) and in a recent review (Montalbetti, C. A. G. N., Falque, V. *Tetrahedron* 2005, 61, 10819-11046). Coupling reagents include, but not limited to, CDI, DIC, and EDCI. Optionally, an intermediate activated ester can be prepared by adding one equivalent of 1-hydroxybenzotriazole or 1-hydroxy-7-azabenzotriazole. Other coupling reagents include, but not limited to, BOP or HATU, which are usually reacted in the presence of a tertiary base such as DIEA or TEA. BOP is a preferred reagent for preparation of compounds of Formula (I). Addition of catalytic or stoichiometric DMAP may improve the reaction rate or yield. The reaction may be conducted in solvents such as, but not limited to, DCE, DCM, DMF, or mixtures thereof. Finally, it may be necessary to run the macrocyclization reaction under dilute conditions (initial concentration of 4<0.1 M) to favor macrocyclization over dimerization. Depending on the particular substituent groups present in the final compounds, deprotection steps may be required before or after the macrocyclization step to afford compounds of Formula (I).

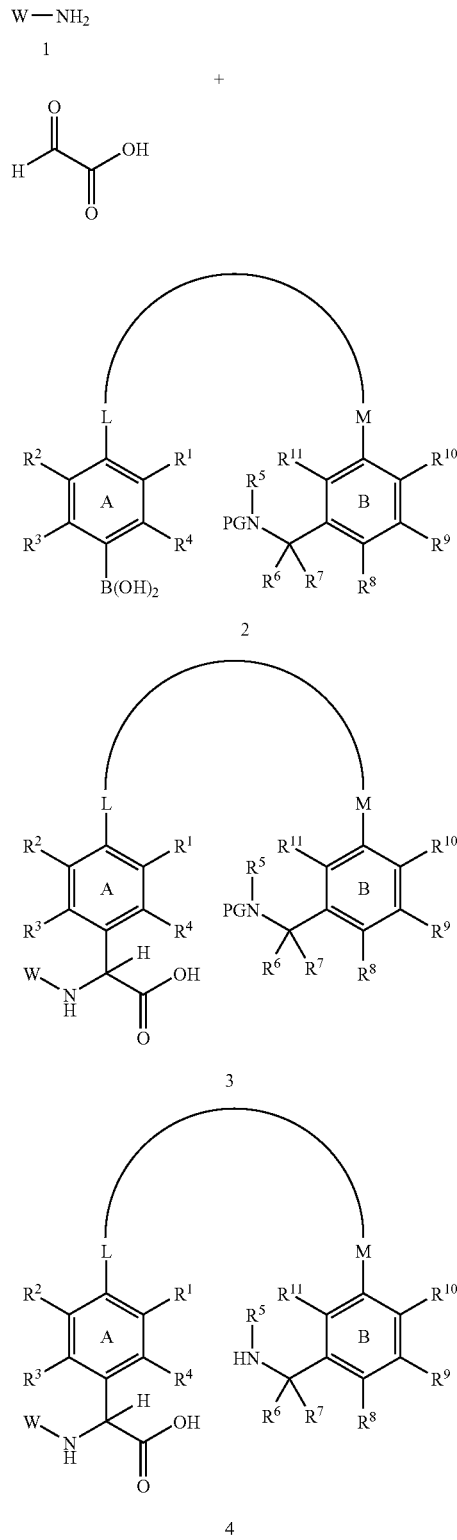

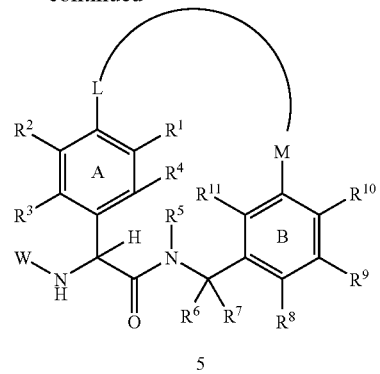

An alternative to the Petasis chemistry, enabling the synthesis of compounds of Formula (I) where Z is either NH or O is shown in Scheme 2. This scheme shows an explicit subset of L and M groups, but the chemistry shown can be readily modified by one skilled in the art to prepare compounds containing other combinations of L and M. Starting aldehydes 6 are commercially available or can be readily prepared by methods known to one skilled in the art of organic synthesis. The aldehydes are converted to the cyanohydrins 7 by treatment, for instance, with potassium cyanide and sodium hydrogensulfite in a mixture of EtOAc and water. The cyanohydrins are reacted with hydrogen chloride in methanol, and the intermediate imidates are hydrolyzed to afford methyl esters 8. The hydroxyl group in 8 is converted to a leaving group (LG) such as halogen or sulfonate. Chloride and triflate are preferred LGs for this reaction. Nucleophiles W-ZH are reacted with 9 in a solvent such as DCM or DMF and in presence of a base such as 2,6-lutidine, TEA, or DIEA to afford 10. The protecting group in 10 is removed and 11, containing nucleophilic groups YH is reacted with phenyl carbamates 12, or their synthetic equivalent isocyanate or carbamoyl halide to give 13. The methyl ester in 13 is hydrolyzed and the nitrogen protecting group (PG) is removed to give amino acids 14. Subsequent cyclization as described in Scheme 1 affords macrocycles 15.

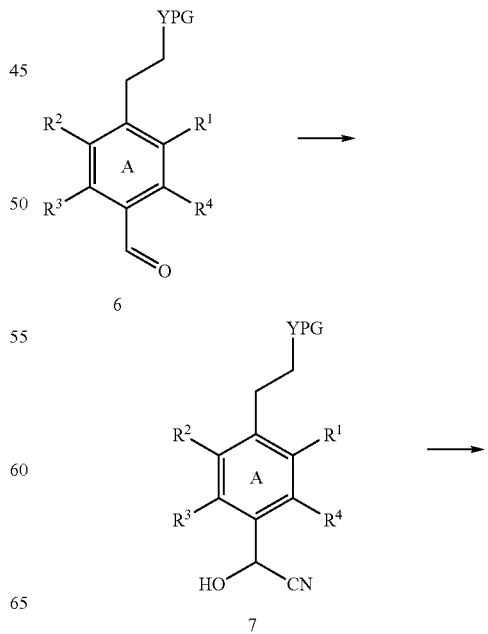

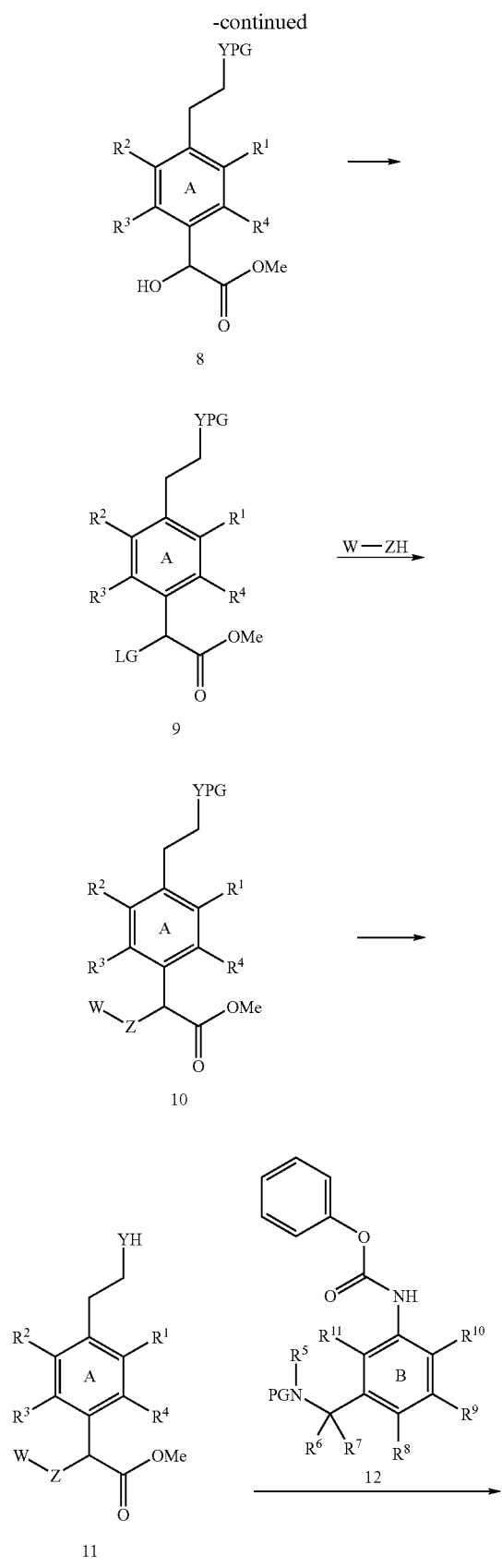
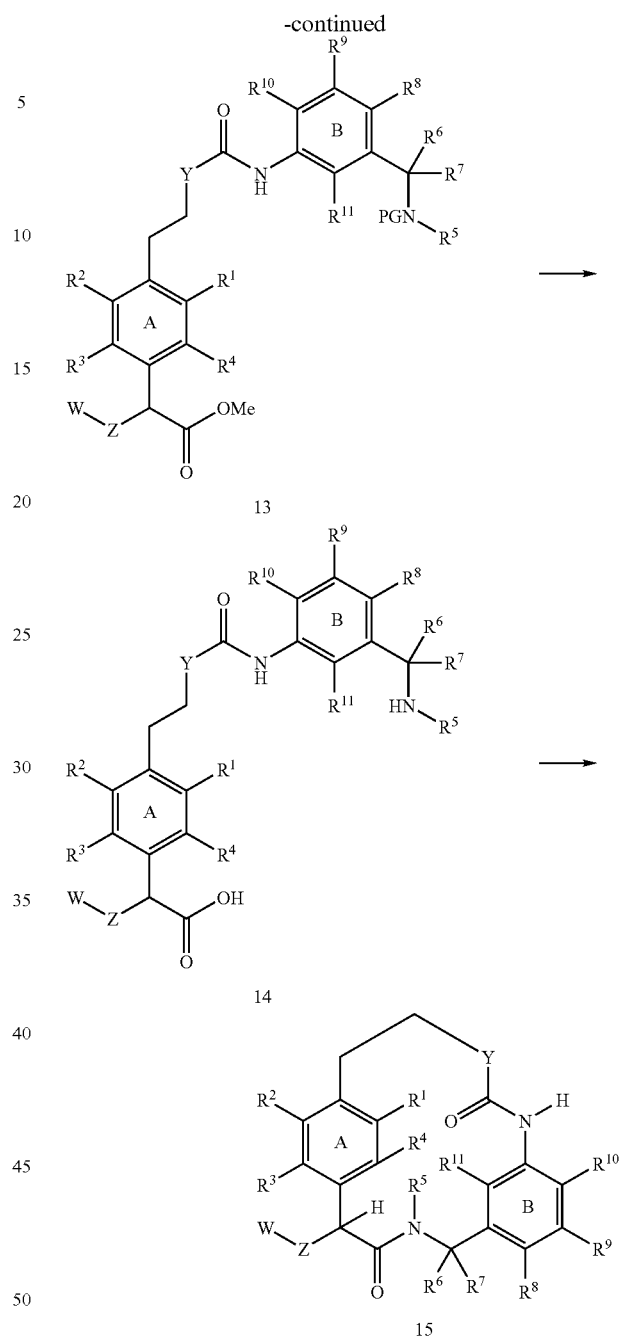

Alternatively to Schemes 1 and 2, as exemplified in Scheme 3, aldehydes 6 can be condensed with trimethylsilyl-cyanide in presence of ammonia to give aminonitriles 16. Treatment of 16 with hydrogen chloride in MeOH, followed by hydrolysis on aqueous workup gives amino esters 17. Amino esters 17 may be coupled with aryl or heteroaryl halides or sulfonates W-LG by methods known in the art. For example, amino esters 17 may be coupled to W-LG in the presence of a palladium catalyst, an appropriate ligand, for example, BINAP, using a base such as cesium carbonate to provide esters 18. Esters 18 are a subset of esters 10 in Scheme 2, and can be converted to compounds of Formula (I) using the subsequent methods described in Scheme 2.

Scheme 3

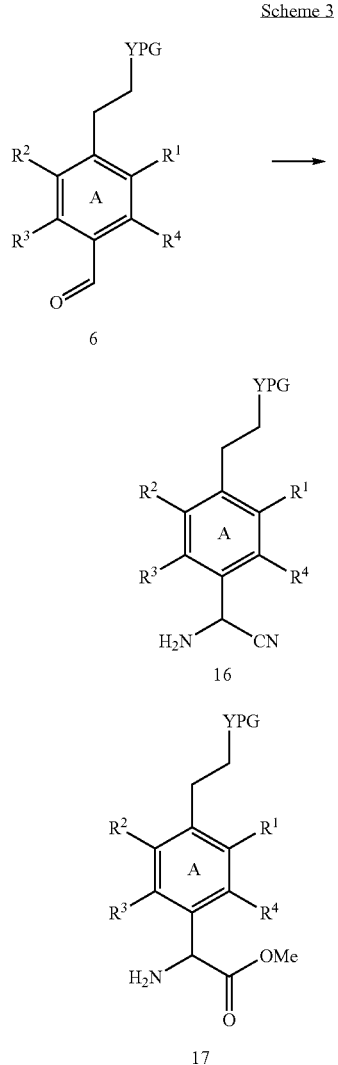

Scheme 4

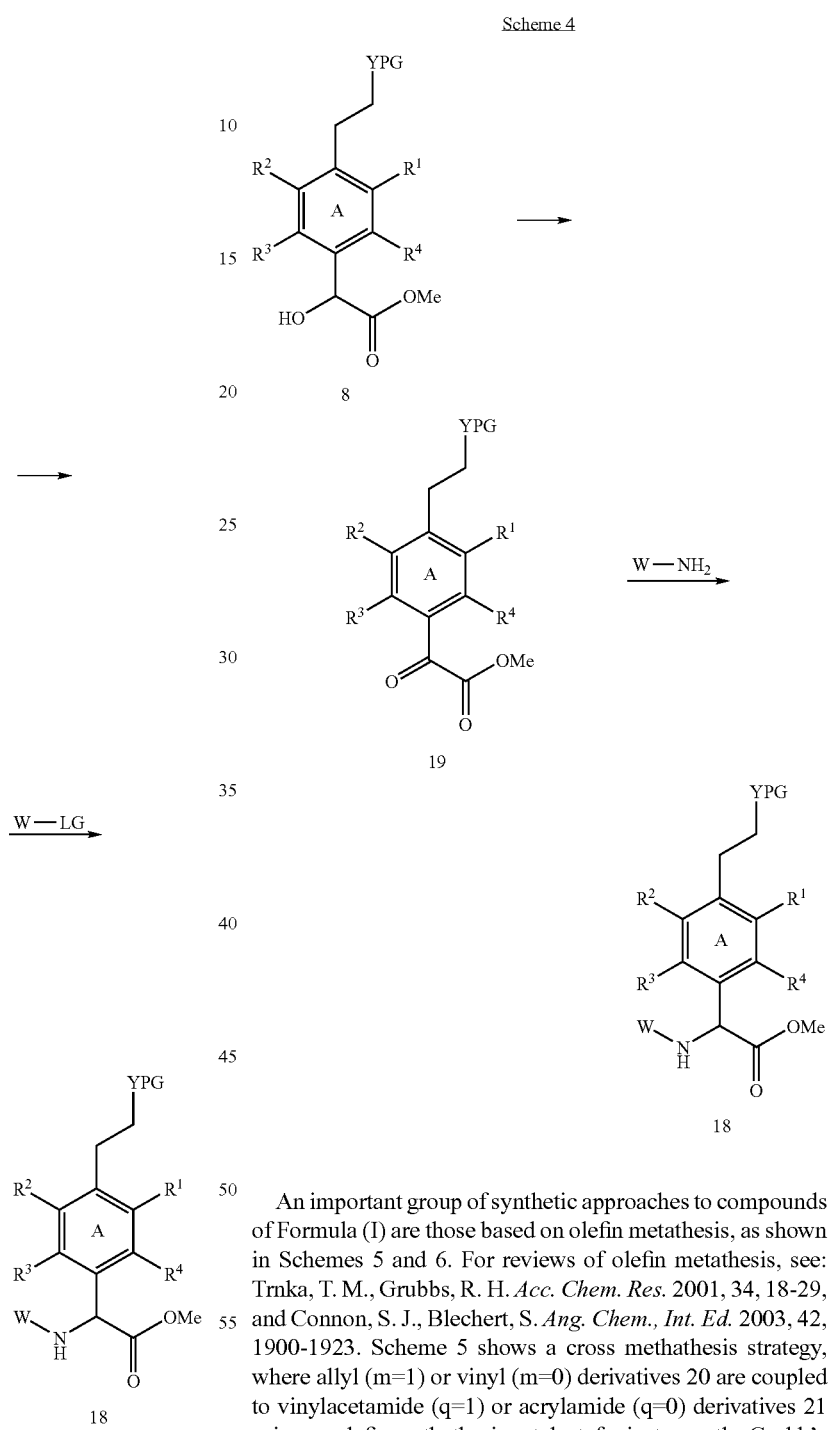

acetonitrile, affords amino esters 18. As indicated in Schemes 2 and 3, compounds 18 may be converted to compounds of Formula (I).

Another alternative for the introduction of the Z group is shown in Scheme 4. Hydroxy esters 8 are oxidized to keto esters 19, using, for instance, Swern conditions or $MnO_2$. Subsequent reductive amination with primary amines W—$NH_2$, using, for instance, sodium cyanoborohydride or sodium triacetoxyborohydride in a solvent such as DCM or acetonitrile, affords amino esters 18.

An important group of synthetic approaches to compounds of Formula (I) are those based on olefin metathesis, as shown in Schemes 5 and 6. For reviews of olefin metathesis, see: Trnka, T. M., Grubbs, R. H. *Acc. Chem. Res.* 2001, 34, 18-29, and Connon, S. J., Blechert, S. *Ang. Chem., Int. Ed.* 2003, 42, 1900-1923. Scheme 5 shows a cross methathesis strategy, where allyl (m=1) or vinyl (m=0) derivatives 20 are coupled to vinylacetamide (q=1) or acrylamide (q=0) derivatives 21 using an olefin methathesis catalyst, for instance, the Grubb's second generation ruthenium catalyst ($Cl_2(PCy_3)(IMes)$ Ru=CHPh). Hydrolysis of the ester and removal of the amine protecting group affords amino acids 23. Subsequent amide coupling as described in Scheme 1 affords macrocycles 24. The double bond may be reduced by catalytic hydrogenation to afford macrocycles 25 with a saturated L group.

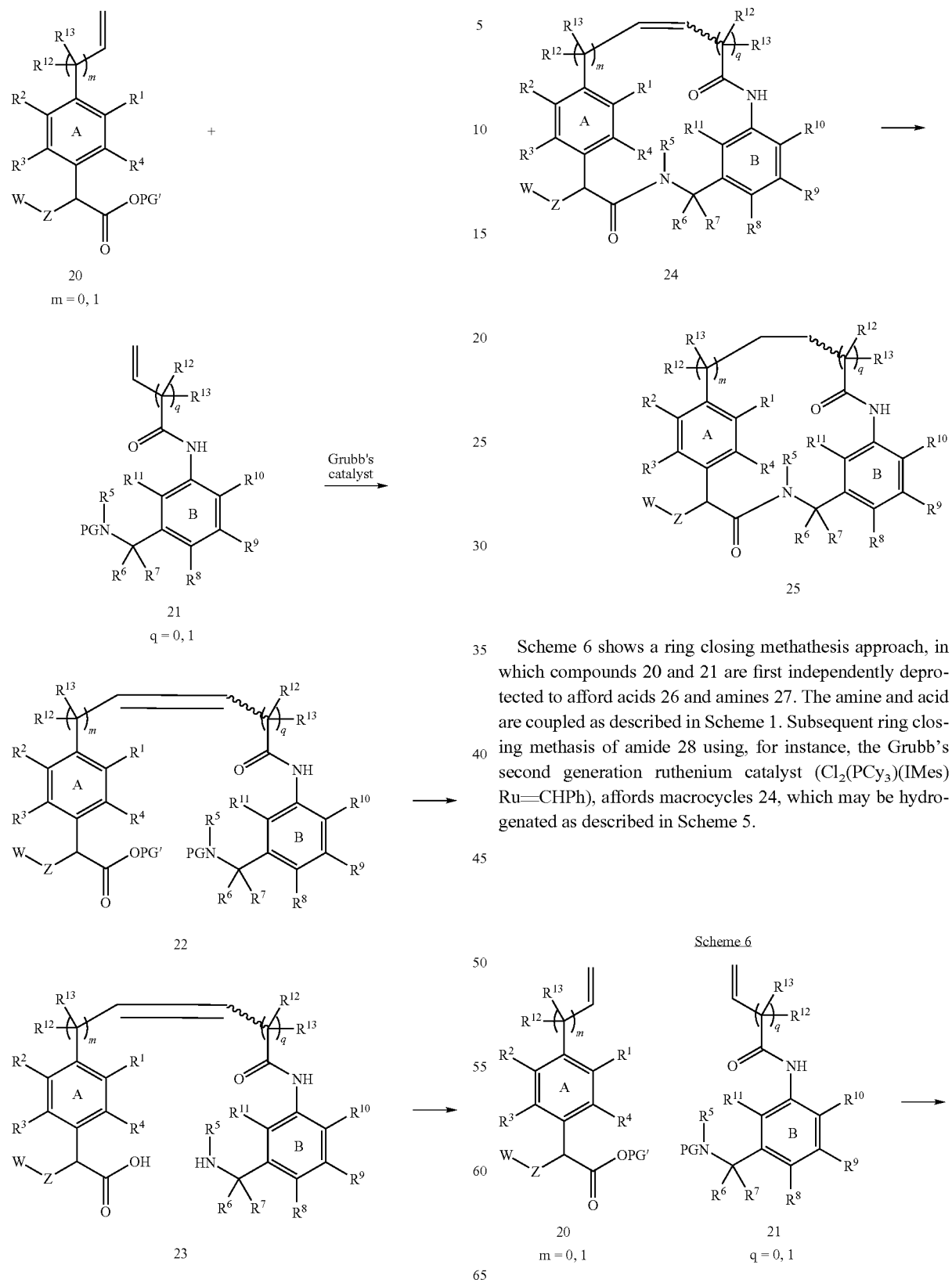

Scheme 6 shows a ring closing methathesis approach, in which compounds 20 and 21 are first independently deprotected to afford acids 26 and amines 27. The amine and acid are coupled as described in Scheme 1. Subsequent ring closing methasis of amide 28 using, for instance, the Grubb's second generation ruthenium catalyst ($Cl_2(PCy_3)(IMes)Ru=CHPh$), affords macrocycles 24, which may be hydrogenated as described in Scheme 5.

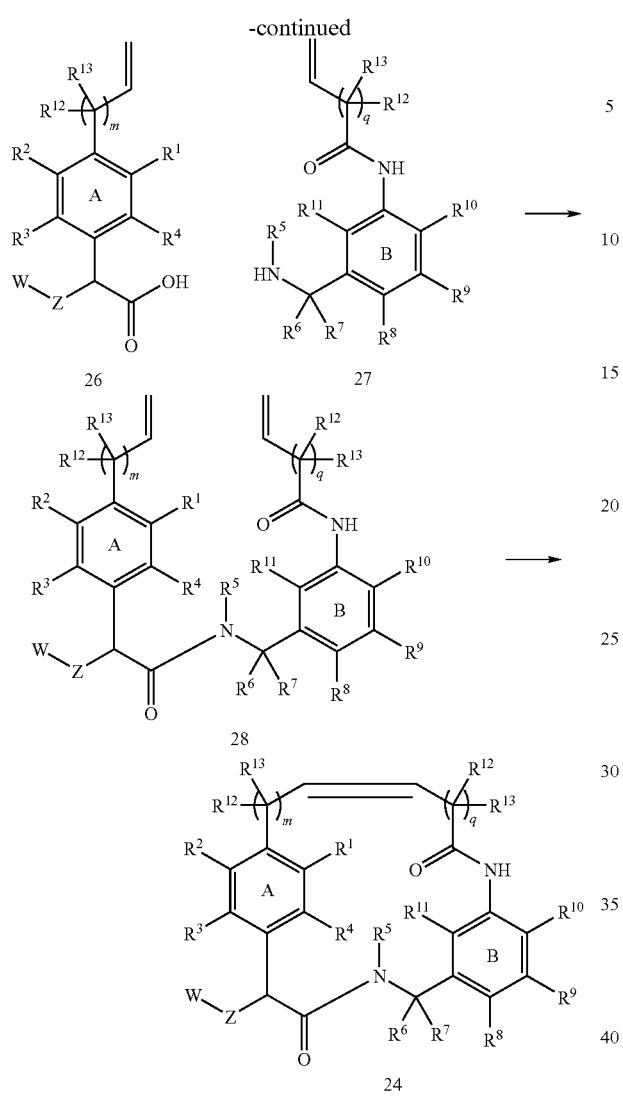

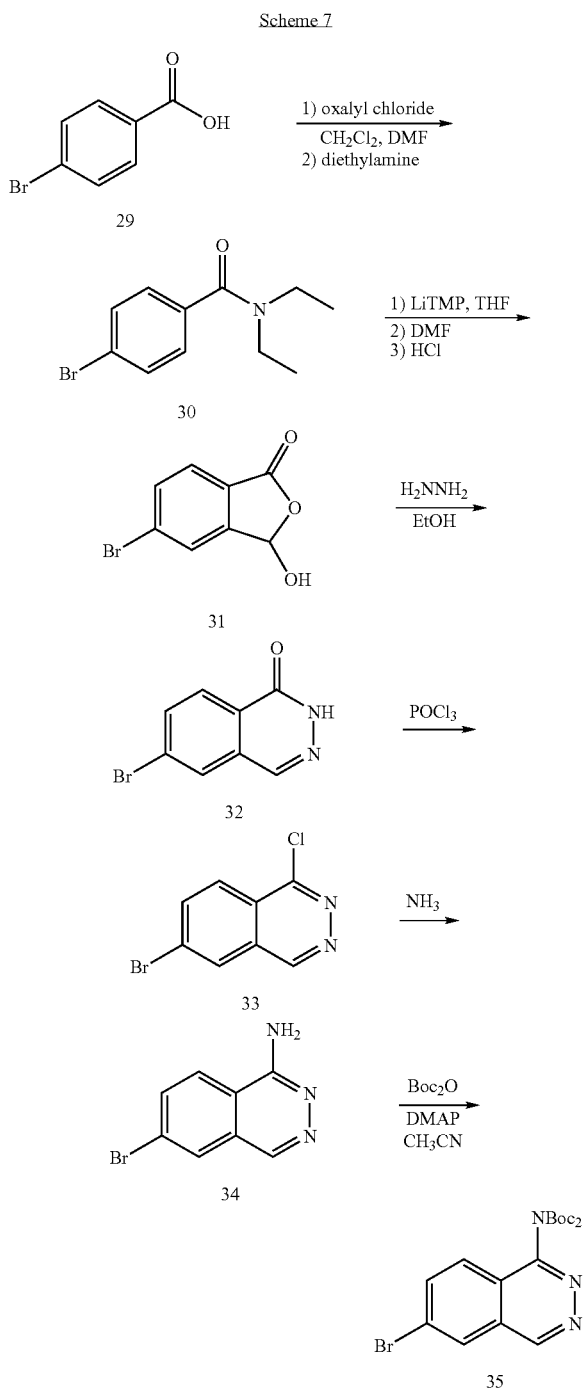

reaction with di-tert-butyl dicarbonate and 4-dimethylaminopyridine in acetonitrile. The resulting bromide 35 can then by coupled to a phenylglycine ester 17 as described in Scheme 3.

The synthesis of an appropriately protected (di-Boc) intermediate W-ZH for W=1-aminoisoquinolin-6-yl and Z=NH is described in the Example section below as Intermediate 1. 4-(N-Boc-aminomethyl)aniline, an appropriately protected intermediate W—NH$_2$ for W=4-aminomethylphenyl and Z=NH is commercially available. 3-Aminobenzamide, an intermediate W—NH$_2$ for W=3-carbamoylphenyl and Z=NH is also commercially available. tert-Butyl (4-aminophenyl)(imino)-methylcarbamate, an appropriately protected intermediate W—NH$_2$ for W=4-amidinophenyl and Z=NH is commercially available. Compounds containing W=1-aminophthalazin-6-yl and Z=NH can be prepared using the methods shown in Scheme 3. Synthesis of an appropriately protected intermediate W-LG is shown below in Scheme 7. 4-Bromobenzoic acid 29 is converted to the acid chloride and reacted with diethylamine. The resulting diethylbenzamide 30 is formulated by treatment with lithium tetramethylpiperidide at −78° C., followed by quenching with DMF. Subsequent cyclization in refluxing hydrochloric acid provides the hydroxyphthalide 31. The hydroxyphthalide 31 is refluxed with hydrazine in ethanol to afford 6-bromophthalazin-1(2H)-one 32. Treatment with phosphorous oxychloride gives 6-bromo-1-chlorophthalazine 33, which is converted to 1-amino-6-bromophthalazine 34 by reaction with ammonia saturated ethylene glycol at 130° C. The amine is protected by Synthesis of benzylamine intermediates for preparation of compounds of Formula (I) is shown in Schemes 8 and 9. Scheme 8 shows the preparation of benzylamine intermediates where R$^5$=H. Nitro fluoride 36 may be treated with thiols to afford sulfides 37. Compounds 37 can be oxidized with mCPBA to sulfones 38. Subsequent catalytic hydrogenation affords anilines 39, which are useful intermediates in the synthesis of macrocycles where M=—CONH— and —SO$_2$NH—. Alternatively, iron/acetic acid reduction of 37 to aniline 40, followed by borane reduction gives benzylamine 41. Subsequent protection, for instance, with Cbz-Cl and base, gives intermediates 42, which are also useful for the synthesis of macrocycles where M=—CONH— and —SO$_2$NH—. Oxidation of the sulfide to the sulfone can be achieved at a later stage in the synthesis using mCPBA. Methods for coupling these benzylamine intermediates to A ring intermediates to afford key intermediates 2 are given in the Examples.

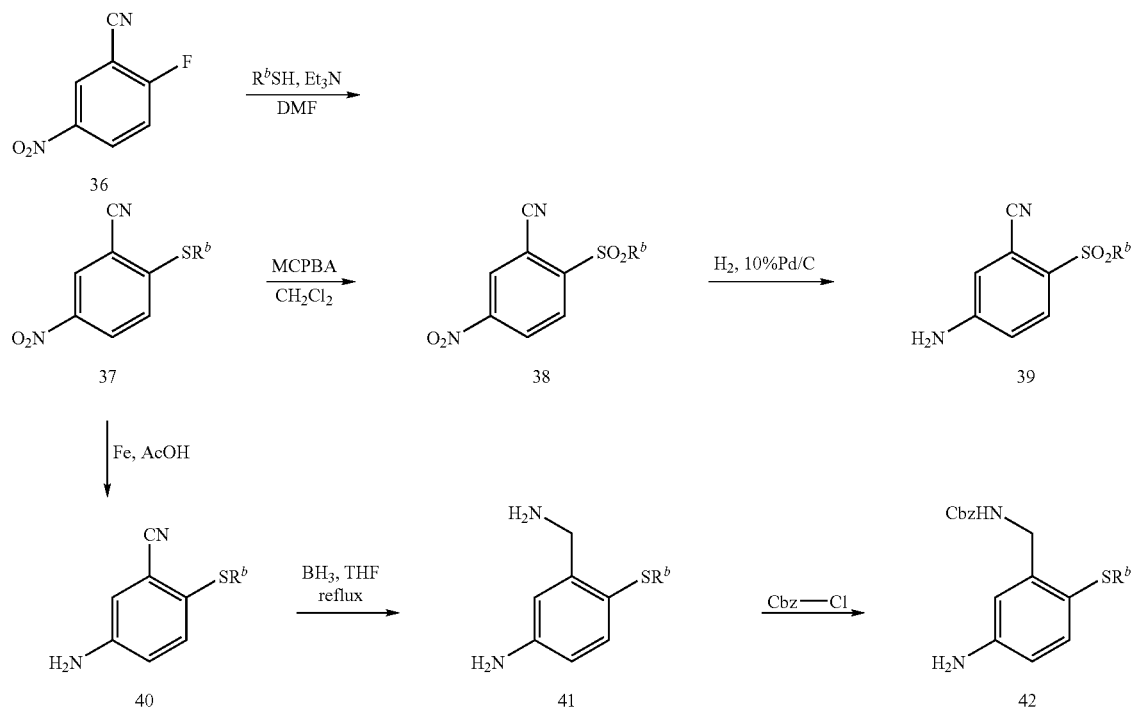

Scheme 8

Synthesis of benzylamine intermediates with R$^5$ substituents other than H can be achieved as shown in Scheme 9. Nitro fluoride 43 may be treated with thiols to afford sulfides. The acid can then be converted to methyl amides 44 through the acid chloride. Subsequent reductions with iron/acetic acid and borane give benzyl amines 46. These may be protected, for instance as the Cbz derivatives 47, which are useful intermediates in the synthesis of macrocycles where M=—CONH— and —SO$_2$NH—. Oxidation of the sulfide to the sulfone can be achieved at a later stage in the synthesis using mCPBA.

Scheme 9

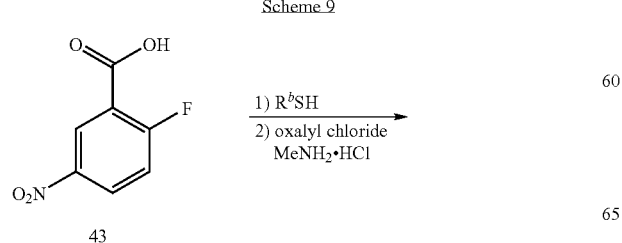

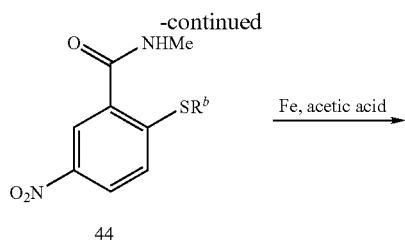

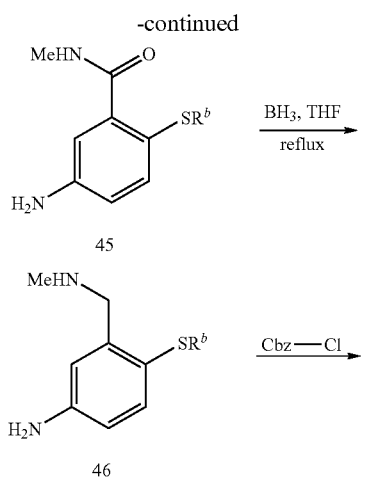

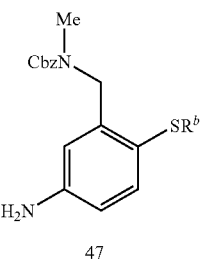

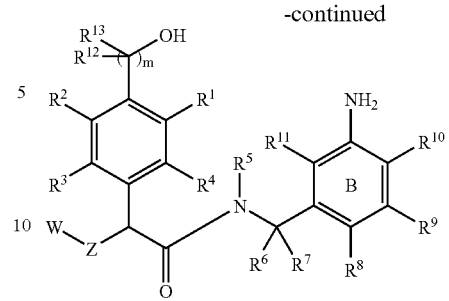

Scheme 10 depicts an alternate approach to compounds where Y═O and M═—CONH—; ring closure is accomplished via carbamate formation. Compounds 48 (prepared according to the Schemes 1-4) are deprotected (PG' protecting group) to afford acids 49, which in turn are coupled with amines 50 to afford amides 51. Following amide bond formation, a second protecting group removal (PG" protecting group) and the nitro functional group reduction (reducing conditions, such as $H_2$, Pd—C or Fe, AcOH) afford amino alcohols 52. Treatment of these intermediates with phosgene (or a phosgene equivalent such as triphosgene) to generate the carbamic chloride intermediate in situ, followed by slow addition of this intermediate into a basic reaction mixture, such as triethylamine or Hunig's base in DCM or acetonitrile, effects macrocyclization to yield compounds 53.

Scheme 10

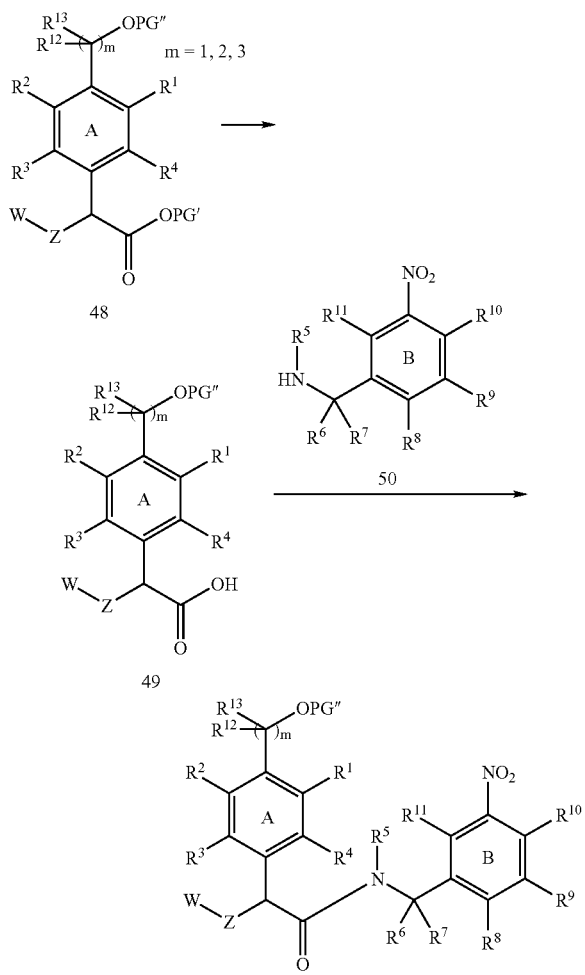

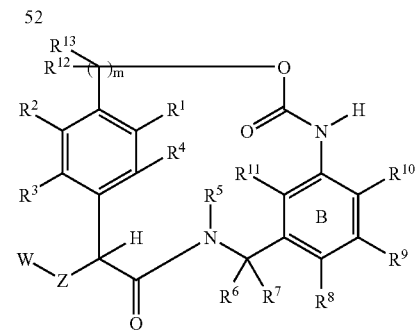

The compounds of the instant invention herein described may have asymmetric centers. For example, the chiral carbon atom in Formula (I) (indicated with an asterisk below) exists either in the S or R configuration. Thus, the stereoisomeric configurations of each compound of Formula (I) are considered part of the invention. In a preferred stereoisomeric embodiment, the present invention provides for the R configuration at the indicated chiral carbon for all embodiments of Formula (I), or tautomers, pharmaceutically acceptable salts, solvates, or prodrug forms thereof.

(I)

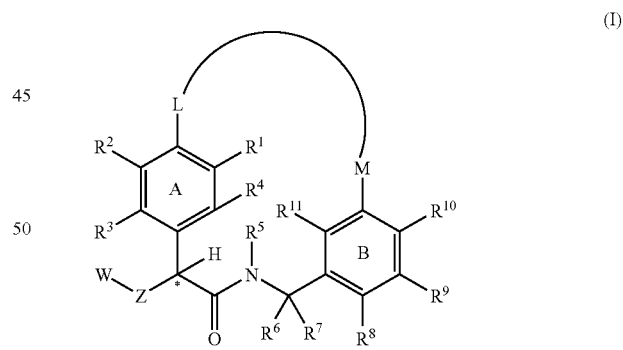

EXAMPLES

The following Examples have been prepared, isolated and characterized using the methods disclosed herein. The following Examples demonstrate a partial scope of the invention and are not meant to be limiting of the scope of the invention.

In the following experimental procedures, solution ratios express a volume relationship, unless stated otherwise. NMR chemical shifts (δ) are reported in parts per million. Flash chromatography (see Still, W. C. et al. *J. Org. Chem.* 1978, 43, Intermediate 1: 6-Amino-1-(di-tert-butoxycarbony-lamino)isoquinoline

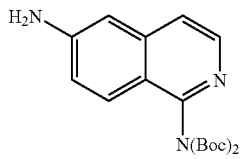

Intermediate 1A: (E)-2-(2-(Dimethylamino)vinyl)-4-nitrobenzonitrile

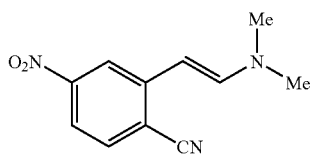

A mixture of 2-methyl-4-nitrobenzonitrile (5.0 g, 31 mmol) and tert-butoxybis(dimethylamino)methane (12.2 mL, 59 mmol) in dry DMF (8 mL) was stirred at 70° C. for 2 h under $N_2$. After cooling to rt, DMF was removed in vacuo and the crude product was triturated with hexanes/EtOAc (5:1). The solid was collected by filtration and washed with hexane to give Intermediate 1A (6.5 g, 97%) as black solid. $^1$H NMR (400 MHz, CDCl$_3$) δ 2.97 (s, 6H), 5.36 (d, J=13.2 Hz, 1H), 7.16 (d, J=13.6 Hz, 1H), 7.52 (d, J=8.8 Hz, 1H), 7.60 (m, 1H), 8.11 (d, J=1.8 Hz, 1H).

Intermediate 1B: 2-(2,4-Dimethoxybenzyl)-6-nitroisoquinolin-1(2H)-imine

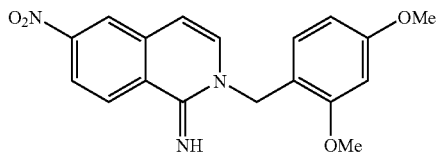

Intermediate 1A (4.6 g, 21.2 mmol) and 2,4-dimethoxylbenzylamine (4.0 mL, 1.25 eq) in DMPU (10 mL) was heated at 140° C. for 3 h. The solvent was removed by vacuum distillation and residue treated with hexanes/EtOAc (1:1). The solid was collected by filtration and washed with hexane to give Intermediate 1B (4.6 g, 64%). $^1$H NMR (400 MHz, DMSO-d$_6$) δ 3.72 (s, 3H), 3.81 (s, 3H), 4.96 (s, 1H), 6.28 (d, J=6.6 Hz, 1H), 6.46 (d, J=7.5 Hz, 1H), 6.58 (d, J=1.8 Hz, 1H), 7.03 (d, J=8.8 Hz, 1H), 7.27 (d, J=6.2 Hz, 1H), 8.02 (dd, J=9.0, 2.4 Hz, 1H), 8.31 (d, J=2.2 Hz, 1H), 8.43 (d, J=8.4 Hz, 1H).

Intermediate 1C: 6-Nitroisoquinolin-1-amine

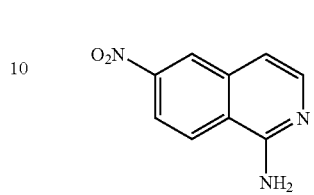

To a solution of Intermediate 1B (11.9 g, 35 mmol) in anisole (24 mL) was added TFA (24 mL). The reaction mixture was stirred at 90° C. for 6 h and the solvent was removed under reduced pressure. The residue was suspended in MeOH (50 mL) and then treated with NaHCO$_3$ (3.3 g, 39 mmol) in water (200 mL). The mixture was stirred at rt for 15 min and the pH was checked to be 9-10. The precipitate was collected by filtration and washed with water to afford Intermediate 1C (6.0 g, 91%). $^1$H NMR (400 MHz, DMSO-d$_6$) δ 7.20 (d, J=5.7 Hz, 1H), 7.36 (s, 2H), 7.95 (d, J=5.7 Hz, 1H), 8.15 (dd, J=9.2, 2.6 Hz, 1H), 8.43 (d, J=9.2 Hz, 1H), 8.67 (d, J=2.6 Hz, 1H).

Intermediate 1D: 6-Nitro-1-di-tert-butoxycarbonylaminoisoquinoline

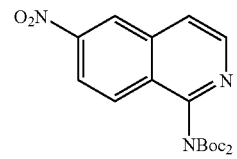

A solution of Intermediate 1C (25.0 g, 0.132 mol), di-tert-butyl dicarbonate (63.4 g, 0.29 mol) and DMAP (750 mg, catalyst) in DMPU (125 mL) was stirred at 70° C. for 30 min. The reaction was quenched with water (300 mL). The reaction mixture was diluted with ethyl acetate (500 mL) and washed with water. The organic layer was separated and the solvent removed under vacuum. The residue was recrystallized from methanol to give Intermediate 1D (54.0 g, 95.0%) as a solid. $^1$H NMR (400 MHz, CDCl$_3$) δ 1.33 (s, 18 H), 7.86 (d, J=5.3 Hz, 1 H), 8.15 (d, J=9.2 Hz, 1 H), 8.39 (dd, J=9.2, 2.20 Hz, 1 H), 8.6 (d, J=5.7 Hz, 1 H), 8.82 (d, J=2.2 Hz, 1 H). MS(ESI) m/z 801 (2M+Na)$^+$.

Intermediate 1

A solution of Intermediate 1D (75.0 g, 0.193 mol) in methanol/THF (500 mL/500 mL) was hydrogenated with a hydrogen balloon in the presence of Pd/C (5%, 5 g) for 2.0 h. Filtration of the Pd/C and concentration gave a solid, which was recrystallized from methanol to give Intermediate 1 as a white solid (65.7 g, 95.0%). $^1$HNMR (400 MHz, CDCl$_3$) δ 1.33 (m, 18 H), 4.18 (s, 2 H), 6.89 (d, J=2.2 Hz, 1 H), 6.99 (dd, J=9.0, 2.4 Hz, 1 H), 7.35 (d, J=6.6 Hz, 1 H), 7.75 (d, J=8.8 Hz, 1 H), 8.22 (d, J=5.7 Hz, 1 H). MS(ESI) m/z 741 (2M+Na)$^+$.

Example 1

2-(1-Amino-isoquinolin-6-ylamino)-16-oxa-4,11-diaza-tricyclo[15.2.2.1$^{6,10}$]docosa-1(20),6,8,10(22),17(21),18-hexaene-3,12-dione trifluoroacetic acid salt

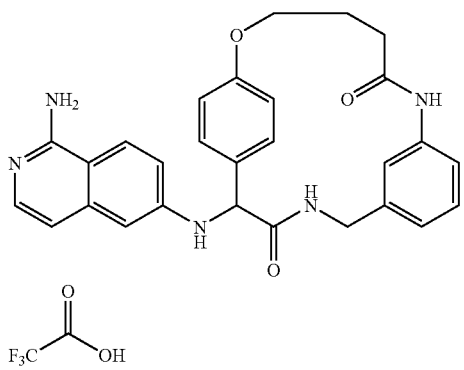

1A: 4-(4-Boronophenoxy)-butyric acid

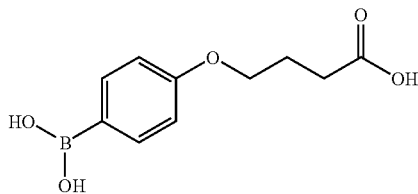

A resealable tube was charged with 4-(4-bromophenoxy)butyric acid (259 mg, 1.0 mmol), 5,5,5',5'-Tetramethyl-[2,2']bi[[1,3,2]dioxaborinanyl] (249 mg, 1.1 mmol), potassium acetate (245 mg, 2.5 mmol), and DMSO (2 mL). The resulting orange suspension was deoxygenated by sparging with nitrogen gas. Dichloro[1,1'-bis(diphenylphosphino)ferrocene]palladium(II) dichloromethane adduct (30 mg, 0.041 mmol) was added, and the tube was sealed tightly and heated at 80° C. overnight. Hydrochloric acid (1N) was added, and the mixture was extracted with EtOAc (2×), washed with water (2×) and brine (1×), and dried (MgSO$_4$). The organic layer was concentrated in vacuo and the residue purified by flash chromatography (0 to 15% MeOH in DCM) to give the 2,2-dimethyl-1,3-propanediol boronic ester of 1A. This material was dissolved in diethyl ether and washed with NaOH (2 N, 2×). The aqueous layers were washed with diethyl ether, combined, and acidified to pH 4 with hydrochloric acid (6 N). The resulting solid precipitate was collected by filtration to afford 1A (210 mg, 94%) as a beige solid. $^1$H NMR (400 MHz, CD$_3$OD) δ 2.06 (m, 2H), 2.48 (t, J=7.5 Hz, 2H), 4.02 (t, J=6.6 Hz, 2H), 6.88 (br s, 2H), 7.62 (br d, 2H).

1B: 4-(3-Benzyloxycarbonyl-propoxy)-phenylboronic acid

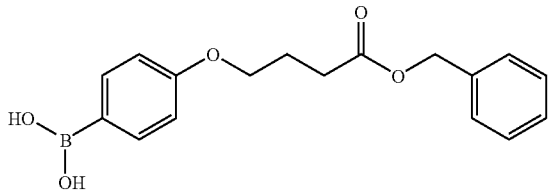

A solution of 1A (200 mg, 0.89 mmol), potassium bicarbonate (313 mg, 3.1 mmol), and benzyl bromide (0.163 mL, 1.4 mmol) in DMF (2 mL) was heated at 60° C. for 8 h. The reaction mixture was concentrated in vacuo and the residue was partitioned between EtOAc and hydrochloric acid (1 N). The aqueous layer was extracted with EtOAc (2×) and then the combined organics were washed with water (3×) and brine, dried (MgSO$_4$), and concentrated in vacuo. The residue was purified by flash chromatography (30 to 100% EtOAc in hexane) to afford 1B (86 mg, 28%) as a white solid. $^1$H NMR (400 MHz, CD$_3$OD) δ 2.08 (m, 2H), 2.56 (t, J=7.0 Hz, 2H), 4.00 (m, 2H), 5.12 (s, 2H), 6.84 (2×d, 2H), 7.32 (m, 5H), 7.7-7.5 (2×d, 2H).

1C: 4-{4-[(1-Di-tert-butoxycarbonylamino-isoquinolin-6-ylamino)-carboxymethyl]-phenoxy}-butyric acid benzyl ester

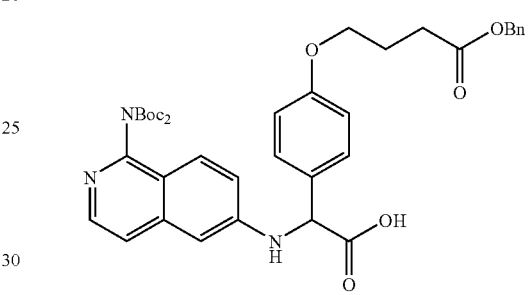

A solution of 1B (82 mg, 0.26 mmol), Intermediate 1 (72 mg, 0.20 mmol), and glyoxylic acid monohydrate (22 mg, 0.24 mmol) in DCE (1 mL) was heated at 100° C. for 10 min in a microwave reactor. This solution was purified by flash chromatography (0 to 15% MeOH in DCM) to give 1C contaminated with 1B (110 mg, 2.5:1 1C/1B, 68% yield based on content of 1C) as a yellow oil. MS (ESI) m/z 686.3 (M+H)$^+$.

1D: 4-{4-[(1-Di-tert-butoxycarbonylamino-isoquinolin-6-ylamino)-(3-nitrobenzylcarbamoyl)-methyl]-phenoxy}-butyric acid benzyl ester

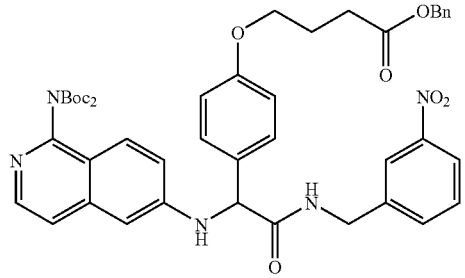

A solution of 1C (110 mg, 0.16 mmol), 3-nitrobenzylamine hydrochloride (36 mg, 0.19 mmol), DIEA (0.084 mL, 0.48 mmol), HOAt (22 mg, 0.16 mmol), and EDCI (62 mg, 0.32 mmol) in a mixture of DCM (2 mL) and DMF (0.5 mL) was stirred at rt overnight. The reaction mixture was concentrated in vacuo and the residue was triturated with water and then purified by flash chromatography (0 to 10% MeOH in DCM) to give 1D (88 mg, 67%). MS (ESI) m/z 820.3 (M+H)$^+$.

1E: 4-{4-[(3-Amino-benzylcarbamoyl)-(1-di-tert-butoxycarbonylamino-isoquinolin-6-ylamino)-methyl]-phenoxy}-butyric acid

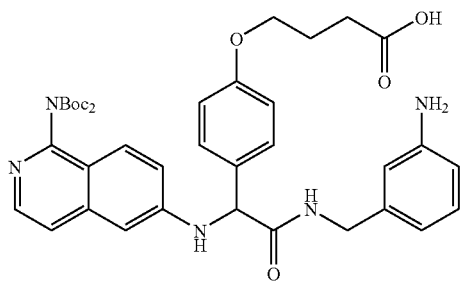

A solution of 1D (88 mg, 0.11 mmol) in MeOH was hydrogenated (55 psi) over 10% palladium on carbon (36 mg) for three h. The reaction mixture was filtered and concentrated in vacuo to give 1E (73 mg, 97%) as a yellow glass. MS (ESI) m/z 700.3 (M+H)$^+$.

1F: 2-(1-Di-tert-butoxycarbonylamino-isoquinolin-6-ylamino)-16-oxa-4,11-diaza-tricyclo[15.2.2.1$^{6,10}$]docosa-1(20),6,8,10(22),17(21),18-hexaene-3,12-dione

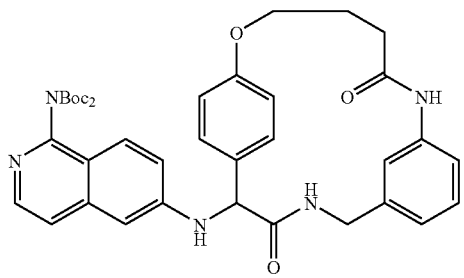

A solution of 1E (63 mg, 0.090 mmol), DIEA (0.047 mL, 0.27 mmol), HOAt (12 mg, 0.088 mmol), and EDCI (35 mg, 0.18 mmol) in a mixture of DCM (10 mL) and DMF (0.5 mL) was stirred at rt overnight. The reaction mixture was concentrated in vacuo and the residue was purified by reverse phase HPLC to give 1F. MS (ESI) m/z 682.3 (M+H)$^+$.

Example 1

A solution of 1F (entire amount from previous step+product from 2 mg and 4 mg scale pilot reactions) in EtOAc (0.5 mL) and hydrogen chloride in dioxane (1 mL, 4N) was stirred at rt for 3 h. The reaction mixture was concentrated in vacuo and the residue was purified by reverse phase HPLC to give Example 1 (15 mg, 26%) as a white solid. $^1$H NMR (400 MHz, CD$_3$OD) δ 2.03-2.19 (m, 2 H), 2.44-2.58 (m, 2 H), 3.95 (dd, J=15.38, 3.52 Hz, 1 H), 4.03-4.19 (m, 2 H), 4.73 (dd, J=15.38, 8.35 Hz, 1 H), 5.09 (s, 1 H), 5.50 (s, 1 H), 6.70 (s, 1 H), 6.82 (d, J=7.03 Hz, 1 H), 6.93 (d, J=8.35 Hz, 3 H), 7.10-7.20 (m, 3 H), 7.29 (d, J=7.03 Hz, 1 H), 7.46 (d, J=7.03 Hz, 2 H), 7.52 (d, J=7.47 Hz, 1 H), 8.05 (d, J=9.23 Hz, 1 H), 8.49 (dd, J=7.91, 3.95 Hz, 1 H). MS (ESI) m/z 482.3 (M+H)$^+$.

Example 2

2-(1-Amino-isoquinolin-6-ylamino)-4,11-diaza-tricyclo[14.2.2.1$^{6,10}$]henicosa-1(19),6,8,10(21),16(20),17-hexaene-3,12-dione trifluoroacetic acid salt

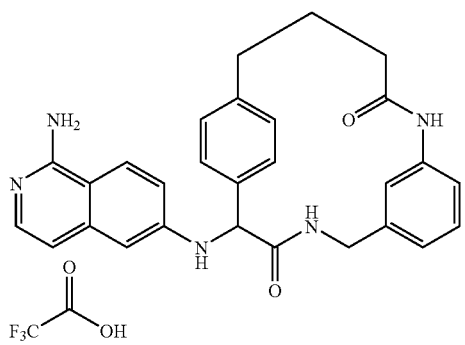

2A: 4-[4-(5,5-Dimethyl-[1,3,2]dioxaborinan-2-yl)-phenyl]-butyric acid

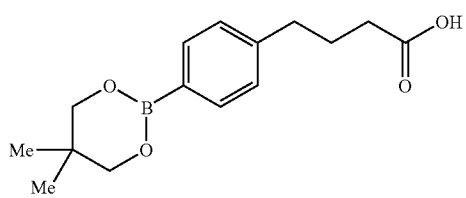

A resealable tube was charged with 4-bromophenyl butyric acid (729 mg, 3.1 mmol), 5,5,5',5'-Tetramethyl-[2,2']bi[[1,3,2]dioxaborinanyl] (746 mg, 3.3 mmol), potassium acetate (736 mg, 7.5 mmol), and DMSO (4 mL). The resulting orange suspension was deoxygenated by sparging with nitrogen gas. Dichloro[1,1'-bis(diphenylphosphino)ferrocene]palladium (II) dichloromethane adduct (66 mg, 0.090 mmol) was added, and the tube was sealed tightly and heated at 80° C. overnight. Hydrochloric acid (IN) was added, and the mixture was extracted with EtOAc (2×), washed with water (2×) and brine (1×), and dried (MgSO$_4$). The organic layer was concentrated in vacuo and the residue purified by flash chromatography (0 to 15% MeOH in DCM) to afford 2A (626 mg, 76%) as an off-white solid. $^1$H NMR (400 MHz, CDCl$_3$) δ 1.02 (s, 6H), 1.97 (m, 2H), 2.36 (t, J=7.5 Hz, 2H), 2.68 (t, J=7.7 Hz, 2H), 3.76 (s, 4H), 7.18 (d, J=7.9 Hz, 2H), 7.72 (d, J=7.5 Hz, 2H).

2B: 4-(4-Boronophenyl)-butyric acid

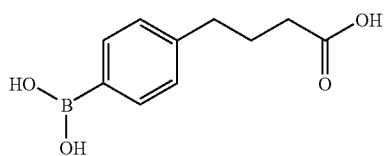

2A (343 mg, 1.24 mmol) was added to a mixture of diethyl ether (10 mL) and NaOH (2 mL, 2 N). The reaction mixture was stirred at rt for 10 min. The ether layer was separated and then treated with an additional portion of NaOH for 5 min. The combined aqueous layers were washed with diethyl ether (2×) and acidified to pH 4 with hydrochloric acid (6 N). The resulting solid precipitate was collected by filtration to afford 2B contaminated with 2A (212 mg, 1:1 2B/2A, 43% yield based on content of 2B) as a beige solid.

2C: 4-(3-Benzyloxycarbonyl-propyl)-phenylboronic acid

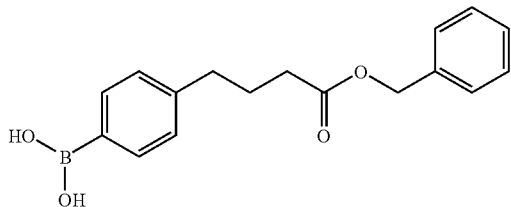

Using a procedure analogous to that used to prepare 1B, 2B (212 mg, 1:1 mixture of 2B and 2A) was reacted with benzyl bromide to afford 2C (90 mg, 69%) as a white solid. $^1$H NMR (400 MHz, CDCl$_3$) δ 1.92 (m, 2H), 2.33 (t, J=7.0 Hz, 2H), 2.62 (t, 2H), 5.08 (s, 2H), 7.11 (d, 2H), 7.25-7.35 (m, 5H), 7.69 (d, 2H).

2D: 4-{4-[(1-Di-tert-butoxycarbonylamino-isoquinolin-6-ylamino)-carboxy-methyl]-phenyl}-butyric acid benzyl ester

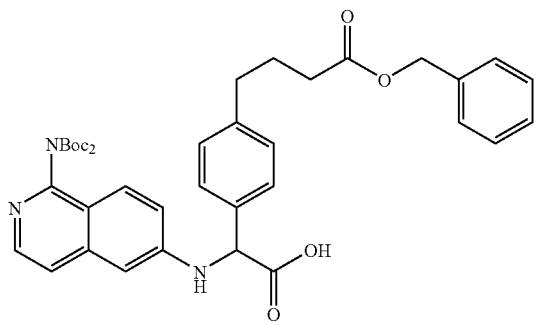

A solution of 2C (179 mg, 0.60 mmol), Intermediate 1 (179 mg, 0.50 mmol), and glyoxylic acid monohydrate (55 mg, 0.60 mmol) in acetonitrile (2 mL) and DMF (0.2 mL) was heated at 100° C. for 10 min in a microwave reactor. The reaction was repeated twice more on the same scale, and the pooled reaction mixtures were concentrated in vacuo, triturated with water, and then purified by flash chromatography (0 to 15% MeOH in DCM) to give 2D (630 mg, 52%) as an orange foam. MS (ESI) m/z 670.4 (M+H)$^+$.

2E: 4-{4-[(1-Di-tert-butoxycarbonylamino-isoquinolin-6-ylamino)-(3-nitro-benzylcarbamoyl)-methyl]-phenyl}-butyric acid benzyl ester

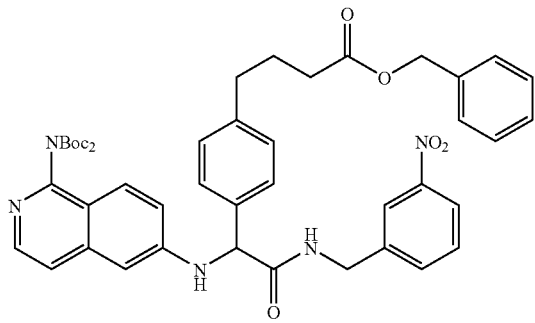

Using a procedure analogous to that used to prepare 1D, 2D (59 mg, 0.089 mmol) was reacted with 3-nitrobenzylamine hydrochloride to give 2E (56 mg, 80%) as a clear oil. MS (ESI) m/z 804.3 (M+H)$^+$.

2F: 4-{4-[(3-Amino-benzylcarbamoyl)-(1-di-tert-butoxycarbonylamino-isoquinolin-6-ylamino)-methyl]-phenyl}-butyric acid

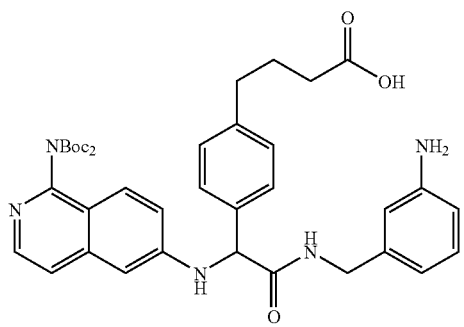

Using a procedure analogous to that used to prepare 1E, 2E (56 mg, 0.070 mmol) was hydrogenated to give 2F (41 mg, 85%) as a clear glass. MS (ESI) m/z 684.3 (M+H)$^+$.

2G: 2-(1-Di-tert-butoxycarbonylamino-isoquinolin-6-ylamino)-4,11-diaza-tricyclo[14.2.2.1$^{6,10}$]henicosa-1(19),6,8,10(21),16(20),17-hexaene-3,12-dione

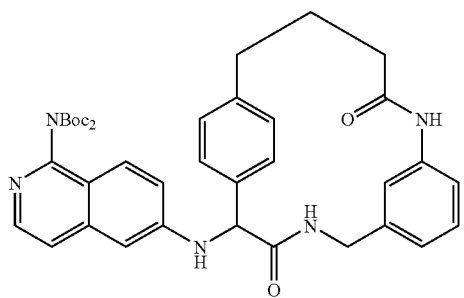

Using a procedure analogous to that used to prepare 1F, 2F (41 mg) was cyclized to give 2G (11 mg, 24%) as a yellow oil. MS (ESI) m/z 666.4 (M+H)$^+$.

Example 2

A solution of 2G (11 mg, 0.016 mmol) was dissolved in 50% TFA/DCM and stirred for 30 min at rt. The solvent was evaporated under a stream of nitrogen and the residue was purified by reverse phase HPLC to give Example 2 (5.3 mg, 57%) as a white solid. $^1$H NMR (400 MHz, CD$_3$OD) δ 2.07-2.19 (m, 1 H), 2.25-2.42 (m, 3 H), 2.61-2.72 (m, 1 H), 2.82-2.94 (m, 1 H), 4.04 (dd, J=15.82, 4.39 Hz, 1 H), 4.70 (dd, J=16.04, 7.69 Hz, 1 H), 5.15 (s, 1 H), 6.01 (s, 1 H), 6.68 (d, J=2.20 Hz, 1 H), 6.72 (d, J=7.91 Hz, 1 H), 6.83 (d, J=7.03 Hz, 1 H), 6.94 (d, J=7.91 Hz, 1 H), 7.11-7.26 (m, 4 H), 7.29 (d, J=7.03 Hz, 1 H), 7.37 (d, J=7.91 Hz, 1 H), 7.58 (d, J=7.91 Hz, 1 H), 8.05 (d, J=9.23 Hz, 1 H), 8.72 (dd, J=7.25, 4.61 Hz, 1 H). MS (ESI) m/z 466.4 (M+H)$^+$.

Example 3

(R)-2-(1-Amino-isoquinolin-6-ylamino)-4,11-diaza-tricyclo[14.2.2.1$^{6,10}$]henicosa-1(19),6,8,10(21),16(20),17-hexaene-3,12-dione

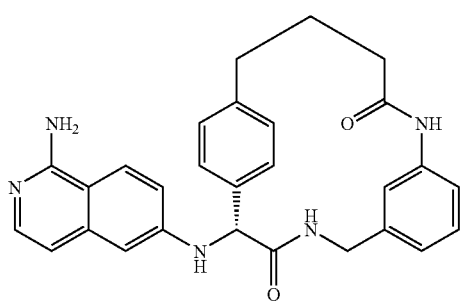

A solution of Example 2 (156 mg, 0.269 mmol) in methanol (6 mL) was purified by chiral HPLC in two injections of 2.0 mL each. The chromatography conditions were the following: Chiralcel OD column (5 cm ID×50 cm L, 20μ, Chiral Technologies, Inc.), 30% (1:1 ethanol/methanol)/70% heptane as eluent, 50 mL/min flow rate, and uv detection at 254 nm. The product fractions were combined with product fractions from an additional separation of Example 2 (46 mg, free base, 0.099 mmol) to give Example 3 (peak 1, 36 mg, 28%), peak 2 (24 mg, 18%), and a mixture of peaks 1 and 2 (28.5 mg, 22%). Peak 1 analytical data: $^1$H NMR (400 MHz, CD$_3$OD) δ 2.07-2.20 (m, 1 H), 2.24-2.44 (m, 3 H), 2.60-2.74 (m, 1 H), 2.79-2.93 (m, 1 H), 4.06 (d, J=16.26 Hz, 1 H), 4.63 (d, J=16.26 Hz, 1 H), 5.07 (s, 1 H), 6.00 (s, 1 H), 6.55 (d, J=2.20 Hz, 1 H), 6.66 (d, J=6.15 Hz, 1 H), 6.71 (d, J=7.91 Hz, 1 H), 6.93 (d, J=7.47 Hz, 1 H), 7.01 (dd, J=9.01, 2.42 Hz, 1 H), 7.15 (t, J=7.69 Hz, 1 H), 7.15-7.22 (m, 1 H), 7.24-7.31 (m, 1 H), 7.34 (dd, J=7.69, 1.54 Hz, 1 H), 7.50 (d, J=6.15 Hz, 1 H), 7.55 (dd, J=7.91, 1.76 Hz, 1 H), 7.80 (d, J=9.23 Hz, 1 H). MS (ESI) m/z 466.4 (M+H)$^+$. Chiral analytical HPLC retention times: peak 1, 6.45 min; peak 2, 7.75 min using the following chromatography conditions: Chiralcel OD column (4.6 mm ID×250 mm L, Chiral Technologies, Inc.), 30% (1:1 ethanol/methanol)/70% heptane as eluent, 1 mL/min flow rate, and uv detection at 254 nm.

Example 4

2-(1-Amino-isoquinolin-6-ylamino)-4,11-diaza-tricyclo[13.2.2.1$^{6,10}$]icosa-1(18),6,8,10(20),15(19),16-hexaene-3,12-dione trifluoroacetic acid salt

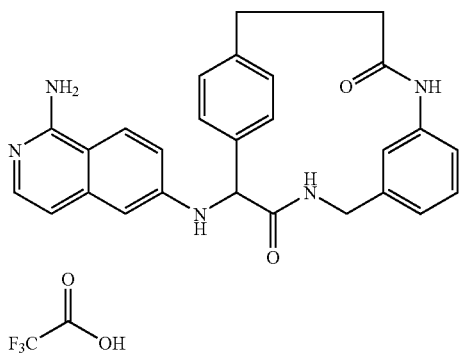

4A: 4-(3-(Benzyloxy)-3-oxopropyl)phenylboronic acid

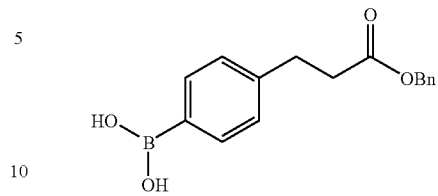

Using a procedure analogous to that used to prepare 1B, 3-(4-boronophenyl)propanoic acid (388 mg, 2.00 mmol) was reacted with benzyl bromide to afford 4A (355 mg, 62%) as a white solid. $^1$H NMR (400 MHz, tetrahydrofuran-d$_8$) δ 2.71 (t, J=7.9 Hz, 2H), 3.02 (t, J=7.5 Hz, 2H), 5.10 (s, 2H), 7.25-7.35 (m, 5H), 8.12 (d, J=7.9 Hz, 2H).

4B: 2-(1-Di-tert-butoxycarbonylaminoisoquinolin-6-ylamino)-2-(4-(3-(benzyloxy)-3-oxopropyl)phenyl)acetic acid

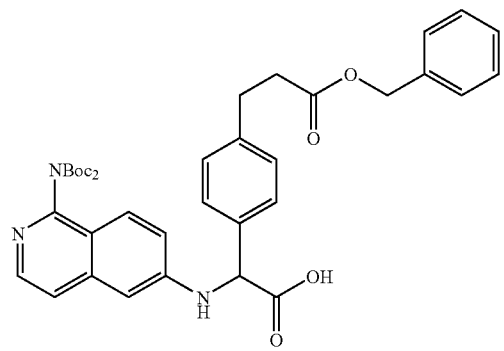

Using a procedure analogous to that used to prepare 2D, 4A (110 mg, 0.387 mmol) was reacted with Intermediate 1 (179 mg, 0.50 mmol), and glyoxylic acid monohydrate (55 mg, 0.60 mmol) to afford 4B (200 mg, 79%) as a yellow solid. MS (ESI) m/z 656.4 (M+H)$^+$.

4C: Benzyl 3-(4-(2-(3-nitrobenzylamino)-1-(1-di-tert-butoxycarbonylaminoisoquinolin-6-ylamino)-2-oxoethyl)phenyl)propanoate

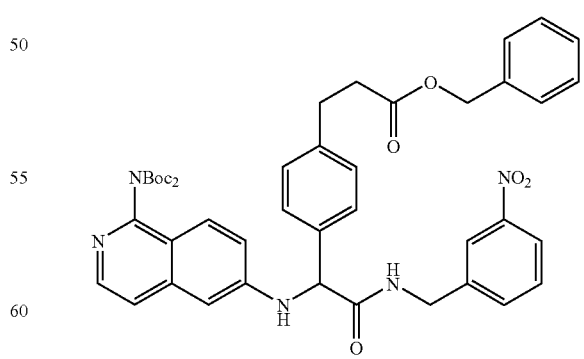

Using a procedure analogous to that used to prepare 1D, 4B (131 mg, 0.200 mmol) was reacted with 3-nitrobenzylamine hydrochloride to give 4C (84 mg, 53%) as a clear oil. MS (ESI) m/z 790.5 (M+H)$^+$.

4D: 3-(4-(2-(3-Aminobenzylamino)-1-(1-di-tert-butoxycarbonylaminoisoquinolin-6-ylamino)-2-oxo-ethyl)phenyl)propanoic acid

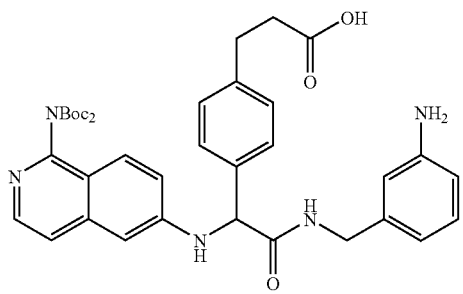

Using a procedure analogous to that used to prepare 1E, 4C (84 mg, 0.11 mmol) was hydrogenated to give 4D (66 mg, 93%). MS (ESI) m/z 670.4 (M+H)$^+$.

Example 4

A solution of 4D (32 mg, 0.048 mmol), DIEA (0.030 mL, 0.17 mmol), HOAt (8 mg, 0.06 mmol), and EDCI (19 mg, 0.099 mmol) in a mixture of DCM (10 mL) and DMF (0.4 mL) was stirred at rt overnight. The reaction mixture was concentrated in vacuo and the residue was purified by reverse phase HPLC (MS (ESI) m/z 652.4 (M+H)$^+$). The residue was dissolved in 50% TFA/DCM (1 mL) and stirred for 1 h at rt. The solvent was evaporated under a stream of nitrogen and the residue was purified by reverse phase HPLC to give Example 4 (4 mg, 15%). $^1$H NMR (400 MHz, CD$_3$OD) δ 2.60 (t, J=7.03 Hz, 2 H), 2.88-3.08 (m, 2 H), 3.95 (dd, J=15.82, 3.95 Hz, 1 H), 4.77 (dd, J=15.38, 8.79 Hz, 1 H), 5.15 (s, 1 H), 6.70 (s, 1 H), 6.84 (d, J=7.03 Hz, 1 H), 6.97 (d, J=7.47 Hz, 1 H), 7.08-7.20 (m, 3 H), 7.22-7.33 (m, 3 H), 7.48 (dd, J=7.91, 1.76 Hz, 1 H), 7.53 (d, J=7.91 Hz, 1 H), 8.09 (d, J=9.23 Hz, 1 H), 8.61 (dd, J=8.35, 3.95 Hz, 1 H). MS (ESI) m/z 452.4 (M+H)$^+$.

Example 5

2-(1-Amino-isoquinolin-6-ylamino)-4,11-diaza-tri-cyclo[15.2.2.1$^{6,10}$]docosa-1(20),6,8,10(22),17(21), 18-hexaene-3,12-dione trifluoroacetic acid salt

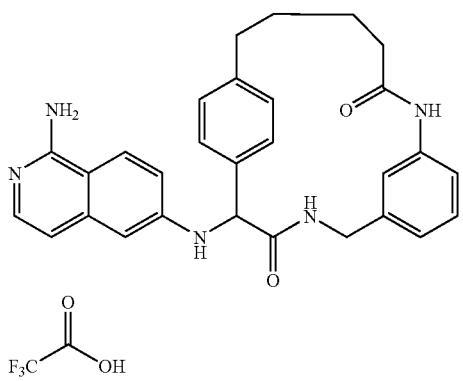

5A: 5-(4-(5,5-dimethyl-1,3,2-dioxaborinan-2-yl) phenyl)pentanoic acid

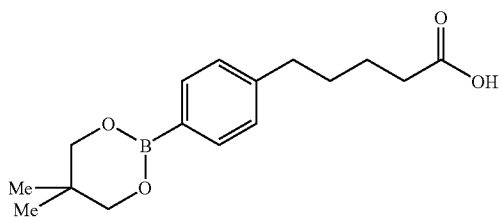

Using a procedure analogous to that used to prepare 2A, 5-(4-bromophenyl)pentanoic acid (537 mg, 2.09 mmol) was reacted with 5,5,5',5'-Tetramethyl-[2,2']bi[[1,3,2]dioxaborinanyl] to afford 5A (429 mg, 71%) as a white solid. $^1$H NMR (400 MHz, tetrahydrofuran-d$_8$) δ 0.99 (s, 6H), 1.55-1.70 (m, 4H), 2.24 (t, J=7.5 Hz, 2H), 2.61 (t, J=7.0 Hz, 2H), 3.73 (s, 4H), 7.12 (d, J=7.9 Hz, 2H), 7.65 (d, J=7.9 Hz, 2H).

5B: 5-(4-boronophenyl)pentanoic acid

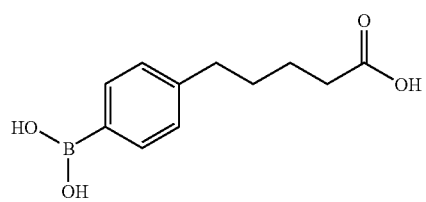

Using a procedure analogous to that used to prepare 2B, 5A (429 mg, 1.48 mmol) was reacted with NaOH to afford 5B (250 mg, 76%) as an off-white solid.

5C: 4-(5-(benzyloxy)-5-oxopentyl)phenylboronic acid

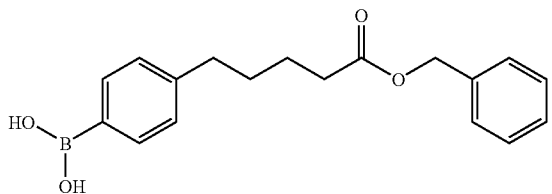

Using a procedure analogous to that used to prepare 1B, 5B (250 mg, 1.13 mmol) was reacted with benzyl bromide to afford 5C (226 mg, 79%) as a clear oil.

5D: 2-(1-Di-tert-butoxycarbonylaminoisoquinolin-6-ylamino)-2-(4-(5-(benzyloxy)-5-oxopentyl)phenyl) acetic acid

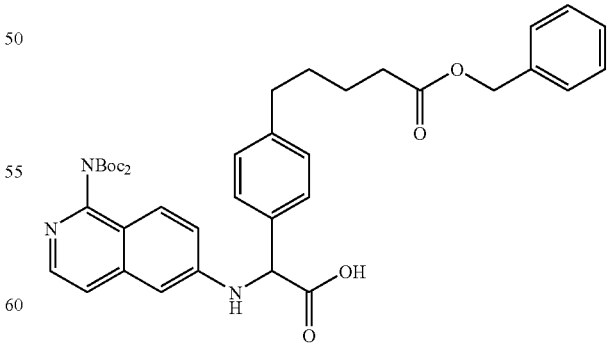

Using a procedure analogous to that used to prepare 2D, 5C (187 mg, 0.599 mmol) was reacted with Intermediate 1 and glyoxylic acid monohydrate to afford 5D (297 mg, 87%) as an orange solid. MS (ESI) m/z 684.4 (M+H)$^+$.

5E: Benzyl 5-(4-(2-(3-nitrobenzylamino)-1-(1-di-tert-butoxycarbonylaminoisoquinolin-6-ylamino)-2-oxoethyl)phenyl)pentanoate

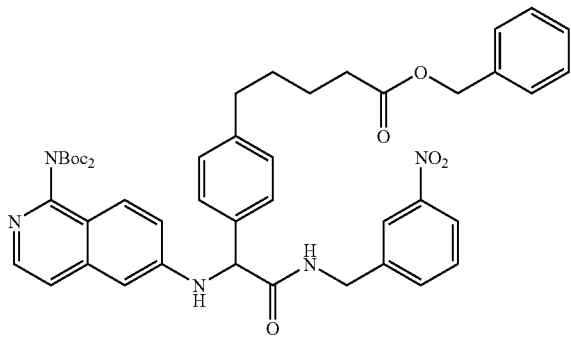

A solution of 5D (204 mg, 0.299 mmol), 3-nitrobenzylamine hydrochloride (68 mg, 0.36 mmol), DIEA (0.16 mL, 0.92 mmol), and BOP (159 mg, 0.360 mmol) in DMF (several mL) was stirred at rt overnight. The reaction mixture was concentrated in vacuo and the residue was triturated with water and then purified by flash chromatography (0 to 30% MeOH in DCM) to give 5E (220 mg, 90%) as a yellow foam. MS (ESI) m/z 818.4 (M+H)$^+$.

5F: 5-(4-(2-(3-Aminobenzylamino)-1-(1-di-tert-butoxycarbonylaminoisoquinolin-6-ylamino)-2-oxoethyl)phenyl)pentanoic acid

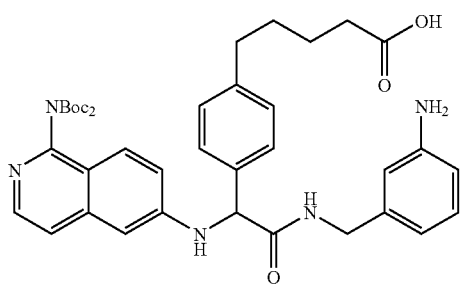

Using a procedure analogous to that used to prepare 1E, 5E (220 mg, 0.269 mmol) was hydrogenated to give 5F (151 mg, 80%) as a yellow glass. MS (ESI) m/z 698.4 (M+H)$^+$.

Example 5

Using a procedure analogous to that used to prepare Example 4, 5F (150 mg, 0.215 mmol) was cyclized and deprotected to give Example 5 (13 mg, 10%) as a white amorphous solid. $^1$H NMR (400 MHz, CD$_3$OD) δ 1.50-1.79 (m, 4 H), 2.15-2.35 (m, 2 H), 2.47-2.70 (m, 2 H), 4.07 (dd, J=15.16, 4.61 Hz, 1 H), 4.72 (dd, J=15.16, 7.69 Hz, 1 H), 5.12 (s, 1 H), 6.00 (s, 1 H), 6.65 (s, 1 H), 6.81 (d, J=7.03 Hz, 1 H), 6.94 (d, J=7.47 Hz, 1 H), 7.10-7.22 (m, 4 H), 7.29 (d, J=7.03 Hz, 1 H), 7.47 (d, J=7.91 Hz, 3 H), 8.05 (d, J=9.23 Hz, 1 H), 8.88 (dd, J=7.69, 4.61 Hz, 1 H). MS (ESI) m/z 480.4 (M+H)$^+$.

Example 6

2-(1-Amino-isoquinolin-6-ylamino)-7-ethanesulfonyl-4,11-diaza-tricyclo[14.2.2.1$^{6,10}$]henicosa-1(19),6,8,10(21),16(20),17-hexaene-3,12-dione trifluoroacetic acid salt

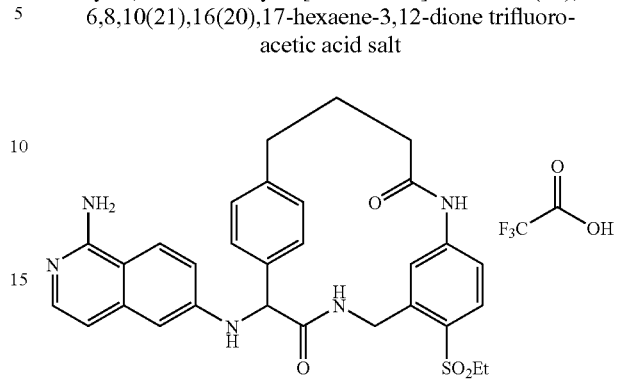

6A: 2-(Ethylsulfonyl)-5-nitrobenzonitrile

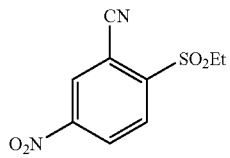

Ethanethiol (2.8 mL, 38 mmol) was added to a solution of 2-fluoro-5-nitrobenzonitrile (5.00 g, 30.1 mmol) and triethylamine (9.3 mL, 67 mmol) in DMF (100 mL). The reaction mixture was stirred for 1 h and then poured into water (500 mL). The resulting precipitate was isolated by filtration, dissolved in DCM, washed with water and brine, dried (MgSO$_4$), and concentrated under reduced pressure. The residue (6.14 g) was dissolved in DCM (100 mL), cooled to 0° C., and treated with MCPBA (16.0 g, 71 mmol) in one portion. The reaction mixture was allowed to stir at rt overnight, and then was extracted with sodium bicarbonate solution (saturated), sodium bisulfite solution (10%), and brine. The organic layer was dried (MgSO$_4$) and concentrated under reduced pressure to afford 6A (5.6 g, 80%) as a pale yellow solid. $^1$H NMR (400 MHz, CDCl$_3$) δ 1.02 (s, 6H), 1.97 (m, 2H), 2.36 (t, J=7.5 Hz, 2H), 2.68 (t, J=7.7 Hz, 2H), 3.76 (s, 4H), 7.18 (d, J=7.9 Hz, 2H), 7.72 (d, J=7.5 Hz, 2H).

6B: 5-Amino-2-(ethylsulfonyl)benzonitrile

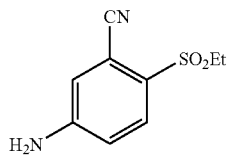

A solution of 6A (0.554 g, 2.31 mmol) in MeOH (60 mL) was hydrogenated (60 psi) over 10% palladium on carbon (99 mg) for 3 h at rt. The reaction mixture was filtered and concentrated under reduced pressure to give 6B (464 mg, 96%) as an off-white solid. $^1$H NMR (400 MHz, CDCl$_3$) δ 1.30 (t, J=7.25 Hz, 3H), 3.30 (q, J=7.47 Hz, 2H), 4.62 (s, 2H), 6.89 (dd, J=8.79, 2.64 Hz, 1H), 7.04 (d, J=2.20 Hz, 1H), 7.83 (d, J=8.79 Hz, 1H).

6C: 4-(4-Bromophenyl)-N-(3-cyano-4-(ethylsulfonyl)phenyl)butanamide

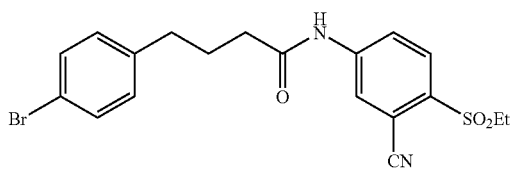

Oxalyl chloride (0.175 mL, 2.0 mmol) was added slowly dropwise to a solution of 4-(4-bromophenyl)butyric acid (243 mg, 1.0 mmol) in DCM (3 mL) and DMF (2 drops). The reaction was stirred for 1 h at rt and then concentrated under reduced pressure. The residue was coevaporated with toluene and then chloroform to give the acid chloride as a crude brown oil. A solution of the crude acid chloride (197 mg, 0.75 mmol) and 6B (106 mg, 0.50 mmol) in DCM (1 mL) was treated with triethylamine (0.140 mL, 1.0 mmol) and DMAP (10 mg, 0.08 mmol). The reaction mixture was stirred for 14 h at rt. DCE (1 mL) was added, and the reaction mixture was heated to reflux for 30 h. The reaction was cooled to rt, diluted with DCM, and washed with 1 N HCl, dried (MgSO$_4$), and concentrated under reduced pressure. The residue was purified by silica gel chromatography (EtOAc/hexanes) and then by reverse phase HPLC to give 6C (83 mg, 38%). MS (ESI) m/z 435.2, 437.2 (M+H)$^+$.

6D: 4-(4-(3-cyano-4-(ethylsulfonyl)phenylamino)-4-oxobutyl)phenylboronic acid

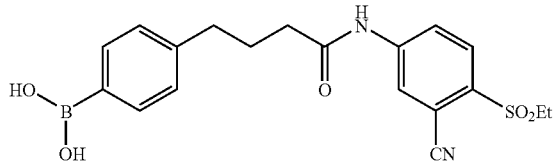

A flask containing 6C (83 mg, 0.19 mmol), 5,5,5',5'-tetramethyl-[2,2']bi[[1,3,2]dioxaborinanyl] (47.6 mg, 0.211 mmol), potassium acetate (83 mg, 0.84 mmol), and dichloro[1,1'-bis(diphenylphosphino)ferrocene]palladium(II) dichloromethane adduct (4.4 mg, 0.0060 mmol) was purged with argon. DMSO (1 mL) was added, and the reaction mixture was degassed with three cycles of vacuum followed by argon backfill. The reaction mixture was heated for 2 h at 80° C., cooled to rt, and diluted with water (100 mL). The aqueous solution was extracted with diethyl ether (3×25 mL), dried (MgSO$_4$), and concentrated under reduced pressure. The residue was dissolved in a mixture of diethyl ether (1 mL), DCM (~0.1 mL), and EtOAc (~0.1 mL). Diethanolamine (22 mg, 0.21 mmol) in isopropanol (0.5 mL) was added, and the reaction mixture was stirred overnight at rt. The reaction mixture was concentrated, and the residue was purified by reverse phase HPLC (under the standard acidic conditions) to give 6D (44 mg, 57%) as a clear oil. MS (ESI) m/z 425.4 (M+CH$_3$OH—H$_2$O+H)$^+$.

6E: 2-(1-Di-tert-butoxycarbonylaminoisoquinolin-6-ylamino)-2-(4-(4-(3-cyano-4-(ethylsulfonyl)phenylamino)-4-oxobutyl)phenyl)acetic acid

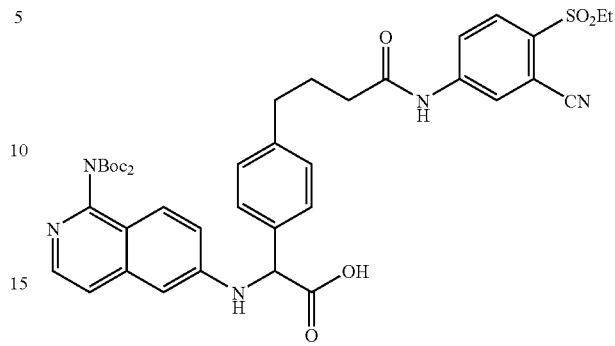

Using a procedure analogous to that used to prepare 2D, 6D (43.6 mg, 0.109 mmol) was reacted with Intermediate 1 and glyoxylic acid monohydrate to afford 6E (42.8 mg, 52%) as a yellow solid. MS (ESI) m/z 772.3 (M+H)$^+$.

6F: 2-(1-Di-tert-butoxycarbonylaminoisoquinolin-6-ylamino)-2-(4-(4-(3-(aminomethyl)-4-(ethylsulfonyl)phenylamino)-4-oxobutyl)phenyl)acetic acid

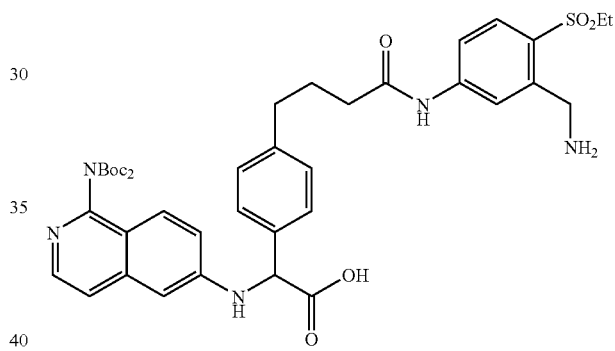

A solution of 6E (17 mg, 0.022 mmol) in a mixture of methanol (5 mL) and 1M hydrochloric acid (0.050 mL) was hydrogenated (60 psi) over 10% palladium on carbon (7 mg) for 17 h. The reaction mixture was filtered and concentrated under reduced pressure to give 6F (7.1 mg, 41%) as a yellow solid. MS (ESI) m/z 776.4 (M+H)$^+$.

Example 6

A solution of 6F (7.1 mg, 0.0092 mmol), DIEA (0.010 mL, 0.057 mmol), and BOP (5.3 mg, 0.012 mmol) in DMF (1.0 mL) was stirred at rt for 1 h. The reaction mixture was concentrated in vacuo and purified by reverse phase HPLC. The residue was dissolved in 50% TFA/DCM (1.5 mL) with 2 drops of water added and stirred for 1.25 h at rt. The solvent was evaporated under a stream of nitrogen and the residue was purified by reverse phase HPLC to give Example 6 (1.30 mg, 21%). $^1$H NMR (400 MHz, CD$_3$OD) δ 1.24 (t, J=7.25 Hz, 3 H), 2.00-2.15 (m, 1 H), 2.28-2.46 (m, 3 H), 2.54-2.66 (m, 1 H), 2.91-2.97 (m, 1 H), 3.32-3.49 (m, 2 H), 4.17 (dd, J=16.92, 5.49 Hz, 1 H), 5.11 (dd, J=17.36, 6.37 Hz, 1 H), 5.18 (s, 1 H), 6.68 (dd, J=15.16, 1.54 Hz, 2 H), 6.87 (d, J=7.03 Hz, 1 H), 6.90 (dd, J=8.35, 2.20 Hz, 1 H), 7.03 (dd, 1 H), 7.12 (dd, 1 H), 7.16 (dd, J=9.23, 2.20 Hz, 1 H), 7.31 (d, J=7.03 Hz, 1 H), 7.38-7.47 (m, 1 H), 7.61 (dd, J=7.47, 1.76 Hz, 1 H), 7.77 (d, J=8.79 Hz, 1 H), 8.04 (d, J=9.23 Hz, 1 H), 8.94 (t, J=5.93 Hz, 1 H). MS (ESI) m/z 558.3 (M+H)$^+$.

Example 7

(R)-2-(1-Amino-isoquinolin-6-ylamino)-7-ethane-sulfonyl-4,11-diaza-tricyclo[14.2.2.1$^{6,10}$]henicosa-1(19),6,8,10(21),16(20),17-hexaene-3,12-dione

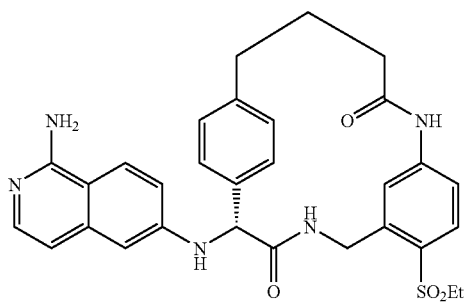

A solution of Example 6 (9 mg, 0.013 mmol) in methanol was purified by chiral HPLC to give peak 1 (2.6 mg, 34%) and Example 7 (peak 2, 2.4 mg, 32%). The chromatography conditions were the following: Chiralcel OD-H column (2.5 cm ID×25 cm L, Chiral Technologies, Inc.), 30% (1:1 ethanol/methanol)/70% heptane as eluent, 15 mL/min flow rate, and uv detection at 254 nm. Peak 2 analytical data: $^1$H NMR (400 MHz, CD$_3$OD) δ 1.24 (t, J=7.51 Hz, 3 H), 2.02-2.16 (m, 1H), 2.27-2.48 (m, 3 H), 2.55-2.69 (m, 1 H), 2.87-3.00 (m, 1 H), 3.32-3.47 (m, 2H), 4.21 (d, J=16.84 Hz, 1 H), 5.05 (d, J=16.84 Hz, 1 H), 5.11 (s, 1 H), 6.58 (d, J=2.20 Hz, 1 H), 6.64 (d, J=1.46 Hz, 1 H), 6.71 (d, J=6.22 Hz, 1 H), 6.91 (dd, J=8.42, 2.20 Hz, 1 H), 7.01 (dd, J=8.97, 2.38 Hz, 1 H), 7.05-7.16 (m, 2 H), 7.40 (d, J=7.69 Hz, 1H), 7.48 (d, J=5.86 Hz, 1 H), 7.59 (dd, J=7.87, 1.65 Hz, 1 H), 7.77 (d, J=8.42 Hz, 1H), 7.83 (d, J=9.15 Hz, 1 H). MS (ESI) m/z 558.3 (M+H)$^+$. Chiral analytical HPLC retention times: peak 1, 8.65 min; peak 2, 10.08 min using the following chromatography conditions: Chiralcel OD column (4.6 mm ID×250 mm L, Chiral Technologies, Inc.), 30% (1:1 ethanol/methanol)/70% heptane as eluent, 1 mL/min flow rate, and uv detection at 254 nm.

Example 8

2-(1-Amino-isoquinolin-6-ylamino)-7-ethanesulfonyl-20-methyl-4,11-diaza-tricyclo[14.2.2.1$^{6,10}$]henicosa-1(19),6,8,10(21),16(20),17-hexaene-3,12-dione trifluoroacetic acid salt

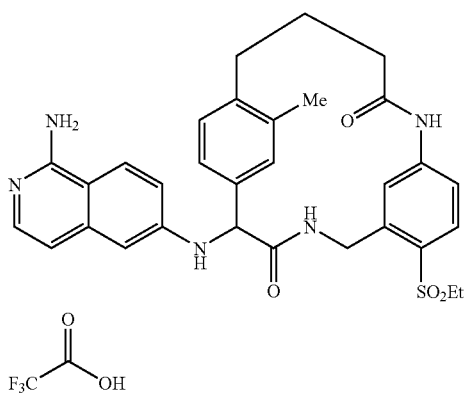

8A: 4-(4-Bromo-2-methylphenyl)butanoic acid

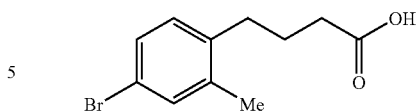

9-Borabicyclo[3.3.1]nonane (10 mL, 5 mmol, 0.5N in THF) was treated with methyl but-3-enoate (0.5 g, 5 mmol) dropwise at rt under argon. The reaction mixture was stirred for 3 h at rt. A resealable tube was charged with 5-bromo-2-iodotoluene (1.48 g, 5 mmol), sodium methoxide (853 mg, 15.8 mmol), and dichloro[1,1'-bis(diphenylphosphino)ferrocene]palladium(II) dichloromethane adduct (110 mg, 0.15 mmol) in THF (15 mL). After the hydroboration reaction was complete, it was added to the resealable tube, and the combined reaction mixture was heated to 70° C. for 4 h, then at rt for several days. The reaction mixture was diluted with water and extracted with EtOAc (2×). The combined organics were extracted with water and brine, dried (MgSO$_4$), and concentrated in vacuo. The residue was purified by silica gel chromatography (EtOAc/hexane) to give 513 mg of impure ester. This material was dissolved in THF (3 mL), MeOH (1.5 mL) and 1 M NaOH (3 mL) and heated for 1 h at 80° C. Most of the solvent was removed in vacuo, 1N HCl (4 mL) was added, and the mixture was extracted with EtOAc (3×). The combined organic layers were washed with brine, dried (MgSO$_4$), and concentrated in vacuo. The residue was purified by reverse phase HPLC to give 8A (287 mg, 22%) as a white solid. $^1$H NMR (400 MHz, CDCl$_3$) δ 1.82-1.96 (m, 2 H), 2.28 (s, 3 H), 2.42 (t, J=7.25 Hz, 2 H), 2.57-2.65 (m, 2 H), 6.99 (d, J=7.91 Hz, 1 H), 7.23-7.26 (m, 1 H), 7.27-7.31 (m, 1 H).

8B: 4-(4-Bromo-2-methylphenyl)-N-(3-cyano-4-(ethylsulfonyl)phenyl)butanamide

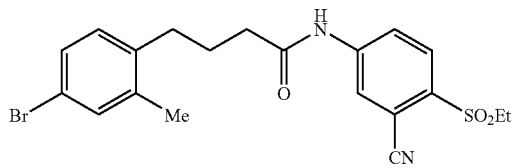

Oxalyl chloride (0.200 mL, 2.29 mmol) was added dropwise to a solution of 8A (287 mg, 1.12 mmol) in DCM (4 mL) and DMF (1 drop). The reaction mixture was stirred for 4 h, and then concentrated in vacuo. The residue was coevaporated with toluene and then dissolved in toluene (10 mL). 6B (227 mg, 1.08 mmol) was added, and the reaction mixture was heated to reflux for 2 h. The reaction mixture was concentrated in vacuo, and the residue was purified by silica gel chromatography (EtOAc/hexane) to give 6B (373 mg, 77%) as an off-white solid. MS (ESI) m/z 449.1, 451.1 (M+H)$^+$.

8C: N-(3-Cyano-4-(ethylsulfonyl)phenyl)-4-(4-(5,5-dimethyl-1,3,2-dioxaborinan-2-yl)-2-methylphenyl)butanamide

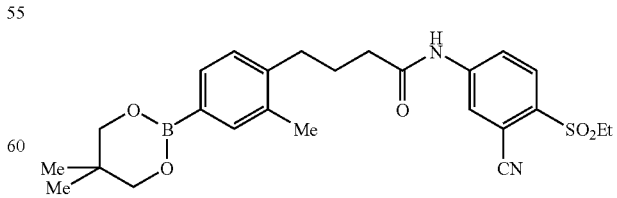

Using a procedure analogous to that used to prepare 2A, 8B (448 mg, 1.00 mmol) was reacted with 5,5,5',5'-Tetramethyl-[2,2']bi[[1,3,2]dioxaborinanyl] to afford 8C (425 mg, 88%) as an off-white solid. MS (ESI) m/z 413.1 (M−H)$^-$ for free boronic acid.

8D: 4-(4-(3-cyano-4-(ethylsulfonyl)phenylamino)-4-oxobutyl)-3-methylphenylboronic acid

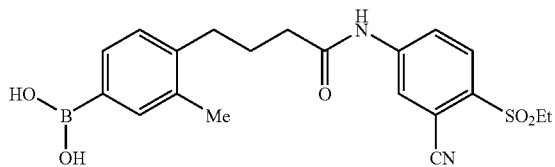

Using a procedure analogous to that used to prepare 2B, 8C (212 mg, 0.44 mmol) was reacted with NaOH and then purified by silica gel chromatography (MeOH/DCM) to afford 8D (113 mg, 62%). $^1$H NMR (400 MHz, THF-d$_8$) δ 1.21 (t, 3 H), 1.94-2.04 (m, 2 H), 2.40 (t, J=7.25 Hz, 2 H), 2.70 (t, J=7.47 Hz, 2 H), 3.31 (q, J=7.47 Hz, 2 H), 7.01 (s, 2 H), 7.08 (d, J=7.47 Hz, 1 H), 7.53 (d, J=7.47 Hz, 1 H), 7.56 (s, 1 H), 7.93 (dd, 1 H), 7.99 (d, 1 H), 1.00 (d, J=2.20 Hz, 1 H), 9.66 (s, 1 H).

8E: 2-(1-Di-tert-butoxycarbonylaminoisoquinolin-6-ylamino)-2-(4-(4-(3-cyano-4-(ethylsulfonyl)phenylamino)-4-oxobutyl)-3-methylphenyl)acetic acid

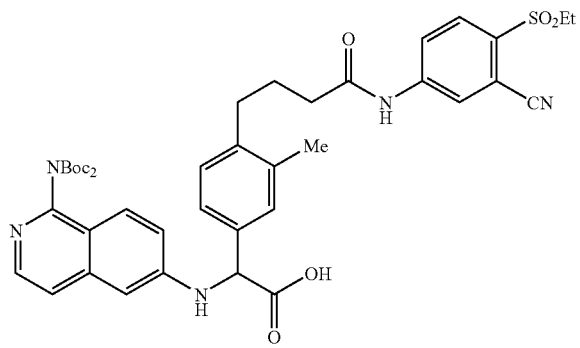

Using a procedure analogous to that used to prepare 2D, 8D (113 mg, 0.273 mmol) was reacted with Intermediate 1 and glyoxylic acid monohydrate to afford 8E (154 mg, 72%) as an off-white solid. MS (ESI) m/z 786.3 (M+H)$^+$.

8F: 2-(1-Di-tert-butoxycarbonyl aminoisoquinolin-6-ylamino)-2-(4-(4-(3-(aminomethyl)-4-(ethylsulfonyl)phenylamino)-4-oxobutyl)-3-methylphenyl)acetic acid

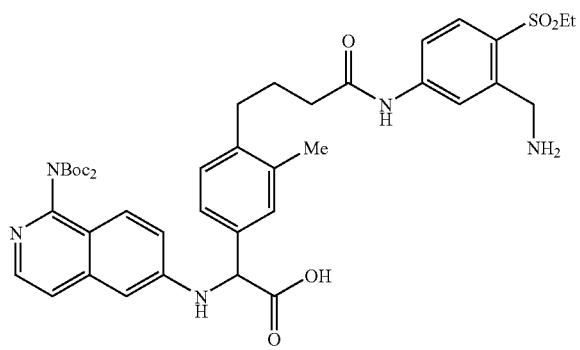

Using a procedure analogous to that used to prepare 6F, 8E (154 mg, 0.196 mmol) was hydrogenated to afford 8F (158 mg, 97%). MS (ESI) m/z 790.2 (M+H)$^+$.

Example 8

Using a procedure analogous to that used to prepare Example 6, 8F (158 mg, 0.192 mmol) was cyclized and deprotected to afford Example 8 (22.6 mg, 17%) as an off-white amorphous solid. NMR and analytical HPLC are consistent with a 1:1 mixture of atropisomers. $^1$H NMR (400 MHz, CD$_3$OD) δ 1.19-1.27 (m, 6 H), 1.86-1.98 (m, 2 H), 2.12-2.21 (m, 1 H), 2.28 (t, J=8.97 Hz, 1 H), 2.35-2.49 (m, 4 H), 2.65-2.75 (m, 1 H), 2.87-2.97 (m, 1 H), 3.08-3.19 (m, 2 H), 3.34-3.45 (m, 4 H), 4.10-4.25 (m, 3 H), 5.09 (dd, J=17.03, 5.68 Hz, 1 H), 5.13 (s, 1 H), 5.14 (s, 1 H), 6.64-6.71 (m, 4 H), 6.80-6.94 (m, 5 H), 6.97 (s, 1 H), 7.05 (d, J=7.69 Hz, 1 H), 7.09-7.17 (m, 2 H), 7.29 (d, J=6.96 Hz, 2 H), 7.33-7.38 (m, 1 H), 7.41-7.46 (m, 1 H), 7.47 (s, 1 H), 7.76 (d, J=8.42 Hz, 2 H), 8.01 (d, J=4.03 Hz, 1 H), 8.02-8.05 (m, 1 H), 8.89 (t, J=5.86 Hz, 1 H), 8.95 (t, J=6.04 Hz, 1 H). MS (ESI) m/z 572.1 (M+H)$^+$.

Example 9

(R)-2-(1-Amino-isoquinolin-6-ylamino)-7-(propane-2-sulfonyl)-4,11-diaza-tricyclo[14.2.2.1$^{6,10}$]henicosa-1(19),6,8,10(21),16(20),17-hexaene-3,12-dione

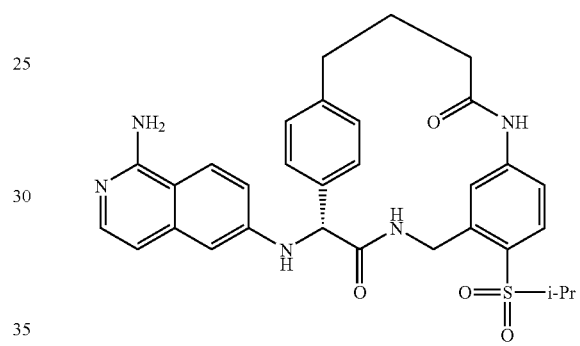

9A: 2-(Isopropylsulfonyl)-5-nitrobenzonitrile

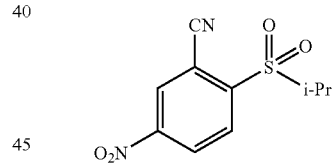

Using a procedure analogous to that used to prepare 6A, 2-fluoro-5-nitrobenzonitrile (2.50 g, 15.6 mmol) was reacted with isopropylthiol and oxidized with mCPBA to afford 9A (3.04 g, 91%) as a white solid. $^1$H NMR (400 MHz, CDCl$_3$) δ 1.40 (d, J=7.03 Hz, 6 H), 3.55-3.76 (m, 1 H), 8.38 (d, J=8.35 Hz, 1 H), 8.63 (dd, J=8.79, 2.20 Hz, 1 H), 8.74 (d, J=2.64 Hz, 1 H).

9B: 5-Amino-2-(isopropylsulfonyl)benzonitrile

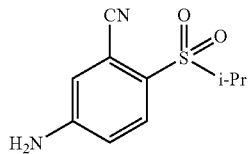

Using a procedure analogous to that used to prepare 6B, 9A (632 mg, 2.48 mmol) was hydrogenated to give 9B (530 mg, 95%) as a white solid. MS (ESI) m/z 225.3 (M+H)$^+$.

9C: 4-(4-Bromophenyl)-N-(3-cyano-4-(isopropylsulfonyl)phenyl)butanamide

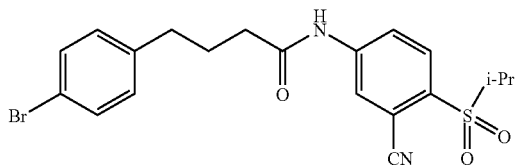

Using a procedure analogous to that used to prepare 8B, 9B (364 mg, 1.62 mmol) was reacted with 4-(4-bromophenyl)butyric acid chloride to give 9C (667 mg, 92%). MS (ESI) m/z 449.1, 451.1 (M+H)$^+$.

9D: N-(3-Cyano-4-(isopropylsulfonyl)phenyl)-4-(4-(5,5-dimethyl-1,3,2-dioxaborinan-2-yl)phenyl)butanamide

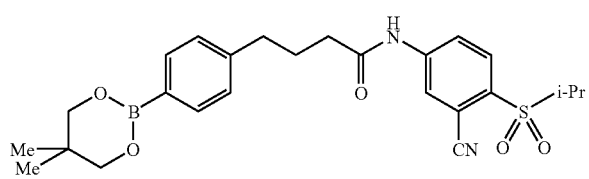

Using a procedure analogous to that used to prepare 2A, 9C (600 mg, 1.34 mmol) was reacted with 5,5',5'-tetramethyl-[2,2']bi[[1,3,2]dioxaborinanyl] to give 9D (625 mg, 97%) as a brown foam. MS (ESI) m/z 413.1 (M−H)$^−$ for free boronic acid.

9E: 4-(4-(3-cyano-4-(isopropylsulfonyl)phenylamino)-4-oxobutyl)phenylboronic acid

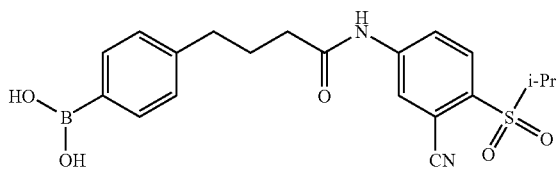

Using a procedure analogous to that used to prepare 2B, 9D (625 mg, 1.29 mmol) was reacted with NaOH to give 9E (508 mg, 95%) as a brown foam. MS (ESI) m/z 413.2 (M−H)$^−$.

9F: 2-(1-Di-tert-butoxycarbonylaminoisoquinolin-6-ylamino)-2-(4-(4-(3-cyano-4-(isopropylsulfonyl)phenylamino)-4-oxobutyl)phenyl)acetic acid

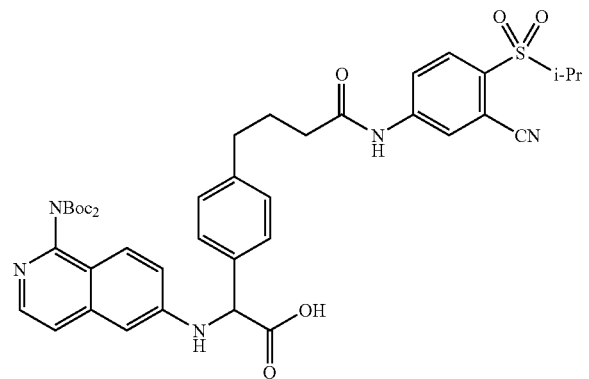

Using a procedure analogous to that used to prepare 2D, 9E (100 mg, 0.241 mmol) was reacted with Intermediate 1 and glyoxylic acid monohydrate to afford 9F (74 mg, 47%) as a yellow oil. MS (ESI) m/z 786.3 (M+H)$^+$.

9G: 2-(1-Di-tert-butoxycarbonylaminoisoquinolin-6-ylamino)-2-(4-(4-(3-(aminomethyl)-4-(isopropylsulfonyl)phenylamino)-4-oxobutyl)phenyl)acetic acid

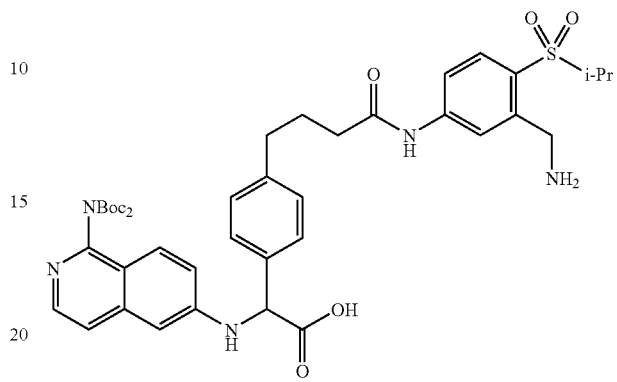

Using a procedure analogous to that used to prepare 6F, 9F (71 mg, 0.090 mmol) was hydrogenated for 48 h to give 9G (98 mg, 100%) as a yellow glass. MS (ESI) m/z 790.3 (M+H)$^+$.

9H: 2-(1-Amino-isoquinolin-6-ylamino)-7-(propane-2-sulfonyl)-4,11-diaza-tricyclo[14.2.2.1$^{6,10}$]henicosa-1(19),6,8,10(21),16(20),17-hexaene-3,12-dione trifluoroacetic acid salt

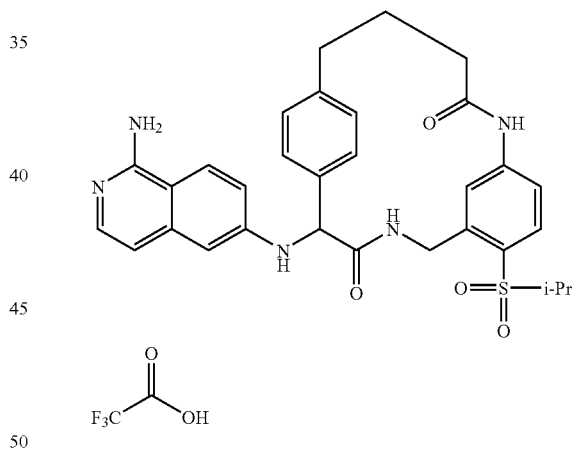

Using a procedure analogous to that used to prepare Example 6, 9G (98 mg, 0.090 mmol) was cyclized with BOP. This material was combined with the product of a 5 mg scale cyclization, deprotected with trifluoroacetic acid, and purified by HPLC to give 9H (20 mg, 27%). MS (ESI) m/z 572.2 (M+H)$^+$.

Example 9

Using a procedure analogous to that used to prepare Example 7, with the modification that 25% (1:1 ethanol/methanol)/75% heptane was used as eluent, 9H (20 mg, 0.029 mmol) was purified by chiral HPLC to give peak 1 (1.65 mg, 10%) and Example 9 (peak 2, 5.5 mg, 33%). Peak 2 analytical data: $^1$H NMR (400 MHz, CD$_3$OD) 1.19 (d, J=6.59 Hz, 3 H), 1.35 (d, J=6.96 Hz, 3 H), 2.03-2.15 (m, 1 H), 2.26-2.46 (m, 3

H), 2.56-2.68 (m, 1 H), 2.87-2.98 (m, 1 H), 3.56-3.73 (m, 1 H), 4.22 (d, J=16.84 Hz, 1 H), 5.04 (d, J=16.84 Hz, 1 H), 5.10 (s, 1 H), 6.57 (d, J=2.20 Hz, 1 H), 6.63 (d, J=1.83 Hz, 1 H), 6.70 (d, J=6.22 Hz, 1 H), 6.90 (dd, J=8.60, 2.01 Hz, 1 H), 6.99 (dd, J=8.97, 2.38 Hz, 1 H), 7.07-7.15 (m, 2 H), 7.39 (d, J=7.69 Hz, 1 H), 7.49 (d, J=5.86 Hz, 1 H), 7.58 (dd, J=7.69, 1.46 Hz, 1 H), 7.74 (d, J=8.79 Hz, 1 H), 7.81 (d, J=9.15 Hz, 1 H). MS (ESI) m/z 572.1 (M+H)$^+$. Chiral analytical HPLC retention times: peak 1, 7.76 min; peak 2, 9.19 min using the following chromatography conditions: Chiralcel OD column (4.6 mm ID×250 mm L, Chiral Technologies, Inc.), 30% (1:1 ethanol/methanol)/70% heptane as eluent, 1 mL/min flow rate, and uv detection at 254 nm.

Example 10

2-(1-Amino-isoquinolin-6-ylamino)-7-(2-methyl-propane-2-sulfonyl)-4,11-diaza-tricyclo[14.2.2.1$^{6,10}$]henicosa-1(19),6,8,10(21),16(20),17-hexaene-3,12-dione trifluoroacetic acid salt

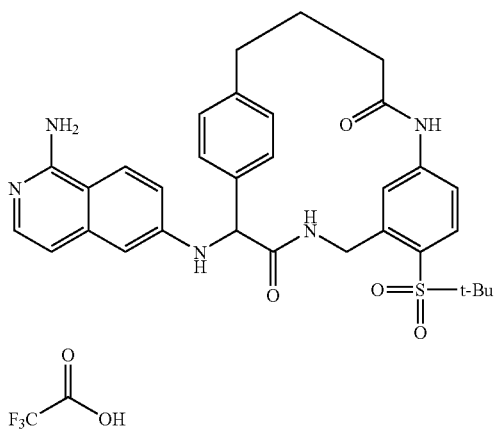

10A: 2-(tert-Butylsulfonyl)-5-nitrobenzonitrile

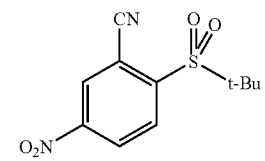

Using a procedure analogous to that used to prepare 6A, 2-fluoro-5-nitrobenzonitrile (2.50 g, 15.6 mmol) was reacted with tert-butylthiol and oxidized with mCPBA to afford 10A (3.14 g, 88%) as a white solid. $^1$H NMR (400 MHz, CDCl$_3$) δ 1.45 (s, 9 H), 7.88 (d, J=8.79 Hz, 1 H), 8.37 (dd, J=8.35, 2.64 Hz, 1 H), 8.55 (d, J=2.64 Hz, 1 H).

10B: 5-Amino-2-(tert-butylsulfonyl)benzonitrile

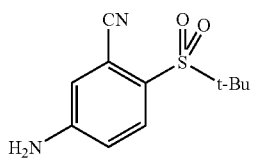

Using a procedure analogous to that used to prepare 6B, 10A (609 mg, 2.27 mmol) was hydrogenated to give 10B (520 mg, 96%) as a white solid. $^1$H NMR (400 MHz, CD$_3$OD) δ 1.35 (s, 9 H), 6.91 (dd, J=8.79, 2.20 Hz, 1 H), 7.07 (d, J=2.20 Hz, 1 H), 7.66 (d, J=8.79 Hz, 1 H).

10C: 4-(4-Bromophenyl)-N-(4-(tert-butylsulfonyl)-3-cyanophenyl)butanamide

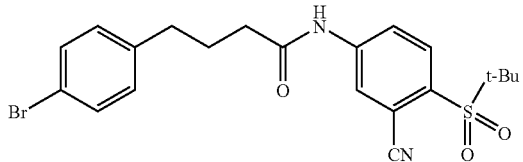

Using a procedure analogous to that used to prepare 8B, 10B (250 mg, 1.05 mmol) was reacted with 4-(4-bromophenyl)butyric acid chloride to give 10C (493 mg, 100%). MS (ESI) m/z 461.2, 463.2 (M+H)$^+$.

10D: N-(4-(tert-butylsulfonyl)-3-cyanophenyl)-4-(4-(5,5-dimethyl-1,3,2-dioxaborinan-2-yl)phenyl)butanamide

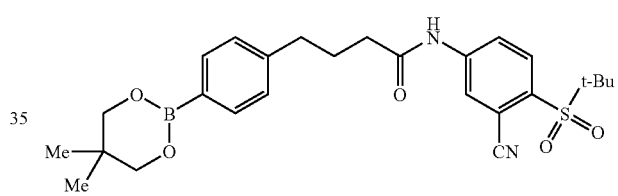

Using a procedure analogous to that used to prepare 2A, 10C (430 mg, 0.930 mmol) was reacted with 5,5',5'-tetramethyl-[2,2']bi[[1,3,2]dioxaborinanyl] to give 10D (431 mg, 93%) as a brown foam. This crude material was taken on to the next step.

10E: 4-(4-(4-(tert-Butylsulfonyl)-3-cyanophenylamino)-4-oxobutyl)phenylboronic acid

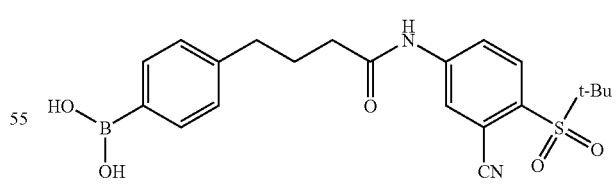

Using a procedure analogous to that used to prepare 2B, 10D (431 mg, 0.869 mmol) was reacted with NaOH to give 10E (263 mg, 71%) as a brown solid. $^1$H NMR (400 MHz, THF-d$_8$) δ 1.34 (s, 9 H), 1.96-2.07 (m, 2 H), 2.35 (t, J=7.25 Hz, 2 H), 2.69 (t, J=7.25 Hz, 2 H), 7.09 (s, 1 H), 7.16 (d, J=7.91 Hz, 2 H), 7.71 (d, J=8.35 Hz, 2 H), 7.92-7.96 (m, 1 H), 8.01 (dd, J=2.20 Hz, 1 H), 8.23 (d, J=2.20 Hz, 1 H), 9.69-9.77 (m, 1 H).

10F: 2-(1-Di-tert-butoxycarbonylaminoisoquinolin-6-ylamino)-2-(4-(4-(4-(tert-butylsulfonyl)-3-cyanophenylamino)-4-oxobutyl)phenyl)acetic acid

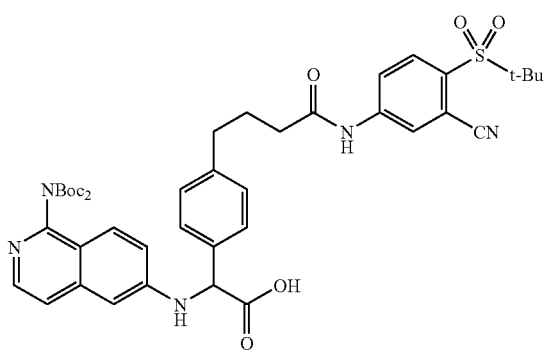

Using a procedure analogous to that used to prepare 2D, 10E (129 mg, 0.301 mmol) was reacted with Intermediate 1 and glyoxylic acid monohydrate to afford 10F (76 mg, 38%). MS (ESI) m/z 800.4 (M+H)+.

10G: 2-(1-Di-tert-butoxycarbonylaminoisoquinolin-6-ylamino)-2-(4-(4-(3-(aminomethyl)-4-(tert-butylsulfonyl)phenylamino)-4-oxobutyl)phenyl)acetic acid

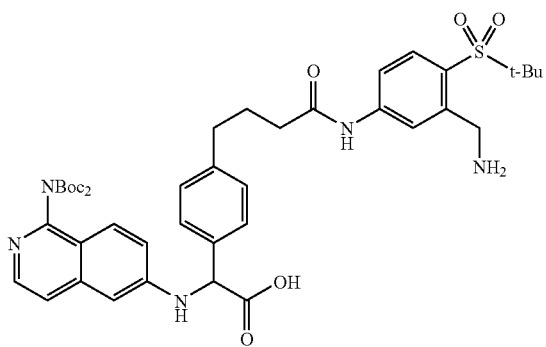

Using a procedure analogous to that used to prepare 6F, 10F (76 mg, 0.095 mmol) was hydrogenated over 20% Pd(OH)$_2$ (64 mg) for 72 h to give 10G (64 mg, 80%) as a yellow glass. MS (ESI) m/z 804.3 (M+H)+.

Example 10

Using a procedure analogous to that used to prepare Example 6, 10G (64 mg, 0.076 mmol) was cyclized with BOP and deprotected with trifluoroacetic acid to give Example 10 (1.58 mg, 3.0%). $^1$H NMR (400 MHz, CD$_3$OD) δ 1.36 (s, 9 H), 2.02-2.16 (m, 1 H), 2.25-2.37 (m, 1 H), 2.39-2.49 (m, 2 H), 2.58-2.70 (m, 1 H), 2.88-2.97 (m, 1 H), 4.36 (dd, J=17.57, 4.39 Hz, 1 H), 5.19 (s, 1 H), 5.25 (dd, J=17.39, 7.14 Hz, 1 H), 6.53 (d, J=1.83 Hz, 1 H), 6.71 (d, J=2.56 Hz, 1 H), 6.87 (d, J=6.96 Hz, 1 H), 6.92 (dd, J=8.42, 2.20 Hz, 1 H), 7.14-7.23 (m, 3 H), 7.31 (d, J=6.96 Hz, 1 H), 7.40 (d, J=8.06 Hz, 1 H), 7.60 (d, J=8.05 Hz, 1 H), 7.75 (d, J=8.42 Hz, 1 H), 8.06 (d, J=9.15 Hz, 1 H), 8.78 (t, J=1 H). MS (ESI) m/z 586.2 (M+H)+.

Example 11

2-(1-Amino-isoquinolin-6-ylamino)-13-oxa-4,11-diaza-tricyclo[14.2.2.1$^{6,10}$]henicosa-1(19),6,8,10(21),16(20),17-hexaene-3,12-dione trifluoroacetic acid salt

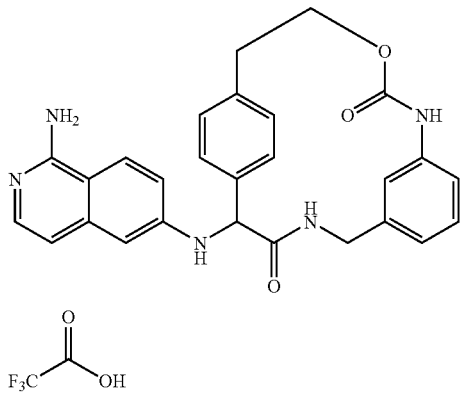

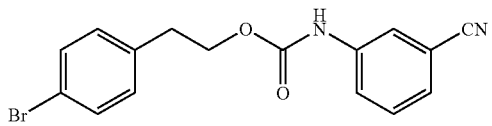

11A: (3-Cyanophenyl)-carbamic acid 2-(4-bromophenyl)ethyl ester

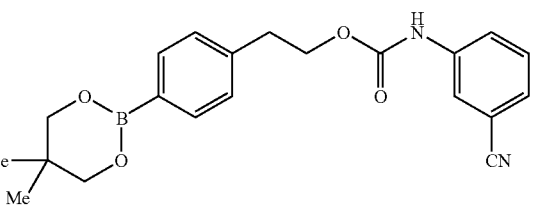

Titanium tetra-tert-butoxide (0.080 mL, 0.21 mmol) was added dropwise to a solution of 3-cyanophenylisocyanate (228 mg, 1.58 mmol) and 2-(4-bromophenyl)ethanol (606 mg, 3.01 mmol) in toluene (10 mL). A precipitate formed immediately and the reaction was stirred for 2 h at rt. The reaction was quenched with saturated ammonium chloride solution and extracted with DCM (3x). The combined organic layers were washed with brine, dried (MgSO$_4$), and concentrated in vacuo. The residual solid was triturated with DCM hexane to give 11A (543 mg, 100%) as a white solid. $^1$H NMR (400 MHz, CDCl$_3$) δ 2.95 (t, J=6.81 Hz, 2 H), 4.38 (t, J=6.81 Hz, 2 H), 6.68 (s, 1 H), 7.11 (d, J=8.35 Hz, 2 H), 7.31-7.35 (m, 1 H), 7.38 (t, J=7.91 Hz, 1 H), 7.44 (d, J=8.35 Hz, 2 H), 7.52 (d, J=7.03 Hz, 1 H), 7.76 (s, 1 H).

11B: (3-Cyanophenyl)carbamic acid 2-[4-(5,5-dimethyl-1,3,2-dioxaborinan-2-yl)-phenyl]ethyl ester Using a procedure analogous to that used to prepare 2A, 11A (516 mg, 1.50 mmol) was reacted with 5,5',5'-tetramethyl-[2,2']bi[[1,3,2]dioxaborinanyl] to give 11B (434 mg, 76%). This crude material was taken on to the next step.

11C: 4-(2-((3-Cyanophenyl)carbamoyloxy)ethyl) phenylboronic acid

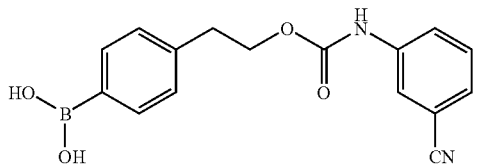

Using a procedure analogous to that used to prepare 2B, 11B (434 mg, 1.15 mmol) was reacted with NaOH to give 11C (170 mg, 48%) as a solid. $^1$H NMR (400 MHz, THF-$d_8$) δ 2.98 (t, J=7.03 Hz, 2 H), 4.38 (t, J=6.81 Hz, 2 H), 7.10 (s, 2 H), 7.22 (d, J=7.91 Hz, 1 H), 7.30 (d, J=7.47 Hz, 1 H), 7.39 (t, J=7.91 Hz, 1 H), 7.68 (d, J=8.35 Hz, 1 H), 7.73 (d, J=8.35 Hz, 2 H), 7.87 (s, 1 H), 9.11 (s, 1 H).

11D: 2-(1-Di-tert-butoxycarbonylaminoisoquinolin-6-ylamino)-2-(4-(2-((3-cyanophenyl)carbamoyloxy) ethyl)phenyl)acetic acid

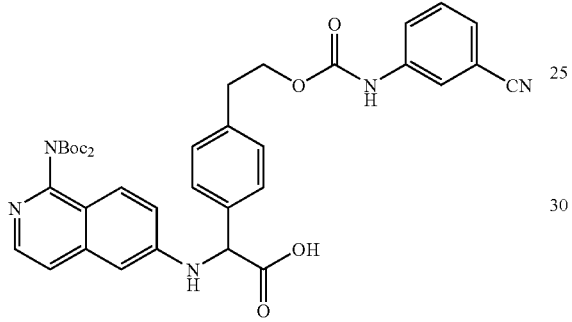

Using a procedure analogous to that used to prepare 2D, 11C (100 mg, 0.32 mmol) was reacted with Intermediate 1 and glyoxylic acid monohydrate to afford 11D (58 mg, 27%). MS (ESI) m/z 682.2 (M+H)$^+$.

11E: 2-(1-Di-tert-butoxycarbonylaminoisoquinolin-6-ylamino)-2-(4-(2-((3-(aminomethyl)phenyl)car-bamoyloxy)ethyl)phenyl)acetic acid

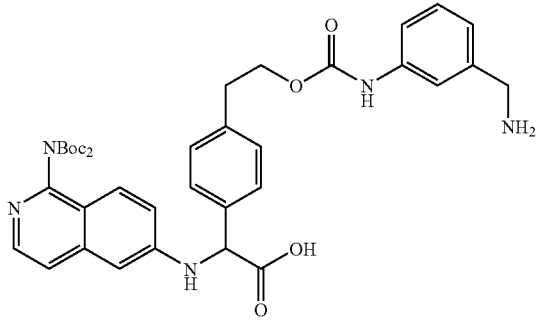

Using a procedure analogous to that used to prepare 6F, 11D (58 mg, 0.085 mmol) was hydrogenated to give 11E (39 mg, 64%) as a yellow glass. MS (ESI) m/z 686.3 (M+H)$^+$.

Example 11

Using a procedure analogous to that used to prepare Example 6, 11E (39 mg, 0.054 mmol) was cyclized with BOP and deprotected with trifluoroacetic acid to give Example 11 (8.5 mg, 27%). $^1$H NMR (400 MHz, CD$_3$OD) δ 2.82-3.06 (m, 4 H), 4.07 (dd, J=16.11, 4.03 Hz, 1 H), 4.27-4.39 (m, 1 H), 5.19 (s, 1 H), 6.19 (s, 1 H), 6.64-6.76 (m, 2 H), 6.85 (d, J=6.96 Hz, 1 H), 6.90 (d, J=7.69 Hz, 1 H), 7.14 (t, J=7.87 Hz, 1 H), 7.20 (dd, J=9.15, 2.56 Hz, 1 H), 7.25 (dd, J=7.87, 1.65 Hz, 1 H), 7.31 (d, J=6.96 Hz, 1 H), 7.33-7.42 (m, 2 H), 7.62 (dd, J=8.06, 1.83 Hz, 1 H), 8.07 (d, J=9.15 Hz, 1 H), 8.69 (s, 1 H). MS (ESI) m/z 468.2 (M+H)$^+$.

Example 12

(R)-2-(1-Amino-isoquinolin-6-ylamino)-7-ethane-sulfonyl-20-methyl-4,11-diaza-tricyclo[14.2.2.1$^{6,10}$] henicosa-1(19),6,8,10(21),16(20),17-hexaene-3,12-dione

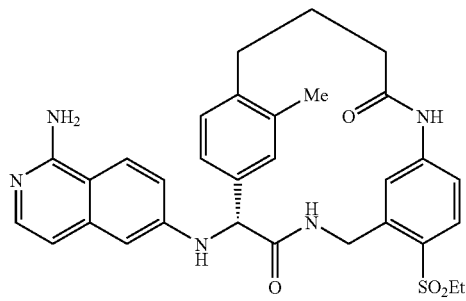

A solution of Example 8 (0.100 g, 0.146 mmol) in methanol was purified by chiral HPLC to give peak 1 (28 mg, 34%) and Example 12 (peak 2, 29 mg, 35%). The chromatography conditions were the following: Chiralpak AS column (3.0 cm ID×25 cm L, 10 micron, Chiral Technologies, Inc.), 75% CO$_2$/25% methanol/0.1% diethylamine as eluent, 100 bar, 40° C., 65 mL/min flow rate, and UV detection at 220 nm. Peak 2 analytical data: $^1$H NMR (400 MHz, CD$_3$OD) δ ppm 1.21-1.33 (m, 3 H) 1.87-2.00 (m, 1 H) 2.26 (s, 1 H) 2.37-2.54 (m, 5 H) 2.66-2.76 (m, 1 H) 2.89-3.00 (m, 1 H) 3.08-3.18 (m, 1 H) 3.33-3.51 (m, 3 H) 4.23 (t, J=17.36 Hz, 1 H) 4.99-5.12 (m, 2 H) 6.55-6.62 (m, 1 H) 6.64-6.69 (m, 1 H) 6.69-6.76 (m, 1 H) 6.85-6.95 (m, 1 H) 6.97-7.10 (m, 2 H) 7.30-7.36 (m, 2 H) 7.38-7.51 (m, 2 H) 7.77 (d, J=8.79 Hz, 1 H) 7.81-7.88 (m, 1 H), mixture of two atropisomers. MS (ESI) m/z 572.10 (M+H)$^+$. Chiral analytical HPLC retention times: peak 1, 20.00 min; peak 2, 24.99 min using the following chromatography conditions: Whelk-01 (R,R) column (4.6 mm ID×250 mm L, 10 micron.), 40% (1:1 ethanol/methanol)/60% heptane/0.1% diethylamine as eluent, 2 mL/min flow rate, and UV detection at 264 nm.

Example 13

(R)-2-(1-Amino-isoquinolin-6-ylamino)-13-oxa-4, 11-diaza-tricyclo[14.2.2.1$^{6,10}$]henicosa-1(19),6,8,10 (21),16(20),17-hexaene-3,12-dione

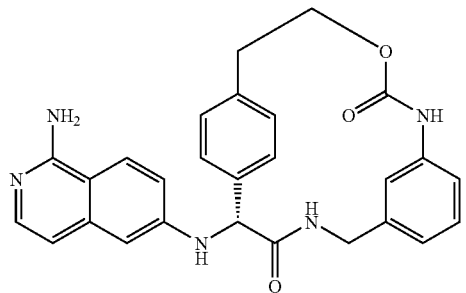

Example 14

(S)-2-(1-Amino-isoquinolin-6-ylamino)-13-oxa-4,
11-diaza-tricyclo[14.2.2.1⁶,¹⁰]henicosa-1(19),6,8,10
(21),16(20),17-hexaene-3,12-dione

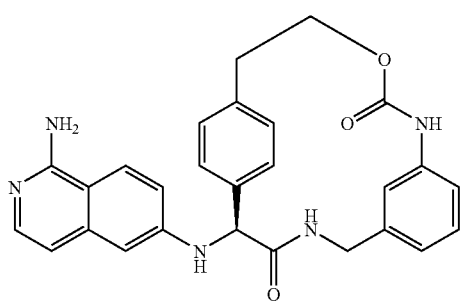

A solution of Example 11 (30 mg, 0.052 mmol) in methanol was purified by chiral HPLC to give Example 13, peak 1 (9 mg, 37%) and Example 14, peak 2 (9 mg, 37%). The chromatography conditions were the following: Chiralcel OD column (2.5 cm ID×25 cm L, Chiral Technologies, Inc.), 30% (1:1 ethanol/methanol)/70% heptane as eluent, 50 mL/min flow rate, and UV detection at 254 nm. Example 13: $^1$H NMR (400 MHz, CD$_3$OD) δ ppm 2.83-2.97 (m, 2 H) 4.10 (d, J=15.82 Hz, 1 H) 4.28-4.38 (m, 1 H) 4.60-4.73 (m, 2 H) 5.11 (s, 1 H) 6.20 (s, 1 H) 6.58 (d, J=2.20 Hz, 1 H) 6.68 (d, J=6.15 Hz, 2 H) 6.89 (d, J=7.91 Hz, 1 H) 7.03 (dd, J=9.01, 2.42 Hz, 1 H) 7.13 (t, J=7.91 Hz, 1 H) 7.24 (dd, J=7.91, 1.76 Hz, 1 H) 7.39 (ddd, J=15.16, 7.91, 1.98 Hz, 2 H) 7.51 (d, J=6.15 Hz, 1 H) 7.58 (dd, J=7.91, 1.76 Hz, 1 H) 7.82 (d, J=9.23 Hz, 1 H). MS (ESI) m/z 468.05 (M+H)$^+$. Example 14: $^1$H NMR (400 MHz, CD$_3$OD) δ ppm 2.82-3.00 (m, 2 H) 4.10 (d, J=16.26 Hz, 1 H) 4.29-4.40 (m, 1 H) 4.68 (d, J=16.26 Hz, 2 H) 5.10 (s, 1 H) 6.20 (s, 1 H) 6.58 (d, J=2.20 Hz, 1 H) 6.68 (d, J=6.15 Hz, 2 H) 6.89 (d, J=7.47 Hz, 1 H) 7.03 (dd, J=9.01, 2.42 Hz, 1 H) 7.13 (t, J=7.91 Hz, 1 H) 7.24 (dd, J=7.91, 1.76 Hz, 1 H) 7.39 (ddd, J=15.16, 7.91, 1.54 Hz, 2 H) 7.51 (d, J=6.15 Hz, 1 H) 7.58 (dd, J=7.91, 1.76 Hz, 1 H) 7.82 (d, J=9.23 Hz, 1 H). MS (ESI) m/z 468.05 (M+H)$^+$. Chiral analytical HPLC retention times: Example 13, 8.18 min; Example 14, 10.94 min using the following chromatography conditions: Chiralcel OD column (4.6 mm ID×250 mm L, Chiral Technologies, Inc.), 30% (1:1 ethanol/methanol)/70% heptane as eluent, 1 mL/min flow rate, and UV detection at 254 nm.

Example 15

4-((R)-7-Ethanesulfonyl-3,12-dioxo-4,11-diaza-tricyclo[14.2.2.1⁶,¹⁰]henicosa-1(19),6,8,10(21),16(20),
17-hexaen-2-ylamino)-benzamidine

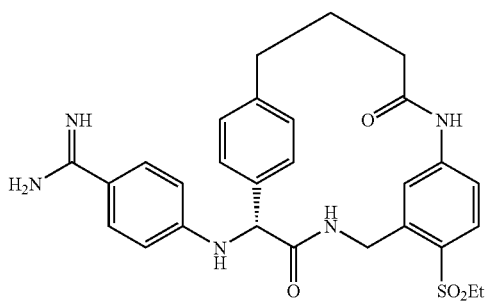

15A: tert-Butyl 5-amino-2-(ethylsulfonyl)benzylcarbamate

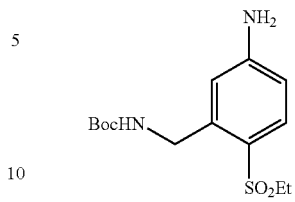

A solution of 6A (2.0 g, 8.32 mmol) in MeOH (100 mL) and hydrochloric acid (1 N, 20 mL) was hydrogenated (60 psi) over 20% Pd(OH)$_2$ (380 mg) for three days. The reaction mixture was filtered and hydrogenated twice more for three days each time over fresh catalyst. The reaction mixture was filtered and then concentrated in vacuo to give a white solid (2.15 g) after trituration with ethyl acetate and ether. 1.0 g of the solid was dissolved in THF (25 mL) and triethylamine (1 mL) and treated with [2-(tert-butoxycarbonyloxyimino)-2-phenylacetonitrile (0.905 g, 3.67 mmol). The reaction mixture was stirred overnight at rt. The reaction mixture was concentrated in vacuo and the residue was extracted twice with DCM and saturated sodium bicarbonate. The combined organics were extracted with brine, dried, and concentrated in vacuo. The residue was purified by silica gel chromatography (gradient from 0 to 50% ethyl acetate in hexanes) to give 15A (1.07 g, 88%) as a clear oil. MS (ESI) m/z 315.12 (M+H)$^+$.

15B: tert-Butyl 5-(4-(4-bromophenyl)butanamido)-2-(ethylsulfonyl)benzylcarbamate

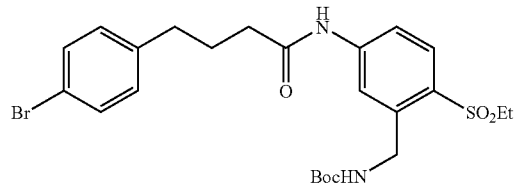

Using a procedure analogous to that used to prepare 6C, except that pyridine was used in place of triethylamine, 15A (0.314 g, 1.00 mmol) was coupled to 4-(4-bromophenyl)butyric acid to give 15B (0.540 g, 100%) as a white foam. $^1$H NMR (400 MHz, CDCl$_3$) δ ppm 1.23-1.31 (m, 3 H) 1.41 (s, 9 H) 1.97-2.08 (m, 2 H) 2.37(t, J=7.47 Hz, 2 H) 2.59-2.70(m, 2 H) 3.11-3.23 (m, 2 H) 4.12(q, J=7.03 Hz, 1 H) 4.50 (d, J=6.15 Hz, 2 H) 5.60 (t, J=5.93 Hz, 1 H) 7.06 (d, J=8.35 Hz, 2 H) 7.39 (d, J=8.35 Hz, 2 H) 7.45-7.50 (m, 1 H) 7.83-7.95 (m, 2 H).

15C: 4-(4-(3-((tert-Butoxycarbonylamino)methyl)-4-(ethylsulfonyl)phenylamino)-4-oxobutyl)phenylboronic acid

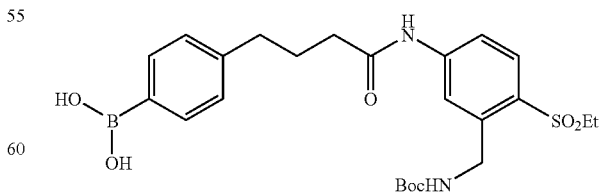

Using a procedure analogous to that used to prepare 6D, 15B (0.541 g, 1.0 mmol) was coupled to 5,5,5',5'-tetramethyl-[2,2']bi[[1,3,2]dioxaborinanyl](0.249 g, 1.1 mmol) and then hydrolyzed to the free boronic acid to give 15C (334 mg, 82%) as a peach colored foam. MS (ESI) m/z 505.03 (M+H)$^+$.

87

15D: 2-(4-(4-(3-((tert-Butoxycarbonylamino)methyl)-4-(ethylsulfonyl)phenylamino)-4-oxobutyl)phenyl)-2-(4-cyanophenylamino)acetic acid

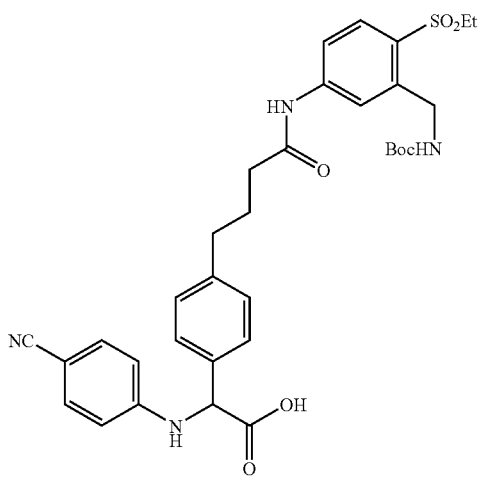

Using a procedure analogous to that used to prepare 2D, 15C (0.101 g, 0.20 mmol) was reacted with 4-aminobenzonitrile (0.024 g, 0.2 mmol) and glyoxylic acid monohydrate (0.018 g, 0.2 mmol) to give, after purification by reverse phase HPLC, 15D (78 mg, 62%) as a white solid. MS (ESI) m/z 634.9 (M+H)+.

15E: 2-(4-(4-(3-(Aminomethyl)-4-(ethylsulfonyl)phenylamino)-4-oxobutyl)phenyl)-2-(4-cyanophenylamino)acetic acid

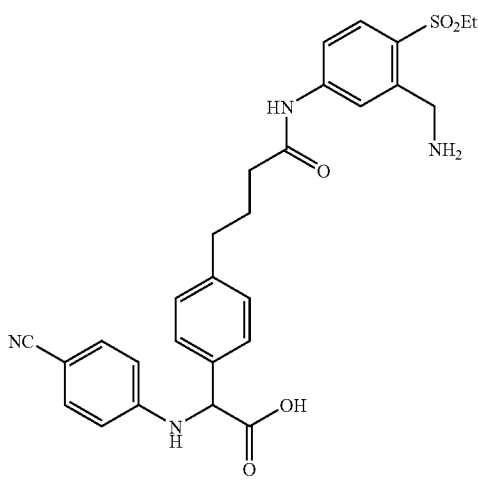

Hydrogen chloride (4N solution in dioxane, 1 mL, 4 mmol) was added to a solution of 15D (78 mg, 0.12 mmol) in ethyl acetate (1 mL). The reaction mixture was stirred at rt overnight and then concentrated to give 15E (65 mg, 100%) as a yellow solid. MS (ESI) m/z 535.0 (M+H)+.

88

15F: 4-((R)-7-Ethanesulfonyl-3,12-dioxo-4,11-diaza-tricyclo[14.2.2.1$^{6,10}$]henicosa-1(19),6,8,10(21),16(20),17-hexaen-2-ylamino)-benzonitrile

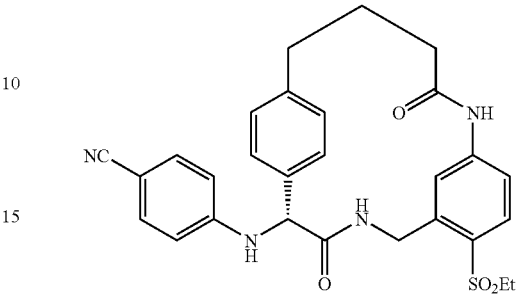

A solution of 15E (200 mg, 0.37 mmol) in DMF (7 mL) was added dropwise over 0.5 h to a solution of BOP (331 mg, 0.74 mmol) and DMAP (226 mg, 1.85 mmol) in DCM (75 mL) at 40° C. The reaction mixture was heated for an additional 0.5 h and then concentrated in vacuo and the residue was purified by reverse phase HPLC to give 81 mg of white solid. This was combined with 31 mg from a previous run, dissolved in MeOH, and purified by chiral HPLC to give peak 1 (48 mg, 43%) and 15F (peak 2, 40 mg, 36%). The preparative chromatography conditions were the following: Chiralcel OD column (5 cm ID×50 cm L, 20 micron, Chiral Technologies, Inc.), 30% (1:1 ethanol/methanol)/70% heptane as eluent, 50 mL/min flow rate, and UV detection at 254 nm. Chiral analytical HPLC retention times: peak 1, 6.15 min; 15F, 8.17 min using the following chromatography conditions: Chiralcel OD column (4.6 mm ID×250 mm L, 10 micron, Chiral Technologies, Inc.), 30% (1:1 ethanol/methanol)/70% heptane as eluent, 1 mL/min flow rate, and UV detection at 254 nm. MS (ESI) m/z 517.1 (M+H)+.

Example 15

15F (30 mg, 0.058 mmol) was dissolved in a solution of hydroxylamine in DMSO (3M, 0.400 mL). The reaction mixture was heated at 70° C. for 3 h. An additional aliquot of hydroxylamine in DMSO (3M, 0.300 mL) was added, and heating was continued for 2 h. The reaction mixture was diluted with ethyl acetate and extracted with water and brine, dried (MgSO$_4$), and concentrated in vacuo. Acetic anhydride (0.030 mL, 0.32 mmol) was added to a solution of the residue dissolved in DCM (3 mL). After 30 min at rt, the reaction mixture was concentrated in vacuo. The residue was dissolved in MeOH and hydrogenated (50 psi) over 10% palladium on carbon (37 mg) for 2.5 h. The reaction mixture was filtered and concentrated in vacuo. The residue was purified by preparative reverse phase HPLC to give Example 15 (7.3 mg, 19%). $^1$H NMR (400 MHz, CD$_3$OD) δ ppm 1.25 (t, J=7.25 Hz, 3 H) 2.00-2.16 (m, 1 H) 2.27-2.49 (m, 3 H) 2.54-2.69 (m, 1 H) 2.87-3.00 (m, 1 H) 3.32-3.51 (m, 2 H) 4.16 (dd, J=16.70, 5.27 Hz, 1 H) 5.00-5.14 (m, 2 H) 6.63 (d, J=1.76 Hz, 1 H) 6.76 (d, J=8.79 Hz, 2 H) 6.90 (dd, J=8.57, 1.98 Hz, 1 H) 7.02 (dd, J=7.91, 2.20 Hz, 1 H) 7.11 (dd, J=7.91, 1.32 Hz, 1 H) 7.39 (dd, J=7.91, 1.76 Hz, 1 H) 7.52-7.62 (m, 3 H) 7.76 (d, J=8.35 Hz, 1 H) 8.91 (t, J=5.71 Hz, 1 H). MS (ESI) m/z 534.0 (M+H)+.

Example 16

3-[(R)-4-Methyl-3,12-dioxo-7-(propane-2-sulfonyl)-13-oxa-4,11-diaza-tricyclo[14.2.2.1$^{6,10}$]henicosa-1(19),6,8,10(21),16(20),17-hexaen-2-ylamino]-benzamide

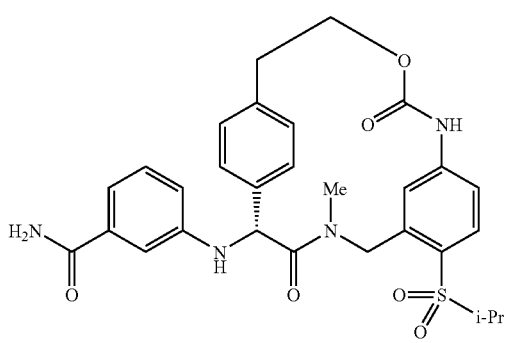

16A: 2-(Isopropylthio)-5-nitrobenzoic acid

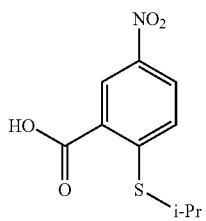

Isopropylthiol (3.06 mL, 32.8 mmol) was added to a solution of 2-fluoro-5-nitrobenzoic acid (5.06 g, 27.3 mmol) and triethylamine (8.4 mL, 60.3 mmol) in DMF (86 mL). The reaction mixture was stirred overnight at rt and then most of the DMF was removed in vacuo. The residual solution was poured into ice water (500 mL) and the resulting yellow solid was isolated by filtration to give 16A (6.5 g, 100%).

16B: 2-(Isopropylthio)-N-methyl-5-nitrobenzamide

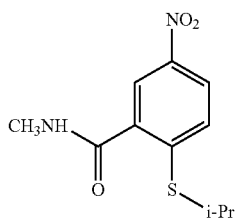

Oxalyl chloride (1.75 mL, 19.6 mmol) was added dropwise to a suspension of 16A (2.41 g, 10 mmol) in DCM (20 mL) containing DMF (2 drops) at 0° C. The reaction mixture was warmed to rt and stirred overnight. The reaction mixture was concentrated in vacuo and coevaporated twice with toluene. The residue was dissolved in DCM (25 mL) and added portionwise to a solution of methylamine hydrochloride (2.03 g, 30.1 mmol) and pyridine (8.1 mL, 100 mmol) in DCM (25 mL) at 0° C. The reaction mixture was stirred overnight at rt. The reaction mixture was concentrated in vacuo and the residue was triturated with water to give 16B (2.08 g, 82%) as a yellow solid.

16C: 5-Amino-2-(isopropylthio)-N-methylbenzamide

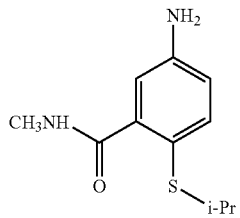

A suspension of 16B (1.2 g, 4.7 mmol) in a mixture of ethanol (30 mL), water (5 mL), and acetic acid (3.3 mL, 5.8 mmol) was heated by a 115° C. oil bath. Iron powder (1.80 g, 32.2 mmol) was added portionwise over 1 h. The reaction mixture was cooled to rt, filtered, and washed with ethyl acetate. Sodium bicarbonate solution was added until it was basic. The reaction mixture was extracted with ethyl acetate (3×) and the combined organics were washed with saturated sodium bicarbonate and brine, dried (MgSO$_4$), and concentrated in vacuo to give 16C (0.98 g, 93%) as a beige solid. MS (ESI) m/z 225.1 (M+H)$^+$.

16D: 4-(Isopropylthio)-3-((methylamino)methyl)aniline

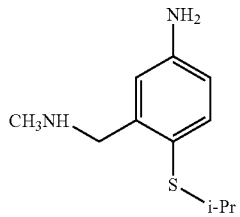

Borane (1M solution in THF, 10 mL, 10 mmol) was added slowly dropwise to a solution of 16C (0.98 g, 4.37 mmol) in THF (60 mL) at 0° C. The reaction mixture was then heated to 70° C. overnight. The reaction mixture was cooled in an ice bath and quenched by cautious addition of hydrochloric acid (2N, 12 mL, 24 mmol). The reaction mixture was refluxed for 2 h and then concentrated almost to dryness in vacuo. The residue was coevaporated with methanol (3×), diluted with ethyl acetate and sodium hydroxide solution (2N). The aqueous layer was extracted with ethyl acetate (3×), dried (MgSO$_4$), and concentrated in vacuo to give 16D (1.03 g, 100%) as a clear oil. MS (ESI) m/z 211.1 (M+H)$^+$.

16E: tert-Butyl-(5-amino-2-(isopropylthio)benzyl)(methyl)carbamate

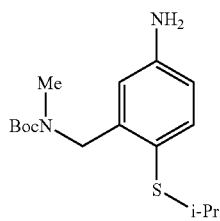

Di-tert-butyl dicarbonate (0.665 g, 3.05 mmol) in acetonitrile (3 mL) was added dropwise to a solution of 16D (560 mg, 2.67 mmol) and DMAP (65 mg, 0.53 mmol) in acetonitrile (5 mL) at 0° C. The reaction mixture was stirred at rt for 4 h. The reaction mixture was diluted with water and extracted with DCM (2×). The combined organic layers were washed with brine, dried (MgSO$_4$), and concentrated in vacuo. The residue

16F: {3-[(tert-Butoxycarbonyl-methyl-amino)-methyl]-4-isopropylsulfanyl-phenyl}-carbamic acid phenyl ester

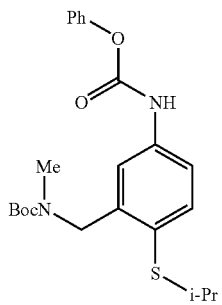

Phenyl chloroformate (0.204 mL, 1.62 mmol) was added dropwise to a solution of 16E (0.48 g, 1.55 mmol) in pyridine (0.193 mL, 2.38 mmol) and DCM (3.5 mL) at 0° C. The reaction mixture was stirred at rt for 1 h. The reaction mixture was diluted with water and extracted with DCM (2×). The combined organic layers were dried (MgSO$_4$) and concentrated in vacuo. The residue was purified by silica gel chromatography (gradient from 0 to 50% ethyl acetate in hexanes) to give 16F (0.609 g, 91%) as a white foam.

16G: [3-[(tert-Butoxycarbonyl-methyl-amino)-methyl]-4-(propane-2-sulfonyl)-phenyl]-carbamic acid phenyl ester

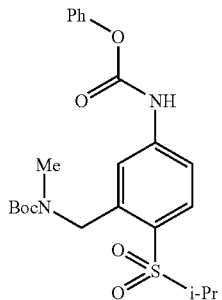

mCPBA (~77%, 0.819 g, 3.65 mmol) was added slowly to a solution of 16F (0.586 g, 1.36 mmol) in DCM (20 mL) at 0° C. The reaction mixture was stirred at rt for 5 h. The reaction mixture was diluted with DCM and extracted with 10% sodium bisulfite (2×), saturated sodium bicarbonate, and brine. The organic layer was dried (MgSO$_4$) and concentrated in vacuo. The residue was purified by silica gel chromatography (gradient from 0 to 50% ethyl acetate in hexanes) to give 16G (0.655 g, 100%) as a clear foam MS (ESI) m/z 463.0 (M+H)$^+$.

16H: [3-[(tert-Butoxycarbonyl-methyl-amino)-methyl]-4-(propane-2-sulfonyl)-phenyl]-carbamic acid 2-(4-bromo-phenyl)-ethyl ester

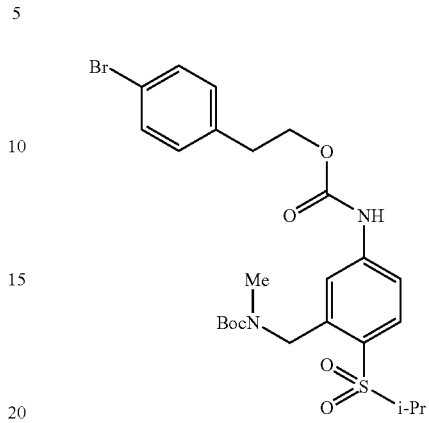

Sodium hydride (60% in oil, 60 mg, 1.5 mmol) was added portionwise to a solution of 4-bromophenethyl alcohol (0.718 g, 3.57) in THF (6 mL) at 0° C. The reaction mixture was cooled to −40° C., and a solution of 16G (0.550 g, 1.19 mmol) in THF (5 mL) was added slowly dropwise. The reaction mixture was slowly warmed to 0° C., and then stirred for 3 h at 0° C. The reaction mixture was diluted with water and extracted with ethyl acetate. The combined organic layers were washed with water and brine, dried (MgSO$_4$) and concentrated in vacuo. The residue was purified by silica gel chromatography (gradient from 0 to 50% ethyl acetate in hexanes) to give 16H (0.503 g, 74%) as a white solid.

16I: 4-(2-(3-((tert-Butoxycarbonyl(methyl)amino)methyl)-4-(isopropylsulfonyl)phenylcarbamoyloxy)ethyl)phenylboronic acid

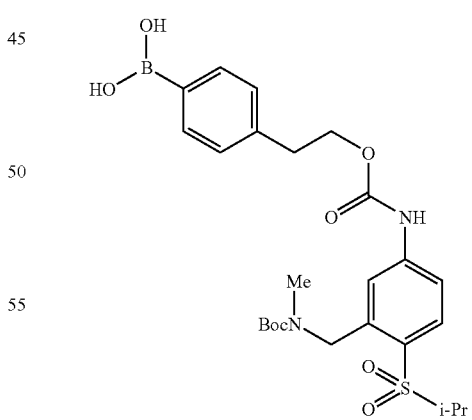

Using a procedure analogous to that used to prepare 6D, 16H (0.653 g, 1.15 mmol) was coupled to 5,5,5',5'-tetramethyl-[2,2']bi[[1,3,2]dioxaborinanyl] (0.286 g, 1.27 mmol) and then hydrolyzed to the free boronic acid to give 16I (0.330 g, 54%) as a white solid.

16J: 2-(4-(2-(3-((tert-Butoxycarbonyl(methyl)amino)methyl)-4-(isopropylsulfonyl)phenylcarbamoyloxy)ethyl)phenyl)-2-(3-carbamoylphenylamino)acetic acid

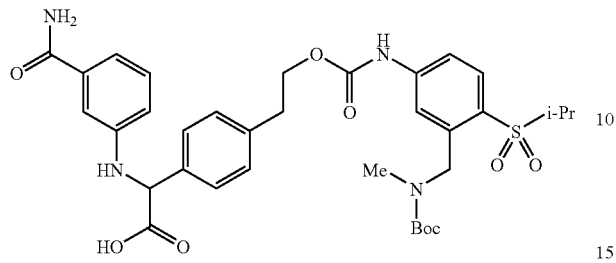

Using a procedure analogous to that used to prepare 2D, 16I (0.134 g, 0.25 mmol) was reacted with m-aminobenzamide (0.035 g, 0.26 mmol) and glyoxylic acid monohydrate (0.023 g, 0.25 mmol) to give, after purification by reverse phase HPLC, 16J (134 mg, 78%) as a pale yellow foam. MS (ESI) m/z 683.1 (M+H)$^+$.

Example 16

Hydrogen chloride (4N solution in dioxanes, 1 mL, 4 mmol) was added to 16J (134 mg, 0.196 mmol) in ethyl acetate (1 mL). The reaction mixture was stirred at rt overnight. The reaction mixture was concentrated in vacuo and then coevaporated with toluene. The residue was then dissolved in DMF (10 mL) and cyclized and purified by reverse phase HPLC according to the procedure described for 15F. The resulting white solid was dissolved in MeOH, and purified by chiral HPLC to give Example 16 (peak 1, 9.8 mg, 9.2%) and peak 2 (7.8 mg, 7.4%). The preparative chromatography conditions were the following: Chiralcel OD column (5 cm ID×50 cm L, 20 micron, Chiral Technologies, Inc.), 30% (1:1 ethanol/methanol)/70% heptane as eluent, 50 mL/min flow rate, and UV detection at 254 nm. Example 16: $^1$H NMR (400 MHz, CD$_3$OD) δ ppm 1.20 (d, J=6.59 Hz, 3 H) 1.32 (d, J=7.03 Hz, 3 H) 2.80-2.99 (m, 2 H) 3.46-3.55 (m, 1 H) 4.02-4.12 (m, 1 H) 4.16 (d, J=17.58 Hz, 1 H) 4.78-4.88 (m, 2 H) 5.53-5.66 (m, 2 H) 6.53 (d, J=2.20 Hz, 1 H) 6.82-6.92 (m, 2 H) 7.06-7.22 (m, 5 H) 7.42 (d, J=7.47 Hz, 1 H) 7.67-7.77 (m, 2 H). MS (ESI) m/z 565.1 (M+H)$^+$. Chiral analytical HPLC retention times: peak 1, 11.56 min; peak 2, 14.01 min using the following chromatography conditions: Chiralcel OD column (4.6 mm ID×250 mm L, 10 micron, Chiral Technologies, Inc.), 30% (1:1 ethanol/methanol)/70% heptane as eluent, 1 mL/min flow rate, and UV detection at 254 nm.

Example 17

(R)-2-(1-Amino-isoquinolin-6-ylamino)-7-ethanesulfonyl-4-methyl-4,11-diaza-tricyclo[14.2.2.1$^{6,10}$]henicosa-1(19),6,8,10(21),16(20),17-hexaene-3,12-dione

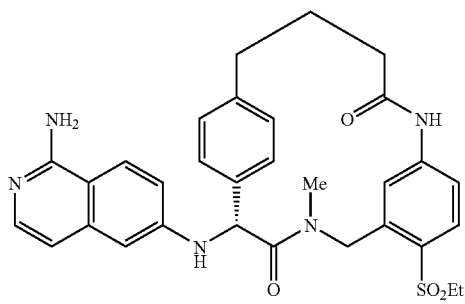

17A: tert-Butyl 5-amino-2-(ethylthio)benzyl(methyl)carbamate

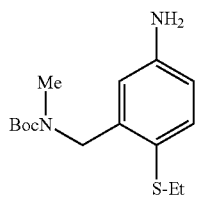

Using a synthetic sequence analogous to that used to convert 2-fluoro-5-nitrobenzoic acid from 16A to 16E, 2-fluoro-5-nitrobenzoic acid was initially reacted with ethanethiol and subsequently converted to 17A. $^1$H NMR (400 MHz, CDCl$_3$) δ ppm 1.19 (t, J=7.25 Hz, 3 H) 1.38-1.57 (m, 9 H) 2.70 (q, J=7.47 Hz, 2 H) 2.76-2.95 (m, 3 H) 3.72 (br. s, 2 H) 4.52-4.75 (m, 2 H) 6.43-6.59 (m, 2 H) 7.27 (d, J=7.91 Hz, 1 H).

17B: tert-Butyl 5-(4-(4-bromophenyl)butanamido)-2-(ethylthio)benzyl(methyl)carbamate

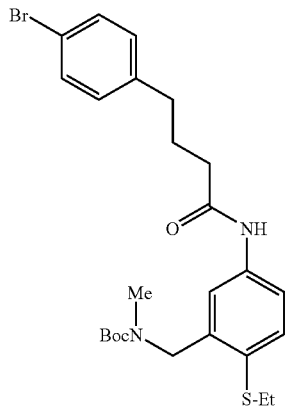

Oxalyl chloride (0.180 mL, 2.06 mmol) was added dropwise to a suspension of 4-bromophenylbutanoic acid (0.250 g, 1.03 mmol) in DCM (3 mL) containing DMF (1 drop) at rt. After 4 h, the reaction mixture was concentrated in vacuo and coevaporated with toluene. The residue was dissolved in DCM (2 mL) and added dropwise to a solution of 17A (0.300 g, 1.01 mmol), DMAP (0.025 g, 0.2 mmol) and pyridine (1.0 mL, 12.3 mmol) in DCM (2 mL) at rt. The reaction mixture was stirred overnight at rt. The reaction mixture was concentrated in vacuo and the residue was triturated with water and then purified by silica gel chromatography (gradient from 0 to 20% ethyl acetate in hexanes) to give 17B (0.46 g, 88%) as a clear oil that solidified on standing. $^1$H NMR (400 MHz, CDCl$_3$) δ ppm 1.26 (t, J=7.03 Hz, 3 H) 1.33-1.58 (m, 9 H) 1.96-2.04 (m, 2 H) 2.33 (t, J=7.47 Hz, 2 H) 2.63 (t, J=7.47 Hz, 2 H) 2.63 (t, J=7.47 Hz, 2 H) 2.74-2.93 (m, 3 H) 4.56 (br. s., 2 H) 6.96-7.02 (m, 0.5 H) 7.05 (d, J=8.35 Hz, 2 H) 7.13 (br. s., 0.4 H) 7.28-7.36 (m, 0.8 H) 7.38 (d, J=8.35 Hz, 2 H) 7.60-7.72 (m, 0.4 H) 7.81-7.98 (m, 0.9 H) 8.33 (br. s., 1 H).

17C: tert-Butyl 5-(4-(4-bromophenyl)butanamido)-2-(ethylsulfonyl)benzyl(methyl)carbamate

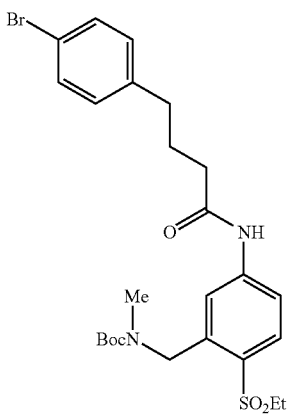

Using a procedure analogous to that used for preparation of 16G, 17B (0.460 g, 0.88 mmol) was reacted with mCPBA (0.500 g, 2.23 mmol) to give 17C (0.428 g, 88%) as a white foam. MS (ESI) m/z 555.0 (M+H)$^+$.

17D: 4-(4-(3-((tert-Butoxycarbonyl(methyl)amino)methyl)-4-(ethylsulfonyl)phenylamino)-4-oxobutyl)phenylboronic acid

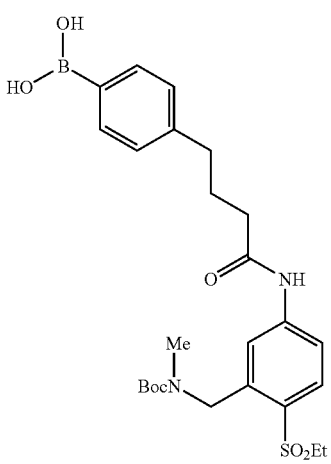

Using a procedure analogous to that used to prepare 6D, 17C (0.428 g, 0.76 mmol) was coupled to 5,5,5',5'-tetramethyl-[2,2']bi[[1,3,2]dioxaborinanyl] (0.202 g, 0.894 mmol) and then hydrolyzed to the free boronic acid to give 17D (0.260 g, 76%) as a white solid. MS (ESI) m/z 519.0 (M+H)$^+$.

17E: 2-(1-(bis(tert-Butoxycarbonyl)amino)isoquinolin-6-ylamino)-2-(4-(4-(3-((tert-butoxycarbonyl(methyl)amino)methyl)-4-(ethylsulfonyl)phenylamino)-4-oxobutyl)phenyl)acetic acid

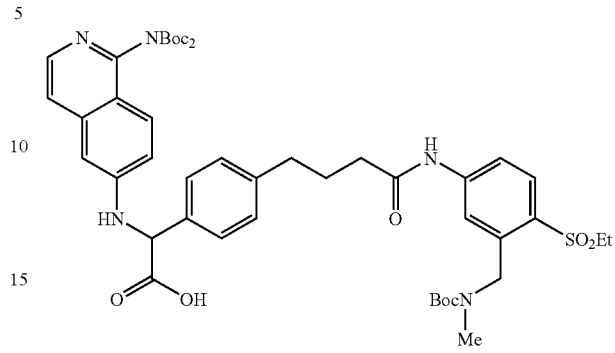

Using a procedure analogous to that used to prepare 2D, 17D (0.130 g, 0.25 mmol) was reacted with Intermediate 1 (0.090 g, 0.25 mmol) and glyoxylic acid monohydrate (0.027 g, 0.29 mmol) to give, after purification by reverse phase HPLC, 17E (109 mg, 49%). MS (ESI) m/z 890.1 (M+H)$^+$.

Example 17

Using a procedure analogous to that used for the final Boc deprotection and cyclization of Example 16, 17E (109 mg, 0.122 mmol) was deprotected with hydrogen chloride and subsequently cyclized and purified by reverse phase HPLC to give 11 mg of yellow foam. This material was dissolved in MeOH, and purified by chiral HPLC using a Chiralcel OJ column to give Example 17 (peak 1) and peak 2. Example 17: $^1$H NMR (400 MHz, CD$_3$OD) δ ppm 1.25 (t, J=7.51 Hz, 3 H) 1.99-2.10 (m, 1 H) 2.23-2.58 (m, 4 H) 2.94-3.04 (m, 1 H) 3.32-3.49 (m, 2 H) 3.43 (s, 3 H) 4.12 (d, J=17.57 Hz, 1 H) 5.63 (d, J=17.21 Hz, 1 H) 5.74 (s, 1 H) 6.62 (s, 1 H) 6.81 (d, J=2.20 Hz, 1 H) 6.89-6.98 (m, 3 H) 7.08-7.12 (m, 1 H) 7.17 (dd, J=9.15, 2.20 Hz, 1 H) 7.31 (d, J=6.96 Hz, 1 H) 7.40 (dd, J=7.87, 1.65 Hz, 1 H) 7.74 (dd, J=8.06, 1.83 Hz, 1 H) 7.80 (d, J=8.42 Hz, 1 H) 8.03 (d, J=9.15 Hz, 1 H). MS (ESI) m/z 572.1 (M+H)$^+$. Chiral analytical HPLC retention times: peak 1, 28 min; peak 2, 49 min using the following chromatography conditions: Chiralcel OJ column (4.6 mm ID×250 mm L, 10 micron, Chiral Technologies, Inc.), 40% (1:1 ethanol/methanol)/70% heptane as eluent, 1 mL/min flow rate, and UV detection at 254 nm.

Example 18

(R)-2-(1-Amino-isoquinolin-6-ylamino)-4-methyl-7-(propane-2-sulfonyl)-4,11-diaza-tricyclo[14.2.2.1$^{6,10}$]henicosa-1(19),6,8,10(21),16(20),17-hexaene-3,12-dione

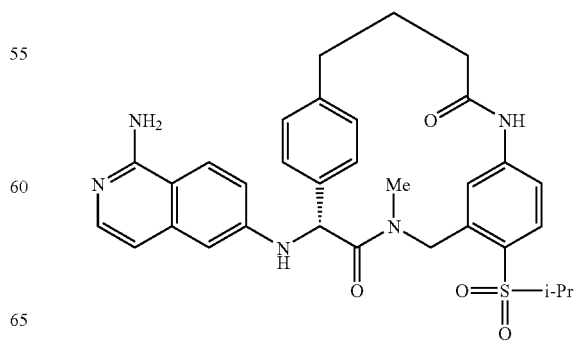

18A: tert-Butyl 5-(4-(4-bromophenyl)butanamido)-2-(isopropylthio)benzyl(methyl)carbamate

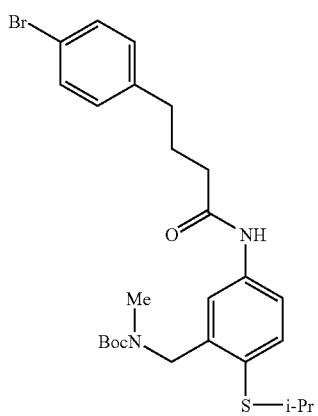

Using a procedure analogous to that used for preparation of 17B, 16E (0.418 g, 1.35 mmol) was reacted with 4-bromophenylbutanoic acid (0.340 g, 1.40 mmol) to give 18A (0.642 g, 89%) as a white solid. MS (ESI) m/z 537.0 (M+H)$^+$.

18B: tert-Butyl 5-(4-(4-bromophenyl)butanamido)-2-(isopropylsulfonyl)benzyl(methyl)carbamate

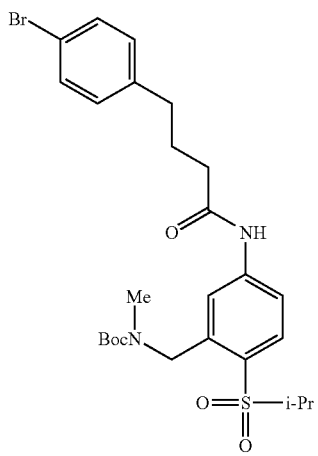

Using a procedure analogous to that used for preparation of 16G, 18A (0.642 g, 1.20 mmol) was reacted with mCPBA (0.672 g, 3.00 mmol) to give 18B (0.660 g, 97%) as a white solid. MS (ESI) m/z 568.9 (M+H)$^+$.

18C: 4-(4-(3-((tert-Butoxycarbonyl(methyl)amino)methyl)-4-(isopropylsulfonyl)phenylamino)-4-oxobutyl)phenylboronic acid

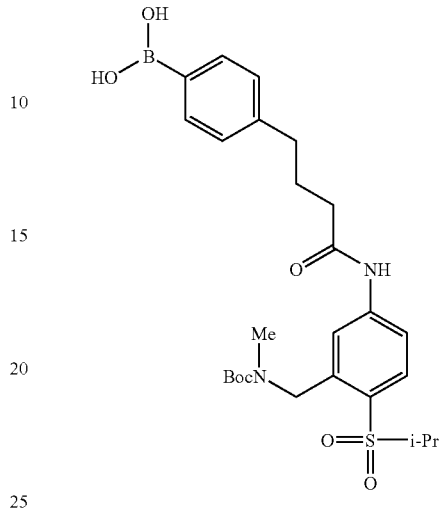

Using a procedure analogous to that used to prepare 6D, 18B (0.660 g, 1.17 mmol) was coupled to 5,5,5',5'-tetramethyl-[2,2']bi[[1,3,2]dioxaborinanyl] (0.290 g, 1.28 mmol) and then hydrolyzed to the free boronic acid to give 18C (0.476 g, 80%) as a white solid. MS (ESI) m/z 533.0 (M+H)$^+$.

18D: 2-(1-(bis(tert-Butoxycarbonyl)amino)isoquinolin-6-ylamino)-2-(4-(4-(3-((tert-butoxycarbonyl(methyl)amino)methyl)-4-(isopropylsulfonyl)phenylamino)-4-oxobutyl)phenyl)acetic acid

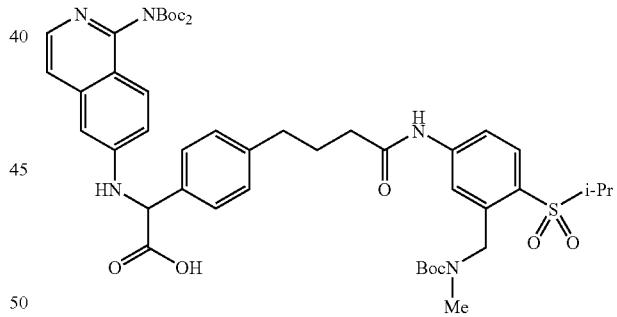

Using a procedure analogous to that used to prepare 2D, 18C (0.151 g, 0.28 mmol) was reacted with Intermediate 1 (0.101 g, 0.28 mmol) and glyoxylic acid monohydrate (0.026 g, 0.28 mmol) to give, after purification by reverse phase HPLC, 18D (168 mg, 66%) as a yellow glass.

Example 18

Using a procedure analogous to that used for the final Boc deprotection and cyclization of Example 16, 18D (168 mg, 0.186 mmol) was deprotected with hydrogen chloride to give 142 mg yellow solid. This was subsequently cyclized in two batches (60 mg and 73 mg) and purified by reverse phase HPLC to give a total 68 mg of racemic product. 43 mg of this material was dissolved in MeOH, and purified by chiral HPLC give Example 18 (peak 1, 16.9 mg, 47%) as a beige solid and peak 2 (15.6 mg, 43%) as a beige solid. The preparative chromatography conditions were the following: Chiralcel OD column (0.21 cm ID×50 cm L, 10 micron, Chiral Technologies, Inc.), 25% methanol/70% CO2/0.1% diethylamine as eluent, 80 mL/min flow rate, and UV detection at 220 nm. Example 18: $^1$H NMR (400 MHz, CD$_3$OD) δ ppm 1.11-1.19 (m, 3 H) 1.24-1.36 (m, 3 H) 1.96-2.06 (m, 1 H) 2.21-2.55 (m, 3 H) 2.62-2.73 (m, 1 H) 2.90-3.01 (m, 1 H) 3.41 (s, 3 H) 3.54-3.68 (m, 1 H) 4.10 (d, J=17.14 Hz, 1 H) 5.60 (d, J=17.58 Hz, 1 H) 5.64 (s, 1 H) 6.57 (s, 1 H) 6.66 (d, J=2.20 Hz, 1 H) 6.73 (d, J=6.15 Hz, 1 H) 6.87-7.00 (m, 3 H) 7.01-7.09 (m, 1 H) 7.37 (d, J=7.91 Hz, 1 H) 7.50 (d, J=5.71 Hz, 1 H) 7.69 (d, J=7.91 Hz, 1 H) 7.76 (dd, J=8.79, 5.27 Hz, 2 H). MS (ESI) m/z 586.0 (M+H)$^+$. Chiral analytical HPLC retention times: peak 1, 13.94 min; peak 2, 18.41 min using the following chromatography conditions: Whelk-01(R,R) column (4.6 mm ID×150 mm L, 10 micron), 50% (1:1 ethanol/methanol)/50% heptane as eluent/0.1% diethylamine, 2 mL/min flow rate, and UV detection at 271 nm.

Example 19

(R)-2-(1-Amino-8-fluoro-isoquinolin-6-ylamino)-13-oxa-4,11-diaza-tricyclo[14.2.2.1$^{6,10}$]henicosa-1(19),6,8,10(21),16(20),17-hexaene-3,12-dione

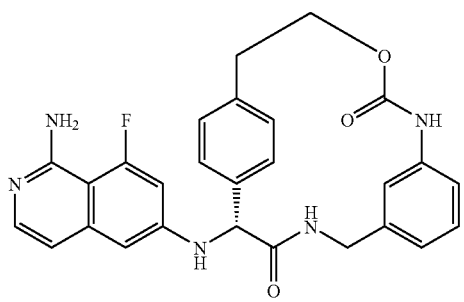

19A: (E)-methyl 3-(3-amino-5-fluorophenyl)acrylate

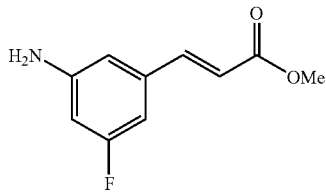

A mixture of 1-fluoro-3-iodo-5-nitrobenzene (1.145 g, 4.29 mmol), sodium acetate (0.430 g, 5.24 mmol), palladium (II) acetate (1.7 mg, 0.0076 mmol), methyl acrylate (0.425 mL, 4.71 mmol), and 1-methyl-2-pyrrolidinone (11 mL) under argon was degassed with three freeze/pump/thaw cycles. The reaction mixture was heated to 130° C. for 35 min and then at 100° C. for 14 h. The reaction mixture was diluted with water and saturated sodium bicarbonate solution and extracted three times with diethyl ether. The combined organic extracts were washed with saturated sodium bicarbonate solution, hydrochloric acid (1 N), and brine, dried (MgSO$_4$), and concentrated under reduced pressure. The residue was suspended in a mixture of ethanol (12 mL), water (2.5 mL), and acetic acid (1.25 mmol) and heated to reflux. Iron powder (0.519 g, 9.28 mmol) was added portionwise over 30 min, and reflux was continued for an additional 30 min. The reaction mixture was concentrated under reduced pressure. The residue was partitioned between ethyl acetate and sodium bicarbonate solution and filtered through a glass fibre filter to remove a fine grey precipitate. The aqueous phase was extracted with ethyl acetate (3×) and the organic phase was dried (MgSO$_4$) and concentrated under reduced pressure to give 19A (0.328 g, 74%) as a pale yellow solid. LC-MS m/z: 196.2 (M+H)$^+$.

19B: (E)-Methyl 3-(3-(dibenzylamino)-5-fluorophenyl)acrylate

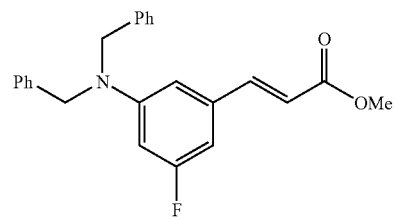

Benzyl bromide (0.440 mL, 3.70 mmol) was added to a solution of 19A (0.328 g, 1.68 mmol) and DIEA (0.880 mL) in acetonitrile (5 mL). The reaction mixture was heated at 60° C. for 14 h and then concentrated under reduced pressure. The residual solid was triturated twice with diethyl ether, dissolved in dichloromethane, and extracted with hydrochloric acid (1N) and saturated sodium bicarbonate solution. The organic layer was dried (MgSO$_4$) and concentrated under reduced pressure. The residue was purified by silica gel chromatography (gradient from 0 to 15% ethyl acetate in hexanes) to give 19B (0.468 g, 74%) as a white solid. LC-MS m/z: 376.5 (M+H)$^+$.

19C: (E)-3-(3-(Dibenzylamino)-5-fluorophenyl)acrylic acid

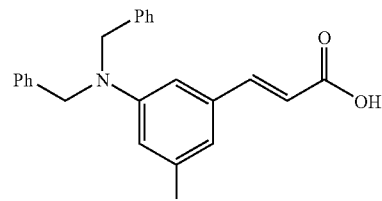

Sodium hydroxide (2 mL, 2 mmol, 1.00 N solution) was added to a solution of 19B (0.467 g, 1.24 mmol) in tetrahydrofuran (2 mL) and methanol (1 mL). The reaction was heated at 80° C. for 1 h. Hydrochloric acid (1 N) was added and the reaction mixture was extracted with ethyl acetate (2×). The combined organic layers were dried (MgSO$_4$) and concentrated under reduced pressure to give 19C (0.411 g, 91%) as a pale yellow solid. LC-MS m/z: 362.4 (M+H)$^+$.

19D: 6-(Dibenzylamino)-8-fluoroisoquinolin-1(2 H)-one

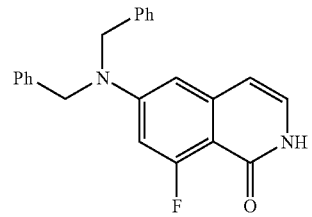

A solution of ethyl chloroformate (0.320 mL, 3.35 mmol) in acetone (5 mL) was added dropwise to a suspension of 19C (1.013 g, 2.80 mmol) in a mixture of acetone (30 mL) and triethylamine (0.90 mL, 6.4 mmol) at 0° C. The reaction mixture was stirred for 45 min and then a solution of sodium azide (0.350 g, 5.4 mmol) in water (8 mL) was added dropwise over 1 h. After an additional 1 h, the reaction was warmed to rt, poured into ice water, and the solid was isolated by filtration and washed with water (Do not allow the solid to dry out). (Caution: this acyl azide intermediate is potentially explosive and should be handled in small quantities behind a safety shield.) The solid was dissolved in DCM, dried (MgSO$_4$), filtered, and the volume reduced to ~2 mL with a stream of nitrogen. Diphenyl ether (2 mL) was added, and the crude acyl azide solution was used directly. The acyl azide solution was added slowly dropwise via addition funnel to a refluxing mixture of diphenyl ether (8.12 g) and tributylamine (2 mL), internal temperature ~230° C. A flow of dry nitrogen was maintained through the reaction vessel to a bubbler during the reaction. Reflux was continued for an additional 1 h, after which time the majority of the solvent was removed in vacuo. The residue was cooled to room temperature and hexanes was added. The solid was collected by filtration and washed with hexanes to give 19D (0.830 g, 83%) as an off-white solid. LC-MS m/z: 359.4 (M+H)$^+$.

19E:
1-Chloro-6-(Dibenzylamino)-8-fluoroisoquinoline

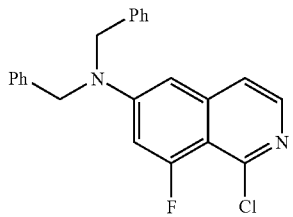

A mixture of 19D (0.622 g, 1.74 mmol) and phosphorous oxychloride (6 mL) was heated at 100° C. for 1.5 h. The reaction mixture was concentrated under reduced pressure and co-evaporated twice with toluene. Ice was added to the residue, followed by sodium hydroxide (1N solution) until the pH was basic. The mixture was extracted with methylene chloride (3x), and the combined organic layers were washed with saturated sodium bicarbonate solution and brine, dried (MgSO$_4$), and dried in vacuo to give 19E (0.583 g, 89%) as a yellow solid.

19F: N$^6$,N$^6$-Dibenzyl-8-fluoroisoquinoline-1,6-diamine

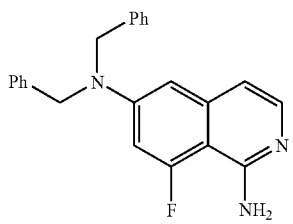

A solution of 19E (0.500 g, 1.33 mmol) in a saturated solution of ammonia in ethylene glycol (30 mL, prepared from 5 g NH$_3$ in 25 g ethylene glycol) was heated to 150° C. (internal temperature) in a Parr stainless steel autoclave with internal thermocouple and heating controller, with a 3000 psi pressure rating and 3000 psi rupture disc. The internal pressure reached 500 psi, so this reaction cannot be run in a glass reaction vessel. After 19 h, the reactor was allowed to cool to RT, and then cooled further in an ice bath. The reaction mixture (still releasing ammonia gas) was poured into ice water, and the resulting precipitate was collected by filtration. The filtrate was extracted with dichloromethane and ethyl acetate and the residue from the organic extracts was combined with precipitate. This material was purified by silica gel chromatography (0 to 30% ethyl acetate/hexanes) to give 19F (328 mg, 69%) as a yellow solid. LC-MS m/z: 358.08 (M+H)$^+$.

19G: N$^6$,N$^6$-Dibenzyl-N$^1$,N$^1$-di-tert-butoxycarbonyl-8-fluoroisoquinoline-1,6-diamine

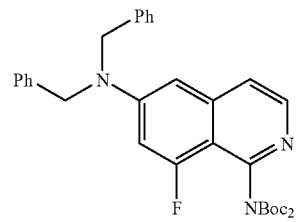

Di-tert-butyl dicarbonate (58 mg, 0.266 mmol) was added to a suspension of 19F (21 mg, 0.059 mmol) and DMAP (5 mg, 0.041 mmol) in acetonitrile (2 mL). The reaction mixture was stirred overnight at rt and then concentrated under reduced pressure. The residue was purified by silica gel chromatography (gradient from 0 to 30% ethyl acetate in hexanes) to afford 19G (23 mg, 70%) as a clear glass. LC-MS m/z: 558.3 (M+H)$^+$.

19H: N$^1$,N$^1$-Di-tert-butoxycarbonyl-8-fluoroisoquinoline-1,6-diamine

A mixture of 19G (77 mg, 0.14 mmol), 20% palladium(II) hydroxide on carbon (94 mg) and ethanol (20 mL) was hydrogenated (55 psi) for 4 h. The reaction mixture was filtered and concentrated under reduced pressure to give 19H (47 mg, 90%) as a yellow solid. LC-MS m/z: 378.3 (M+H)$^+$.

19I: 4-bromophenethyl 3-cyanophenylcarbamate

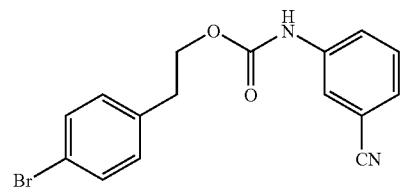

2-(4-Bromophenyl)ethanol (1.2 g, 5.97 mmol) was added to a solution of 3-cyanophenyl isocyanate (0.475 g, 3.3 mmol) in dry toluene (20 mL), followed by titanium tetra-tert-butoxide (0.16 mL, 0.42 mmol). The reaction mixture was stirred overnight at rt. The reaction was quenched by addition of saturated ammonium chloride solution and extracted with DCM (3x). The combined organics were dried and concentrated in vacuo to give 19I (1.08 g, 95%). $^1$H NMR (400 MHz, CDCl$_3$) δ ppm 2.96 (t, J=6.81 Hz, 2 H) 4.39 (t, J=6.81 Hz, 2 H) 6.70 (br. s., 1 H) 7.13 (d, J=8.35 Hz, 2 H) 7.32-7.43 (m, 2 H) 7.45 (d, J=8.35 Hz, 2 H) 7.53 (d, J=7.03 Hz, 1 H) 7.78 (br. s., 1 H).

19J: 4-(2-(3-Cyanophenylcarbamoyloxy)ethyl)phenylboronic acid

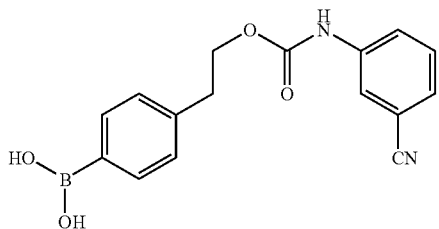

Using procedures analogous to those used to prepare 2A and hydrolyze it to 2B, 19I (1.08 g, 2.86 mmol) was coupled to 5,5,5',5'-tetramethyl-[2,2']bi[[1,3,2]dioxaborinanyl] (0.710 g, 3.14 mmol) and then a portion of this material was hydrolyzed to the free boronic acid to give 19J (0.340 g, 72%, two steps) as a crude white solid.

19K: 2-(1-(bis(tert-Butoxycarbonyl)amino)-8-fluoroisoquinolin-6-ylamino)-2-(4-(2-(3-cyanophenylcarbamoyloxy)ethyl)phenyl)acetic acid

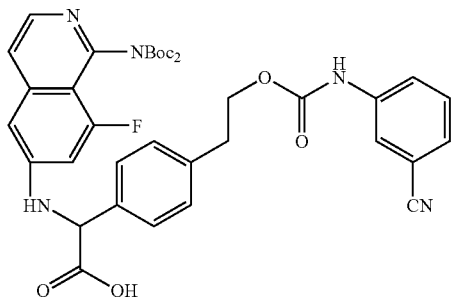

Using a procedure analogous to that used to prepare 2D, 19J (0.048 g, 0.15 mmol) was reacted with 19H (0.054 g, 0.14 mmol) and glyoxylic acid monohydrate (0.015 g, 0.16 mmol) using a reaction time of 900 sec to give, after purification by reverse phase HPLC, 19K. MS (ESI) m/z 700.05 (M+H)$^+$.

19L: 2-(4-(2-(3-(Aminomethyl)phenylcarbamoyloxy)ethyl)phenyl)-2-(1-(bis(tert-butoxycarbonyl)amino)-8-fluoroisoquinolin-6-ylamino)acetic acid

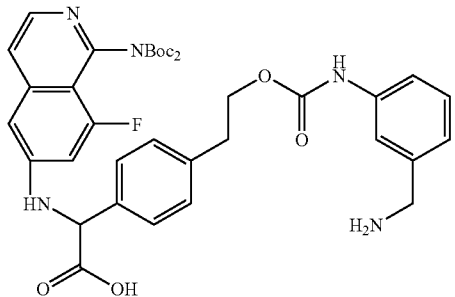

Using a procedure analogous to that used to prepare 6F, 19K (0.030 g, 0.043 mmol) was hydrogenated to give 19L (27 mg, 90%). MS (ESI) m/z 704.2 (M+H)$^+$.

Example 19

Using a procedure analogous to that used to prepare 15F, except that BOP was replaced with PyBOP (40 mg, 0.077 mmol), 19L (27 mg, 0.038 mmol) was cyclized and purified by reverse phase HPLC. This material was subsequently deprotected using a procedure analogous to that used for the final step of Example 1. The resulting material was dissolved in MeOH, and purified by chiral HPLC to give peak 1 (4 mg, 22%) and Example 19 (peak 2, 2.5 mg, 14%). The preparative chromatography conditions were the following: Whelk-01 (R,R) column (2.11 cm ID×25 cm L, Regis), 40% (1:1 ethanol/methanol)/60% heptane as eluent, 15 mL/min flow rate, and UV detection at 254 nm. Example 19: $^1$H NMR (400 MHz, CD$_3$OD) δ ppm 2.83-2.99 (m, 3 H) 4.05 (dd, J=16.29, 4.21 Hz, 1 H) 4.26-4.35 (m, 1 H) 6.17 (s, 1 H) 6.59 (br. s., 1 H) 6.68 (d, J=8.05 Hz, 1 H) 6.83 (dd, J=7.32, 2.20 Hz, 1 H) 6.87-6.98 (m, 2 H) 7.14 (t, J=7.69 Hz, 1 H) 7.22-7.27 (m, 1 H) 7.30 (d, J=7.32 Hz, 1 H) 7.32-7.36 (m, 1 H) 7.38-7.43 (m, 1 H) 7.60 (dd, J=7.87, 1.65 Hz, 1H) 8.66 (br. s., 1 H). MS (ESI) m/z 485.97 (M+H)$^+$. Chiral analytical HPLC retention times: peak 1, 6.47 min; Example 19, 10.43 min using the following chromatography conditions: Whelk-01 (R,R) column (4.6 mm ID×250 mm L, 10 micron), 50% (1:1 ethanol/methanol)/50% heptane as eluent, 1 mL/min flow rate, and UV detection at 254 nm.

Example 20

(R)-2-(1-Amino-8-fluoro-isoquinolin-6-ylamino)-4-methyl-7-(propane-2-sulfonyl)-13-oxa-4,11-diazatricyclo[14.2.2.1$^{6,10}$]henicosa-1(19),6,8,10(21),16(20),17-hexaene-3,12-dione

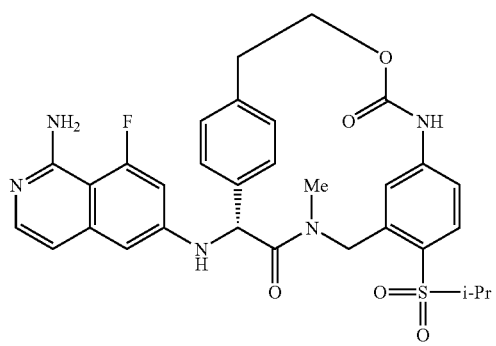

20A: 2-(1-(bis(tert-butoxycarbonyl)amino)-8-fluoroisoquinolin-6-ylamino)-2-(4-(2-(3-((tert-butoxycarbonyl(methyl)amino)methyl)-4-(isopropylsulfonyl)phenylcarbamoyloxy)ethyl)phenyl)acetic acid

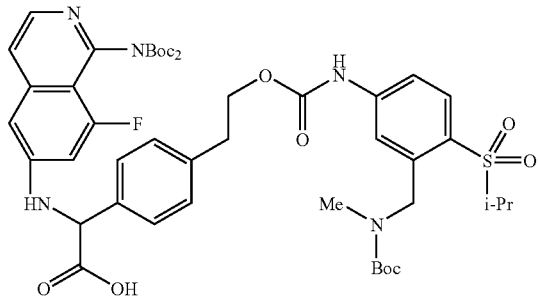

Using a procedure analogous to that used to prepare 2D, 16I (0.160 g, 0.300 mmol) was reacted with 19H (0.113 g, 0.300 mmol) and glyoxylic acid monohydrate (0.028 g, 0.30 mmol) using a 900 sec reaction time to give, after purification by reverse phase HPLC, 20A (121 mg, 43%). MS (ESI) m/z 924.1 (M+H)$^+$.

20B: 2-(1-amino-8-fluoroisoquinolin-6-ylamino)-2-(4-(2-(4-(isopropylsulfonyl)-3-((methylamino)methyl)phenylcarbamoyloxy)ethyl)phenyl)acetic acid

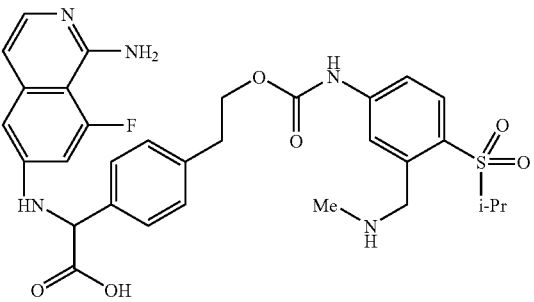

Using a procedure analogous to that used in the final step of Example 1, 20A (0.152 g, 0.16 mmol) was deprotected using hydrogen chloride to give 20B (0.132 g, 100%). MS (ESI) m/z 623.97 (M+H)$^+$.

Example 20

Using a procedure analogous to that used to prepare 15F, except that BOP was replaced with PyBOP (172 mg, 0.33 mmol), 20B (132 mg, 0.16 mmol) was cyclized and purified by reverse phase HPLC. The resulting material was dissolved in MeOH, and purified by chiral HPLC to give peak 1 (6.8 mg, 14%) and Example 20 (peak 2, 4.8 mg, 9.6%). The preparative chromatography conditions were the following: Whelk-01 (R,R) column (2.11 cm ID×25 cm L, Regis), 40% (1:1 ethanol/methanol)/60% heptane as eluent, 15 mL/min flow rate, and UV detection at 254 nm. Example 20: $^1$H NMR (400 MHz, CD$_3$OD) δ ppm 2.83-2.99 (m, 3 H) 4.05 (dd, J=16.29, 4.21 Hz, 1 H) 4.26-4.35 (m, 1 H) 6.17 (s, 1 H) 6.59 (br. s., 1H) 6.68 (d, J=8.05 Hz, 1 H) 6.83 (dd, J=7.32, 2.20 Hz, 1 H) 6.87-6.98 (m, 2 H) 7.14 (t, J=7.69 Hz, 1 H) 7.22-7.27 (m, 1 H) 7.30 (d, J=7.32 Hz, 1 H) 7.32-7.36 (m, 1 H) 7.38-7.43 (m, 1 H) 7.60 (dd, J=7.87, 1.65 Hz, 1 H) 8.66 (br. s., 1 H). MS (ESI) m/z 485.97 (M+H)$^+$. Chiral analytical HPLC retention times: peak 1, 8.35 min; Example 20, 10.21 min using the following chromatography conditions: Whelk-01 (R,R) column (4.6 mm ID×250 mm L, 10 micron), 60% (1:1 ethanol/methanol)/40% heptane as eluent, 1 mL/min flow rate, and UV detection at 254 nm.

Example 21

3-[17-Ethyl-4-methyl-3,12-dioxo-7-(propane-2-sulfonyl)-4,11-diaza-tricyclo[14.2.2.1$^{6,10}$]henicosa-1(19),6,8,10(21),16(20),17-hexaen-2-ylamino]-benzamide trifluoroacetic acid salt

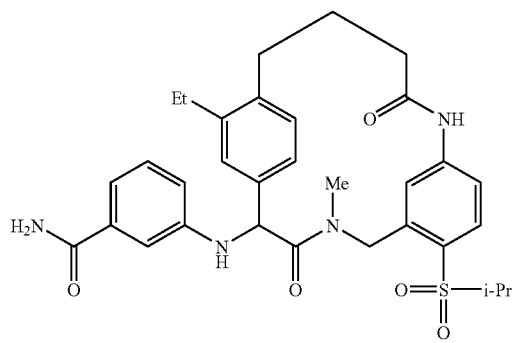

-continued

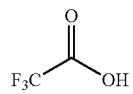

21A: Benzyl 4-(4-bromo-2-ethylphenyl)butanoate

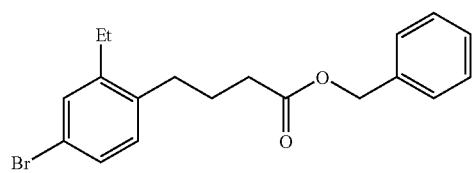

Using a procedure analogous to that used to prepare 8A, benzyl but-3-enoate (3.63 g, 0.020 mmol, reference for preparation: Cardillo, G.; De Simone, A.; Mingardi, A.; Tomasini, C. Synlett 1995, 11, 1131-2) was reacted with 4-bromo-2-ethyl-iodobenzene (6.23 g, 0.020 mmol) to give 21A (1.5 g, 21%). $^1$H NMR (400 MHz, CDCl$_3$) δ ppm 1.18 (t, J=7.69 Hz, 3 H) 1.84-1.94 (m, 2 H) 2.41 (t, J=7.25 Hz, 2 H) 2.55-2.62 (m, 4 H) 5.12 (s, 1 H) 6.96 (d, J=7.91 Hz, 1 H) 7.22 (dd, J=7.91, 2.20 Hz, 1 H) 7.29 (d, J=2.20 Hz, 1 H) 7.30-7.40 (m, 5 H).

21B: tert-Butyl 5-(4-(4-bromo-2-ethylphenyl)butanamido)-2-(isopropylthio)benzyl(methyl)carbamate

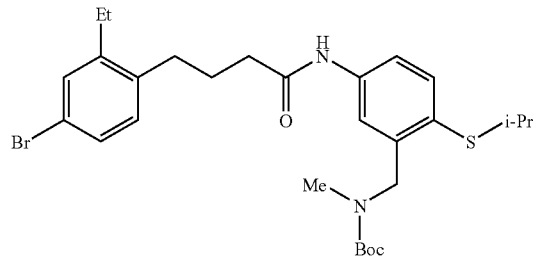

Lithium hydroxide monohydrate (0.176 g, 4.19 mmol) was added to a solution of 21A (0.504 g, 1.4 mmol) in a mixture of THF (2 mL), water (2 mL), and methanol (several drops). After 1 h, additional lithium hydroxide was added. The reaction mixture was concentrated in vacuo to remove most of the THF and methanol, acidified with hydrochloric acid (1N), and extracted with ethyl acetate (3×). The combined organics were washed with brine, dried, and concentrated in vacuo to give the acid (0.376 g) as a clear oil. This material was converted to the acid chloride and then coupled to aniline 16E (0.434 g, 1.4 mmol) using a procedure analogous to that described for preparation of 17B, to give 21B (0.700 g, 89%) as a yellow oil.

21C: tert-Butyl 5-(4-(4-bromo-2-ethylphenyl)butanamido)-2-(isopropylsulfonyl)benzyl(methyl)carbamate

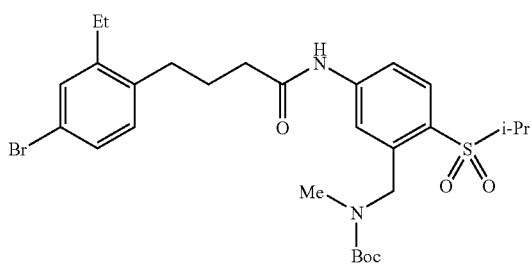

Using a procedure analogous to that described for the preparation of 16G, 21B (0.700 g, 1.25 mmol) was reacted with mCPBA (0.695 g, 3.10 mmol) to give 21C (0.513 g, 69%). MS (ESI) m/z 595, 597.4 (M+H)+.

21D: 4-(4-(3-((tert-Butoxycarbonyl(methyl)amino) methyl)-4-(isopropylsulfonyl)phenylamino)-4-oxobutyl)-3-ethylphenylboronic acid

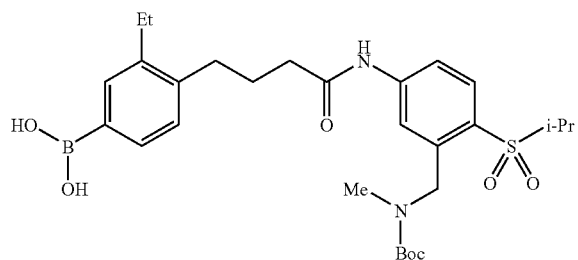

Using a procedure analogous to that described for the preparation of 6D, 21C (0.513 g, 0.86 mmol) was coupled to 5,5,5',5'-tetramethyl-[2,2']bi[[1,3,2]dioxaborinanyl] (0.215 g, 0.952 mmol) and hydrolyzed to give boronic acid 21D (0.278 g, 67%). MS (ESI) m/z 561.48 (M+H)+.

21E: 2-(4-(4-(3-((tert-Butoxycarbonyl(methyl) amino)methyl)-4-(isopropylsulfonyl)phenylamino)-4-oxobutyl)-3-ethylphenyl)-2-(3-carbamoylphenylamino)acetic acid

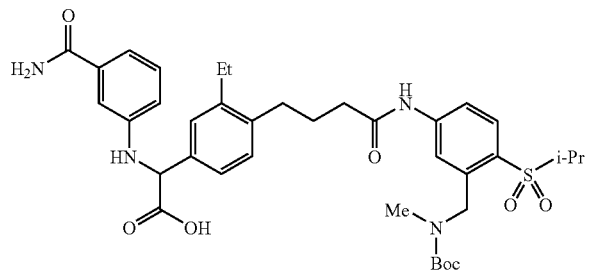

Using a procedure analogous to that used to prepare 2D, 21D (0.0.168 g, 0.300 mmol) was reacted with 3-aminobenzamide (0.041 g, 0.300 mmol) and glyoxylic acid monohydrate (0.028 g, 0.30 mmol) to give, after purification by reverse phase HPLC, 21E (134 mg, 63%) as a foam. MS (ESI) m/z 709.52 (M+H)+.

Example 21

Using a procedure analogous to that described for the preparation of 15E, 21D (134 mg, 0.189 mmol) was deprotected with hydrogen chloride. This material was coevaporated with toluene (2×) and then cyclized using a procedure analogous to that described for preparation of 15F, with the exception that pyBOP was substituted for BOP, to give Example 21 (39 mg, 30%) as 2:1 mixture of two atropisomers. 1H NMR (400 MHz, CD3OD) δ ppm 1.00 (t, J=7.51 Hz, 1 H) 1.18-1.25 (m, 3 H) 1.25-1.40 (m, 5 H) 1.87-1.99 (m, 0.5 H) 2.04-2.17 (m, 0.5H) 2.19-2.58 (m, 3.5 H) 2.68-2.92 (m, 2.5 H) 3.10-3.25 (m, 0.6 H) 3.53-3.69 (m, 0.7 H) 4.05-4.18 (m, 0.6 H) 5.55-5.71 (m, 1 H) 6.57-6.66 (m, 1 H) 6.80 (dd, J=7.87, 1.65 Hz, 1 H) 6.90 (dt, J=8.42, 2.38 Hz, 1 H) 6.94-7.03 (m, 1.4 H) 7.06 (d, J=8.06 Hz, 0.7 H) 7.18-7.36 (m, 3 H) 7.37-7.42 (m, 0.4 H) 7.47 (d, J=1.46 Hz, 0.5 H) 7.74-7.79 (m, 1 H). MS (ESI) m/z 591.4 (M+H)+.

Example 22

2-(1-Amino-isoquinolin-6-ylamino)-13-methyl-4,11, 13-triaza-tricyclo[15.2.2.1^{6,10}]docosa-1(20),6,8,10 (22),17(21),18-hexaene-3,12-dione trifluoroacetic acid salt

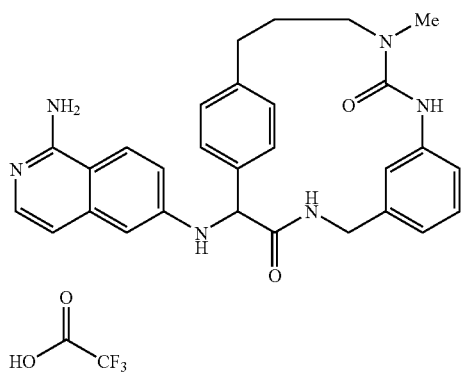

22A: 3-(4-bromophenyl)-N-methylpropanamide

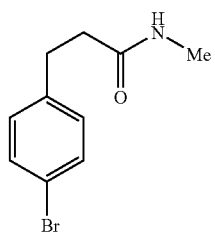

EDAC (1.56 g, 8.1 mmol) was added in one portion to 3-(4-bromophenyl)propanoic acid (2.5 g, 7.4 mmol) and HOBt (1.1 g, 8.1 mmol) in DMF (6 mL) and the reaction mixture was stirred for 2 h. The reaction mixture was cooled to 0° C. and NH2Me (2.0 M in MeOH, 29 mL, 58 mmol) was added dropwise. The solution was stirred at 0° C. for 30 min and 10 h at ambient temperature. The reaction mixture was diluted with water (25 mL), extracted with diethyl either (3×50 mL). The combined organics were washed with brine, dried over Na2SO4 and concentrated in vacuo to yield 22A (1.7 g, 67%) as an off-white solid. MS (ESI) m/z 242.22/ 244.22 (M+H)+.

22B: 3-(4-bromophenyl)-N-methylpropan-1-amine

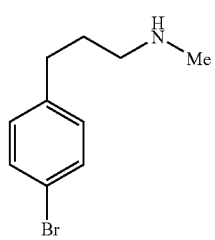

Borane in THF (1.0 M, 28 mL, 28 mmol) was added dropwise to a solution of 22A (1.6 g, 7.0 mmol) in THF (17.5 mL). After stirring the reaction mixture for 30 min at 0° C. the mixture was refluxed for 4 h. Methanol (20 mL) was added to the mixture at 0° C. followed by the addition of 20 mL 6.0 M HCl dropwise. After refluxing for 30 min the volatiles were removed in vacuo. 50% NaOH (12 mL) was added dropwise while maintaining the temperature below 30° C. The resulting mixture was diluted with water (100 mL) and extracted with diethyl ether (3×100 mL). The organics were combined, washed with brine, dried over Na$_2$SO$_4$ and concentrated in vacuo to yield 22B (1.57 g, 97%) as a clear oil. MS (ESI) m/z 227.99/229.99 (M+H)$^+$.

22C: 1-(3-(4-bromophenyl)propyl)-3-(3-cyanophenyl)-1-methylurea

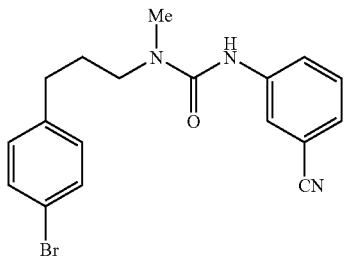

3-Isocyanatobenzonitrile (202 mg, 1.4 mmol) was added in one portion to a solution of 22B (320 mg, 1.4 mmol) in methylene chloride (10 mL). After stirring overnight the reaction mixture was concentrated in vacuo and purified by flash chromatography (0 to 100% EtOAc in hexanes) to yield 22C (430 mg, 88%) as a clear oil. MS (ESI) m/z 371.92/373.92 (M+H)$^+$.

22D: 4-(3-(3-(3-cyanophenyl)-1-methylureido)propyl)phenylboronic acid

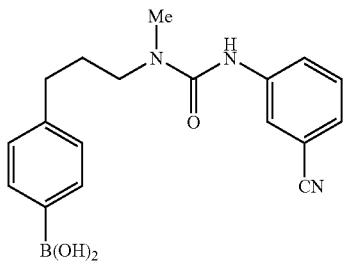

Using a procedure analogous to that used to prepare 6D, 22C (210 mg, 0.54 mmol) was reacted with 5,5',5'-tetramethyl-[2,2']bi[[1,3,2]dioxaborinanyl] to give 22D (146 mg, 91%) as a clear oil. MS (ESI) m/z 338.3 (M+H)$^+$.

22E: 2-(1-(bis(tert-butoxycarbonyl)amino)isoquinolin-6-ylamino)-2-(4-(3-(3-(3-cyanophenyl)-1-methylureido)propyl)phenyl)acetic acid

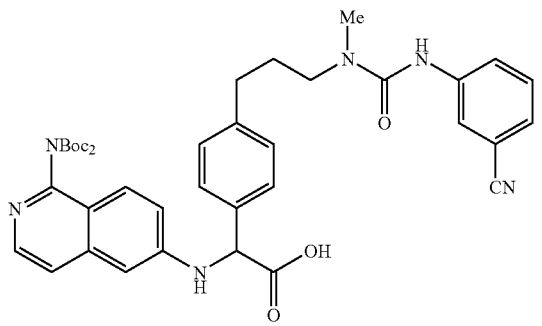

Using a procedure analogous to that used to prepare 2D, 22D (146 mg, 0.43 mmol) was reacted with Intermediate 1 and glyoxylic acid monohydrate to afford 22E (124 mg, 41%) as a yellow solid. MS (ESI) m/z 709.08 (M+H)$^+$.

22F: 2-(4-(3-(3-(3-(aminomethyl)phenyl)-1-methylureido)propyl)phenyl)-2-(1-(bis(tert-butoxycarbonyl)amino)isoquinolin-6-ylamino)acetic acid

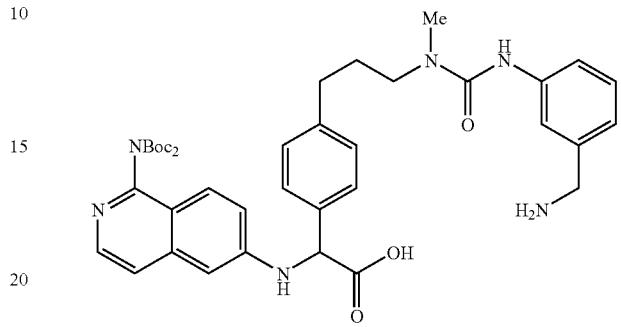

Using a procedure analogous to that used to prepare 6F, 22E (124 mg, 0.18 mmol) was hydrogenated for 14 h to give 22F (95 mg, 76%) as a yellow glass. MS (ESI) m/z 713.20 (M+H)$^+$.

Example 22

Using a procedure analogous to that used to prepare Example 6, 22F (94 mg, 0.12 mmol) was cyclized with BOP. This material was deprotected with trifluoroacetic acid, and purified by HPLC to give Example 22 (8 mg, 13%). $^1$H NMR (400 MHz, CD$_{30}$D) δ ppm 1.87-2.14 (m, 2 H) 2.57-2.78 (m, 2 H) 4.06 (dd, J=15.82, 4.39 Hz, 1 H) 4.77 (dd, J=16.26, 7.91 Hz, 1 H) 5.19-5.19 (m, 1 H) 5.34 (s, 1 H) 6.69 (d, J=1.76 Hz, 1 H) 6.78 (d, J=7.47 Hz, 1 H) 6.83 (d, J=7.03 Hz, 1 H) 7.08-7.15 (m, J=7.91, 7.91 Hz, 1 H) 7.22 (dd, J=9.23, 2.20 Hz, 1 H) 7.30 (d, J=7.03 Hz, 1 H) 7.32-7.39 (m, 2 H) 7.56-7.70 (m, J=8.79 Hz, 2 H) 7.73 (d, J=8.35 Hz, 1 H) 8.08 (d, J=8.79 Hz, 1 H) 8.86 (dd, J=7.91, 4.39 Hz, 1 H). MS (ESI) m/z 495.08 (M+H)$^+$.

Example 23

2-(1-Amino-isoquinolin-6-ylamino)-13-methyl-4,11,13-triaza-tricyclo[14.2.2.1$^{6,10}$]henicosa-1(19),6,8,10(21),16(20),17-hexaene-3,12-dione trifluoroacetic acid salt

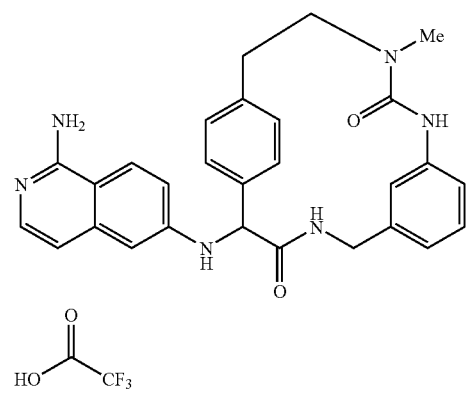

23A: 2-(4-bromophenyl)-N-methylacetamide

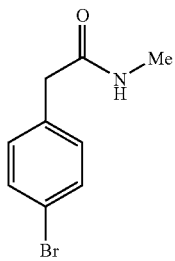

Using a procedure analogous to that used to prepare 22A, 2-(4-bromophenyl)acetic acid (1.6 g, 7.0 mmol) was coupled to methylamine to yield 23A (2.0 g, 75%) as a white solid. MS (ESI) m/z 228.20/230.20 (M+H)$^+$.

23B: 2-(4-bromophenyl)-N-methylethanamine

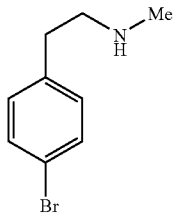

Using a procedure analogous to that used to prepare 22B, 23A (1.6 g, 7.0 mmol) was reduced with borane in THF to yield 23B (1.45 g, 97%) as a clear oil. MS (ESI) m/z 214.22/216.22 (M+H)$^+$.

23C: 1-(4-bromophenethyl)-3-(3-cyanophenyl)-1-methylurea

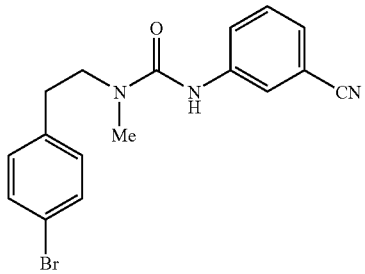

Using a procedure analogous to that used to prepare 22C, 23B (300 mg, 1.4 mmol) was reacted with 3-isocyanatobenzonitrile to yield 23C (406 g, 81%) as a clear oil. MS (ESI) m/z 358.31/360.29 (M+H)$^+$.

23D: 4-(2-(3-(3-cyanophenyl)-1-methylureido)ethyl)phenylboronic acid

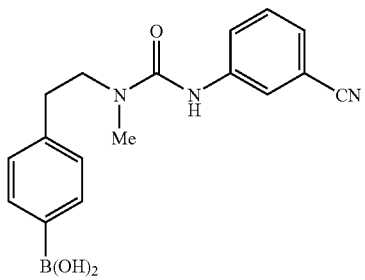

Using a procedure analogous to that used to prepare 6D, 23C (200 mg, 0.70 mmol) was reacted with 5,5',5'-tetramethyl-[2,2']bi[[1,3,2]dioxaborinanyl] to give 23D (165 mg, 91%) as a yellow oil. MS (ESI) m/z 324.03 (M+H)$^+$.

23E: 2-(1-(bis(tert-butoxycarbonyl)amino)isoquinolin-6-ylamino)-2-(4-(2-(3-(3-cyanophenyl)-1-methylureido)ethyl)phenyl)acetic acid

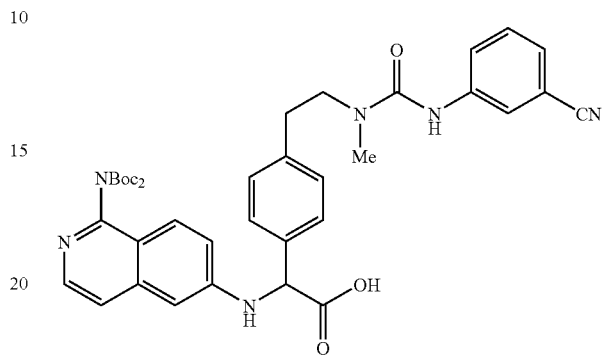

Using a procedure analogous to that used to prepare 2D, 23D (164 mg, 0.50 mmol) was reacted with Intermediate 1 and glyoxylic acid monohydrate to afford 23E (128 mg, 44%) as a yellow oil. MS (ESI) m/z 695.19 (M+H)$^+$.

23F: 2-(4-(2-(3-(3-(aminomethyl)phenyl)-1-methylureido)ethyl)phenyl)-2-(1-(bis(tert-butoxycarbonyl)amino)isoquinolin-6-ylamino)acetic acid

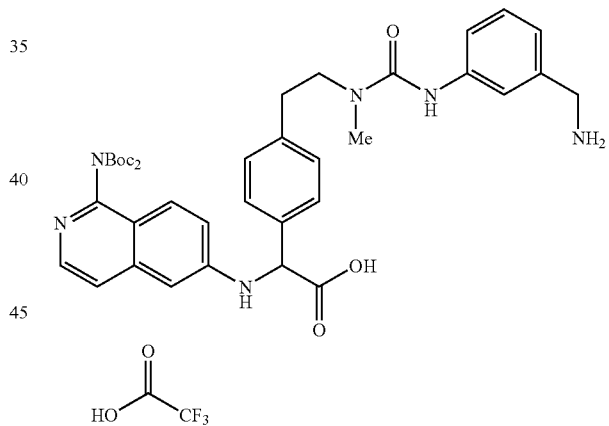

Using a procedure analogous to that used to prepare 6F, 23E (128 mg, 0.18 mmol) was hydrogenated for 14 h to give 23F (60 mg, 46%) as a yellow glass. MS (ESI) m/z 699.19 (M+H)$^+$.

Example 23

Using a procedure analogous to that used to prepare Example 6, 23F (60 mg, 0.084 mmol) was cyclized with BOP. This material was deprotected with trifluoroacetic acid, and purified by HPLC to give Example 23 (7 mg, 17%). $^1$H NMR (400 MHz, CD$_3$OD) δ ppm 2.79-2.96 (m, 2 H) 3.05 (s, 3 H) 4.02 (dd, J=16.04, 3.74 Hz, 1 H) 4.76 (dd, J=16.26, 7.47 Hz, 1 H) 4.91 (s, 1 H) 5.19 (s, 1 H) 5.67 (bs, 1 H) 6.66-6.72 (m, J=2.20 Hz, 1 H) 6.76-6.89 (m, 3 H) 7.05-7.14 (m, J=7.69, 7.69 Hz, 1 H) 7.14-7.25 (m, 2 H) 7.29 (d, J=7.03 Hz, 1 H) 7.32-

7.46 (m, 2 H) 7.61-7.73 (m, 1 H) 8.05 (d, J=9.23 Hz, 1 H) 8.65-8.78 (m, J=2.64 Hz, 1 H). MS (ESI) m/z 481.11 (M+H)$^+$.

Example 24

(R)-2-(1-Amino-isoquinolin-6-ylamino)-13-methyl-4,11,13-triaza-tricyclo[14.2.2.1$^{6,10}$]henicosa-1(19),6,8,10(21),16(20),17-hexaene-3,12-dione trifluoroacetic acid salt

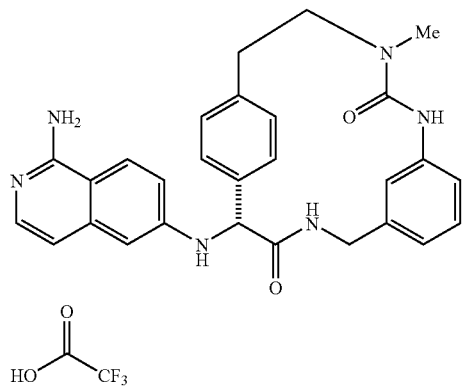

Example 23 (100 mg) was purified by chiral HPLC then again by reverse phase HPLC to give Example 24 (peak 1, 19 mg) and peak 2 (19 mg). The chromatography conditions were the following: Chiralcel OD-H (2.0 cm×25 cm, 5 micron, Chiral Technologies, Inc.), 30% MeOH/EtOH (1:1)/70% Heptane, 20 mL/min flow rate, and UV detection at 220 nm. Peak 1 analytical data: $^1$H NMR (400 MHz, CD$_3$OD) δ ppm 2.79-2.95 (m, 2 H) 3.05 (s, 3 H) 4.04 (d, J=16.26 Hz, 1 H) 4.70 (d, J=16.26 Hz, 1 H) 5.13 (s, 1 H) 6.60 (d, J=2.20 Hz, 1 H) 6.71 (d, J=6.15 Hz, 1 H) 6.77-6.88 (m, 2 H) 7.01-7.14 (m, 2 H) 7.22 (d, J=7.91 Hz, 1 H) 7.34 (d, J=7.47 Hz, 1 H) 7.41-7.51 (m, 2 H) 7.65 (dd, J=7.91, 1.76 Hz, 1 H) 7.88 (d, J=9.23 Hz, 1 H). MS (ESI) m/z 481.2 (M+H)$^+$. Chiral analytical HPLC retention times: peak 1, 8.05 min; peak 2, 10.45 min using the following chromatography conditions: Chiral OD (4.6×250 mm, 10 micron), 30% (1:1 ethanol methanol)/70% heptane as eluent, 1 mL/min flow rate and UV detection at 254 nm.

Example 25

(R)-2-(1-Amino-isoquinolin-6-ylamino)-7-ethanesulfonyl-13-methyl-4,11,13-triaza-tricyclo[14.2.2.1$^{6,10}$]henicosa-1(19),6,8,10(21),16(20),17-hexaene-3,12-dione

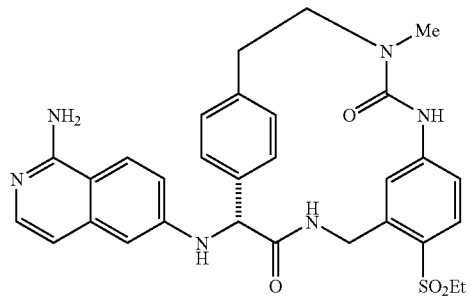

25A: phenyl 3-cyano-4-(ethylsulfonyl)phenylcarbamate

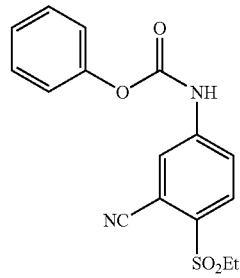

Phenylchloroformate (0.63 mL, 5 mmol) was added dropwise to a solution of 6B in methylene chloride (10 mL) and pyridine (0.60 mL, 7.1 mmol) at 0° C. After stirring for 1 h, the reaction mixture was partitioned between 1.0 M HCl (150 mL) and EtOAc (150 mL). The layers were separated and the organic phase was washed with saturated NaHCO$_3$, brine, dried over Na$_2$SO$_4$ and concentrated. The crude product was purified by flash chromatography (0% to 100% EtOAc in hexanes) to yield 25A (1.34 g, 85%) as a white solid. $^1$H NMR (400 MHz, CD$_3$OD) δ ppm 1.32 (t, J=7.45 Hz, 3 H) 3.36 (q, J=7.33 Hz, 2 H) 7.14-7.21 (m, J=7.58 Hz, 2 H) 7.26-7.31 (m, J=7.45, 7.45 Hz, 1 H) 7.37-7.45 (m, J=7.83, 7.83 Hz, 2 H) 7.66 (bs, 1 H) 7.83 (dd, J=8.72, 2.15 Hz, 1 H).

25B: 1-(4-bromophenethyl)-3-(3-cyano-4-(ethylsulfonyl)phenyl)-1-methylurea

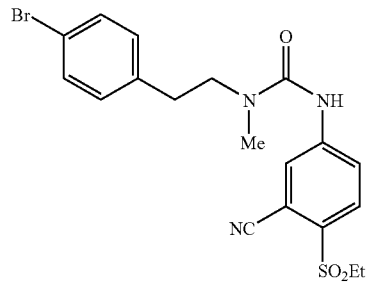

A solution of 25A (750 mg, 2.3 mmol) and 23B (486 mg, 4.5 mmol) with potassium carbonate (627 mg, 2.3 mmol) in DMF (6 mL) were heated at 50° C. for 15 h. The mixture was diluted with water (100 mL) and extracted with EtOAc (3×100 mL). The organics were washed with brine, dried over Na$_2$SO$_4$ and concentrated. The crude product was purified by flash chromatography (0% to 100% EtOAc in hexanes) to yield give 25B (950 mg, 93%) as a colorless oil. MS (ESI) m/z 449.89/451.91 (M+H)$^+$.

25C: 4-(2-(3-(3-cyano-4-(ethylsulfonyl)phenyl)-1-methylureido)ethyl)phenylboronic acid

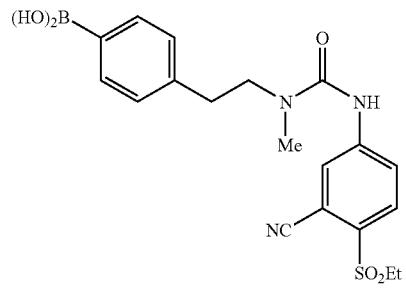

Using a procedure analogous to that used to prepare 6D, 25B (950 mg, 2.1 mmol) was reacted with 5,5',5'-tetramethyl-

[2,2']bi[[1,3,2]dioxaborinanyl] to give 25C (679 mg, 78%) as an white solid. MS (ESI) m/z 415.93 (M+H)+.

25D: 2-(1-(bis(tert-butoxycarbonyl)amino)isoquinolin-6-ylamino)-2-(4-(2-(3-(3-cyano-4-(ethylsulfonyl)phenyl)-1-methylureido)ethyl)phenyl)acetic acid

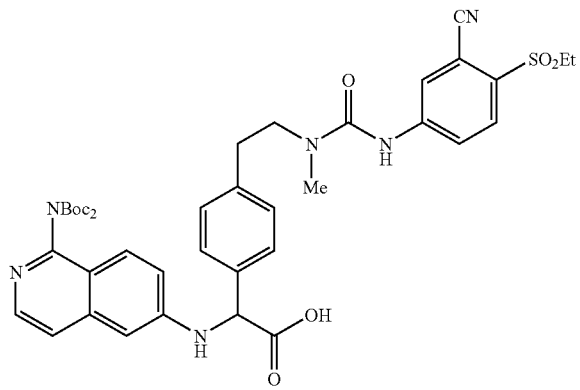

Using a procedure analogous to that used to prepare 2D, 25C (277 mg, 0.67 mmol) was reacted with Intermediate 1 and glyoxylic acid monohydrate to afford 25D (460 mg, 88%) as a yellow solid. MS (ESI) m/z 787.00 (M+H)+.

25E: 2-(4-(2-(3-(3-(aminomethyl)-4-(ethylsulfonyl)phenyl)-1-methylureido)ethyl)phenyl)-2-(1-(bis(tert-butoxycarbonyl)amino)isoquinolin-6-ylamino)acetic acid

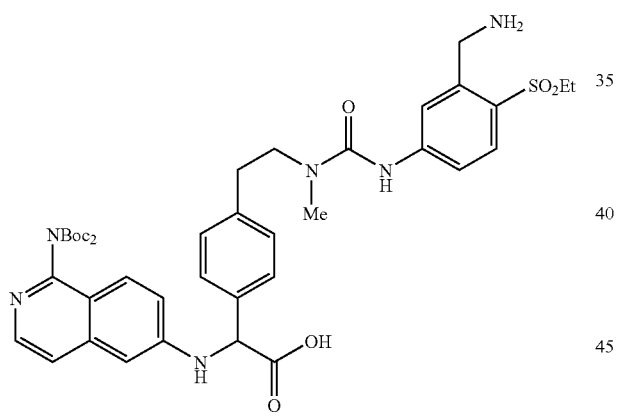

A solution of 25D (460 mg, 0.59 mmol) in MeOH (50 mL) with catalytic Raney Ni was stirred under an atmosphere of H$_2$ (70 psi) for 20 h. The reaction mixture was filtered through Celite and concentrated to give 25E (340 mg, 73%) as a yellow oil. MS (ESI) m/z 790.95 (M+H)+.

Example 25

BOP (380 mg, 0.86 mmol) and DIEA (0.375 mL, 2.2 mmol) were added to a solution of 25E (340 mg, 0.49 mmol) in CH$_2$Cl$_2$ (100 mL) and stirred for 15 h. The mixture was concentrated in vacuo. The residue was redissolved in CH$_2$Cl$_2$ (4 mL) and TFA (2 mL) with 5 drops of water and stirred at 40° C. for 1 h. The mixture was concentrated and purified by reverse phase HPLC and chiral HPLC to yield peak 1 (3.5 mg) and Example 25 (peak 2, 2.5 mg, 5%) as a white solid. The chromatography conditions were the following: Chiralcel OD-H (2.0 cm×25 cm, 5 micron, Chiral Technologies, Inc.), 24% MeOH/EtOH (1:1)/75% Heptane, 15 mL/min flow rate, and UV detection at 220 nm. Peak 2 analytical data $^1$H NMR (400 MHz, CD$_3$OD) δ ppm 1.22 (t, J=7.45 Hz, 3 H) 2.79-2.95 (m, 2 H) 3.08 (s, 3 H) 3.28 (q, J=7.45 Hz, 2 H) 4.19-4.38 (m, 1 H) 4.99-5.14 (m, J=24.25 Hz, 1 H) 5.23 (s, 1 H) 5.25 (none, 1 H) 6.71 (d, J=2.02 Hz, 1 H) 6.85 (d, J=7.07 Hz, 1 H) 7.01 (s, 1 H) 7.10-7.23 (m, J=9.22, 2.40 Hz, 2 H) 7.25-7.34 (m, J=7.07 Hz, 2 H) 7.37-7.46 (m, 1 H) 7.70 (d, J=8.59 Hz, 2 H) 8.06 (d, J=9.09 Hz, 1 H) 8.74-8.85 (m, 1 H). MS (ESI) m/z 572.93 (M+H)+. Chiral analytical HPLC retention times: peak 1, 19.26 min; peak 2, 21.62 min using the following chromatography conditions: Chiral OD (4.6×250 mm, 10 micron), 25% (1:1 ethanol/methanol)/75% heptane as eluent, 1 mL/min flow rate and UV detection at 254 nm.

Example 26

2-(1-Amino-isoquinolin-6-ylamino)-7-ethanesulfonyl-13-oxa-4,11-diaza-tricyclo[14.2.2.1$^{6,10}$]henicosa-1(19),6,8,10(21),16(20),17-hexaene-3,12-dione trifluoroacetic acid salt

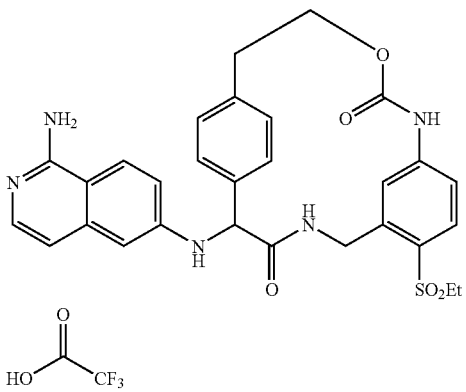

26A: 4-bromophenethyl 3-cyano-4-(ethylsulfonyl)phenylcarbamate

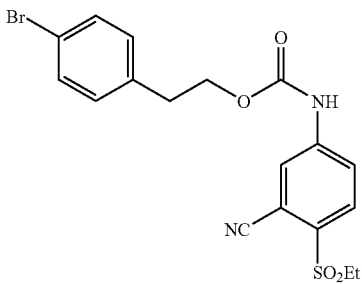

NaH (138 mg, 3.45 mmol, 60% dispersion in oil) was added to a solution of 2-(4-bromophenyl)ethanol (833 mg, 4.1 mmol) in THF (7 mL) at 0° C. and stirred for 10 min. The mixture was cooled to −40° C. and 25A (500 mg, 1.38 mmol) in THF (7 mL) was added. After stirring warming to 0° C. over 1 h and stirring at 0° C. for 3 h the mixture was partitioned between EtOAc and brine (100 mL each). The layers were separated and the organic layer washed with 5% NaOH, brine and concentrated in vacuo. The crude solid was purified by flash chromatography (0% to 50% EtOAc in Hexanes) to yield 26A (600 mg, 99%) as a white solid. $^1$H NMR (400 MHz, DMSO-D$_6$) δ ppm 1.12 (t, J=7.47 Hz, 2 H) 2.95 (t, J=6.59 Hz, 2 H) 3.38 (q, J=7.18 Hz, 2 H) 4.36 (t, J=6.59 Hz, 2 H) 7.27 (d, J=8.35 Hz, 2 H) 7.92 (dd, 1 H) 8.00 (d, 1 H) 8.08 (d, J=2.20 Hz, 1 H) 10.51 (s, 1 H).

117

26B: 4-(2-(3-cyano-4-(ethylsulfonyl)phenylcarbamoyloxy)ethyl)phenylboronic acid

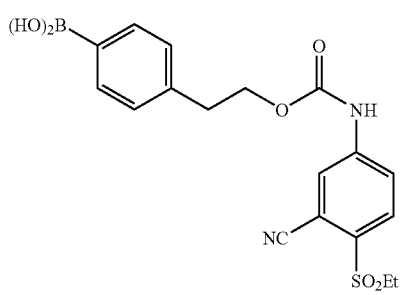

Using a procedure analogous to that used to prepare 6D, 26A (600 mg, 2.54 mmol) was reacted with 5,5',5'-tetramethyl-[2,2']bi[[1,3,2]dioxaborinanyl] to give 26B (455 mg, 82%) as a white solid. $^1$H NMR (400 MHz, CD$_3$OD) δ ppm 1.24 (t, J=7.47 Hz, 3 H) 3.01 (t, J=6.81 Hz, 2 H) 3.35 (q, J=7.32 Hz, 2 H) 4.42 (t, J=6.59 Hz, 2 H) 7.29 (d, J=7.91 Hz, 2 H) 7.56 (d, J=7.91 Hz, 2 H) 7.86 (dd, J=9.01, 1.98 Hz, 1 H) 7.99 (d, J=8.79 Hz, 1 H) 8.11 (d, J=2.20 Hz, 1 H) 10.12 (s, 1 H).

26C: 2-(1-(bis(tert-butoxycarbonyl)amino)isoquinolin-6-ylamino)-2-(4-(2-(3-cyano-4-(ethylsulfonyl)phenylcarbamoyloxy)ethyl)phenyl)acetic acid

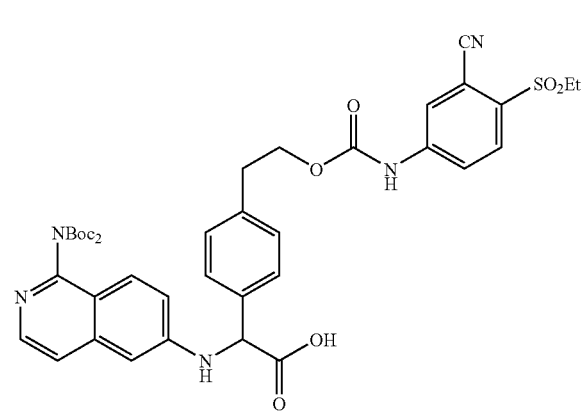

Using a procedure analogous to that used to prepare 2D, 26B (225 mg, 0.57 mmol) was reacted with Intermediate 1 and glyoxylic acid monohydrate to afford 26C (374 mg, 86%) as a yellow solid. MS (ESI) m/z 773.86 (M+H)$^+$.

118

26D: 2-(4-(2-(3-(aminomethyl)-4-(ethylsulfonyl)phenylcarbamoyloxy)ethyl)phenyl)-2-(1-(bis(tert-butoxycarbonyl)amino)isoquinolin-6-ylamino)acetic acid

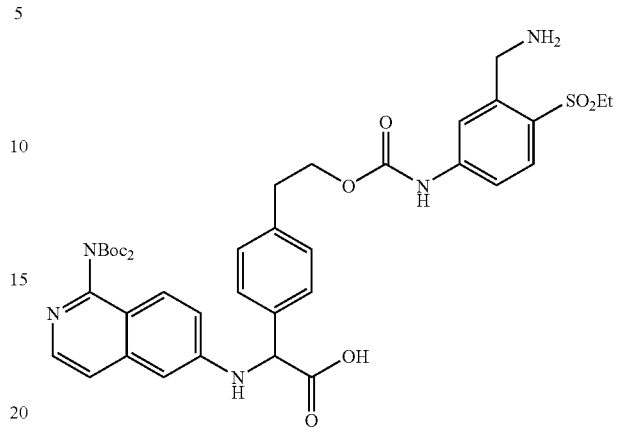

Using a procedure analogous to that used to prepare 25E, 26C (374 mg, 0.21 mmol) was hydrogenated for 15 h to give 26D (270 mg, 72%) as a yellow glass. MS (ESI) m/z 777.93 (M+H)$^+$.

Example 26

Using a procedure analogous to that used to prepare Example 25, 26D (270 mg, 0.35 mmol) was cyclized with BOP. This material was deprotected with trifluoroacetic acid, and purified by HPLC to give Example 26 (40 mg, 21%). $^1$H NMR (400 MHz, DMSO-D$_6$) δ ppm 1.12 (t, J=7.25 Hz, 3 H) 2.71-2.83 (m, 1 H) 2.85-3.01 (m, 1 H) 3.27-3.37(m, 2 H) 4.18(d, J=11.86 Hz, 2 H) 4.64-4.75(m, 1 H) 4.91 (dd, J=16.92, 6.37 Hz, 1 H) 5.20 (d, J=6.59 Hz, 1 H) 6.55 (d, J=2.20 Hz, 1 H) 6.66 (s, 1 H) 6.78-6.89 (m, 2 H) 7.02-7.13 (m, 2 H) 7.22-7.44 (m, 3H) 7.58 (d, J=7.03 Hz, 1 H) 7.63-7.72 (m, 2 H) 8.13 (d, J=9.23 Hz, 1 H) 8.42 (s, 2 H) 9.72 (s, 1 H) 12.40 (s, 1 H). MS (ESI) m/z 559.84 (M+H)$^+$.

Example 27

(R)-2-(1-Amino-isoquinolin-6-ylamino)-7-ethanesulfonyl-13-oxa-4,11-diaza-tricyclo[14.2.2.1$^{6,10}$]henicosa-1(19),6,8,10(21),16(20),17-hexaene-3,12-dione

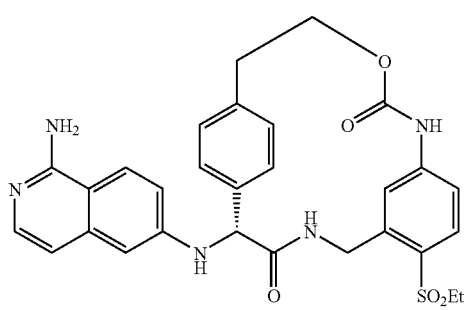

Example 26 (60 mg) was purified was purified by chiral HPLC to give peak 1 (14 mg) and Example 27 (peak 2, 14 mg). The chromatography conditions were the following: Whelk-O 1 (R,R) (500×21.1 mm ID; 10 micron, Regis Technologies), 60% MeOH/EtOH (1:1), 40% Heptane, 0.1% DEA, 15 mL/min flow rate, and UV detection at 254 nm. Peak 2 analytical data: $^1$H NMR (400 MHz, CD$_3$OD) δ ppm 1.22 (t, J=7.42 Hz, 3 H) 1.22 (t, J=7.42 Hz, 3 H) 2.82-3.01 (m, 2 H) 3.32-3.35 (m, 2 H) 4.15-4.24 (m, 1 H) 4.30 (d, J=17.04 Hz, 1 H) 4.76-4.83 (m, 1 H) 5.02 (d, J=17.04 Hz, 1 H) 5.13 (s, 1 H) 6.59 (d, J=2.20 Hz, 1 H) 6.66-6.75 (m, 2 H) 6.83 (dd, J=8.52, 1.92 Hz, 1 H) 6.99 (dd, J=9.07, 2.47 Hz, 1 H) 7.10-7.17 (m, 1 H) 7.19-7.25 (m, 1 H) 7.43 (dd, J=7.97, 1.37 Hz, 1 H) 7.51 (d, J=6.05 Hz, 1 H) 7.61 (dd, J=7.70, 1.65 Hz, 1 H) 7.73 (d, J=8.24 Hz, 1 H) 7.80 (d, J=8.79 Hz, 1 H). Chiral analytical HPLC retention times: peak 1, 17.75 min; peak 2, 20.50 min using the following chromatography conditions: Welko-O1 (R,R) column (250×4.6 mm ID; 5 micron, 60% MeOH/EtOH (1:1), 40% Heptane, 0.1% DEA as eluent, 1 mL/min flow rate and UV detection at 254 nm.

Example 28

3-(7-Ethanesulfonyl-13-methyl-3,12-dioxo-4,11,13-triaza-tricyclo[14.2.2.1$^{6,10}$]henicosa-1(19),6,8,10(21),16(20),17-hexaen-2-ylamino)-benzamide

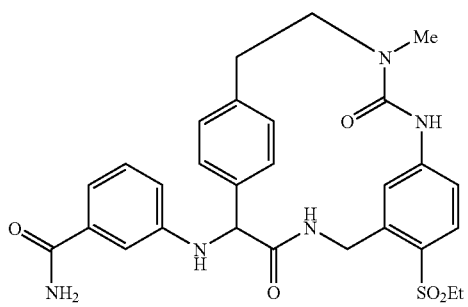

28A: Benzyl 5-amino-2-(ethylsulfonyl)benzylcarbamate

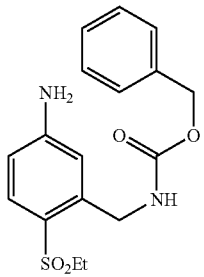

To a solution of 3-(aminomethyl)-4-(ethylsulfonyl)aniline (1.1 g, 5.1 mmol) in DMF (5 mL) and TEA (2.75 mL) was added benzyl 2,5-dioxopyrrolidin-1-yl carbonate (1.4 g, 5.7 mmol) in DCM (15 mL). The solution was stirred for 18 h before quenching with water (25 mL). The reaction mixture was extracted with DCM (2×30 mL), washed with brine and dried (MgSO$_4$). The organic layer was concentrated in vacuo and the residue purified by flash chromatography (0-100% EtOAc/Hexane) to afford 28A (1.0 g, 59%) as an oil. MS (ESI) m/z 349.2 (M+H)$^+$.

28B: 3-((benzyloxycarbonylamino)methyl)-4-(ethylsulfonyl)phenyl phenyl carbamic acid

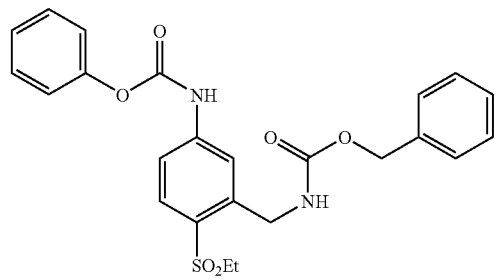

To a solution of 28A (1 g, 3 mmol), DCM (10 mL) and pyridine (10 mL) at 0° C. was added phenyl chloroformate (0.38 mL, 3 mmol) dropwise over 30 min. The reaction was quenched with 1 N HCl (50 mL) and extracted with EtOAc (3×30 mL). The combined organics were washed with saturated NaHCO$_3$, brine and dried (MgSO$_4$). The organic layer was concentrated in vacuo and the residue purified by flash chromatography (0-100% EtoAc/Hexane) to afford 28B (877 mg, 62%) as an oil. $^1$H NMR (400 MHz, CDCl$_3$) δ ppm 1.25 (t, 3 H) 5.06 (d, J=8.35 Hz, 4 H) 7.09-7.19 (m, 5 H) 7.31-7.36 (m, 5 H) 7.42-7.47 (m, 1 H) 7.70 (d, J=8.79 Hz, 1 H) 7.83 (d, J=8.35 Hz, 1 H).

28C: benzyl 4-bromophenethyl(methyl)carbamate

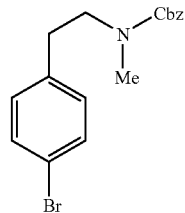

Benzyl chloroformate (0.97 mL, 6.7 mmol) was added dropwise to a solution of 23B (1.1 g, 5.1 mmol) in CH$_2$Cl$_2$ (26 mL) and triethylamine (1 mL, 7.5 mmol). The reaction mixture washed with brine, dried over Na$_2$SO$_4$ and concentrated in vacuo. Purification by flash chromatography (0% to 50% EtOAc in hexanes) afforded 28C (1.15 g, 65%) as a clear oil. $^1$H NMR (400 MHz, CDCl$_3$) δ ppm 2.70-2.94 (m, 5 H) 3.47 (m, 2 H) 5.08 (m, 2 H) 6.90-7.12 (m, 2 H) 7.26-7.44 (m, 7 H).

28D: 4-(2-((benzyloxycarbonyl)(methyl)amino)ethyl)phenylboronic acid

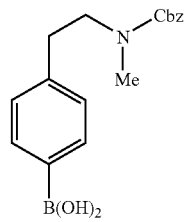

Using a procedure analogous to that used to prepare 6D, 28C (1.14 g, 3.3 mmol) was 5',5'-tetramethyl-[2,2']bi[[1,3,2]dioxaborinanyl] to give 28D (760 mg, 74%) as a white solid. MS (ESI) m/z 313.97 (M+H)$^+$.

28E: 2-(4-(2-((benzyloxycarbonyl)(methyl)amino) ethyl)phenyl)-2-(3-carbamoylphenylamino)acetic acid

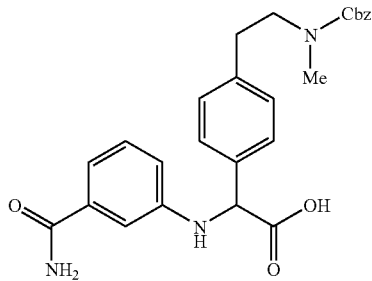

Using a procedure analogous to that used to prepare 2D, 28D (400 mg, 1.3 mmol) was reacted with 3-aminobenzamide and glyoxylic acid monohydrate to afford 28E (661 mg, 76%) as a yellow solid. MS (ESI) m/z 462.32 (M+H)$^+$.

28F: 2-(3-carbamoylphenylamino)-2-(4-(2-(methylamino)ethyl)phenyl)acetic acid

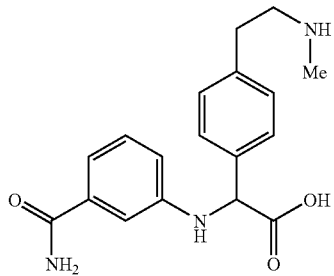

A solution of 28E (265 mg, 0.39 mmol) and Pd/C (10%, 40 mg) was stirred under H$_2$ (1 atm) for 15 h. The reaction was filtered through Celite and concentrated to yield 28F (126 mg, 99%) as a yellow oil. MS (ESI) m/z 328.29 (M+H)$^+$.

28G: 2-(4-(2-(3-(3-((benzyloxycarbonylamino)methyl)-4-(ethylsulfonyl)phenyl)-1-methylureido)ethyl) phenyl)-2-(3-carbamoylphenylamino)acetic acid

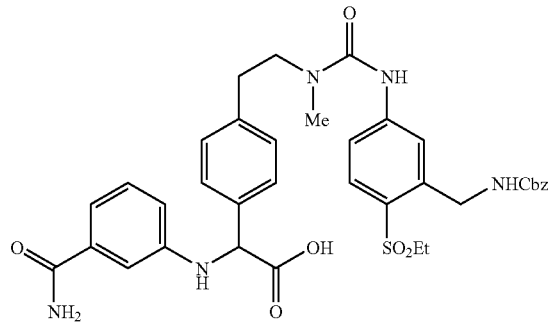

Using a procedure analogous to that used to synthesize 25B, 28F (227 mg, 0.69 mmol) was reacted with 28B to yield 28G (230 mg, 49%) as a yellow solid. MS (ESI) m/z 702.44 (M+H)$^+$.

28H: 2-(4-(2-(3-(3-(aminomethyl)-4-(ethylsulfonyl) phenyl)-1-methylureido)ethyl)phenyl)-2-(3-carbamoylphenylamino)acetic acid

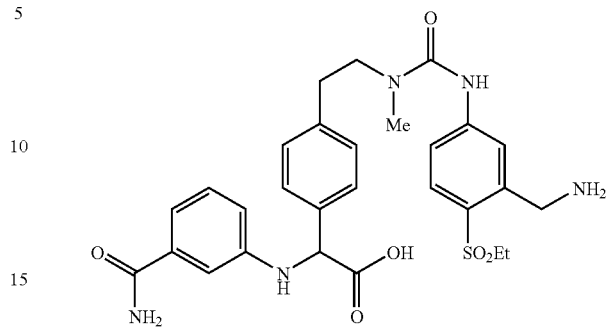

A solution of 28G (225 mg, 0.32 mmol) in THF/MeOH/EtOAc (1:1:1) and HCl (1.0 M, 1.5 mL) with Pd/C (50 mg, 10%) was stirred under H$_2$ (60 psi) for 20 h. The mixture was filtered through Celite and concentrated in vacuo to yield 28H (160 mg, 83%). MS (ESI) m/z 568.3 (M+H)$^+$.

Example 28

A solution of 28H (160 mg, 0.27 mmol) in DMF (4 mL) was added dropwise over 2 h to a solution of BOP (235 mg, 0.53 mmol), DMAP (162 mg, 1.33 mmol) and DIEA (0.23 mL, 1.33 mmol) at 40° C. After stirring an additional 2 h at rt, the mixture was concentrated in vacuo and purified by reverse phase HPLC to yield Example 28 (30 mg, 21%) as a white solid. $^1$H NMR (400 MHz, CD$_3$OD) δ ppm 1.22 (t, J=7.15 Hz, 3 H) 2.80-2.96 (m, 2 H) 3.06 (s, 3 H) 3.30 (m, 2 H) 4.18-4.40 (m, 1 H) 4.89-4.99 (m, 1 H) 5.07 (s, 1 H) 6.78-6.93 (m, 1 H) 7.04-7.22 (m, 5 H) 7.27-7.42 (m, 2 H) 7.62 (d, J=6.60 Hz, 1 H) 7.69 (d, J=8.24 Hz, 1 H) 8.82 (s, 1 H). MS (ESI) m/z 550.3 (M+H)$^+$.

Example 29

3-((R)-7-Ethanesulfonyl-13-methyl-3,12-dioxo-4,11, 13-triaza-tricyclo[14.2.2.1$^{6,10}$]henicosa-1(19),6,8,10 (21),16(20),17-hexaen-2-ylamino)-benzamide

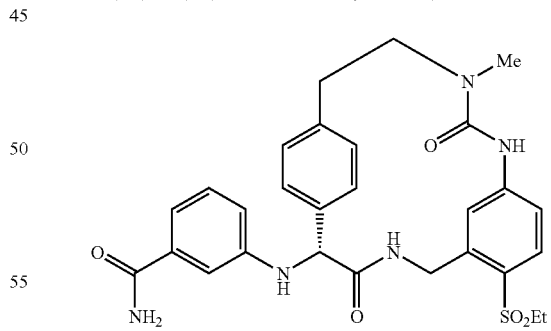

Example 28 (30 mg) was purified by chiral HPLC and then again by reverse phase HPLC to give peak 1 (5 mg) and Example 28 (peak 2, 5 mg). The chromatography conditions were the following: Chiralcel AD-H (2.0 cm×25 cm, 5 micron, Chiral Technologies, Inc.), 60% MeOH/EtOH (1:1)/40% Heptane, 15 mL/min flow rate, and UV detection at 220 nm. Peak 2 analytical data: $^1$H NMR (400 MHz, CD$_3$OD) δ ppm 1.21 (t, J=7.47 Hz, 3 H) 2.80-2.94 (m, J=3.08 Hz, 2 H) 3.06 (s, 3 H) 3.30 (m, 2 H) 4.18-4.40 (m, 1 H) 4.91-4.99 (m, 1 H) 5.07 (s, 1 H) 6.73-6.85 (m, 1 H) 6.93-7.20 (m, 5 H) 7.26-7.40 (m, J=7.47 Hz, 2 H) 7.63 (d, J=6.59 Hz, 1 H) 7.69 (d, J=8.79 Hz, 1 H). MS (ESI) m/z 550.21 (M+H)$^+$. Chiral analytical HPLC retention times: peak 1, 13.42 min; peak 2, 18.30 min using the following chromatography conditions: Chiral AD (4.6×250 mm, 10 micron), 40% (1:1 ethanol/methanol)/60% heptane as eluent, 1 mL/min flow rate and UV detection at 254 nm.

Example 30

2-(1-Amino-isoquinolin-6-ylamino)-20-methyl-13-oxa-4,11-diaza-tricyclo[14.2.2.1$^{6,10}$]henicosa-1(19),6,8,10(21),16(20),17-hexaene-3,12-dione trifluoroacetic acid salt

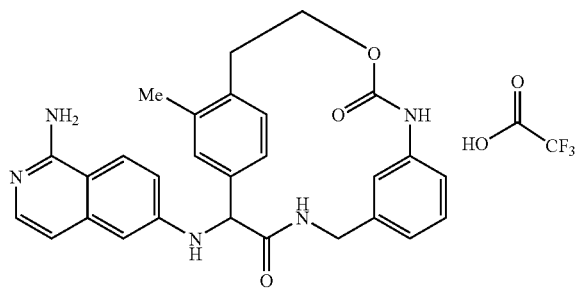

30A: 4-bromo-2-methyl-1-vinylbenzene

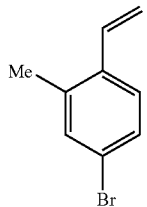

KF (870 mg, 15 mmol), n-Bu$_4$NCl (2.77 g, 10 mmol), Pd(dba)$_2$ (145 mg, 0.25 mmol), molecular sieves (4 Ang, 200 mg, activated balls), 5-bromo-2-iodo-1-methylbenzene (1.49 g, 5 mmol), trimethyl(vinyl)silane (2.7 mL, 20 mmol), and toluene (10 mL) were added to a pressure vessel and sparged with Ar. The vial was sealed and microwaved at 170° C. for 30 min. The mixture was cooled to ambient temperature, diluted with hexanes, filtered and concentrated. The crude oil was purified by flash chromatography (100% hexanes) to yield 30A (750 mg, 76%) as a clear oil. $^1$H NMR (400 MHz, CDCl$_3$) δ ppm 2.31 (s, 3 H) 5.31 (dd, J=10.99, 1.10 Hz, 1 H) 5.62 (dd, J=17.59, 1.10 Hz, 1 H) 6.84 (dd, J=17.04, 10.99 Hz, 1 H) 7.26-7.35 (m, 3 H).

30B: 2-(4-bromo-2-methylphenyl)ethanol

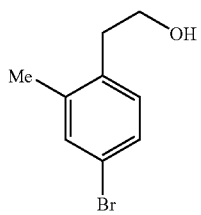

A solution of 30A (1.5 g, 7.6 mmol) in 0.5 M 9-BBN in THF (40 mL, 20 mmol) was heated at 120° C. in a sealed tube for 15 min in a microwave. The mixture was cooled to 0° C. in a 250 mL Erlenmeyer flask. NaOH (1.0 M, 40 mL) then H$_2$O$_2$ (30%, 40 mL) were added slowly dropwise while maintaining the internal temperature below 30° C. HCl (1.0 M, 40 mL) was added and the mixture was extracted with Et$_2$O (2×100 mL). The organics were combined, washed with NaHCO$_3$, brine, dried over Na$_2$SO$_4$ and concentrated in vacuo. The crude oil was purified by flash chromatography (0% to 50% hexanes in EtOAc) to yield 30B (1.05 g, 64%) as a clear oil. $^1$H NMR (400 MHz, MeOD) δ ppm 2.30 (s, 3 H) 2.80 (t, J=7.20 Hz, 2 H) 3.69 (t, J=7.07 Hz, 2 H) 7.06 (d, J=8.08 Hz, 1 H) 7.23 (dd, J=8.21, 1.89 Hz, 1 H) 7.28-7.31 (m, 1 H).

30C: 4-bromo-2-methylphenethyl 3-cyanophenylcarbamate

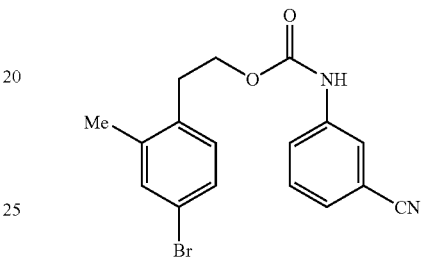

NaH (150 mg, 60% dispersion in oil) was added portionwise to a solution of 30B (570 mg, 2.65 mmol) in THF (26.5 mL) and the mixture was stirred for 30 min. The solution was cooled to −78° C. and 3-isocyanatobenzonitrile (382 mg, 2.65 mmol) was added in one portion. The cooling bath was removed and the reaction was stirred for 2 h. Water (100 mL) was added to the reaction mixture and it was extracted with EtOAc (2×75 mL). The organics were combined, washed with brine, dried over Na$_2$SO$_4$ and concentrated in vacuo. The crude product was purified by flash chromoatography (0 to 100% EtOAc in hexanes) to yield 30C (590 mg, 62%). $^1$H NMR (400 MHz, DMSO-D$_6$) δ ppm 2.30 (s, 3 H) 2.92 (t, J=6.95 Hz, 2 H) 4.28 (t, J=6.95 Hz, 2 H) 7.17 (d, J=8.34 Hz, 1 H) 7.32 (dd, J=8.21, 1.89 Hz, 1 H) 7.39 (d, J=1.77 Hz, 1 H) 7.41-7.55 (m, 2 H) 7.70 (d, J=8.08 Hz, 1 H) 7.85 (s, 1 H) 9.97 (s, 1 H).

30D: 4-(2-(3-cyanophenylcarbamoyloxy)ethyl)-3-methylphenylboronic acid

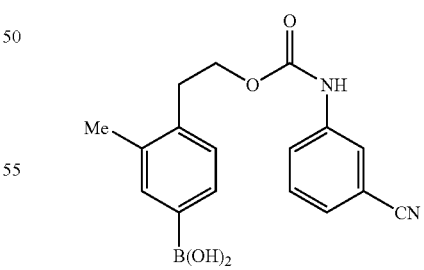

Using a procedure analogous to that used to prepare 6D, 30C (730 mg, 2.0 mmol) was reacted with 5,5',5'-tetramethyl-[2,2']bi[[1,3,2]dioxaborinanyl] to give 30D (420 mg, 64%) as a brown oil. $^1$H NMR (400 MHz, MeOD) δ ppm 2.29 (s, 3 H) 2.94 (t, J=7.07 Hz, 2 H) 4.26 (t, J=7.07 Hz, 2 H) 7.11 (d, J=7.33 Hz, 1 H) 7.24 (d, J=7.58 Hz, 1 H) 7.33 (t, J=7.96 Hz, 1 H) 7.36-7.52 (m, 2 H) 7.56 (d, J=7.83 Hz, 1 H) 7.77 (s, 1 H).

30E: 2-(1-(bis(tert-butoxycarbonyl)amino)isoquinolin-6-ylamino)-2-(4-(2-(3-cyanophenylcarbamoyloxy)ethyl)-3-methylphenyl)acetic acid

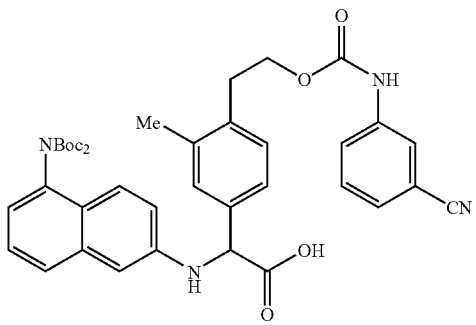

Using a procedure analogous to that used to prepare 2D, 30D (420 mg, 1.30 mmol) was reacted with Intermediate 1 and glyoxylic acid monohydrate to afford 30E (308 mg) as a tan solid. MS (ESI) m/z 696.15 (M+H)+.

30F: 2-(4-(2-(3-(aminomethyl)phenylcarbamoyloxy)ethyl)-3-methylphenyl)-2-(1-(bis(tert-butoxycarbonyl)amino)isoquinolin-6-ylamino)acetic acid

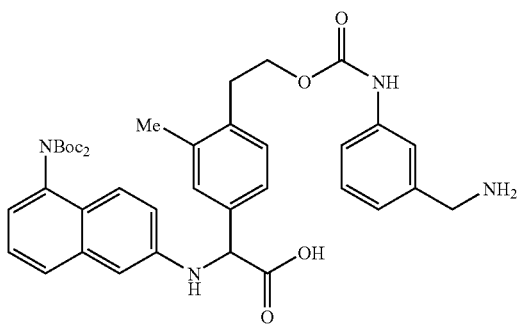

Using a procedure analogous to that used to prepare 25E, 30E (308 mg, 0.44 mmol) was hydrogenated for 15 h and purified by reverse phase HPLC to give 30F (140 mg, 45%) as a yellow solid. MS (ESI) m/z 700.15 (M+H)+.

Example 30

Using a procedure analogous to that used to prepare Example 28, 30F (140 mg, 0.2 mmol) was cyclized with PyBOP instead of BOP, deprotected with TFA, and purified by reverse phase HPLC to give Example 30 (40 mg, 42%) as a white solid. $^1$H NMR (400 MHz, CD$_3$OD) δ ppm 2.32 (s, 1.5 H) 2.48 (s, 1.5 H) 2.70-2.88 (m, 1 H) 3.04-3.22 (m, 1 H) 3.88-4.23 (m, 2 H) 4.41-4.61 (m, 1 H) 4.64-4.80 (m, 1 H) 5.09-5.17 (m, J=3.54 Hz, 1 H) 6.09-6.26 (m, J=12.13 Hz, 1 H) 6.61-6.72 (m, 2 H) 6.72-6.83 (m, J=12.88, 7.07 Hz, 1 H) 6.83-6.94 (m, J=7.58 Hz, 1 H) 7.03-7.20 (m, 3 H) 7.21-7.33 (m, 2 H) 7.36-7.54 (m, 1 H) 7.98-8.10 (m, J=9.09, 5.05 Hz, 1 H) 8.50-8.70 (m, 1 H), mixture of two atropisomers. MS (ESI) m/z 482.20 (M+H)+.

Example 31

2-(1-Amino-isoquinolin-6-ylamino)-7-ethanesulfonyl-20-methyl-13-oxa-4,11-diaza-tricyclo[14.2.2.1$^{6,10}$]henicosa-1(19),6,8,10(21),16(20),17-hexaene-3,12-dione trifluoroacetic acid salt

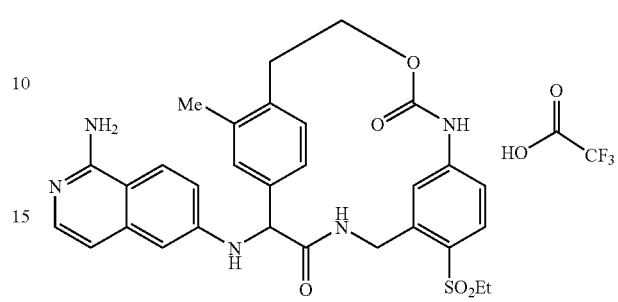

31A: 4-bromo-2-methylphenethyl 3-cyano-4-(ethylsulfonyl)phenylcarbamate

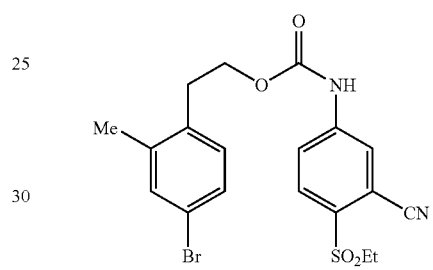

NaH (230 mg, 4.4 mmol, 60% disperson in oil) was added portionwise to a solution of 30B (490 mg, 2.3 mmol) in THF (12 mL) and the mixture was stirred for 30 min. The solution was cooled to −40° C. and 25A (760 mg, 2.3 mmol) was added in one portion. The cooling bath was removed and the reaction was stirred for 2 h. The reaction mixture was cooled to −40° C. and quenched by the addition of NH$_4$Cl (5 mL, sat. aq.). The resulting mixture was partitioned between water (50 mL) and EtOAc (100 mL). The organic phase washed with brine, dried over Na$_2$SO$_4$ and concentrated in vacuo. The crude product was purified by flash chromoatography (0 to 100% EtOAc in hexanes) to yield 31A (745 mg, 72%) as a white solid. $^1$H NMR (400 MHz, MeOD) δ ppm 1.94 (t, J=7.42 Hz, 3 H) 3.11 (s, 3 H) 4.19 (q, J=7.15 Hz, 2 H) 5.14 (t, J=6.87 Hz, 2 H) 7.99 (d, J=8.24 Hz, 1 H) 8.14 (dd, J=7.70, 2.20 Hz, 1 H) 8.21 (d, J=1.65 Hz, 1 H) 8.72-8.77 (m, 1 H) 8.79-8.84 (m, 1 H) 8.90 (d, J=2.20 Hz, 1 H).

31B: 4-(2-(3-cyano-4-(ethylsulfonyl)phenylcarbamoyloxy)ethyl)-3-methylphenylboronic acid

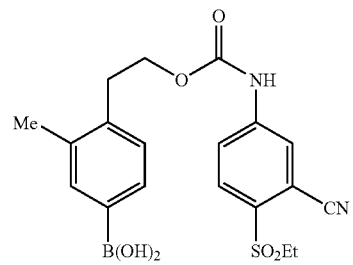

Using a procedure analogous to that used to prepare 6D, 31A (745 mg, 1.66 mmol) was reacted with 5,5',5'-tetramethyl-[2,2']bi[[1,3,2]dioxaborinanyl] to give 31B (468 mg, 68%) as a tan foam. $^1$H NMR (400 MHz, MeOD) δ ppm 1.25 (t, J=7.33 Hz, 3 H) 2.34-2.40 (m, 3 H) 3.03 (t, J=6.95 Hz, 2 H) 3.35 (q, J=7.33 Hz, 2 H) 4.39 (t, J=7.07 Hz, 2 H) 7.20 (d, J=7.33 Hz, 1 H) 7.30-7.43 (m, 2 H) 7.86 (dd, J=8.84, 1.77 Hz, 1 H) 7.99 (d, J=8.84 Hz, 1 H) 8.11 (d, J=2.02 Hz, 1 H) 10.05 (s, 1 H).

31C: 2-(1-(bis(tert-butoxycarbonyl)amino)isoquinolin-6-ylamino)-2-(4-(2-(3-cyano-4-(ethylsulfonyl)phenylcarbamoyloxy)ethyl)-3-methylphenyl)acetic acid

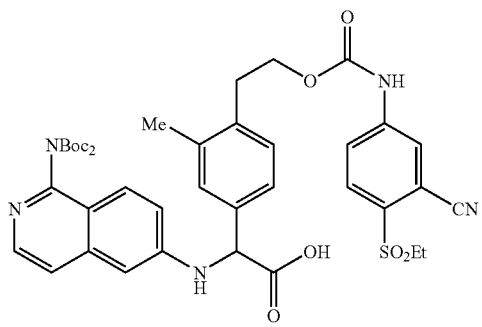

Using a procedure analogous to that used to prepare 2D, 31B (468 mg, 1.1 mmol) was reacted with Intermediate 1 and glyoxylic acid monohydrate to afford 31C (419 mg, 44%) as a pale yellow solid. MS (ESI) m/z 788.07 (M+H)$^+$.

31D: 2-(4-(2-(3-(aminomethyl)-4-(ethylsulfonyl)phenylcarbamoyloxy)ethyl)-3-methylphenyl)-2-(1-(bis(tert-butoxycarbonyl)amino)isoquinolin-6-ylamino)acetic acid

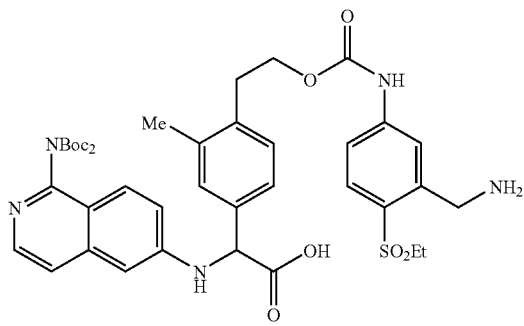

Using a procedure analogous to that used to prepare 25E, 31C (419 mg) was hydrogenated for 15 h to give 31D (400 mg, 95%) as a yellow glass. MS (ESI) m/z 792.43 (M+H)$^+$.

Example 31

Using a procedure analogous to that used to prepare Example 28, 31D (400 mg, 0.51 mmol) was cyclized with PyBOP instead of BOP, deprotected with TFA, and purified by reverse phase HPLC to give Example 31 (100 mg, 35%) as a tan solid. $^1$H NMR (400 MHz, CD$_3$OD) δ ppm 1.09-1.24 (m, 3 H) 2.27 (s, 2 H) 2.49 (s, 2 H) 2.67-2.88 (m, 1 H) 3.05-3.17 (m, 1 H) 3.22-3.28 (m, 2 H) 4.05 (d, J=9.89 Hz, 0.5 H) 4.13-4.25 (m, 0.5 H) 4.29-4.39 (m, 1 H) 5.01-5.12 (m, 2 H) 5.14-5.18 (m, J=3.30 Hz, 1 H) 6.43 (none, 1 H) 6.68 (d, J=2.75 Hz, 1 H) 6.70-6.78 (m, J=5.50 Hz, 1 H) 6.78-6.86 (m, 1 H) 6.92-7.16 (m, 2.5 H) 7.21 (m, 0.5 H) 7.44 (m, 0.5 H) 7.51 (s, 0.5 H) 7.65-7.74 (m, 1 H) 7.90-8.02 (m, 1 H) 8.76-8.92 (m, J=6.05 Hz, 1 H). MS (ESI) m/z 574.18 (M+H)$^+$.

Example 32

2-(1-Amino-isoquinolin-6-ylamino)-7-ethanesulfonyl-17,20-dimethyl-13-oxa-4,11-diaza-tricyclo[14.2.2.1$^{6,10}$]henicosa-1(19),6,8,10(21),16(20),17-hexaene-3,12-dione trifluoroacetic acid salt

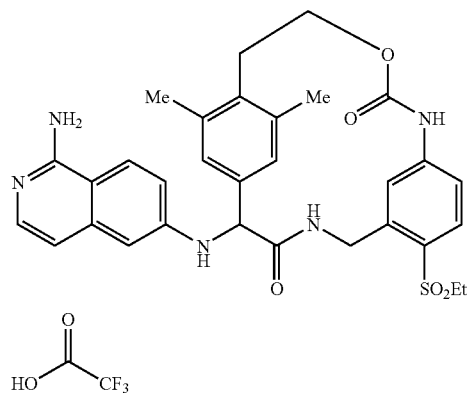

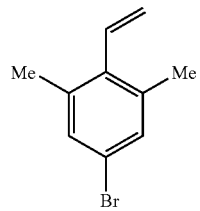

32A: 5-bromo-1,3-dimethyl-2-vinylbenzene

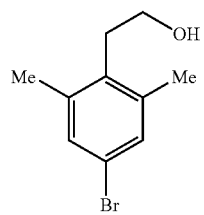

Using a procedure analogous to that used to prepare 30A, 5-bromo-2-iodo-1,3-dimethylbenzene (15.6 g, 48 mmol) was reacted with trimethyl(vinyl)silane in a pressure vessel at 160° C. for 1 h to yield 32A (10.0 g, 94%) as a clear oil. $^1$H NMR (400 MHz, CDCl$_3$) δ ppm 2.26 (s, 6 H) 5.24 (dd, J=17.86, 1.92 Hz, 1 H) 5.55 (dd, J=11.54, 2.20 Hz, 1 H) 7.18 (s, 2 H).

32B: 2-(4-bromo-2,6-dimethylphenyl)ethanol

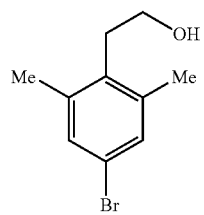

Using a procedure analogous to that used to prepare 30B, 32A was heated in a pressure vessel with 9-BBN at 100° C. for 10 h to yield 32B (6.7 g, 62%) as a clear oil. $^1$H NMR (400

MHz, CDCl$_3$) δ ppm 2.31 (s, 6 H) 2.89 (t, J=7.33 Hz, 2 H) 3.73 (t, J=7.33 Hz, 2 H) 7.16 (s, 2 H).

32C: 4-bromo-2,6-dimethylphenethyl 3-cyano-4-(ethylsulfonyl)phenylcarbamate

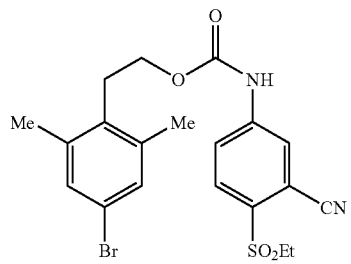

Using a procedure analogous to that used to prepare 31A, 32B (400 mg, 1.75 mmol) was reacted with 25A (579 mg, 1.75 mmol) to give 32C (480 mg, 59%) as a white solid. MS (ESI) m/z 465.1/467.1 (M+H)$^+$.

32D: 4-(2-(3-cyano-4-(ethylsulfonyl)phenylcarbamoyloxy)ethyl)-3,5-dimethylphenylboronic acid

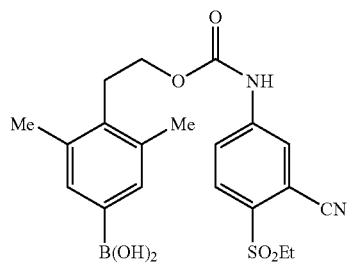

Using a procedure analogous to that used to prepare 6D, 32C (480 mg, 1.0 mmol) was reacted with 5,5',5'-tetramethyl-[2,2']bi[[1,3,2]dioxaborinanyl] to give 32D (240 mg, 54%) as a tan solid. MS (ESI) m/z 453.12 (M+Na)$^+$.

32E: 2-(1-(bis(tert-butoxycarbonyl)amino)isoquinolin-6-ylamino)-2-(4-(2-(3-cyano-4-(ethylsulfonyl)phenylcarbamoyloxy)ethyl)-3,5-dimethylphenyl)acetic acid

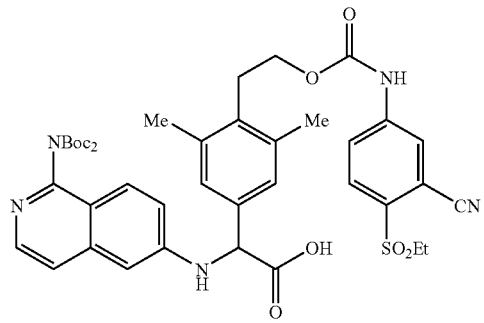

Using a procedure analogous to that used to prepare 2D, 32D (240 mg, 0.56 mmol) was reacted with Intermediate 1 and glyoxylic acid monohydrate to afford 32E (560 mg, 69%) as a yellow solid. MS (ESI) m/z 802.07 (M+H)$^+$.

32F: 2-(4-(2-(3-(aminomethyl)-4-(ethylsulfonyl)phenylcarbamoyloxy)ethyl)-3,5-dimethylphenyl)-2-(1-(bis(tert-butoxycarbonyl)amino)isoquinolin-6-ylamino)acetic acid

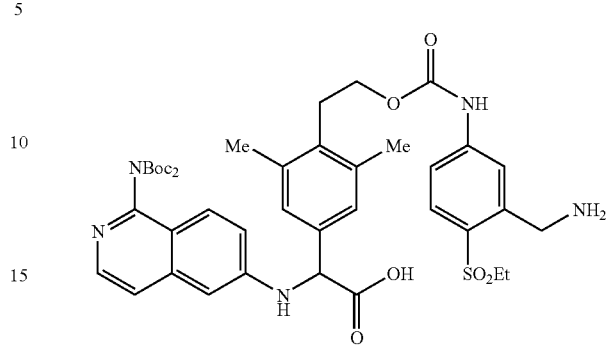

Using a procedure analogous to that used to prepare 6F, 32E (560 mg, 0.70) was hydrogenated for 14 h to give 32F (547 mg, 97%) as a yellow solid. MS (ESI) m/z 806.12 (M+H)$^+$.

Example 32

Using a procedure analogous to that used to prepare Example 28, 32F (547 mg, 0.68 mmol) was cyclized with PyBOP instead of BOP, deprotected with TFA, and purified by reverse phase HPLC to give Example 32 (139 mg, 35%) as a tan solid. $^1$H NMR (400 MHz, CD$_3$OD) δ ppm 1.18 (t, J=7.42 Hz, 3 H) 2.26 (s, 3 H) 2.48 (s, 3 H) 2.87-2.98 (m, 1 H) 3.07-3.18 (m, 1 H) 3.19-3.28 (m, 2 H) 4.03-4.36 (m, 2 H) 5.03-5.08 (m, 2 H) 5.11 (s, 1 H) 6.64 (d, J=13.74 Hz, 2 H) 6.68-6.76 (m, 1 H) 6.80 (d, J=8.25 Hz, 1 H) 6.93 (s, 1 H) 7.07 (d, J=9.34 Hz, 1 H) 7.20 (d, J=6.60 Hz, 1 H) 7.36 (s, 1 H) 7.70 (d, J=8.24 Hz, 1 H) 7.94 (d, J=7.70 Hz, 1 H) 7.96 (none, 1 H) 8.70-8.87 (m, 1 H). MS (ESI) m/z 589.21 (M+H)$^+$.

Example 33

(R)-2-(1-Amino-isoquinolin-6-ylamino)-7-ethanesulfonyl-17,20-dimethyl-13-oxa-4,11-diaza-tricyclo[14.2.2.1$^{6,10}$]henicosa-1(19),6,8,10(21),16(20),17-hexaene-3,12-dione

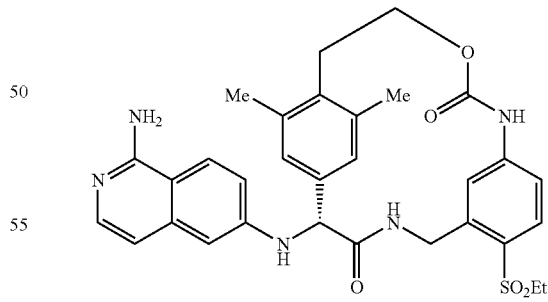

Example 32 (139 mg) was purified was purified by chiral HPLC then again by reverse phase HPLC to give peak 1 (40 mg) and Example 32 (peak 2, 35 mg). The chromatography conditions were the following: Chiralcel OD-H (2.0 cm×25 cm, 5 micron, Chiral Technologies, Inc.), 40% MeOH/EtOH (1:1)/60% Heptane, 15 mL/min flow rate, and UV detection at 220 nm. Peak 2 analytical data: $^1$H NMR (400 MHz, CD$_3$OD) δ ppm 2.27 (s, 3 H) 2.48 (s, 3 H) 2.86-2.95 (m, J=13.19 Hz, 1

H) 3.07-3.20 (m, 1 H) 3.21-3.33 (m, 2 H) 4.04-4.40 (m, 2 H) 4.94-5.02 (m, 2 H) 5.05 (s, 1 H) 6.60 (d, J=1.65 Hz, 1 H) 6.66 (d, J=1.65 Hz, 1 H) 6.71 (d, J=6.60 Hz, 1 H) 6.80 (dd, J=8.24, 2.20 Hz, 1 H) 6.95 (s, 1 H) 7.02 (dd, J=9.07, 1.92 Hz, 1 H) 7.33 (s, 1 H) 7.40 (d, J=6.05 Hz, 1 H) 7.72 (d, J=8.25 Hz, 1 H) 7.85 (d, J=9.34 Hz, 1 H). MS (ESI) m/z 588.2 (M+H)$^+$. Chiral analytical HPLC retention times: peak 1, 7.55 min; peak 2, 10.87 min using the following chromatography conditions: Chiral AD (4.6×250 mm, 10 micron), 40% (1:1 ethanol methanol)/60% heptane/0.1% DEA as eluent, 0.7 mL/min flow rate and UV detection at 270 nm.

Example 34

[(S)-2-(1-Amino-isoquinolin-6-ylamino)-20-methyl-3,12-dioxo-13-oxa-4,11-diaza-tricyclo[14.2.2.1$^{6,10}$]henicosa-1(19),6,8,10(21),16(20),17-hexaen-5-yl]-acetic acid ethyl ester trifluoroacetic acid salt

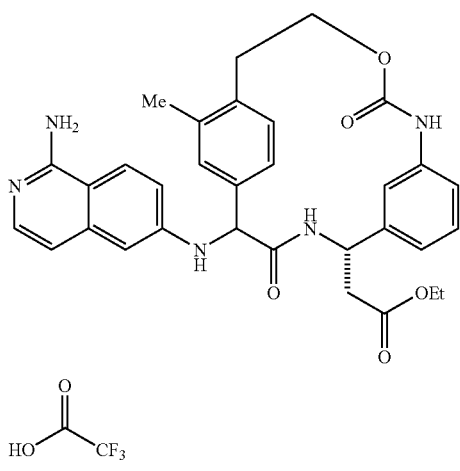

34A: (S)-ethyl 3-amino-3-(3-nitrophenyl)propanoate hydrochloride salt

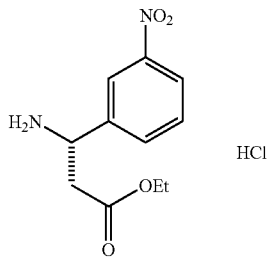

(S)-3-Amino-3-(3-nitrophenyl)propanoic acid (500 mg, 2.4 mmol) was dissolved in 2.0HCl in dioxane (2 mL) and concentrated in vacuo. In a separate flask thionyl chloride (0.21 mL, 2.8 mmol) was added to ethanol at −10° C. The ethanolic solution was stirred for 20 min at −10° C. then added to the HCl salt of (S)-3-amino-3-(3-nitrophenyl)propanoic acid. The resulting solution was stirred at ambient temperature for 1 h and at 40° C. for 3 h. The reaction mixture was concentrated in vacuo to yield 34A (600 mg, 92%) as a white solid. MS (ESI) m/z 239.09 (M+H)$^+$.

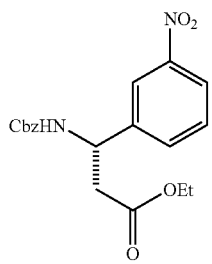

N-(Benzyloxycarbonyloxy)succinimide (1.3 g, 5.2 mmol) was added to a solution of 34A (1.3 g, 4.7 mmol) and DIEA in CH$_2$Cl$_2$ (20 mL). The resulting solution was stirred for 1 h at ambient temperature then diluted with CH$_2$Cl$_2$ (40 mL), washed with ammonium chloride, NaHCO$_3$, brine, dried over Na$_2$SO$_4$ and concentrated in vacuo. The crude material was purified by flash chromatography (0% to 60% EtOAc in hexanes) to yield 34B (1.49 g, 70%) as a clear oil. MS (ESI) m/z 395.07 (M+Na)$^+$.

34C: (S)-ethyl 3-(3-aminophenyl)-3-(benzyloxycarbonylamino)propanoate

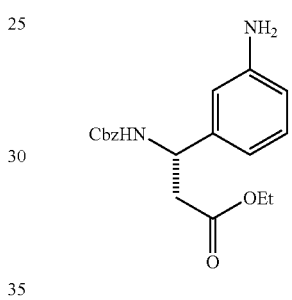

Fe (1 g, 18.5 mmol, powder) was added portionwise to a refluxing solution of 34B (1.38 g, 3.7 mmol) in EtOH (75 mL)/water (16 mL)/AcOH (4 mL). After refluxing for 1 h, the reaction mixture was cooled to ambient temperature. The mixture was neutralized with saturated NaHCO$_3$, diluted with water and extracted with EtOAc. The combined organics were washed with brine and concentrated. The crude solid was purified by flashchromatography (0% to 100% EtOAc in hexanes) to yield 34C (1.19 g, 94%) as a yellow solid. 343.23 (M+H)$^+$.

34D: (S)-ethyl 3-(benzyloxycarbonylamino)-3-(3-((4-bromo-2-methylphenethoxy)carbonylamino)phenyl)propanoate

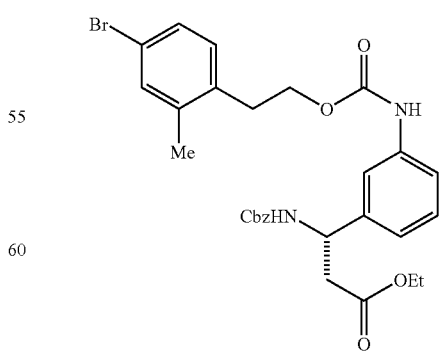

Phosgene (3.5 mmol, 1.75 mL, 20% in toluene) was added to a solution of 34C (600 mg, 1.75 mmol) and NaHCO$_3$ (1.47 g, 17.5 mmol) at 0° C. After stirring for 1 h at rt, the solution was filtered and concentrated in vacuo. 30B (375 mg, 1.75 mmol) in THF (20 mL) was added to the crude isocyanate and the solution was cooled to −45° C. NaH (93 mg) was added in one portion and the mixture was warmed to 0° C. and stirred for 2 h at 0° C. and 15 h at ambient temperature. Ammonium chloride (5 mL, saturated) was added and the reaction mixture was diluted with water and extracted with EtOAc. The organics were combined, washed with brine, dried over $Na_2SO_4$ and concentrated in vacuo. The crude product was purified by flash chromatography (0% to 50% EtOAc in hexanes) to yield 34D (578 mg, 57%) as a yellow oil. $^1$H NMR (400 MHz, $CDCl_3$) δ ppm 1.15 (t, J=7.15 Hz, 3 H) 2.32 (s, 3 H) 2.80-2.87 (m, J=6.87, 6.87 Hz, 2 H) 2.93 (t, J=7.15 Hz, 2 H) 4.05 (q, J=7.15 Hz, 2 H) 4.30 (t, J=7.15 Hz, 2 H) 5.02-5.18 (m, 3 H) 6.95-7.09 (m, 2 H) 7.23-7.37 (m, 10 H).

34E: (S)-4-(2-(3-(1-(benzyloxycarbonylamino)-3-ethoxy-3-oxopropyl)phenylcarbamoyloxy)ethyl)-3-methylphenylboronic acid

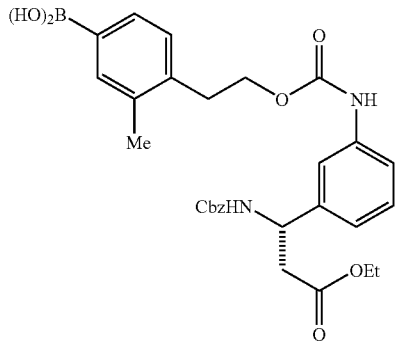

Using a procedure analogous to that used to prepare 6D, 34D (800 mg, 1.37 mmol) was reacted with 5,5',5'-tetramethyl-[2,2']bi[[1,3,2]dioxaborinanyl] to give 34E (530 mg, 70%) as an oily brown solid. $^1$H NMR (400 MHz, MeOD) δ ppm 1.16 (t, J=7.20 Hz, 3 H) 2.36 (s, 3 H) 2.67-2.85 (m, 2 H) 3.01 (t, J=7.07 Hz, 2 H) 4.06 (q, J=7.16 Hz, 2 H) 4.31 (t, J=7.07 Hz, 2 H) 4.96-5.11 (m, J=12.55, 12.55, 12.55 Hz, 3 H) 6.99 (d, J=7.33 Hz, 1 H) 7.15-7.25 (m, J=7.83, 7.83 Hz, 3 H) 7.31 (s, H) 7.35-7.43 (m, 3 H).

34F: 2-(4-(2-(3-((S)-1-(benzyloxycarbonylamino)-3-ethoxy-3-oxopropyl)phenylcarbamoyloxy)ethyl)-3-methylphenyl)-2-(1-(bis(tert-butoxycarbonyl)amino)isoquinolin-6-ylamino)acetic acid

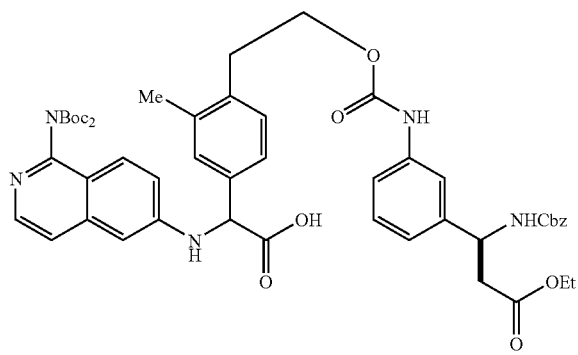

Using a procedure analogous to that used to prepare 2D, 34E (400 mg, 0.73 mmol) was reacted with Intermediate 1 and glyoxylic acid monohydrate to afford 34F (670 mg, 96%) as a yellow foam. MS (ESI) m/z 697.15 (M+H)$^+$.

34G: 2-(4-(2-(3-((S)-1-amino-3-ethoxy-3-oxopropyl)phenylcarbamoyloxy)ethyl)-3-methylphenyl)-2-(1-(bis(tert-butoxycarbonyl)amino)isoquinolin-6-ylamino)acetic acid

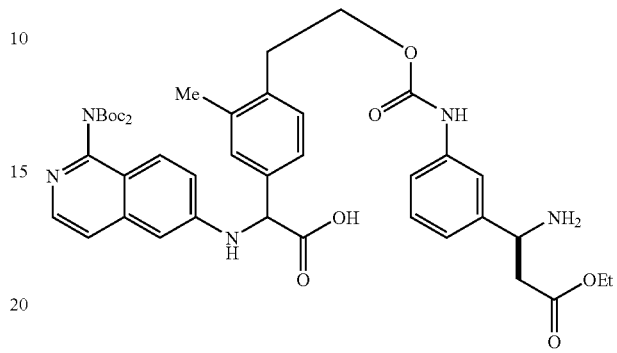

A solution of 34F (670 mg, 0.96 mmol) in MeOH (60 mL) and HCl (2.5 mL, 1.0 M aqueous) and Pd/C (60 mg) was stirred under an atmosphere of $H_2$ (60 psi) for 8 h. The solution was filtered and concentrated in vacuo to yield 34G (600 mg, 89%) as a yellow solid. MS (ESI) m/z 786.4 (M+H)$^+$.

Example 34

Using a procedure analogous to that used to prepare Example 28, 34F (600 mg, 0.73 mmol) was cyclized with PyBOP instead of BOP, deprotected with TFA, and purified by reverse phase HPLC to give Example 34 (50 mg, 23% yield) and its diastereomer (49 mg) as a tan solids. MS (ESI) m/z 568.12 (M+H)$^+$.

Example 35

[(S)-2-(1-Amino-isoquinolin-6-ylamino)-20-methyl-3,12-dioxo-13-oxa-4,11-diaza-tricyclo[14.2.2.1$^{6,10}$] henicosa-1(19),6,8,10(2 1),16(20),17-hexaen-5-yl]-acetic acid trifluoroacetic acid salt

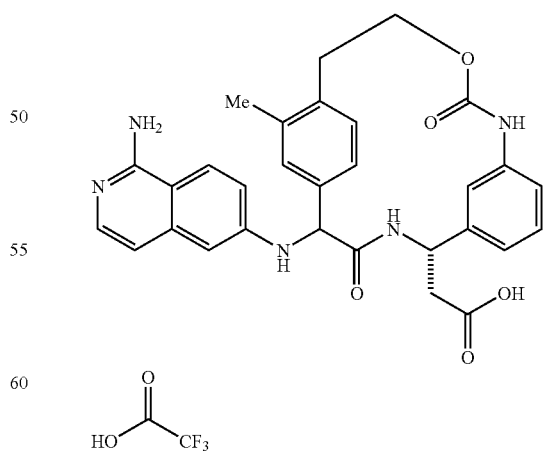

LiOH (1.0 M, 0.75 mL, aqueous) was added to a solution of Example 34 (46 mg, 0.08 mmol) in THF (1 mL) and stirred for 30 min at ambient temperature. The reaction mixture was concentrated in vacuo and purified by reverse phase HPLC to afford Example 35 (10 mg, 23%) as a white solid. MS (ESI) m/z 539.3 (M+H)+.

Example 36

3-(20-Ethyl-13-methyl-3,12-dioxo-4,11,13-triaza-tricyclo[14.2.2.1⁶,¹⁰]henicosa-1(19),6,8,10(21),16(20),17-hexaen-2-ylamino)-benzamide

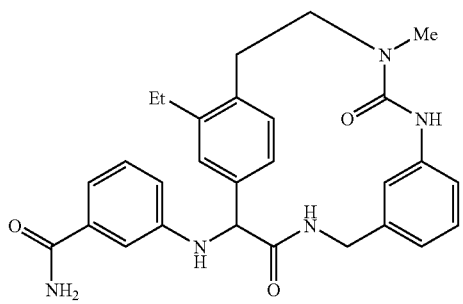

36A: 4-bromo-2-ethyl-1-vinylbenzene

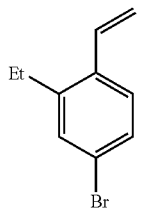

Using a procedure analogous to that used to prepare 30A, 4-bromo-2-ethyl-1-iodobenzene (2.1 g, 6.9 mmol) was reacted with trimethyl(vinyl)silane in a pressure vessel at 175° C. for 45 min to yield 36A (1.1 g, 77%) as a clear oil. $^1$H NMR (400 MHz, CDCl$_3$) δ ppm 1.03 (t, J=7.58 Hz, 3 H) 2.51 (q, J=7.66 Hz, 2 H) 5.15 (dd, J=10.99, 1.14 Hz, 1 H) 5.47 (dd, J=17.31, 1.14 Hz, 1 H) 6.74 (dd, J=17.43, 11.12 Hz, 1 H) 7.08-7.20 (m, 3 H).

36B: 2-(4-bromo-2-ethylphenyl)ethanol

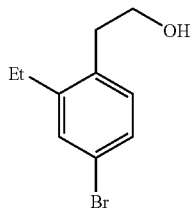

Using a procedure analogous to that used to prepare 30B, 36A (1.98 g, 5.1 mmol) was heated in a pressure vessel with 9-BBN at 100° C. for 15 h to yield 36B (0.95 g, 81%) as a clear oil. $^1$H NMR (400 MHz, CDCl$_3$) δ ppm 1.23 (t, J=7.58 Hz, 3 H) 2.66 (q, J=7.58 Hz, 2 H) 2.87 (t, J=6.82 Hz, 2 H) 3.83 (t, J=6.82 Hz, 2 H) 7.06 (d, J=8.08 Hz, 1 H) 7.25-7.31 (m, 1 H) 7.32-7.37 (m, 1 H).

36C: 2-(4-bromo-2-ethylphenyl)-N-methylethanamine

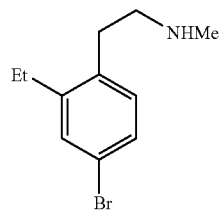

Mesyl anhydride (430 mg, 2.46 mmol) was added portionwise to a solution of 36B (470 mg, 2.05 mmol) in CH$_2$Cl$_2$ (10 mL) and Et$_3$N (0.57 mL, 4.1 mmol) at 0° C. After stirring for 15 h at ambient temperature, the mixture was diluted with CH$_2$Cl$_2$ (80 mL), washed with 1.0 M HCl, NaHCO$_3$, brine, dried over Na$_2$SO$_4$ and concentrated in vacuo. The crude mesylate was dissolved in EtOAc (20 mL) and methyl amine (33%, 5 mL) and heated in a pressure tube for 2 h. The reaction mixture was concentrated in vacuo to afford 36C (500 mg, 99%) as a yellow oil. MS (ESI) m/z 242.0/244.0 (M+H)+.

36D: 1-(4-bromo-2-ethylphenethyl)-3-(3-cyanophenyl)-1-methylurea

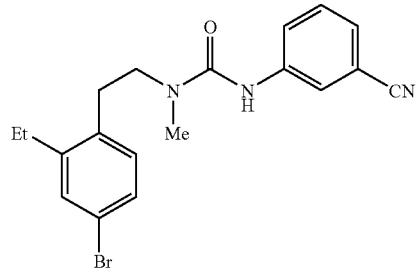

A solution of 36C (250 mg, 1.03 mmol) and 3-isocyanatobenzonitrile (164 mg, 1.03 mg) in CH$_2$Cl$_2$ (10 mL) was refluxed for 30 min. The solution was concentrated in vacuo and purified by flash chromatography (0% to 100% EtOAc in hexanes) to afford 36D (250 mg, 63%) as a yellow solid. MS (ESI) m/z 386.04/388.05 (M+H)+.

36E: 4-(2-(3-(3-cyanophenyl)-1-methylureido)ethyl)-3-ethylphenylboronic acid

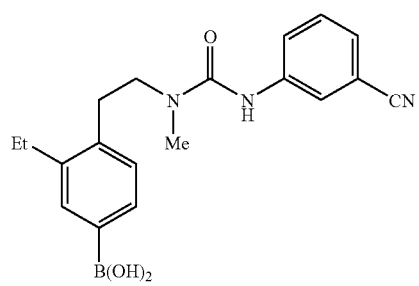

Using a procedure analogous to that used to prepare 6D, 36D (500 mg, 1.3 mmol) was reacted with 5,5',5'-tetramethyl-[2,2']bi[[1,3,2]dioxaborinanyl] to give 36E (183 mg, 40%) as a tan foam. MS (ESI) m/z 352.6 (M+H)+.

36F: 2-(3-carbamoylphenylamino)-2-(4-(2-(3-(3-cyanophenyl)-1-methylureido)ethyl)-3-ethylphenyl)acetic acid

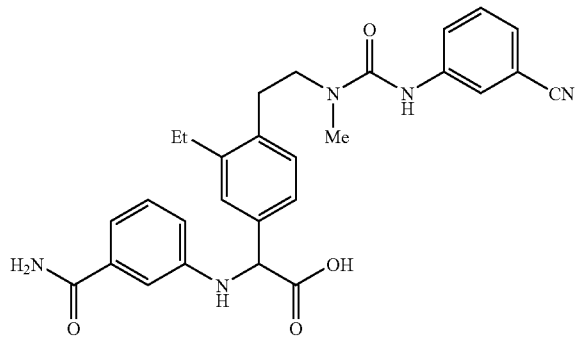

Using a procedure analogous to that used to prepare 2D, 36E (183 mg, 0.52 mmol) was reacted with 3-aminobenzamide and glyoxylic acid monohydrate to afford 36F (95 mg, 37%) as a yellow film. MS (ESI) m/z 500.3 (M+H)$^+$.

36G: 2-(4-(2-(3-(3-(aminomethyl)phenyl)-1-methylureido)ethyl)-3-ethylphenyl)-2-(3-carbamoylphenylamino)acetic acid

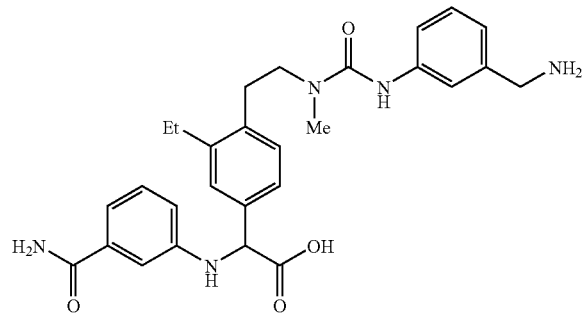

Using a procedure analogous to that used to prepare 6F, 36F (92 mg, 0.19 mmol) was hydrogenated for 4 h and purified by preparatory HPLC to yield 36G (91 mg, 98%) as a yellow solid. MS (ESI) m/z 504.3 (M+H)$^+$.

Example 36

Using a procedure analogous to that used to prepare Example 28, 36G (91 mg, 0.18 mmol) was cyclized with PyBOP instead of BOP and purified by reverse phase HPLC to give Example 36 (10 mg, 11%) as a yellow solid. $^1$H NMR (400 MHz, CD$_3$OD) δ ppm 1.11 (t, J=7.45 Hz, 1.5 H) 1.27 (t, J=7.45 Hz, 1.5 H) 2.98 (s, 3 H) 3.06 (d, J=2.27 Hz, 2 H) 3.21 (q, J=7.33 Hz, 2 H) 3.66-3.79 (m, 2 H) 4.04 (dd, J=16.80, 5.94 Hz, 1 H) 4.57-4.74 (m, 1 H) 5.00-5.12 (m, J=5.05 Hz, 1 H) 6.73-6.90 (m, J=21.85, 7.20 Hz, 3 H) 6.99-7.24 (m, 6 H) 7.29-7.40 (m, J=6.32 Hz, 1 H) 7.41-7.57 (m, 1 H) 7.97 (s, 1 H). MS (ESI) m/z 486.4 (M+H)$^+$.

Example 37

3-(17,20-Diethyl-3,12-dioxo-13-oxa-4,11-diaza-tricyclo[14.2.2.1$^{6,10}$]henicosa-1(19),6,8,10(21),16(20),17-hexaen-2-ylamino)-benzamide

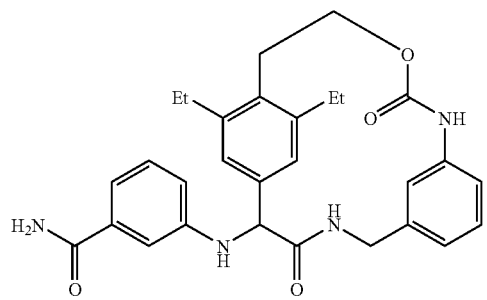

37A: 5-bromo-1,3-diethyl-2-iodobenzene

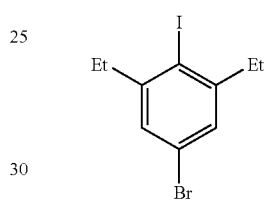

A solution of 4-bromo-2,6-diethylaniline (10 g, 44 mmol) in acetonitrile (20 mL) was added dropwise to a solution of I$_2$ (33.4 g, 131.6 mmol), tert-butylnitrite (7.4 mL, 65.8 mmol) in acetonitrile (80 mL), never allowing the internal temperature to exceed 30° C. After stirring 4 h at ambient temperature, Na$_2$SO$_3$ (100 mL, saturated aqueous) was added and stirred for 1 h. The mixture was extracted with hexanes (3×200 mL). The organics were combined, washed with brine, dried over Na$_2$SO$_4$ and concentrated. The crude oil was purified by flash chromatography (100% hexanes) to afford 37A (1.9 g, 13%) as a red oil. $^1$H NMR (400 MHz, CDCl$_3$) δ ppm 1.20 (t, J=7.45 Hz, 6 H) 2.77 (q, J=7.58 Hz, 4 H) 7.18 (s, 2 H).

37B: 5-bromo-1,3-diethyl-2-vinylbenzene

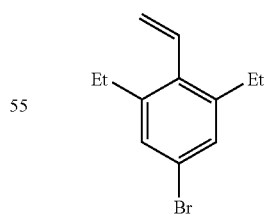

Using a procedure analogous to that used to prepare 30A, 37A (1.9 g, 5.6 mmol) was reacted with trimethyl(vinyl)silane to yield 37B (1.2 g, 90%) as a red oil. $^1$H NMR (400 MHz, CDCl$_3$) δ ppm 1.14 (t, J=7.47 Hz, 6 H) 2.60 (q, J=7.62 Hz, 4 H) 5.21 (dd, J=17.80, 1.98 Hz, 1 H) 5.51 (dd, J=11.42, 1.76 Hz, 1 H) 6.64 (dd, J=18.02, 11.42 Hz, 1 H) 7.18 (s, 2 H).

37C: 2-(4-bromo-2,6-diethylphenyl)ethanol

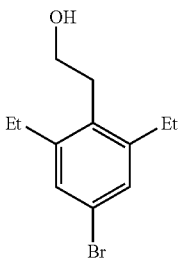

Using a procedure analogous to that used to prepare 30B, 37B (1.2 g, 5 mmol) was heated in a pressure vessel with 9-BBN at 115° C. for 1 h to yield 37C (735 mg, 58%) as an orange oil. $^1$H NMR (400 MHz, CDCl$_3$) δ ppm 1.21 (t, J=7.58 Hz, 6 H) 2.66 (q, J=7.49 Hz, 4 H) 2.92 (t, J=7.58 Hz, 2 H) 3.66-3.77 (t, J=7.57 Hz, 2 H) 7.17 (s, 2 H).

37D: 4-bromo-2,6-diethylphenethyl 3-cyanophenylcarbamate

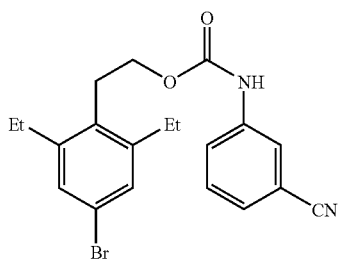

Using a procedure analogous to that used to prepare 30C, 37C (280 mg, 1.95 mmol) was reacted with 3-isocyanatobenzonitrile to yield 37D (670 mg, 86%) as an yellow oil. $^1$H NMR (400 MHz, CD$_3$OD) δ ppm 1.22 (t, J=7.58 Hz, 6 H) 2.73 (q, J=7.58 Hz, 4 H) 3.06 (t, J=8.1 Hz, 2 H) 4.21 (t, J=8.1 Hz, 2H) 7.19 (s, 2 H) 7.32-7.39 (m, 1 H) 7.40-7.50 (m, J=8.08, 8.08 Hz, 1 H) 7.66 (d, J=8.34 Hz, 1 H) 7.86 (s, 1 H).

37E: 4-(2-(3-cyanophenylcarbamoyloxy)ethyl)-3,5-diethylphenylboronic acid

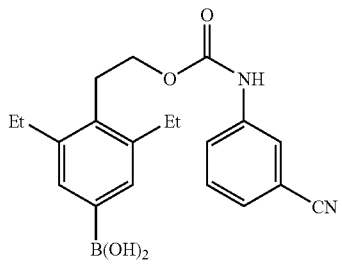

Using a procedure analogous to that used to prepare 6D, 37D (670 mg, 1.7 mmol) was reacted with 5,5',5'-tetramethyl-[2,2']bi[[1,3,2]dioxaborinanyl] to give 37E (278 mg, 45%) as a brown oil. $^1$H NMR (400 MHz, CD$_3$OD) δ ppm 1.16 (t, J=7.45 Hz, 6 H) 2.68 (q, J=7.41 Hz, 4 H) 3.03 (t, J=7.83 Hz, 2 H) 4.14 (t, J=7.82 Hz, 2 H) 7.13-7.29 (m, 2 H) 7.30-7.45 (m, 2 H) 7.59 (d, J=7.83 Hz, 1 H) 7.80 (s, 1 H) 9.42 (s, 1 H).

37F: 2-(3-carbamoylphenylamino)-2-(4-(2-(3-cyanophenylcarbamoyloxy)ethyl)-3,5-diethylphenyl)acetic acid

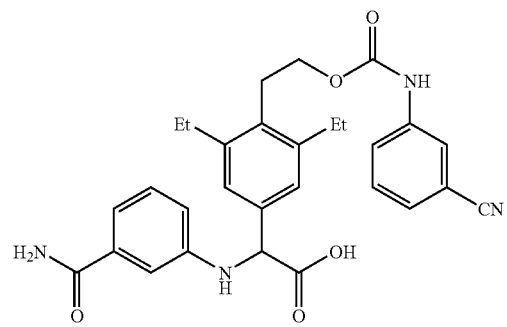

Using a procedure analogous to that used to prepare 2D, 37E (80 mg, 0.22 mmol) was reacted with 3-aminobenzamide and glyoxylic acid monohydrate to afford 37F (81 mg, 70%) as a yellow oil. MS (ESI) m/z 515.21 (M+H)$^+$.

37G: 2-(4-(2-(3-(aminomethyl)phenylcarbamoyloxy)ethyl)-3,5-diethylphenyl)-2-(3-carbamoylphenylamino)acetic acid

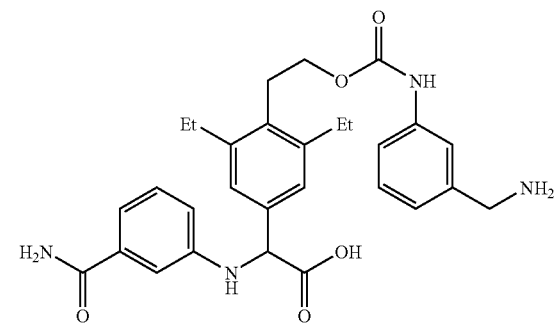

Using a procedure analogous to that used to prepare 6F, 37F (81 mg, 0.16 mmol) was hydrogenated for 16 h to yield 37G (85 mg, 99%) as a yellow solid. MS (ESI) m/z 519.3 (M+H)$^+$.

Example 37

Using a procedure analogous to that used to prepare Example 28, 37F (90 mg, 0.15 mmol) was cyclized with PyBOP instead of BOP and purified by reverse phase HPLC to give Example 37 (5 mg, 6%) as a white solid. $^1$H NMR (400 MHz, CD$_3$OD) δ ppm 1.11 (t, J=7.45 Hz, 3 H) 1.28 (t, J=7.33 Hz, 3 H) 2.48-2.81 (m, 2 H) 2.83-3.21 (m, 4 H) 4.12 (s, 1 H) 4.63 (s, 1 H) 4.98 (s, 1 H) 6.17 (s, 1 H) 6.65 (d, J=8.08 Hz, 1 H) 6.78-6.95 (m, 2 H) 7.03-7.22 (m, 5 H) 7.29 (s, 1 H) 8.39-8.57 (m, 1 H) 8.72 (s, 1 H). MS (ESI) m/z 501.3 (M+H)$^+$.

Example 38

(R)-2-(1-Amino-isoquinolin-6-ylamino)-17,20-diethyl-13-oxa-4,11-diaza-tricyclo[14.2.2.1$^{6,10}$]henicosa-1(19),6,8,10(21),16(20),17-hexaene-3,12-dione

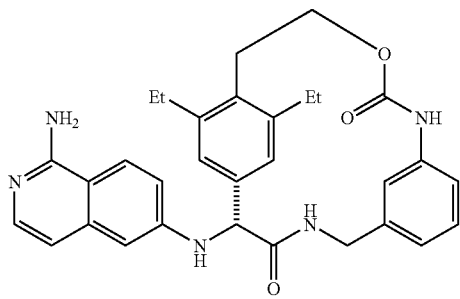

38A: 2-(1-(bis(tert-butoxycarbonyl)amino)isoquinolin-6-ylamino)-2-(4-(2-(3-cyanophenylcarbamoyloxy)ethyl)-3,5-diethylphenyl)acetic acid

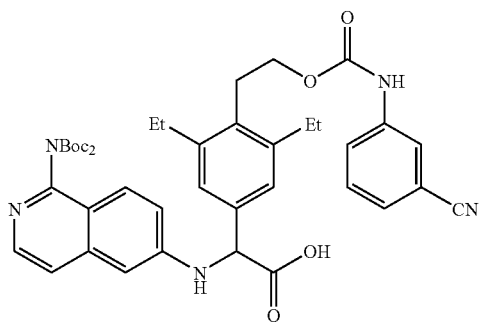

Using a procedure analogous to that used to prepare 2D, 37E (200 mg, 0.55 mmol) was reacted with Intermediate 1 and glyoxylic acid monohydrate to afford 38A (304 mg, 75%) as a yellow oil. MS (ESI) m/z 738.22 (M+H)$^+$.

38B: 2-(4-(2-(3-(aminomethyl)phenylcarbamoyloxy)ethyl)-3,5-diethylphenyl)-2-(1-(bis(tert-butoxycarbonyl)amino)isoquinolin-6-ylamino)acetic acid

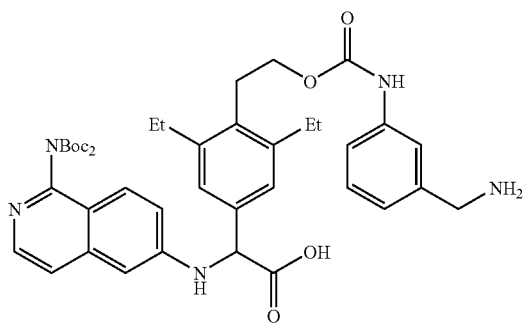

Using a procedure analogous to that used to prepare 6F, 38A (304 mg, 0.41 mmol) was hydrogenated and purified by prep HPLC to yield 38B (150 mg, 49%) as a yellow solid. MS (ESI) m/z 742.5 (M+H)$^+$.

Example 38

Using a procedure analogous to that used to prepare Example 28, 38B (150 mg, 0.2 mmol) was cyclized with PyBOP instead of BOP, deprotected with TFA, and purified by reverse phase HPLC to give racemic Example 38 (20 mg, 27%) as a white solid. The racemate was purified was purified by chiral HPLC to give peak 1 (5 mg) and Example 38 (peak 2, 5 mg). The chromatography conditions were the following: Whelk-O1 (R,R) (500×21.1 mm ID; 10 micron, Regis Technologies), 40% MeOH/EtOH (1:1), 60% Heptane 15 mL/min flow rate, and UV detection at 220 nm. Peak 2 analytical data: $^1$H NMR (400 MHz, CD$_3$OD) δ ppm 1.11 (t, J=7.42 Hz, 3 H) 1.30 (t, 3 H) 2.50-3.22 (m, 6 H) 4.08 (d, J=16.49 Hz, 1 H) 4.74 (d, J=15.94 Hz, 1 H) 5.10 (s, 1 H) 6.19 (s, 1 H) 6.59-6.74 (m, 2 H) 6.79 (d, J=6.60 Hz, 1 H) 6.88 (d, J=7.70 Hz, 1 H) 7.00-7.20 (m, 3 H) 7.31-7.42 (m, 2 H) 7.98 (d, J=9.34 Hz, 1 H). MS (ESI) m/z 524.2 (M+H)$^+$. Chiral analytical HPLC retention times: peak 1, 7.94 min; peak 2, 11.40 min using the following chromatography conditions: Welko-O1 (R, R) column (250×4.6 mm ID; 5 micron, 50% MeOH/EtOH (1:1), 50% Heptane, 0.1% DEA as eluent, 1 mL/min flow rate and UV detection at 254 nm.

Example 39

[(R)-2-(1-Amino-isoquinolin-6-ylamino)-20-methyl-3,12-dioxo-13-oxa-4,11-diaza-tricyclo[14.2.2.1$^{6,10}$]henicosa-1(19),6,8,10(21),16(20),17-hexaen-5-yl]-acetic acid ethyl ester trifluoroacetic acid salt

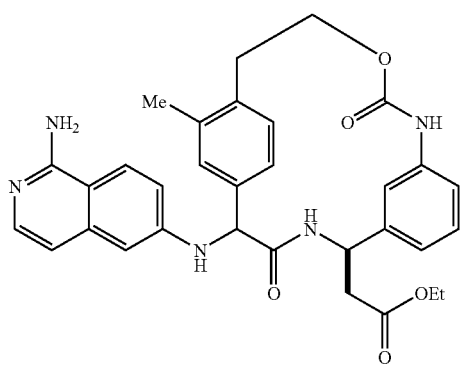

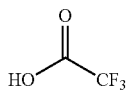

39A: (R)-ethyl 3-amino-3-(3-nitrophenyl)propanoate hydrochloride salt

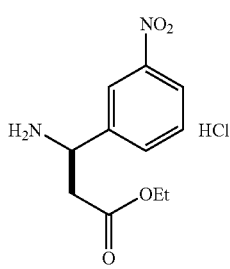

Using a procedure analogous to that used to prepare 34A, (S)-3-amino-3-(3-nitrophenyl)propanoic acid (2.1 g, 10 mmol) was reacted with thionyl chloride to 10 afford 39A (2.75 g, 99%) as a white solid. MS (ESI) m/z 239.08 (M+H)$^+$.

39B: (R)-ethyl 3-(benzyloxycarbonylamino)-3-(3-nitrophenyl)propanoate

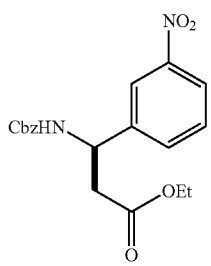

Using a procedure analogous to that used to prepare 34B, 39A (2.75 g, 10 mmol) was reacted with N-(Benzyloxycarbonyloxy)succinimide to afford 39B (3.1 g, 83%) as a white solid. MS (ESI) m/z 395.13 (M+Na)+.

39C: (R)-ethyl 3-(3-aminophenyl)-3-(benzyloxycarbonylamino)propanoate

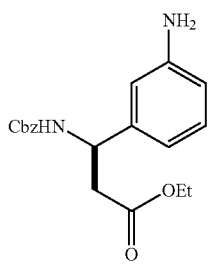

Using a procedure analogous to that used to prepare 34C, 39B (3.1 g, 8.3 mmol) was reacted with Fe to afford 39C (2.7 g, 95%) as a white solid. MS (ESI) m/z 343.35 (M+H)+.

39D: (R)-ethyl 3-(benzyloxycarbonylamino)-3-(3-((4-bromo-2-methylphenethoxy)carbonylamino)phenyl)propanoate

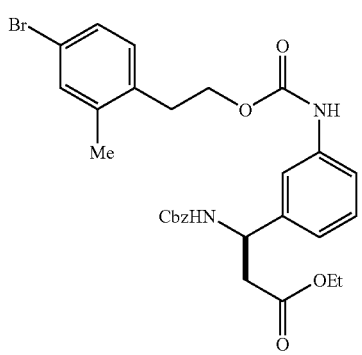

Using a procedure analogous to that used to prepare 34D, 39C (1.12 g, 3.3 mmol) was reacted with 30B (700 mg, 3.3 mmol) to afford 39D (1.07 g, 56%) as a colorless oil. MS (ESI) m/z 583.13/585.13 (M+H)+.

39E: (R)-4-(2-(3-(1-(benzyloxycarbonylamino)-3-ethoxy-3-oxopropyl)phenylcarbamoyloxy)ethyl)-3-methylphenylboronic acid

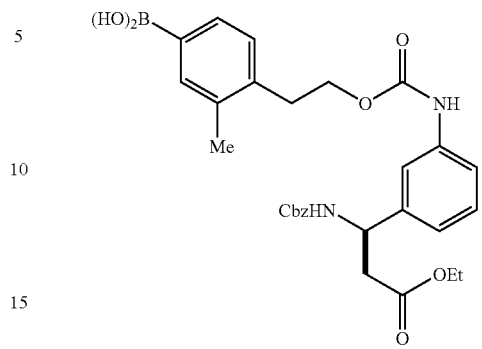

Using a procedure analogous to that used to prepare 6D, 39D (1.07 g, 1.84 mmol) was reacted with 5,5',5'-tetramethyl-[2,2']bi[[1,3,2]dioxaborinanyl] to give 39E (640 mg, 64%) as a tan foam. $^1$H NMR (400 MHz, CD$_3$OD) δ ppm 1.14 (t, J=7.15 Hz, 3 H) 2.65-2.86 (m, 2 H) 2.99 (t, J=7.15 Hz, 2 H) 4.05 (q, J=7.15 Hz, 2 H) 4.19-4.35 (m, 2 H) 4.93-5.14 (m, 3 H) 6.98 (d, J=7.70 Hz, 1 H) 7.12-7.33 (m, 8 H) 7.34-7.45 (m, 2 H) 7.45-7.59 (m, 1 H) 9.14 (s, 1 H)

39F: 2-(4-(2-(3-((R)-1-(benzyloxycarbonylamino)-3-ethoxy-3-oxopropyl)phenylcarbamoyloxy)ethyl)-3-methylphenyl)-2-(1-(bis(tert-butoxycarbonyl)amino)isoquinolin-6-ylamino)acetic acid

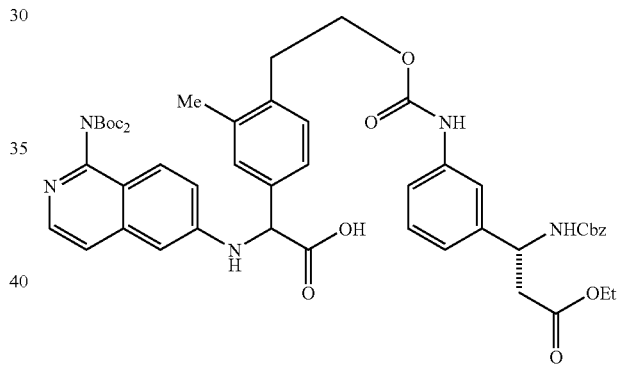

Using a procedure analogous to that used to prepare 2D, 39E (440 mg, 0.8 mmol) was reacted with Intermediate 1 and glyoxylic acid monohydrate to afford 39F (538 mg, 44%) as a brown oil. MS (ESI) m/z 920.6 (M+H)+.

39G: 2-(4-(2-(3-((R)-1-amino-3-ethoxy-3-oxopropyl)phenylcarbamoyloxy)ethyl)-3-methylphenyl)-2-(1-(bis(tert-butoxycarbonyl)amino)isoquinolin-6-ylamino)acetic acid

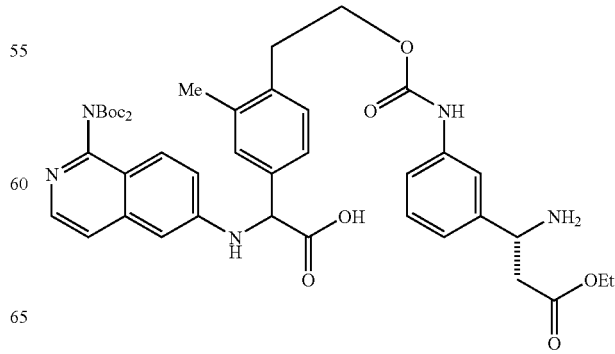

Using a procedure analogous to that used to prepare 6F, 39F (538 mg, 0.58 mmol) was hydrogenated and purified by prep HPLC to yield 39G (270 mg, 59%) as a yellow film. MS (ESI) m/z 786.4 (M+H)+.

Example 39

Using a procedure analogous to that used to prepare Example 28, 39F (600 mg, 0.73 mmol) was cyclized, deprotected with TFA, and purified by reverse phase HPLC to give Example 39 (80 mg, 41%) as a brown solid. MS (ESI) m/z 568.43 (M+H)+.

Example 40

[(R)-2-(1-Amino-isoquinolin-6-ylamino)-20-methyl-3,12-dioxo-13-oxa-4,11-diaza-tricyclo[14.2.2.1$^{6,10}$]henicosa-1(19),6,8,10(21),16(20),17-hexaen-5-yl]-acetic acid trifluoroacetic acid salt

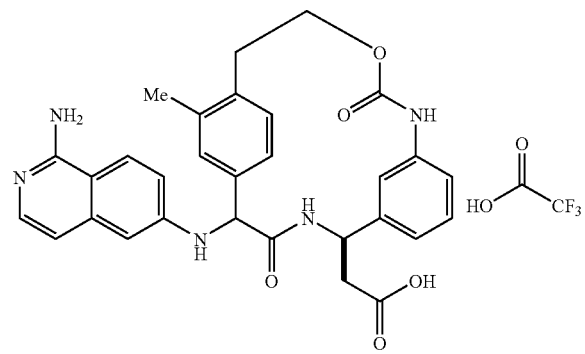

Using a procedure analogous to that used to prepare Example 35, Example 39 (40 mg, 0.07 mmol) was reacted with LiOH, and purified by reverse phase HPLC to give Example 40 (12 mg, 32%) as a tan solid. MS (ESI) m/z 539.4 (M+H)+.

Example 41

[(R)-2-(3-Carbamoyl-phenylamino)-20-methyl-3,12-dioxo-13-oxa-4,11-diaza-tricyclo[14.2.2.1$^{6,10}$]henicosa-1(19),6,8,10(21),16(20),17-hexaen-5-yl]-acetic acid ethyl ester

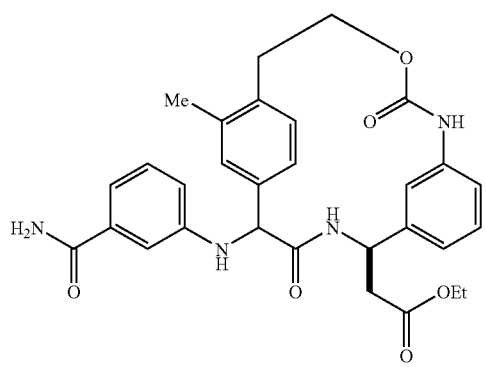

41A: 2-(4-(2-(3-((R)-1-(benzyloxycarbonylamino)-3-ethoxy-3-oxopropyl)phenylcarbamoyloxy)ethyl)-3-methylphenyl)-2-(3-carbamoylphenylamino)acetic acid

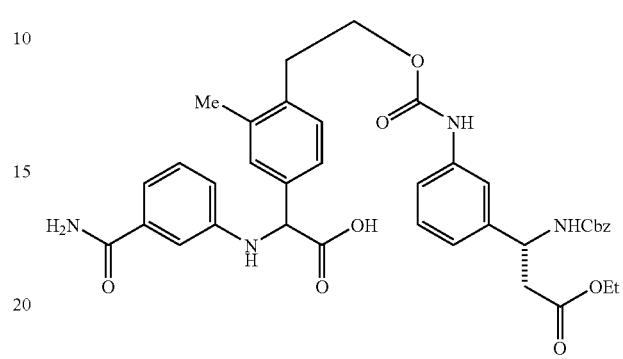

Using a procedure analogous to that used to prepare 2D, 39E (200 mg, 0.36 mmol) was reacted with 3-aminobenzamide and glyoxylic acid monohydrate to afford 41A (232 mg, 44%) as a brown oil. MS (ESI) m/z 697.4 (M+H)+.

41B: 2-(4-(2-(3-((R)-1-amino-3-ethoxy-3-oxopropyl)phenylcarbamoyloxy)ethyl)-3-methylphenyl)-2-(3-carbamoylphenylamino)acetic acid

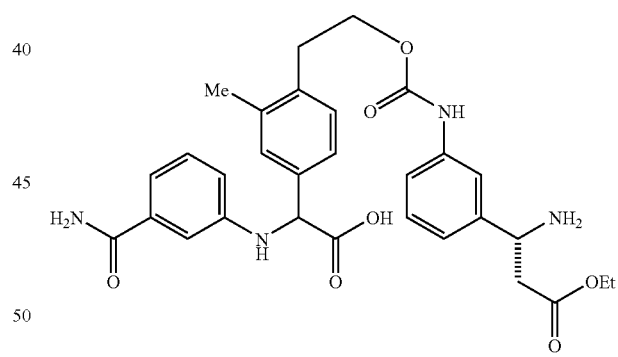

Using a procedure analogous to that used to prepare 6F, 41A (232 mg, 0.33 mmol) was hydrogenated to afford 41B (202 mg, 87%) as a yellow solid. MS (ESI) m/z 563.2 (M+H)+.

Example 41

Using a procedure analogous to that used to prepare Example 28, 41B (202 mg, 0.31 mmol) was cyclized with BOP and purified by reverse phase HPLC to give Example 41 (50 mg, 26%) as a brown solid. MS (ESI) m/z 545.2 (M+H)+.

Example 42

[(R)-2-(3-Carbamoyl-phenylamino)-20-methyl-3,12-dioxo-13-oxa-4,11-diaza-tricyclo[14.2.2.1$^{6,10}$]henicosa-1(19),6,8,10(21),16(20),17-hexaen-5-yl]-acetic acid

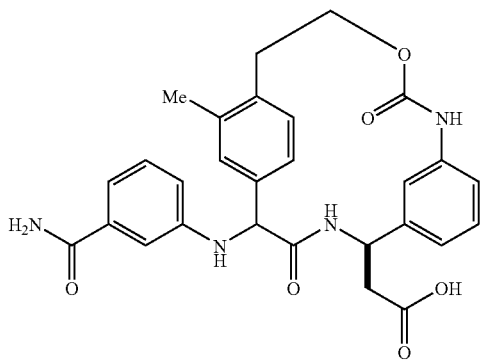

Using a procedure analogous to that used to prepare Example 35, Example 41 (40 mg, 0.07) was reacted with LiOH, and purified by reverse phase HPLC to give Example 42 (15 mg, 39%) as a yellow solid. MS (ESI) m/z 517.2 (M+H)$^+$.

Example 43

3-[20-Ethyl-3,12-dioxo-7-(propane-2-sulfonyl)-13-oxa-4,11-diaza-tricyclo[14.2.2.1$^{6,10}$]henicosa-1(19),6,8,10(21),16(20),17-hexaen-2-ylamino]-4-fluoro-benzamide

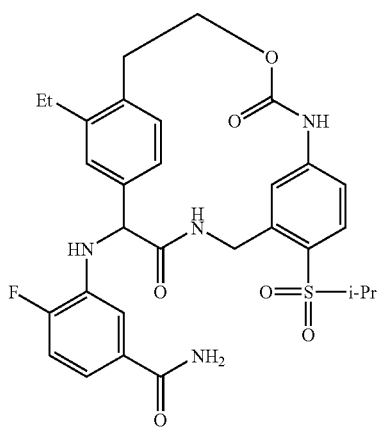

43A: [3-[(tert-Butoxycarbonyl-methyl-amino)-methyl]-4-(propane-2-sulfonyl)-phenyl]-carbamic acid 2-(4-bromo-2-ethyl-phenyl)-ethyl ester

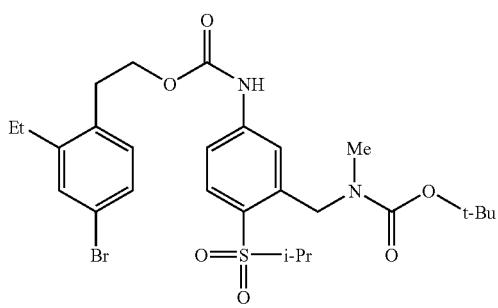

NaH (190 mg, 4.7 mmol) was added in one portion to a solution of 16G (547 mg, 1.2 mmol) and 36B (1000 mg, 4.4 mmol) in THF (20 mL) at −40° C. The reaction was warmed slowly to ambient temperature over 2 h and stirred for 15 h. The reaction was quenched with saturated citric acid and diluted with EtOAc. The mixture washed with brine, dried over Na$_2$SO$_4$ and concentrated in vacuo. The crude product was purified by flash chromatography (0% to 100% EtOAc in hexanes) to afford 43A (650 mg, 92%) as a yellow solid. MS (ESI) m/z 597.1/599.1 (M+H)$^+$.

43B: 4-(2-(3-((tert-butoxycarbonyl(methyl)amino)methyl)-4-(isopropylsulfonyl)phenylcarbamoyloxy)ethyl)-3-ethylphenylboronic acid

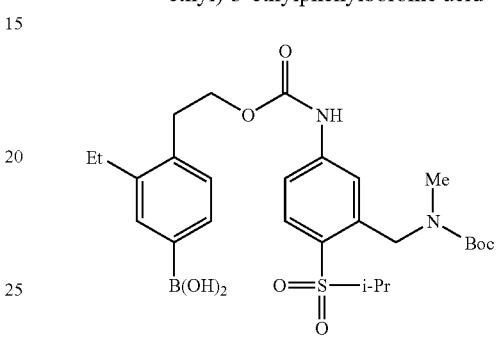

Using a procedure analogous to that used to prepare 6D, 43A (650 mg, 1.1 mmol) was reacted with 5,5',5'-tetramethyl-[2,2']bi[[1,3,2]dioxaborinanyl] to give 43B (362 mg, 59%) as a brown oil. MS (ESI) m/z 563.2 (M+H)$^+$.

43C: 2-(4-(2-(3-((tert-butoxycarbonyl(methyl)amino)methyl)-4-(isopropylsulfonyl)phenylcarbamoyloxy)ethyl)-3-ethylphenyl)-2-(5-carbamoyl-2-fluorophenylamino)acetic acid

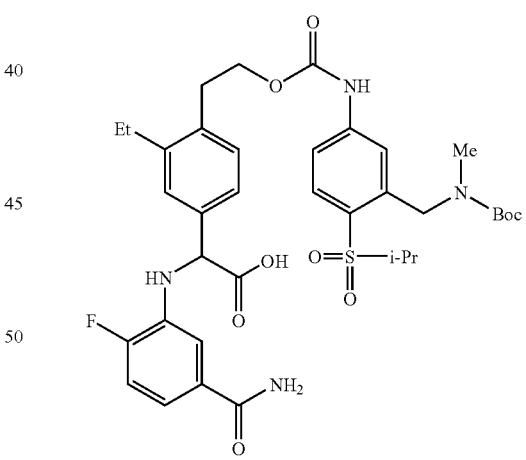

Using a procedure analogous to that used to prepare 2D, 43B (362 mg, 0.65 mmol) was reacted with 3-amino-4-fluorobenzamide and glyoxylic acid monohydrate to afford 43C (296 mg, 62%) as a yellow oil. MS (ESI) m/z 729.3 (M+H)$^+$.

Example 43

HCl (4.0 M in dioxane, 10 mL) was added to a solution 43C (296 mg, 0.41 mmol) in EtOAc (10 mL) and stirred to 1 h. The solution was concentrated in vacuo. Using a procedure analogous to that used to prepare Example 28, the solid was cyclized with BOP and purified by reverse phase HPLC to give Example 43 (40 mg, 16%) as an off-white solid which consists of a mixture of atropisomers. $^1$H NMR (400 MHz, DMSO-D$_6$) δ ppm 1.71 (t, J=7.70 Hz, 1.5 H) 1.94-2.05 (m, 6 H) 2.09 (t, J=7.42 Hz, 1.5 H) 3.14-3.27 (m, 0.5 H) 3.35-3.69 (m, 3 H) 3.78-3.99 (m, 2.5 H) 4.04 (s, 1.5 H) 4.04 (s, 1.5 H) 4.17-4.37 (m, 1 H) 4.73-5.03 (m, 3 H) 5.47-5.64 (m, 1 H) 6.25-6.44 (m, J=21.71, 17.31 Hz, 1 H) 6.48-6.61 (m, J=5.50 Hz, 1 H) 7.04-7.20 (m, 1 H) 7.52 (d, J=7.70 Hz, 0.5 H) 7.61-7.77 (m, 2 H) 7.79-7.95 (m, 2.5 H) 8.02-8.16 (m, 1 H) 8.22-8.33 (m, 1 H) 8.37-8.64 (m, 2 H). MS (ESI) m/z 611.20 (M+H)$^+$.

Example 44

3-[(R)-20-Ethyl-3,12-dioxo-7-(propane-2-sulfonyl)-13-oxa-4,11-diaza-tricyclo[14.2.2.1$^{6,10}$]henicosa-1(19),6,8,10(21),16(20),17-hexaen-2-ylamino]-4-fluoro-benzamide atropisomer 1

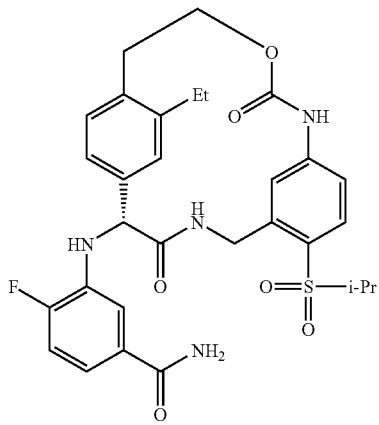

Example 45

3-[(R)-20-Ethyl-3,12-dioxo-7-(propane-2-sulfonyl)-13-oxa-4,11-diaza-tricyclo[14.2.2.1$^{6,10}$]henicosa-1(19),6,8,10(21),16(20),17-hexaen-2-ylamino]-4-fluoro-benzamide atropisomer 2

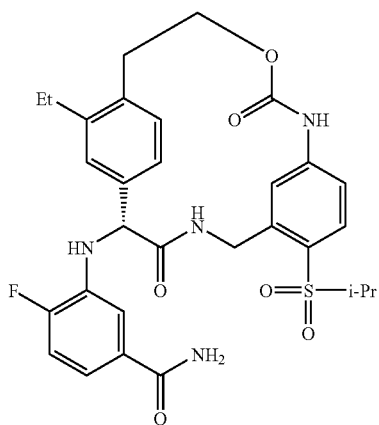

Example 43 (37 mg) was purified by chiral HPLC to separate the enantiomers and atropisomers: peak 1 (2.5 mg), peak 2 (3.5 mg), Example 44 (2.5 mg) and Example 45 (3.5 mg). The chromatography conditions were the following: Chiralpack AD (250×20 mm ID; 10 micron, Chiral Technologies, Inc.), 30% IPA, 30% EtOH, 40% Heptane, 0.1% DEA, 18 mL/min flow rate, and UV detection at 270 nm. Peak 3 analytical data: $^1$H NMR (400 MHz, CD$_3$OD) δ ppm 0.99 (t, J=7.70 Hz, 3 H) 1.23 (d, J=7.15 Hz, 3 H) 1.33 (d, J=6.60 Hz, 3 H) 2.39-2.53 (m, J=14.57, 7.42 Hz, 1 H) 2.68-2.78 (m, J=13.74 Hz, 1 H) 2.81-2.94 (m, 1 H) 3.33 (s, 3 H) 3.43-3.56 (m, 1 H) 3.74-3.88 (m, 1 H) 4.08-4.30 (m, 2 H) 4.59 (s, 1 H) 5.52-5.71 (m, 2 H) 6.48 (d, J=2.20 Hz, 1 H) 6.84 (dd, J=8.25, 2.20 Hz, 1 H) 6.95-7.04 (m, 2 H) 7.07-7.18 (m, 1 H) 7.31-7.40 (m, 2 H) 7.52-7.62 (m, 1 H) 7.74 (d, J=8.79 Hz, 1 H). MS (ESI) m/z 611.3 (M+H)$^+$. Peak 4 analytical data: $^1$H NMR (400 MHz, CD$_3$OD) δ ppm 1.19-1.40 (m, 9 H) 2.67-2.94 (m, 3 H) 3.17 (d, J=13.74 Hz, 1 H) 3.32 (s, 3 H) 3.46-3.60 (m, 1 H) 3.76-3.85 (m, 1 H) 4.02 (dd, J=10.99, 2.75 Hz, 1 H) 4.17 (d, J=17.04 Hz, 1 H) 4.59 (s, 1 H) 5.54-5.68 (m, 2 H). MS (ESI) m/z 611.3 (M+H)$^+$. Chiral analytical HPLC retention times: peak 1, 7.62 min; peak 2, 11.75 min; peak 3, 15.88 min; peak 4, 21.12 min using the following chromatography conditions: Chiralpack AD (250×4.6 mm ID; 10 micron, Chiral Technologies, Inc.), 30% IPA, 30% EtOH, 40% Heptane, 0.1% DEA, 1 mL/min flow rate, and UV detection at 270 nm.

Example 46

3-(20-Ethyl-7-isopropylsulfanyl-4-methyl-3,12-dioxo-13-oxa-4,11-diaza-tricyclo[14.2.2.1$^{6,10}$]henicosa-1(19),6,8,10(21),16(20),17-hexaen-2-ylamino)-benzamide

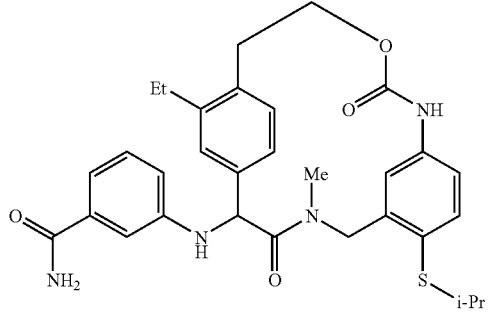

46A: (4-bromo-2-ethylphenethoxy)(tert-butyl)dimethylsilane

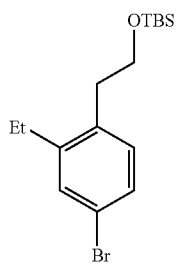

Imidazole (2.1 g, 30.6 mmol) followed by tert-butylchlorodimethylsilane (2.5 g, 16.8 mmol) were added to a solution of 36B (3.5 g, 15.3 mmol) in CH$_2$Cl$_2$ (100 mL). The reaction mixture was stirred for 2 h then washed with water and brine, dried over Na$_2$SO$_4$ and concentrated in vacuo. The crude product was purified by flash chromatography (0% to 30% EtOAc in hexanes) to yield 46A (4.3 g, 82%) as a colorless oil. $^1$H NMR (400 MHz, CDCl$_3$) δ ppm −0.02 (s, 6 H) 0.86 (s, 9 H) 1.20 (t, J=7.42 Hz, 3 H) 2.63 (q, J=7.51 Hz, 2 H) 2.79 (t, J=7.15 Hz, 2 H) 3.74 (t, J=7.15 Hz, 2 H) 7.22 (dd, J=7.97, 1.92 Hz, 1 H) 7.29 (d, J=2.20 Hz, 1 H).

46B: 4-(2-(tert-butyldimethylsilyloxy)ethyl)-3-ethylphenylboronic acid

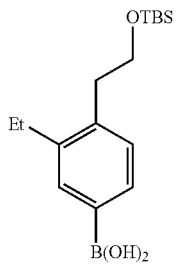

n-Butyl Lithium (4.7 mL) was added to a solution of 46A (2.1 g, 6.1 mmol) in THF at −78° C. After stirring to 10 min at −78° C., trimethyl borate (1.0 mL, 12.3 mmol) was added dropwise. After warming to ambient temperature, the reaction mixture was stirred an additional 2 h. HCl (1.0 M, 30 mL, aqueous) was added to the mixture at −40° C. and stirred at −20° C. for 30 min. The solution was extracted with diethyl ether. The combined organics were washed with brine, dried over $Na_2SO_4$ and concentrated in vacuo. The resulting oil was purified by flash chromatography (0% to 20% MeOH in $CH_2Cl_2$) to yield 46B (0.90 mg, 48%) as a clear oil. MS (ESI) m/z 307.4 (M−H)⁻.

46C: 2-(3-carbamoylphenylamino)-2-(3-ethyl-4-(2-hydroxyethyl)phenyl)acetic acid

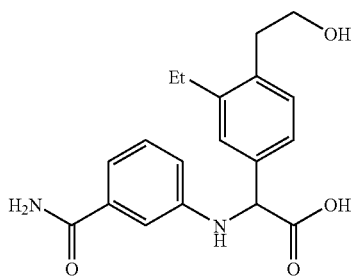

Using a procedure analogous to that used to prepare 2D, 46B (1.4 g, 4.1 mmol) was reacted with 3-aminobenzamide and glyoxylic acid monohydrate to afford 46C (1.25 g, 88%) as a yellow solid. MS (ESI) m/z 343.3 (M+H)⁺.

46D: 3-(2-((5-amino-2-(isopropylthio)benzyl)(methyl)amino)-1-(3-ethyl-4-(2-hydroxyethyl)phenyl)-2-oxoethylamino)benzamide

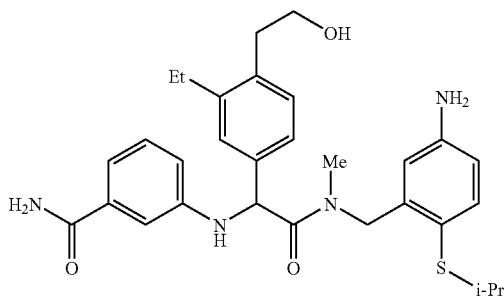

EDCI (67 mg, 0.35 mmol), HOAt (80 mg, 0.58 mmol) and triethylamine (0.79 mL, 0.58 mmol) were added to a solution of 46C (100 mg, 0.3 mmol) and 16D (67 mg, 0.3 mmol) and stirred at 50° C. for 4 h. The reaction mixture was diluted with EtOAc, washed with water, brine, dried over $Na_2SO_4$ and concentrated in vacuo. The crude oil was purified by flash chromatography (0% to 20% MeOH in $CH_2Cl_2$) to yield 46D as a yellow solid. MS (ESI) m/z 535.4 (M+H)⁺.

Example 46

Phosgene (0.072 mL, 0.14 mmol, 20% in toluene) was added dropwise to a solution of 46D (70 mg, 0.13 mmol) in acetonitrile (20 mL) at 0° C. The mixture was stirred for 30 min at ambient temperature. DMPU (0.5 mL) was added and the solution was added via syringe pump over 4 h to a solution of triethylamine (0.18 mL, 1.3 mmol) in acetonitrile (150 mL) at 40° C. The solution was concentrated in vacuo, combined with an earlier run (30 mg 46D) and purified by HPLC to yield two atropisomers: peak 1 (16 mg, 15%) and Example 46 (peak 2, 31 mg, 30%). ¹H NMR (400 MHz, $CD_3OD$) δ ppm 1.23 (t, J=6.87 Hz, 6 H) 1.30 (t, J=7.70 Hz, 3 H) 2.70-2.90 (m, 4 H) 3.19 (s, 3 H) 3.18-3.18 (m, 1 H) 4.00-4.04 (m, 2 H) 5.44 (d, J=17.04 Hz, 1 H) 5.63 (s, 1 H) 6.07 (d, J=2.75 Hz, 1 H) 6.70 (dd, J=8.24, 2.20 Hz, 1 H) 6.95-7.04 (m, 1 H) 7.11 (s, 2 H) 7.19-7.27 (m, 2 H) 7.29-7.36 (m, 2 H) 7.52 (s, 1 H). MS (ESI) m/z 561.4 (M+H)⁺. Analytical HPLC retention times: peak 1, 6.52 min; peak 2, 6.76 min using the following chromatography conditions: Phenomenex Luna (S-5) C-18 (4.6× 750 mm, 5 micron), 10% to 90% gradient MeOH in water with 0.2% $H_3PO_4$ as eluent, 2.5 mL/min flow rate and UV detection at 220 nm.

Example 47

3-(20-Ethyl-7-isopropylsulfonyl-4-methyl-3,12-dioxo-13-oxa-4,11-diaza-tricyclo[14.2.2.1⁶,¹⁰]henicosa-1(19),6,8,10(21),16(20),17-hexaen-2-ylamino)-benzamide

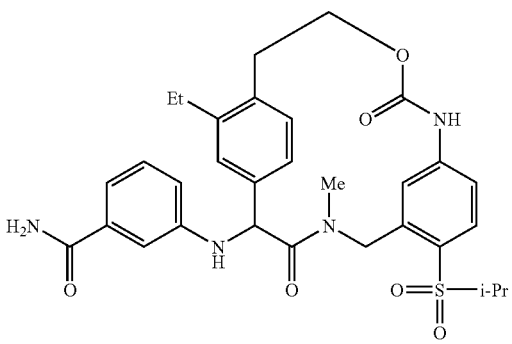

Hydrogen peroxide (50%, 0.2 mL) was added dropwise to a solution of Example 46 (31 mg, 0.055 mmol) in TFA (0.4 mL) and water (0.4 mL) at −40° C. The reaction mixture was stirred for 30 min and 2 h at −20° C. the reaction mixture was partitioned between EtOAc and sat. $NaHCO_3$. The organic layer washed with brine, dried over $Na_2SO_4$ and concentrated in vacuo. The crude material was purified by HPLC to yield Example 47 (6 mg, 18%) as a white solid. ¹H NMR (400 MHz, $CD_3OD$) δ ppm 1.21 (d, J=7.15 Hz, 3 H) 1.27-1.35 (m, 6 H) 2.68-2.97 (m, 3 H) 3.18 (d, J=13.74 Hz, 1 H) 3.28 (s, 3 H) 3.42-3.57 (m, 1 H) 4.03 (dd, J=10.99, 2.20 Hz, 1 H) 4.16 (d, J=17.59 Hz, 1 H) 5.54-5.64 (m, 2 H) 6.52 (s, 1 H) 6.85 (dd, J=8.24, 2.20 Hz, 1 H) 6.97 (dd, J=13.19, 7.70 Hz, 2 H) 7.03-7.12 (m, 1 H) 7.18-7.30 (m, 2 H) 7.30-7.37 (m, 1 H) 7.53 (s, 1 H) 7.73 (d, J=8.24 Hz, 1 H). MS (ESI) m/z 593.4 (M+H)+.

Example 48

3-((R)-20-Ethyl-7-isopropylsulfanyl-4-methyl-3,12-dioxo-13-oxa-4,11-diaza-tricyclo[14.2.2.1[6,10]]henicosa-1(19),6,8,10(21),16(20),17-hexaen-2-ylamino)-benzamide

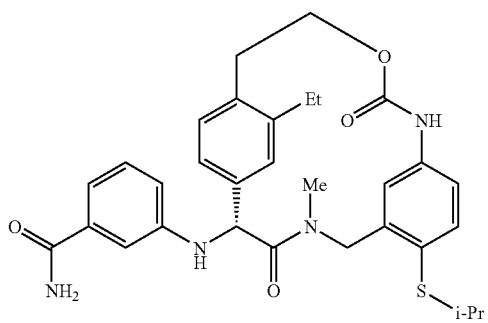

48A: (R)-3-(2-((5-amino-2-(isopropylthio)benzyl)(methyl)amino)-1-(3-ethyl-4-(2-hydroxyethyl)phenyl)-2-oxoethylamino)benzamide

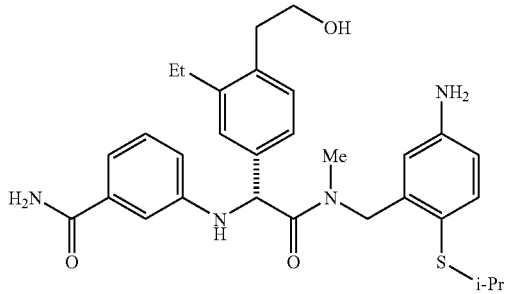

46D (660 mg) was separated by chiral HPLC to yield 48A (peak 1, 250 mg) and its entantiomer (peak 2, 250 mg). The chromatography conditions were the following: Chiralcel OD-H (5.0 cm×50 cm, 520 micron, Chiral Technologies, Inc.), MeOH/EtOH (1:1) 0.1% DEA, 50 mL/min flow rate, and UV detection at 220 nm. MS (ESI) m/z 535.5 (M+H)+.

Example 48

Using a procedure analogous to that used to prepare Example 46, 48A (200 mg, 0.36 mmol) was reacted phosgene and purified by HPLC to afford Example 48 (peak 1, 38 mg, 18%) and peak 2 (72 mg, 34%) as white solids. Analytical data for peak 1: $^1$H NMR (400 MHz, CD$_3$OD) δ ppm 1.10 (t, J=7.42 Hz, 3 H) 1.18-1.28 (m, J=9.34, 6.60 Hz, 6 H) 2.51-2.64 (m, 1 H) 2.73 (d, J=14.29 Hz, 1 H) 2.81-2.86 (m, 1 H) 2.88-2.99 (m, 1 H) 3.13-3.18 (m, 1 H) 3.18 (s, 3 H) 3.94-4.03 (m, 1 H) 4.08-4.19 (m, 1 H) 5.46 (d, J=17.04 Hz, 1 H) 5.64 (s, 1 H) 5.94-6.12 (m, 1 H) 6.69 (dd, J=7.70, 2.20 Hz, 1 H) 7.05 (d, J=9.34 Hz, 1 H) 7.21-7.48 (m, 7 H). MS (ESI) m/z 561.6 (M+H)+.

Example 49

3-((R)-20-Ethyl-7-isopropylsulfonyl-4-methyl-3,12-dioxo-13-oxa-4,11-diaza-tricyclo[14.2.2.1[6,10]]henicosa-1(19),6,8,10(21),16(20),17-hexaen-2-ylamino)-benzamide

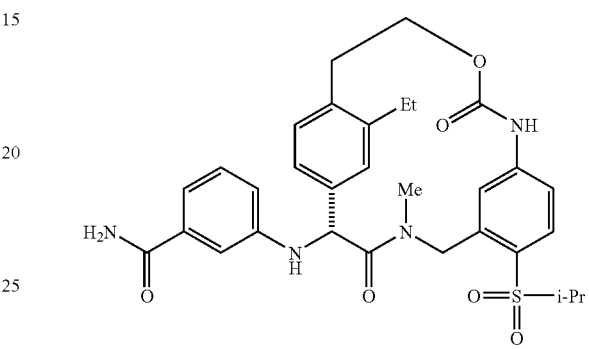

Using a procedure analogous to that used to prepare Example 47, Example 48 (40 mg, 0.07 mmol) was reacted with hydrogen peroxide to afford Example 49 (7 mg, 17%) as a white solid. $^1$H NMR (400 MHz, CD$_3$OD) δ ppm 0.95 (t, J=7.42 Hz, 3 H) 1.09-1.24 (m, J=6.87, 1.37 Hz, 6 H) 2.34-2.46 (m, 2 H) 2.63-2.80 (m, 4 H) 3.01-3.13 (m, 2 H) 3.22 (s, 3 H) 3.40-3.51 (m, 2 H) 4.02-4.19 (m, 3 H) 4.70-4.81 (m, 2 H) 5.52 (d, J=17.04 Hz, 1 H) 5.60 (s, 1 H) 6.30 (s, 1 H) 6.84 (dd, J=8.52, 1.92 Hz, 1 H) 6.90 (dd, J=7.97, 1.37 Hz, 1 H) 6.95 (s, 1 H) 6.99-7.05 (m, 1 H) 7.05-7.13 (m, 1 H) 7.16-7.24 (m, 2 H) 7.30 (d, J=7.70 Hz, 1 H) 7.53 (dd, J=7.70, 1.65 Hz, 1 H) 7.66 (d, J=8.25 Hz, 1 H) 7.72 (s, 1 H) 9.73 (s, 1 H). MS (ESI) m/z 593.3 (M+H)+.

Example 50

[(2R,5R)-2-(1-Amino-isoquinolin-6-ylamino)-17,20-dimethyl-3,12-dioxo-13-oxa-4,11-diaza-tricyclo[14.2.2.1[6,10]]henicosa-1(19),6,8,10(21),16(20),17-hexaen-5-yl]-acetic acid ethyl ester trifluoroacetic acid salt

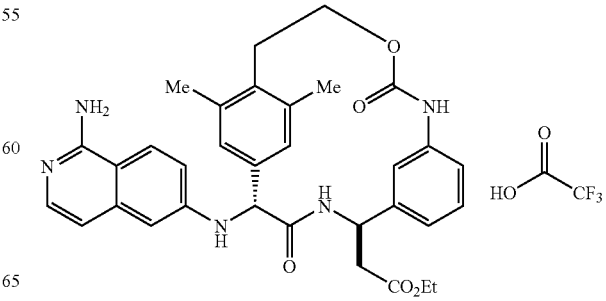

50A: (4-bromo-2,6-dimethylphenethoxy)(tert-butyl)dimethylsilane

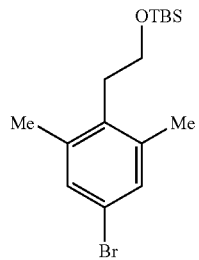

Using a procedure analogous to that used to prepare 46A, 32B (3.0 g, 13.1 mmol) was reacted tert-butylchlorodimethylsilane to afford 50A (3.58 g, 80%) as a clear oil. $^1$H NMR (400 MHz, CDCl$_3$) δ ppm −0.01 (s, 9 H) 2.30 (s, 6 H) 2.84 (t, J=7.70 Hz, 2 H) 3.66 (t, J=7.70 Hz, 2 H) 7.13 (s, 2 H).

50B: 4-(2-(tert-butyldimethylsilyloxy)ethyl)-3,5-dimethylphenylboronic acid

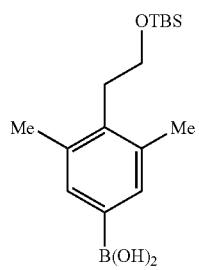

Using a procedure analogous to that used to prepare 46B, 50A (3.58 g, 10.5 mmol) was reacted trimethylborate to afford 50B (1.45 g, 45%) as a white solid. $^1$H NMR (400 MHz, MeOD) δ ppm −0.03 (s, 6 H) 0.85 (s, 9 H) 2.33 (s, 6 H) 2.92 (t, J=7.15 Hz, 2 H) 3.75 (t, J=7.42 Hz, 2 H) 7.20 (s, 2 H).

50C: 2-(1-(bis(tert-butoxycarbonyl)amino)isoquinolin-6-ylamino)-2-(4-(2-hydroxyethyl)-3,5-dimethylphenyl)acetic acid

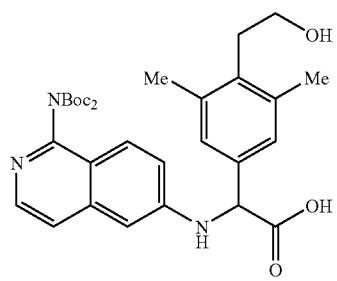

Using a procedure analogous to that used to prepare 2D, 50B (1.43 g, 4.6 mmol) was reacted with Intermediate 1 and glyoxylic acid monohydrate to afford 50C (1.1 g, 39%) as an orange solid. MS (ESI) m/z 566.6 (M+H)$^+$.

50D: (3R)-ethyl 3-(2-(1-(bis(tert-butoxycarbonyl)amino)isoquinolin-6-ylamino)-2-(4-(2-hydroxyethyl)-3,5-dimethylphenyl)acetamido)-3-(3-nitrophenyl)propanoate

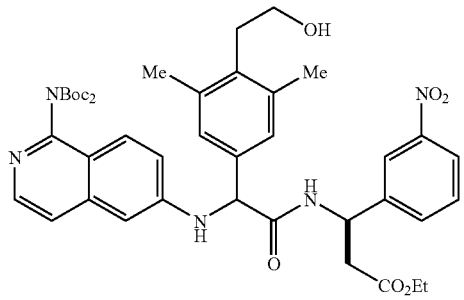

EDC (187 mg, 0.97 mmol) and HOAt (132 mg, 0.97 mmol) were added to a solution of 39A (268 mg, 0.97 mmol) and 50C (500 mg, 0.89 mmol) in DMF (10 mL). Triethylamine (0.36 mL, 2.7 mmol) was added to the reaction mixture and it was stirred at 50° C. for 3 h. The reaction mixture was diluted with EtOAc, washed with water and brine, dried over Na$_2$SO$_4$ and concentrated in vacuo. The crude product was purified by flash chromatography (0% to 20% MeOH in CH$_2$Cl$_2$) to yield 50D (580 mg, 83%) as a yellow solid. MS (ESI) m/z 786.9 (M+H)$^+$.

50E: (3R)-ethyl 3-(3-aminophenyl)-3-(2-(1-(bis(tert-butoxycarbonyl)amino)isoquinolin-6-ylamino)-2-(4-(2-hydroxyethyl)-3,5-dimethylphenyl)acetamido)propanoate

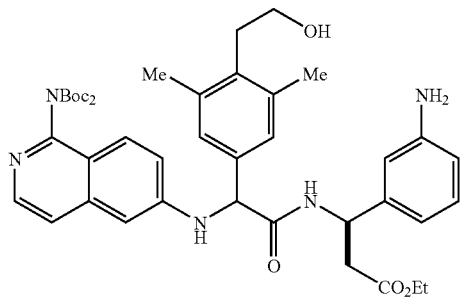

A solution of 50D (580 mg, 0.74 mmol) in MeOH (30 mL) with Pd/C (35 mg) was stirred under H$_2$ (50 psi) for 2 h. The reaction mixture was filtered and concentrated in vacuo. The crude solid was purified by flash chromatography (0% to 20% MeOH in CH$_2$Cl$_2$) to afford 50E (400 mg, 72%) as a yellow solid. MS (ESI) m/z 756.6 (M+H)$^+$.

Example 50

Phosgene (0.16 mL, 0.32 mmol, 20% in toluene) was added dropwise to a solution of 50E (200 mg, 0.26 mmol) in acetonitrile (20 mL) at 0° C. After stirring for 30 min at ambient temperature, Ar was bubbled through the reaction mixture for 5 min. The reaction mixture was added dropwise to triethylamine (0.37 mL) in CH$_2$Cl$_2$ (100 mL) at 40° C. over 4 h. The reaction mixture was stirred at ambient temperature for 15 h, concentrated in vacuo, dissolved in CH$_2$Cl$_2$/TFA (1:1) and stirred for 1 h. The solution was concentrated in vacuo and purified by reverse phase HPLC to yield Example 50 (33 mg, 43%) and its diastereomer (37 mg). ¹H NMR (400 MHz, MeOD) δ ppm 1.25 (t, J=7.07 Hz, 3 H) 2.31 (s, 3 H) 2.50 (s, 3 H) 2.66-2.81 (m, 1 H) 2.82-3.05 (m, 3 H) 3.09-3.25 (m, 1 H) 4.18 (q, J=7.07 Hz, 2 H) 5.06 (s, 1 H) 5.26-5.41 (m, 1 H) 6.29 (s, 1 H) 6.62-6.72 (m, 2 H) 6.89 (dd, J=17.05, 7.45 Hz, 2 H) 7.00 (s, 1 H) 7.07-7.20 (m, 2 H) 7.25 (d, J=7.07 Hz, 1 H) 7.36 (s, 1 H) 7.98 (d, J=9.09 Hz, 1 H) 8.57 (d, J=7.33 Hz, 1 H). MS (ESI) m/z 582.6 (M+H)⁺.

Example 51

[(2R,5R)-2-(1-Amino-isoquinolin-6-ylamino)-17,20-dimethyl-3,12-dioxo-13-oxa-4,11-diaza-tricyclo[14.2.2.1$^{6,10}$]henicosa-1(19),6,8,10(21),16(20),17-hexaen-5-yl]-acetic acid, trifluoroacetic acid salt

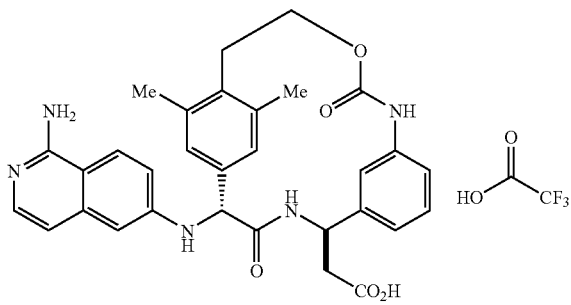

Using a procedure analogous to that used to prepare Example 35, Example 50 (30 mg, 0.05 mmol) was reacted with LiOH, and purified by reverse phase HPLC to give Example 51 (20 mg, 71%) as a white solid. ¹H NMR (400 MHz, MeOD) δ ppm 2.32 (s, 3 H) 2.51 (s, 3 H) 2.66-2.79 (m, 1 H) 2.81-3.00 (m, 2 H) 3.09-3.27 (m, 1 H) 5.05 (s, 1 H) 5.30 (dd, J=10.23, 4.17 Hz, 1 H) 6.28 (s, 1 H) 6.60-6.77 (m, 2 H) 6.89-7.05 (m, 3 H) 7.10-7.20 (m, 2 H) 7.28 (d, J=7.07 Hz, 1 H) 7.36 (s, 1 H) 8.00 (d, J=9.09 Hz, 1 H). MS (ESI) m/z 545.2 (M+H)⁺.

Example 52

[2-(1-Amino-isoquinolin-6-ylamino)-17,20-dimethyl-3,12-dioxo-13-oxa-4,11-diaza-tricyclo[14.2.2.1$^{6,10}$]henicosa-1(19),6,8,10(21),16(20),17-hexaen-4-yl]-acetic acid trifluoroacetic acid salt

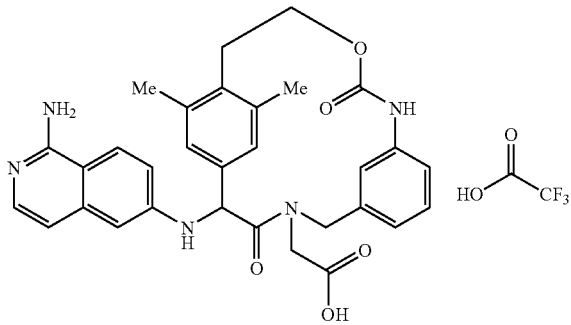

52A: 2,2,2-trifluoro-N-(3-nitrobenzyl)acetamide

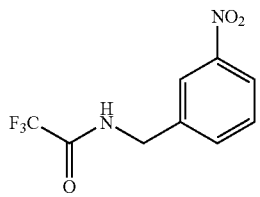

Trifluoroacetic anhydride (1.6 mL, 11.7 mmol) was added to a solution of (3-nitrophenyl)methanamine hydrochloride (2.0 g, 10.6 mmol) and Et₃N (3.7 mL, 26.6 mmol). The reaction mixture was diluted with CH₂Cl₂, washed with Na₂CO₃, brine, dried over Na₂SO₄ and concentrated in vacuo to afford 52A (2.0 g, 76%) as an off-white solid. 247.3 (M−H)⁻.

52B: tert-butyl 2-(2,2,2-trifluoro-N-(3-nitrobenzyl)acetamido)acetate

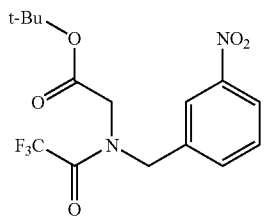

tert-Butyl 2-bromoacetate was added to a solution of 52A (950 mg, 3.8 mmol) in DMF (8 mL) with Cs₂CO₃ (1.5 g, 4.6 mmol) and stirred 15 h. The reaction mixture was diluted with EtOAc, washed with water, brine, dried over Na₂SO₄ and concentrated in vacuo. The crude product was purified by flash chromatography (0% to 60% EtOAc in hexanes) to afford 52B (850 mg, 61%) as a clear oil. MS (ESI) m/z 361.3 (M−H)⁻.

52C: tert-butyl 2-(3-nitrobenzylamino)acetate

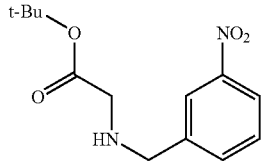

K₂CO₃ (1.5 g, 11 mmol) was added to a solution of 52B (800 mg, 2.2 mmol) in MeOH/H₂O (2:1, 9 mL) and the mixture was refluxed for 2 h. Volatiles were removed in vacuo and the remaining aqueous mixture was extracted with EtOAc. The combined organics were washed with brine, dried over Na₂SO₄ and concentrated in vacuo. The crude product was purified by flash chromatography (0% to 100% EtOAc in hexanes) to yield 52C (275 mg, 47%) as a clear oil. MS (ESI) m/z 267.1 (M+H)⁺.

52D: tert-butyl 2-(2-(1-(bis(tert-butoxycarbonyl)amino)isoquinolin-6-ylamino)-2-(4-(2-hydroxyethyl)-3,5-dimethylphenyl)-N-(3-nitrobenzyl)acetamido)acetate

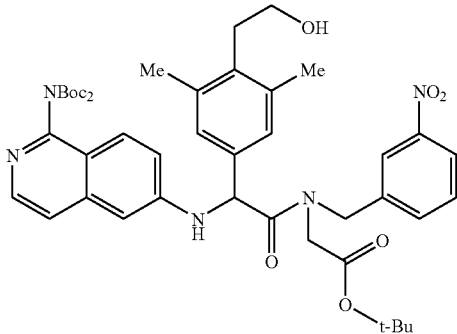

EDCI (142 mg, 0.74), HOAt (101 mg, 0.74 mmol), and triethylamine (0.18 mL, 1.35 mmol) were added to a solution of 50C (380 mg, 0.67 mmol) and 52C (197 mg, 0.74 mmol) in that order. The reaction mixture was stirred at 60° C. for 3 h. The solution was diluted with EtOAc, washed with brine, dried over $Na_2SO_4$ and concentrated in vacuo. The crude solid was purified by flash chromatography (0% to 100% EtOAc in hexanes) to afford 52D (230 mg, 42%) as a yellow solid. MS (ESI) m/z 814.9 $(M+H)^+$.

52E: tert-butyl 2-(N-(3-aminobenzyl)-2-(1-(bis(tert-butoxycarbonyl)amino)isoquinolin-6-ylamino)-2-(4-(2-hydroxyethyl)-3,5-dimethylphenyl)acetamido)acetate

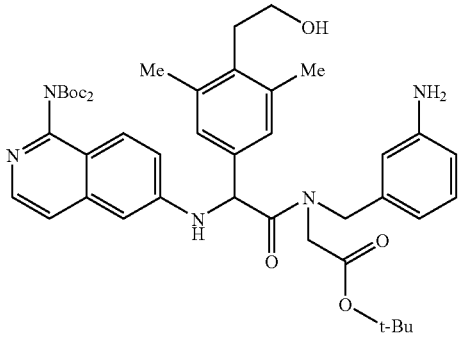

A solution of 52D (230 mg, 0.28 mmol) in MeOH (5 mL) with Pd/C (15 mg) was stirred under $H_2$ (60 psi) for 3 h. The reaction mixture was filtered through Celite and concentrated in vacuo to afford 52E (200 mg, 90%) as a yellow solid. MS (ESI) m/z 784.85 $(M+H)^+$.

Example 52

Using a procedure analogous to that used to prepare Example 50, 52E (200 mg, 0.25 mmol) was cyclized, deprotected with TFA, and purified by reverse phase HPLC to give Example 52 (100 mg, 71%) as an off-white solid. $^1$H NMR (400 MHz, MeOD) δ ppm 2.39 (s, 3 H) 2.49 (s, 3 H) 3.77-3.99 (m, 2 H) 4.02-4.20 (m, 1 H) 4.79 (d, J=18.69 Hz, 1 H) 5.04 (s, 1 H) 5.36 (s, 1 H) 5.42 (d, J=17.04 Hz, 1 H) 6.08 (s, 1 H) 6.70 (d, J=7.70 Hz, 1 H) 6.89 (d, J=7.70 Hz, 1 H) 6.94-7.02 (m, 2 H) 7.08-7.25 (m, 3 H) 7.32 (d, J=6.60 Hz, 1 H) 7.38 (s, 1 H) 8.04 (d, J=8.79 Hz, 1 H). MS (ESI) m/z 554.5 $(M+H)^+$.

Example 53

[(2R,5R)-2-(1-Amino-isoquinolin-6-ylamino)-17,20-dimethyl-3,12-dioxo-4,11-diaza-tricyclo[14.2.2.1$^{6,10}$]henicosa-1(19),6,8,10(21),16(20),17-hexaen-5-yl]-acetic acid ethyl ester trifluoroacetic acid salt

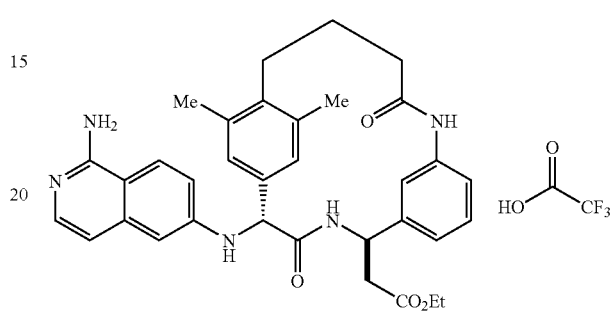

53A: 2-(4-bromo-2,6-dimethylphenyl)acetaldehyde

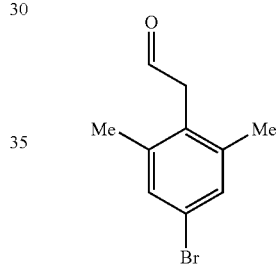

Dess-Martin Periodinane (5.2 g, 12.5 mmol) was added portionwise to a solution of 32B (2.6 g, 11.4 mmol) in $CH_2Cl_2$ (60 mL) at 0° C. and the mixture was stirred at ambient temperature for 2 h. The reaction mixture was filtered and stirred with NaOH (1.0 M, 40 mL) for 10 min. The organic layer washed with brine, dried over $Na_2SO_4$ and concentrated to yield 53A (2.6 g, 99%) as a light yellow oil. $^1$H NMR (400 MHz, CDCl$_3$) δ ppm 2.24 (s, 6 H) 3.71 (d, J=1.77 Hz, 2 H) 7.20-7.20 (m, 2 H) 9.66 (t, J=1.89 Hz, 1 H).

53B: (E)-tert-butyl 4-(4-bromo-2,6-dimethylphenyl)but-2-enoate

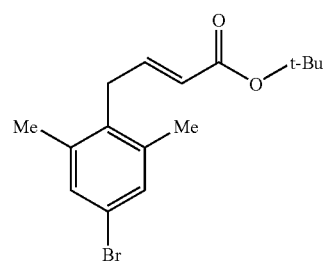

tert-Butyl 2-(dimethoxyphosphoryl)acetate (2.5 mL, 12.7 mmol) was added dropwise to a suspension of NaH (490 mg, 12.7 mmol, 60% dispersion in oil) in THF (60 mL) at 0° C. After stirring for 30 min at ambient temperature a solution of 53A (2.6 g, 11.4 mmol) in THF (10 mL) and stirred for 1 h at ambient temperature. The reaction mixture was poured into 50 mL saturated NaHCO$_3$/400 mL water and extracted with diethyl ether. The combined organics were dried over Na$_2$SO$_4$ and concentrated in vacuo. The crude solid was purified by flash chromatography (0% to 50% EtOAc in hexanes) to yield 53B (2.35 g, 63%) as a white solid. $^1$H NMR (400 MHz, CDCl$_3$) δ ppm 1.44 (s, 9 H) 2.22 (s, 6 H) 3.43 (dd, J=5.56, 1.77 Hz, 2 H) 5.43 (dt, J=15.54, 2.02, 1.89 Hz, 1 H) 6.92 (dt, J=15.66, 5.56 Hz, 1 H) 7.17 (s, 2 H).

53C: (E)-4-(4-bromo-2,6-dimethylphenyl)but-2-enoic acid

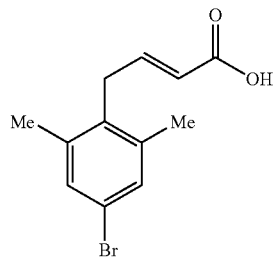

TFA (10 mL) was added to a solution of 53B (2.35 g) in CH$_2$Cl$_2$ (20 mL) at 0° C. and stirred for 4 h. The reaction mixture was concentrated to yield 53C (1.95 g, 99%) as an off-white solid. MS (ESI) m/z 267.2/269.2 (M−H)$^−$.

53D: (R,E)-ethyl 3-(benzyloxycarbonylamino)-3-(3-(4-(4-bromo-2,6-dimethylphenyl)but-2-enamido) phenyl)propanoate

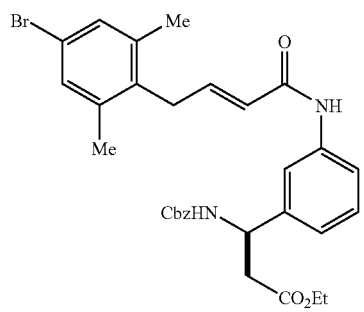

BOP (1.3 g, 3.0 mmol) was added to a solution of 53C (675 mg, 2.5 mmol), 39C (1.0 g, 2.75 mmol) and triethylamine (5.0 mmol) in acetonitrile (25 mL) at 0° C. The mixture was stirred at 0° C. for 2 h and at ambient temperature for 15 h. The mixture was concentrated in vacuo and purified by flash chromatography (0% to 60% EtOAc in hexanes) to afford 53D (800 mg, 54%) as a white solid. MS (ESI) m/z 593.3/595.3 (M+H)$^+$.

53E: (R,E)-4-(4-(3-(1-(benzyloxycarbonylamino)-3-ethoxy-3-oxopropyl)phenylamino)-4-oxobut-2-phenyl)-3,5-dimethylphenylboronic acid

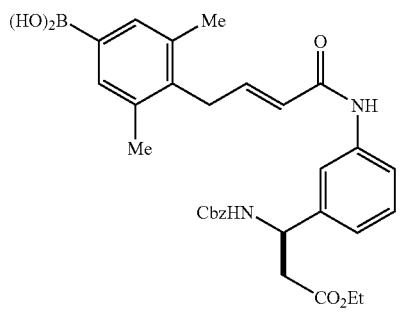

Using a procedure analogous to that used to prepare 6D, 53D (1000 mg, 2.2 mmol) was reacted with 5,5',5'-tetramethyl-[2,2']bi[[1,3,2]dioxaborinanyl] to give 53E (775 mg, 82%) as a yellow powder. MS (ESI) m/z 559.54 (M+H)$^+$.

53F: (R)-2-(4-((Z)-4-(3-((R)-1-(benzyloxycarbonylamino)-3-ethoxy-3-oxopropyl)phenylamino)-4-oxobut-2-phenyl)-3,5-dimethylphenyl)-2-(1-(bis(tert-butoxycarbonyl)amino)isoquinolin-6-ylamino)acetic acid

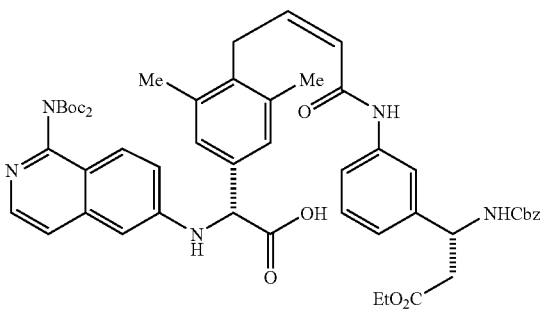

Using a procedure analogous to that used to prepare 2D, 53D (718 mg, 1.3 mmol) was reacted with Intermediate 1 and glyoxylic acid monohydrate to afford 53E (900 mg, 75%) as an orange foam. MS (ESI) m/z 930.8 (M+H)$^+$.

53E: (R)-2-(4-(4-(3-((R)-1-amino-3-ethoxy-3-oxopropyl)phenylamino)-4-oxobutyl)-3,5-dimethylphenyl)-2-(1-(bis(tert-butoxycarbonyl)amino)isoquinolin-6-ylamino)acetic acid

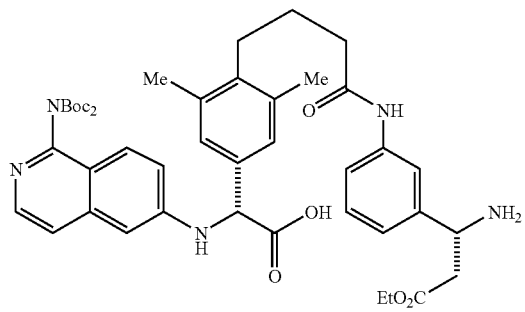

A solution of 53D (400 mg, 0.43 mmol) in MeOH (10 mL) and HCl (0.50 mL, 1.0 M) with Pd/C (80 mg) were stirred under H$_2$ (60 psi) for 15 h. The reaction mixture was filter and concentrated to afford 53E (300 mg, 87%) as a yellow solid. MS (ESI) m/z 798.6 (M+H)$^+$.

Example 53

Using a procedure analogous to that used to prepare Example 28, 53E (300 mg, 0.38 mmol) was cyclized with BOP, deprotected with TFA, and purified by reverse phase HPLC to give Example 53 (50 mg, 46%) and its diastereomer (12 mg) as a white solids. $^1$H NMR (400 MHz, MeOD) δ ppm 1.94-2.11 (m, 1 H) 2.29 (s, 3 H) 2.35-2.49 (m, 3 H) 2.52 (s, 3 H) 2.67-2.94 (m, 4 H) 4.18 (q, J=7.24 Hz, 2 H) 5.04 (s, 1 H) 5.21-5.35 (m, 1 H) 6.28 (s, 1 H) 6.62-6.75 (m, 2 H) 6.81-6.92 (m, 2 H) 6.97 (d, J=7.58 Hz, 1 H) 7.09-7.22 (m, 1 H) 7.24-7.36 (m, 2 H) 8.02 (d, J=9.35 Hz, 1 H) 8.59 (d, J=7.33 Hz, 1 H). MS (ESI) m/z 580.6 (M+H)$^+$.

Example 54

[(2R,5R)-2-(1-Amino-isoquinolin-6-ylamino)-17,20-dimethyl-3,12-dioxo-4,11-diaza-tricyclo[14.2.2.1$^{6,10}$]henicosa-1(19),6,8,10(21),16(20),17-hexaen-5-yl]-acetic acid trifluoroacetic acid salt

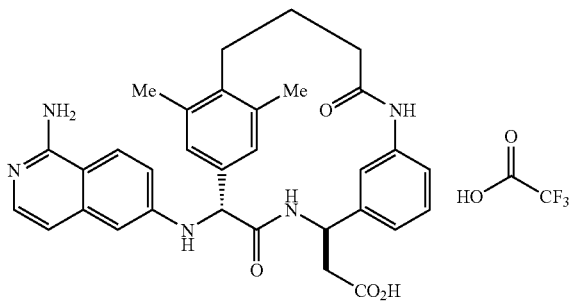

Using a procedure analogous to that used to prepare Example 35, Example 53 (47 mg, 0.08 mmol) was reacted with LiOH, and purified by reverse phase HPLC to give Example 54 (28 mg, 63%) as a white solid. $^1$H NMR (400 MHz, CD$_3$OD) δ ppm 1.96-2.10 (m, 1 H) 2.27 (s, 3 H) 2.37-2.49 (m, 3 H) 2.52 (s, 3 H) 2.72-2.91 (m, 4 H) 5.04 (s, 1 H) 5.24-5.35 (m, 1 H) 6.28 (s, 1 H) 6.63 (d, J=2.27 Hz, 1 H) 6.66-6.74 (m, 1 H) 6.81-6.90 (m, 2 H) 6.99 (d, J=7.83 Hz, 1 H) 7.09 (dd, J=9.35, 2.27 Hz, 1 H) 7.12-7.19 (m, J=7.83, 7.83 Hz, 1 H) 7.23 (d, J=7.07 Hz, 1 H) 7.34 (s, 1 H) 7.95 (d, J=9.09 Hz, 1 H) 8.66 (d, J=7.33 Hz, 1 H).

Example 55

2-(1-Amino-isoquinolin-6-ylamino)-17-methyl-4,11-diaza-tricyclo[14.2.2.1$^{6,10}$]henicosa-1(19),6,8,10(21),16(20),17-hexaene-3,12-dione

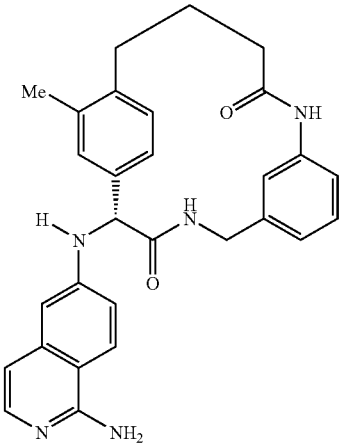

55A: 4-(4-bromo-2-methylphenyl)-4-oxobutanoic acid

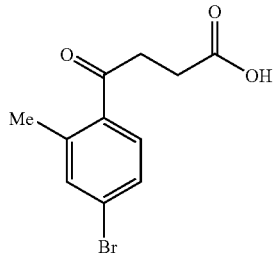

To a solution of 4-bromo-1-iodo-2-methylbenzene (148 mg, 0.5 mmol) in THF (10 mL) at −25° C. was added isopropylmagnesium bromide (0.5 mL, 0.5 mmol) and stirred 3 h. Succinic anhydride (55 mg, 0.55 mmol) was added and the reaction was stirred 18 h. The mixture was quenched with water (10 mL) and washed with 1N NaOH (10 mL), 1N HCl (10 mL), brine (10 mL) and dried (MgSO$_4$). The organic layer was concentrated in vacuo and the residue purified by flash chromatography (0-100% EtOAc/Hexane) to afford 55A (42 mg, 31%) as a crystalline solid. $^1$H NMR (400 MHz, CDCl$_3$) δ ppm 0.98 (t, 3 H) 2.42 (q, 2 H) 2.73 (t, 2 H) 4.10 (t, 2 H) 6.82 (d, 1 H) 7.02 (d, 1 H) 7.09 (t, 2 H) 7.15 (t, 1 H) 7.36 (d, 1 H) 7.58-7.63 (m, 1 H).

55B: 4-(4-bromo-2-methylphenyl)butanoic acid

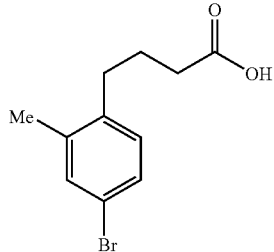

To a solution of 55A (542 mg, 2 mmol) in TFA (5 mL) was added triethylsilane (0.8 mL, 5 mmol) and the mixture heated at 90° C. for 7 h. The reaction was quenched with 1N NaOH (20 mL) and washed with EtOAc (20 mL). Aqueous layer was acidified to pH 1 with 1N HCl and extracted with EtOAc (2×20 mL). The combined organics were washed with brine (10 mL) and dried (MgSO₄). The organic layer was concentrated in vacuo and the residue purified by flash chromatography (0-100% EtOAc/Hexane) to afford 55B (216 mg, 42%) as an oil. ¹H NMR (400 MHz, CDCl₃) δ ppm 0.98 (t, 3 H) 2.42 (q, 2 H) 2.73 (t, 2 H) 4.10 (t, 2 H) 6.82 (d, 1 H) 7.02 (d, H) 7.09 (t, 2 H) 7.15 (t, 1 H) 7.36 (d, 1 H) 7.58-7.63 (m, 1 H).

55C: 4-(4-bromo-2-methylphenyl)-N-(3-cyanophenyl)butanamide

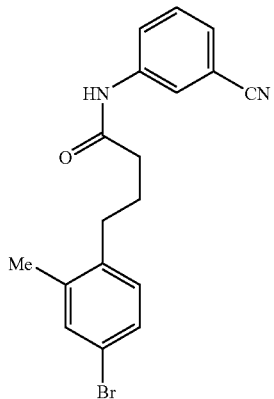

Using a procedure analogous to that used to prepare 6C, 55B (216 mg, 0.84 mmol) was reacted with 3-aminobenzonitrile to afford 55C (228 mg, 76%) as a solid. MS (ESI) m/z 358.1 (M+H)⁺.

55D: 4-(4-(3-cyanophenylamino)-4-oxobutyl)-3-methylphenylboronic acid

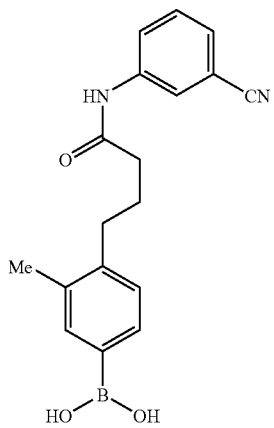

Using a procedure analogous to that used to prepare 6D, 55C (200 mg, 0.56 mmol) was reacted with 5,5',5'-tetramethyl-[2,2']bi[[1,3,2]dioxaborinanyl] to give 55D (200 mg, 56%) as a solid. MS (ESI) m/z 323.2 (M+H)⁺.

55E: 2-(1-(bis(tert-butoxycarbonyl)amino)isoquinolin-6-ylamino)-2-(4-(4-(3-cyanophenylamino)-4-oxobutyl)-3-methylphenyl)acetic acid

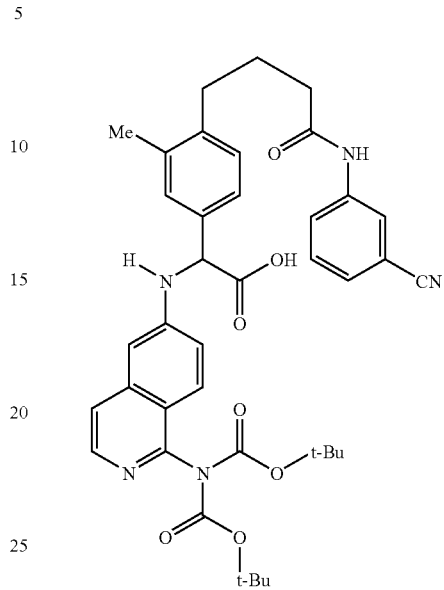

Using a procedure analogous to that used to prepare 2D, 55D (200 mg, 0.623 mmol) was reacted with Intermediate 1 and glyoxylic acid monohydrate to afford 55E (200 mg, 46%) as an oil. MS (ESI) m/z 694.4 (M+H)⁺.

55F: 2-(4-(4-(3-(aminomethyl)phenylamino)-4-oxobutyl)-3-methylphenyl)-2-(1-(bis(tert-butoxycarbonyl)amino)isoquinolin-6-ylamino)acetic acid

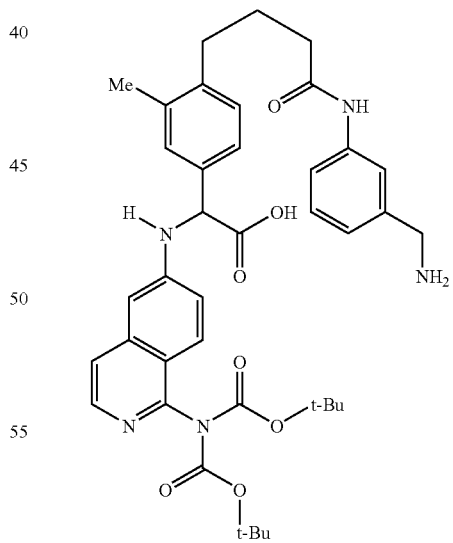

Using a procedure analogous to that used to prepare 6F, 55E (220 mg, 0.289 mmol) was hydrogenated for 18 h to give 55F (164 mg, 82%) as a solid. ¹H NMR (400 MHz, MeOD-d₄) δ ppm 1.22-1.28 (m, 18 H) 1.93 (q, 2 H) 2.31 (s, 3 H) 2.40 (t, J=7.25 Hz, 2 H) 2.67 (t, 2 H) 3.35 (s, 1 H) 3.82 (s, 2 H) 6.59-6.63 (m, J=1.76 Hz, 1 H) 7.10 (t, J=8.35 Hz, 2 H) 7.18-7.44 (m, 6 H) 7.57 (t, 2 H) 7.98 (d, J=5.71 Hz, 1 H).

Example 55

Using a procedure analogous to that used to prepare Example 6, 55F (200 mg, 0.287 mmol) was cyclized with BOP. This material was deprotected with trifluoroacetic acid, and purified by reverse phase HPLC and chiral HPLC to give Example 55 (peak 1, 10 mg, 15%) and peak 2 (10 mg, 15%). The chromatography conditions were the following: Whelk-O1 (R,R) (500×21.1 mm ID; 10 micron, Regis Technologies), 60% MeOH/EtOH (1:1), 40% Heptane, 0.1% DEA, 20 mL/min flow rate, and UV detection at 254 nm. Peak 1 analytical data: $^1$H NMR (400 MHz, CD$_3$OD) δ ppm 2.00 (m, 1 H) 2.18-2.28 (m, 1 H) 2.30 (s, 1.5 H) 2.34-2.43 (m, 2 H) 2.46 (s, 1.5 H) 2.48-2.69 (m, 2 H) 2.91-3.11 (m, 1 H) 4.08 (t, J=16.76 Hz, 1 H) 4.64 (dd, J=21.44, 15.94 Hz, 1 H) 5.03 (d, Chiral analytical HPLC retention times: peak 1, 11.22 min; peak 2, 16.00 min using the following chromatography conditions: Welko-O1 (R, R) column (250×4.6 mm ID; 5 micron, 60% MeOH/EtOH (1:1), 40% Heptane, 0.1% DEA as eluent, 1 mL/min flow rate and UV detection at 254 nm.

Example 56

3-(17-Ethyl-3,12-dioxo-13-oxa-4,11-diaza-tricyclo[14.2.2.1$^{6,10}$]henicosa-1(19),6,8,10(21), 16(20),17-hexaen-2-ylamino)-benzamide

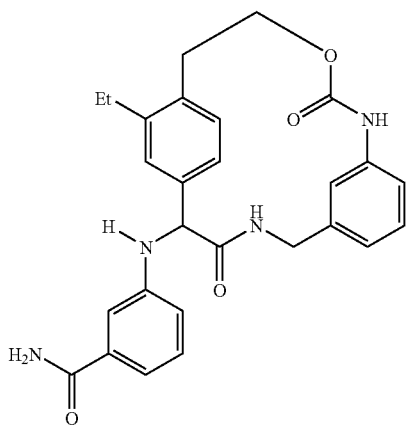

56A: 4-bromo-2-ethylphenethyl 3-cyanophenylcarbamate

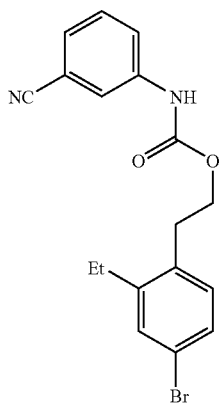

Using a procedure analogous to that used to prepare 30C, 36B (687 mg, 3 mmol) was reacted with 3-isocyanatobenzonitrile (432 mg, 3 mmol) to give 56A (630 mg, 57%) as an oil. MS (ESI) m/z 373.2 (M+H)$^+$.

56B: 4-(2-(3-cyanophenylcarbamoyloxy)ethyl)-3-ethylphenylboronic acid

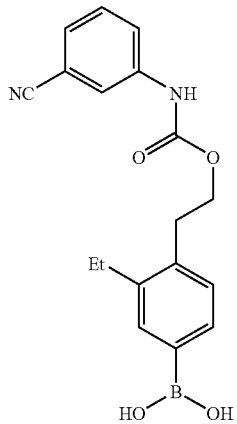

Using a procedure analogous to that used to prepare 6D, 56A (630 mg, 1.69 mmol) was reacted with 5,5',5'-tetramethyl-[2,2']bi[[1,3,2]dioxaborinanyl] to give 56B (350 mg, 61%) as a solid. $^1$H NMR (400 MHz, MeOD-d$_4$) δ ppm 0.98 (t, 3 H) 2.42 (q, 2 H) 2.73 (t, 2 H) 4.10 (t, 2 H) 6.82 (d, 1 H) 7.02 (d, 1 H) 7.09 (t, 2 H) 7.15 (t, 1 H) 7.36 (d, 1 H) 7.58-7.63 (m, 1 H).

56C: 2-(3-carbamoylphenylamino)-2-(4-(2-(3-cyanophenylcarbamoyloxy)ethyl)-3-ethylphenyl)acetic acid

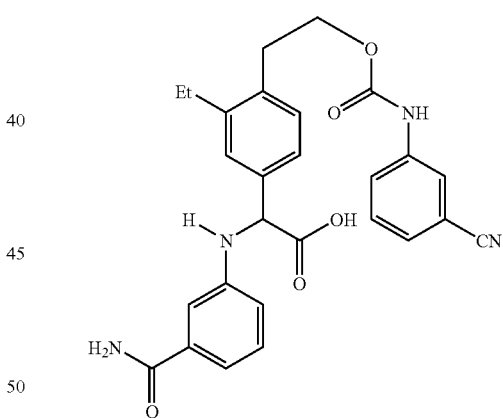

Using a procedure analogous to that used to prepare 2D, 56B (175 mg, 0.52 mmol) was reacted with 3-aminobenzamide and glyoxylic acid monohydrate to afford 56C (175 mg, 72%) as an oil. MS (ESI) m/z 487.3 (M+H)$^+$.

Example 56

Using a procedure analogous to that used to prepare 6F, 56C (175 mg, 0.36 mmol) was hydrogenated for 5 h to give 2-(4-(2-(3-(aminomethyl)phenylcarbamoyloxy)ethyl)-3-ethylphenyl)-2-(3-carbamoylphenylamino)acetic acid (170 mg, 97%) as an oil. Using a procedure analogous to that used to prepare Example 28, the crude material was cyclized with BOP and purified by HPLC to give Example 56 (13 mg, 8%). $^1$H NMR (400 MHz, CD$_3$OD) δ ppm 1.15 (t, J=7.70 Hz, 1 H)

1.29 (t, J=7.42 Hz, 2 H) 2.55-2.68 (m, 1 H) 2.69-2.98 (m, 3 H) 3.06-3.26 (m, 1 H) 3.93-4.25 (m, 1.6 H) 4.37-4.51 (m, 0.4 H) 4.55-4.86 (m, 2 H) 5.00-5.10 (m, J=5.50 Hz, 1 H) 6.19 (s, 1 H) 6.66 (d, J=7.70 Hz, 1 H) 6.87 (d, J=7.15 Hz, 1 H) 6.91-6.98 (m, 1 H) 7.07-7.20 (m, 2 H) 7.20-7.27 (m, 2 H) 7.27-7.36 (m, 2 H) 7.40 (s, 1 H). MS (ESI) m/z 473.3 (M+H)+.

Example 57

2-(1-Amino-isoquinolin-6-ylamino)-17-ethyl-13-oxa-4,11-diaza-tricyclo[14.2.2.1$^{6,10}$]henicosa-1(19),6,8,10(21),16(20),17-hexaene-3,12-dione trifluoroacetic acid salt

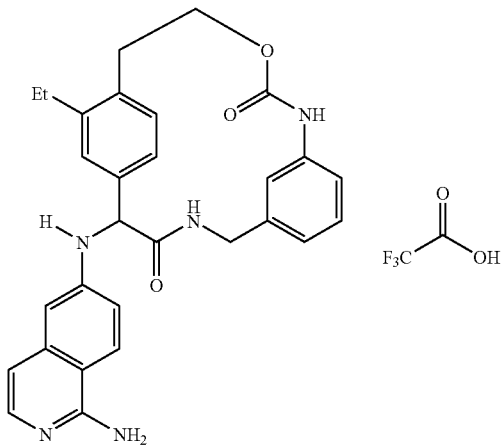

57A: 2-(1-(bis(tert-butoxycarbonyl)amino)isoquinolin-6-ylamino)-2-(4-(2-(3-cyanophenylcarbamoyloxy)ethyl)-3-ethylphenyl)acetic acid

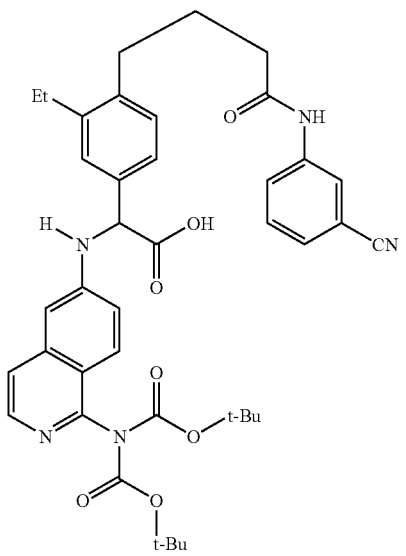

Using a procedure analogous to that used to prepare 2D, 56B (175 mg, 0.52 mmol) was reacted with Intermediate 1 and glyoxylic acid monohydrate to afford 57A (186 mg, 52%) as an oil. MS (ESI) m/z 710.5 (M+H)+.

Example 57

Using a procedure analogous to that used to prepare 6F, 57A (180 mg, 0.25 mmol) was hydrogenated for 5 h to give 2-(4-(2-(3-(aminomethyl)phenylcarbamoyloxy)ethyl)-3-ethylphenyl)-2-(1-(bis(tert-butoxycarbonyl)amino)isoquinolin-6-ylamino)acetic acid (180 mg) as an oil. Using a procedure analogous to that used to prepare Example 28, the crude oil was cyclized with BOP, deprotected with trifluoroacetic acid, and purified by HPLC to give Example 57 (16 mg, 13%). $^1$H NMR (400 MHz, CD$_3$OD) δ ppm 1.13 (t, J=7.70 Hz, 1 H) 1.34 (t, J=7.42 Hz, 2 H) 2.70-3.01 (m, 3 H) 3.09-3.25 (m, 1 H) 3.95-4.38 (m, 2 H) 4.40-4.83 (m, 2 H) 5.10-5.19 (m, 1 H) 6.19 (s, 1 H) 6.63-6.76 (m, 2 H) 6.82-6.93 (m, 2 H) 7.07-7.27 (m, 4 H) 7.28-7.34 (m, 2 H) 7.39-7.55 (m, 1 H) 8.00-8.12 (m, 1 H) 8.56-8.76 (m, 1 H). MS (ESI) m/z 496.3 (M+H)+.

Example 58

3-(13-Methyl-3,12-dioxo-4,11,13-triaza-tricyclo[14.2.2.1$^{6,10}$]henicosa-1(19),6,8,10(21),16(20),17-hexaen-2-ylamino)-benzamide

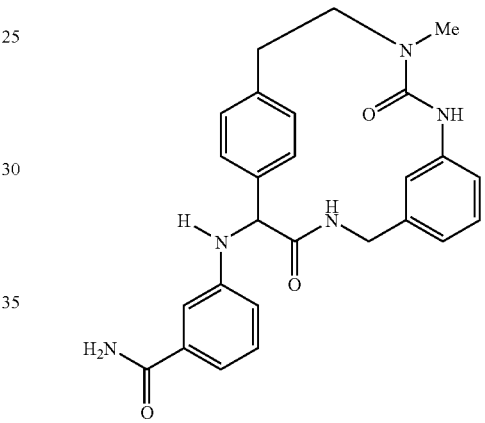

58A: 2-(3-carbamoylphenylamino)-2-(4-(2-(3-(3-cyanophenyl)-1-methylureido)ethyl)phenyl)acetic acid

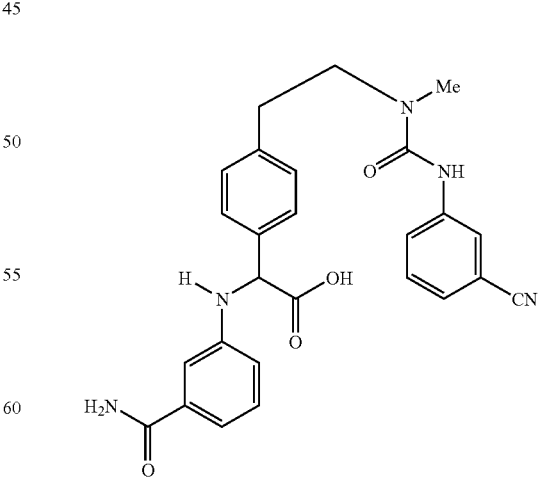

Using a procedure analogous to that used to prepare 2D, 23D (170 mg, 0.52 mmol) was reacted with 3-aminobenzamide and glyoxylic acid monohydrate to afford 58A (157 mg, 64%) as an oil. MS (ESI) m/z 472.3 (M+H)+.

58B: 2-(4-(2-(3-(3-(aminomethyl)phenyl)-1-methy-lureido)ethyl)phenyl)-2-(3-carbamoylphenylamino)acetic acid

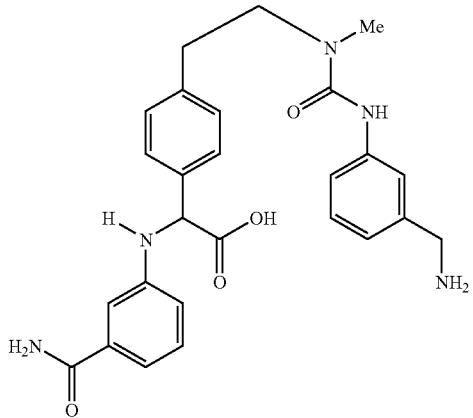

Using a procedure analogous to that used to prepare 6F, 58A (245 mg, 0.52 mmol) was hydrogenated for 5 h to give 58B (239 mg, 97%) as an oil. MS (ESI) m/z 476.1 (M+H)+.

Example 58

Using a procedure analogous to that used to prepare Example 28, 58B (150 mg, 0.316 mmol) was cyclized with BOP and purified by HPLC to give Example 58 (47 mg, 33%). $^1$H NMR (400 MHz, MeOD-$d_4$) δ ppm 2.86 (t, J=5.93 Hz, 3 H) 3.05 (s, 3 H) 4.03 (d, J=15.82 Hz, 1 H) 4.63 (d, 1 H) 5.09 (s, 1 H) 6.82 (d, J=6.59 Hz, 2 H) 6.88-6.94 (m, 1 H) 7.16-7.24 (m, 4 H) 7.27 (d, 2 H) 7.31 (d, J=7.47 Hz, 1 H) 7.46 (d, J=8.35 Hz, 1 H) 7.57 (d, J=7.91 Hz, 1 H). MS (ESI) m/z 458.3 (M+H)+.

Example 59

(S)-2-(1-Amino-isoquinolin-6-ylamino)-5,17-dimethyl-13-oxa-4,11-diaza-tricyclo[14.2.2.1$^{6,10}$]henicosa-1(19),6,8,10(21),16(20),17-hexaene-3,12-dione trifluoroacetic acid salt

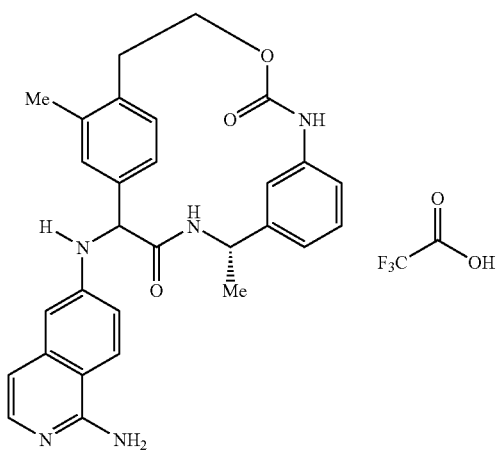

59A: (S)-benzyl 1-(3-nitrophenyl)ethylcarbamate

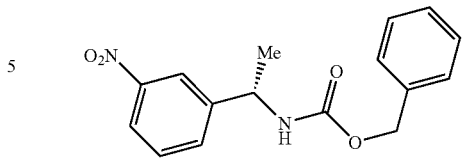

Benzyl 2,5-dioxopyrrolidin-1-yl carbonate (1.36 g, 5.5 mmol) was added to a solution of (S)-1-(3-nitrophenyl)ethanamine HCl (1 g, 4.95 mmol) in $CH_2Cl_2$ (70 mL) and DIEA (2.2 mL, 12.4 mmol) and the reaction mixture was stirred for 1 h. The mixture was diluted with $CH_2Cl_2$ (100 mL), washed with $NaHCO_3$, brine, dried over $Na_2SO_4$ and concentrated in vacuo to yield 59A (1.76 g, 99%) as a white solid. MS (ESI) m/z 323.02 (M+Na)+.

59B: (S)-benzyl 1-(3-aminophenyl)ethylcarbamate

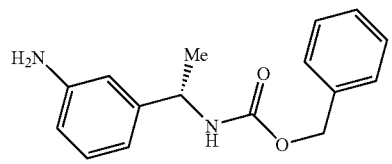

To a refluxing solution of 59A (1.7 g, 5.9 mmol), EtOH (60 mL), water (15 mL) and AcOH (4 mL) was added portionwise Fe powder (1.6 g, 29.5 mmol) over 30 min. Mixture was heated for 45 min. before cooling to ambient temperature and filtering through celite. Filtration and concentration in vacuo afforded 59B (1.5 g, 94%) as an oil. $^1$H NMR (400 MHz, CDCl$_3$) δ ppm 1.43 (d, J=6.59 Hz, 3 H) 5.00-5.17 (m, 2 H) 5.40 (d, J=7.47 Hz, 1 H) 6.53-6.60 (m, 2 H) 6.69 (d, J=7.47 Hz, 1 H) 7.11 (t, J=7.69 Hz, 1 H) 7.29-7.39 (m, 5 H).

59C: (S)-4-(2-(3-(1-(benzyloxycarbonylamino)ethyl)phenylcarbamoyloxy)ethyl)-3-methylphenylbromide

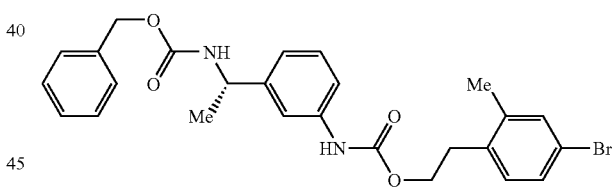

Using a procedure analogous to that used to prepare 34D, 59B (1.5 g 5.5 mmol) was reacted with 30B to give 59C (2.46 g, 9%) as an oil. MS (ESI) m/z 512.2 (M+H)+.

59D: (S)-4-(2-(3-(1-(benzyloxycarbonylamino)ethyl)phenylcarbamoyloxy)ethyl)-3-methylphenylboronic acid

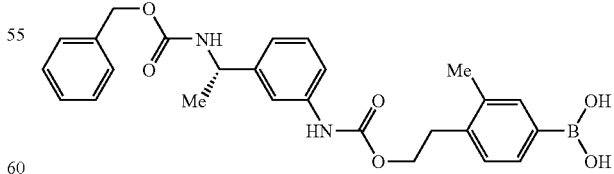

Using a procedure analogous to that used to prepare 6D, 59C (2.46 g, 4.8 mmol) was reacted with 5,5',5'-tetramethyl-[2,2']bi[[1,3,2]dioxaborinanyl] to give 59D (560 mg, 22%) as a solid. $^1$H NMR (400 MHz, MeOD-$d_4$) δ ppm 1.25-1.41 (m, J=4.39 Hz, 3 H) 2.27 (s, 3 H) 2.61 (s, 2 H) 2.92 (s, 2 H) 4.22 (s, 2 H) 4.64 (s, 1 H) 6.84-7.56 (m, 12 H).

59E: 2-(4-(2-(3-((S)-1-(benzyloxycarbonylamino)ethyl)phenylcarbamoyloxy)ethyl)-3-methylphenyl)-2-(1-(bis(tert-butoxycarbonyl)amino)isoquinolin-6-ylamino)acetic acid

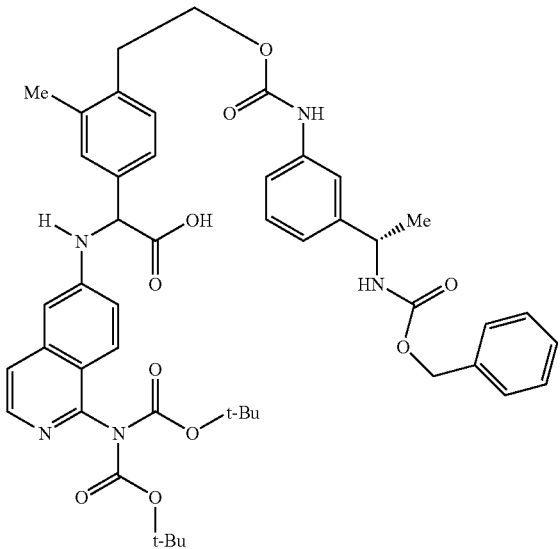

Using a procedure analogous to that used to prepare 2D, 59D (280 mg, 0.588 mmol) was reacted with Intermediate 1 and glyoxylic acid monohydrate to afford 59E (313 mg, 63%) as an oil. MS (ESI) m/z 848.7 (M+H)$^+$.

Example 59

Using a procedure analogous to that used to prepare 6F, 59E (313 mg, 0.37 mmol) was hydrogenated for 18 h to give 2-(4-(2-(3-((S)-1-aminoethyl)phenylcarbamoyloxy)ethyl)-3-methylphenyl)-2-(1-(bis(tert-butoxycarbonyl)amino)isoquinolin-6-ylamino)acetic acid (188 mg) as an oil. Using a procedure analogous to that used to prepare Example 28, the crude oil (188 mg, 0.26 mmol) was cyclized with BOP, deprotected with trifluoroacetic acid, and purified by HPLC to give Example 59 (15 mg, 4%). MS (ESI) m/z 496.3 (M+H)$^+$.

Example 60

2-(1-Amino-isoquinolin-6-ylamino)-4,17-dimethyl-13-oxa-4,11-diaza-tricyclo[14.2.2.1$^{6,10}$]henicosa-1(19),6,8,10(21),16(20),17-hexaene-3,12-dione trifluoroacetic acid salt

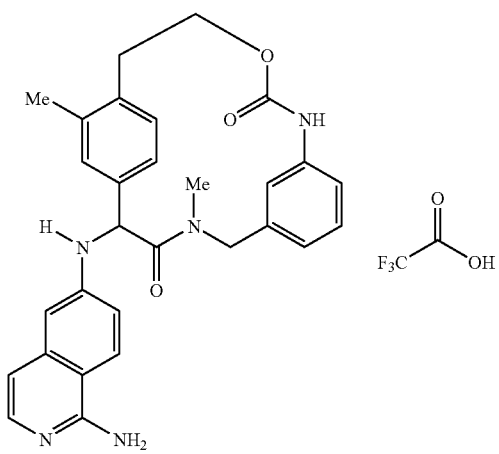

60A: benzyl methyl(3-nitrobenzyl)carbamate

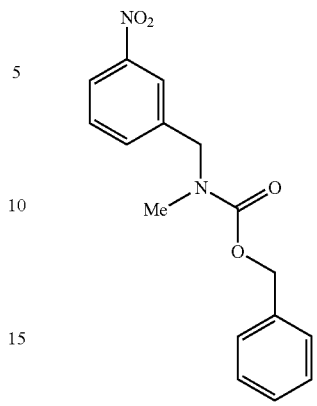

Benzyl 2,5-dioxopyrrolidin-1-yl carbonate (1.65 g, 6.6 mmol) was added to a solution of N-methyl-1-(3-nitrophenyl)methanamine (1 g, 6 mmol) in CH$_2$Cl$_2$ (24 mL) and DIEA (2.7 mL, 15 mmol) and the reaction mixture was stirred for 1 h. The mixture was diluted with CH$_2$Cl$_2$ (100 mL), washed with NH$_4$Cl, NaHCO$_3$, brine, dried over Na$_2$SO$_4$ and concentrated in vacuo to yield 60A (1.75 g, 99%) as a white solid. MS (ESI) m/z 301.03 (M+H)$^+$.

60B: benzyl 3-aminobenzyl(methyl)carbamate

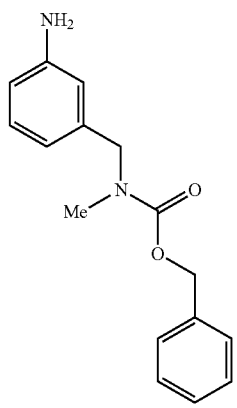

To a refluxing solution of 60A (1.7 g, 5.8 mmol), EtOH (60 mL), water (15 mL) and AcOH (4 mL) was added portionwise Fe powder (1.63 g, 29.0 mmol) over 30 min. The mixture was heated for 45 min. before cooling to ambient temperature and filtered through celite. Filtrate concentrated in vacuo to afford 60B (1.5 g, 95%) as an oil. $^1$H NMR (400 MHz, CDCl$_3$) δ ppm 1.25-1.41 (m, J=4.39 Hz, 3 H) 2.27 (s, 3 H) 2.61 (s, 2 H) 2.92 (s, 2 H) 4.22 (s, 2 H) 4.64 (s, 1 H) 6.84-7.56 (m, 12 H)

60C: 4-(2-(3-(((benzyloxycarbonyl)(methyl)amino)methyl)phenylcarbamoyloxy)ethyl)-3-methylphenyl-bromide

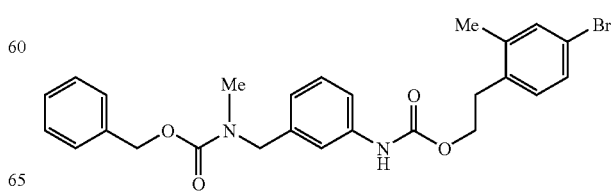

Using a procedure analogous to that used to prepare 34D, 60B (1.6 g, 5.9 mmol) was reacted with 30B to give 60C (2.0 g, 69%) as an oil. MS (ESI) m/z 512.2 (M+H)⁺.

60D: 4-(2-(3-(((benzyloxycarbonyl)(methyl)amino) methyl)phenylcarbamoyloxy)ethyl)-3-methylphenyl- boronic acid

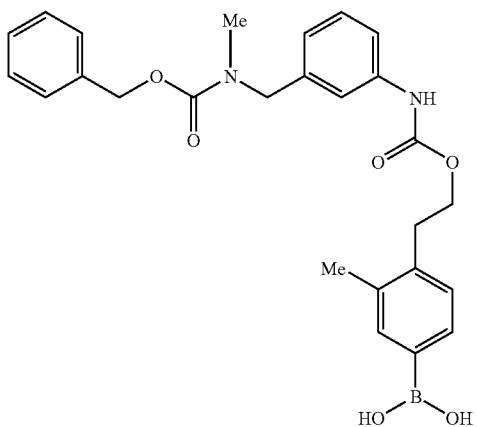

Using a procedure analogous to that used to prepare 6D, 60C (2.9 g, 5.6 mmol) was reacted with 5,5',5'-tetramethyl- [2,2']bi[[1,3,2]dioxaborinanyl] to give 60D (720 mg, 28%) as a solid. MS (ESI) m/z 475.3 (M−H)⁻.

60E: 2-(4-(2-(3-(((benzyloxycarbonyl)(methyl) amino)methyl)phenylcarbamoyloxy)ethyl)-3-meth- ylphenyl)-2-(1-(bis(tert-butoxycarbonyl)amino)iso- quinolin-6-ylamino)acetic acid

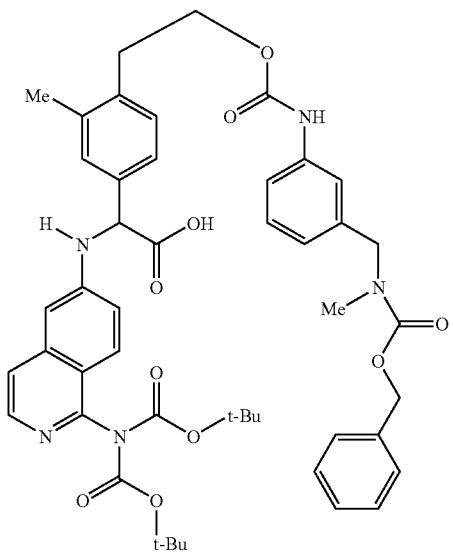

Using a procedure analogous to that used to prepare 2D, 60D (350 mg, 0.73 mmol) was reacted with Intermediate 1 and glyoxylic acid monohydrate 60E (535 mg, 87%) as an oil. MS (ESI) m/z 848.1 (M+H)⁺.

Example 60

Using a procedure analogous to that used to prepare 6F, 60E (535 mg, 0.63 mmol)) was hydrogenated for 18 h to give 2-(1-(bis(tert-butoxycarbonyl)amino)isoquinolin-6-ylamino)-2-(3-methyl-4-(2-(3-((methylamino)methyl)phe- nylcarbamoyloxy)ethyl)phenyl)acetic acid (350 mg, 77%) as an oil. Using a procedure analogous to that used to prepare Example 28, the crude oil was cyclized with BOP, depro- tected with trifluoroacetic acid, and purified by HPLC to give Example 60 (2.88 mg, 1.2%). ¹H NMR (400 MHz, CD₃OD) δ ppm 2.33 (s, 1.5 H) 2.49 (s, 1.5 H) 2.65-2.84 (m, 1 H) 3.05-3.19 (m, 1 H) 3.24 (s, 1.5 H) 3.26 (s, 1.5 H) 3.81-4.06 (m, 1.5 H) 4.32-4.35 (m, 0.5 H) 5.28-5.51 (m, 1 H) 5.62-5.76 (m, 1 H) 5.94-6.04 (m, 1 H) 6.69 (d, J=7.91 Hz, 1 H) 6.78-6.85 (m, 1 H) 6.84-6.94 (m, 2 H) 7.07-7.36 (m, 6 H) 7.51-7.66 (m, 1 H) 8.02 (d, J=9.23 Hz, 1 H). MS (ESI) m/z 496.4 (M+H)⁺.

Example 61

2-(1-Amino-isoquinolin-6-ylamino)-17-chloro-13- oxa-4,11-diaza-tricyclo[14.2.2.1⁶,¹⁰]henicosa-1(19), 6,8,10(21),16(20),17-hexaene-3,12-dione trifluoro- acetic acid salt

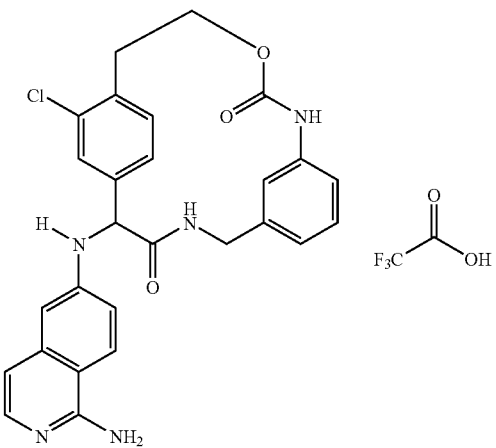

61A: 4-bromo-2-chloro-1-vinylbenzene

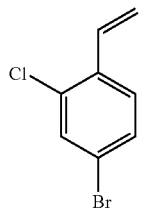

Using a procedure analogous to that used to prepare 30A, 4-bromo-2-chloro-1-iodobenzene (8 g, 25 mmol) was reacted with trimethyl(vinyl)silane in a pressure vessel at 160° C. for 1 h and worked up in a manner similar as in 30A to yield 61A (5.2 g, 96%) as an oil. ¹H NMR (400 MHz, CDCl₃) δ ppm 5.41 (d, J=11.86 Hz, 1 H) 7.02 (dd, J=17.36, 11.21 Hz, 1 H) 7.35 (dd, 1 H) 7.41 (d, 1 H) 7.52 (d, J=1.76 Hz, 1 H).

61B: 2-(4-bromo-2-chlorophenyl)ethanol

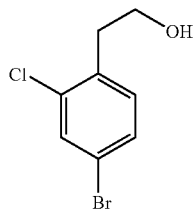

Using a procedure analogous to that used to prepare 30B, 61A (5 g, 23 mmol) was heated in a pressure vessel with 9-BBN at 100° C. for 10 h and worked up as in 30B to yield 61B (2.9 g, 54%) as an oil. ¹H NMR (400 MHz, CDCl₃) δ ppm 2.95 (t, J=6.59 Hz, 2 H) 3.85 (t, J=6.59 Hz, 2 H) 7.14 (d, J=7.91 Hz, 1 H) 7.33 (dd, J=8.13, 1.98 Hz, 1 H) 7.52 (d, J=2.20 Hz, 1 H).

61C: tert-butyl 3-isocyanatobenzylcarbamate

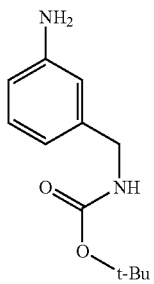

To a solution of 3-(aminomethyl)aniline (25 g, 205 mmol) and TEA (80 mL, 451 mmol) in DCM (500 mL) and acetonitrile (200 mL) at 0° C. was added dropwise a solution of di-tert-butyl dicarbonate (45 g, 205 mmol) in DCM (70 mL). The mixture was stirred for 1 h before concentrating in vacuo. The residue purified by flash chromatography (0-100% EtoAc/Hexane) to afford 61C (43 g, 94%) as a crystalline solid. ¹H NMR (400 MHz, CDCl₃) δ ppm 1.42-1.47 (m, 9 H) 4.18 (d, J=5.71 Hz, 2 H) 6.52-6.65 (m, 3 H) 7.07 (t, J=7.91 Hz, 1 H).

61D: 4-(2-(3-((tert-butoxycarbonylamino)methyl)phenylcarbamoyloxy)ethyl)-3-chlorophenylbromide

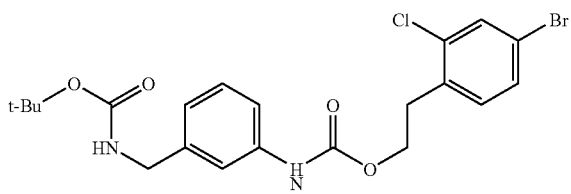

Using a procedure analogous to that used to prepare 34D, 61C (1.94 g, 8.73 mmol) was reacted with 61B to give 61D (1.84 g, 50%) as an oil. MS (ESI) m/z 385.1 (M+H)⁺.

61E: 4-(2-(3-((tert-butoxycarbonylamino)methyl)phenylcarbamoyloxy)ethyl)-3-chlorophenylboronic acid

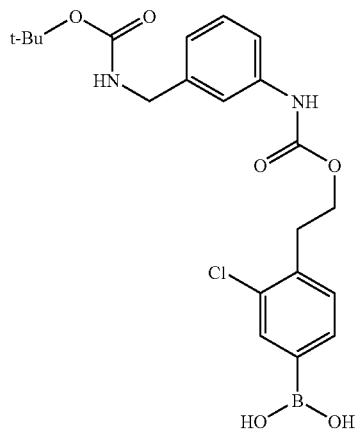

Using a procedure analogous to that used to prepare 6D, 61D (1.84 g, 3.8 mmol) was reacted with 5,5',5'-tetramethyl-[2,2']bi[[1,3,2]dioxaborinanyl] to give 61E (750 mg, 44%) as a solid. MS (ESI) m/z 447.1 (M−H)⁻.

61F: 2-(1-(bis(tert-butoxycarbonyl)amino)isoquinolin-6-ylamino)-2-(4-(2-(3-((tert-butoxycarbonylamino)methyl)phenylcarbamoyloxy)ethyl)-3-chlorophenyl)acetic acid

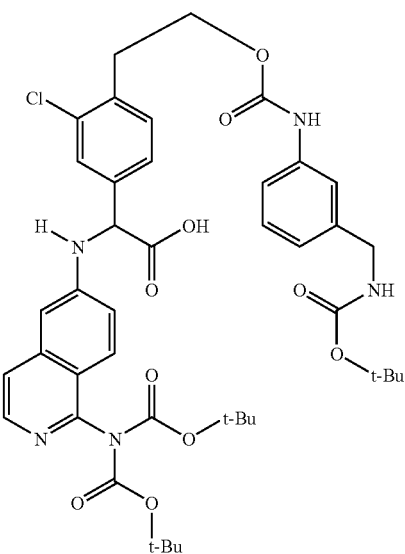

Using a procedure analogous to that used to prepare 2D, 61E (350 mg, 0.781 mmol) was reacted with Intermediate 1 and glyoxylic acid monohydrate to afford 61F (547 mg, 86%) as an oil. MS (ESI) m/z 822.0 (M+2 H)⁺.

Example 61

61F (547 mg, 0.67 mmol) was stirred in dioxane (10 mL) and 4M HCl/dioxane (5 mL) at ambient temperature for 6 h and concentrated to give crude benzyl amine (346 mg, 98%) as an oil. Using a procedure analogous to that used to prepare Example 28, the oil was cyclized with BOP before concentrating and purifying by HPLC to give Example 61 (6.2 mg, 2.0%). MS (ESI) m/z 502.3 (M+H)⁺.

Example 62

3-(17-Ethoxy-3,12-dioxo-13-oxa-4,11-diaza-tricyclo[14.2.2.1⁶,¹⁰]henicosa-1(19),6,8,10(21), 16(20),17-hexaen-2-ylamino)-benzamide

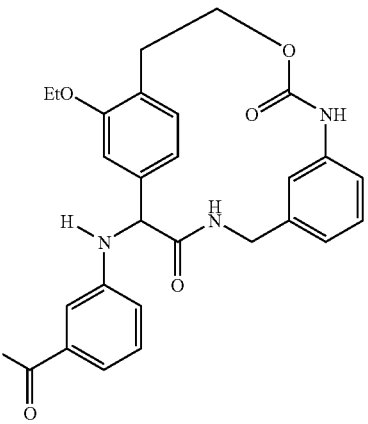

62A: 4-bromo-2-ethoxy-1-nitrobenzene

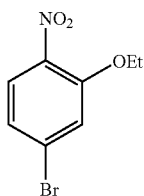

To a solution of 4-bromo-2-fluoro-1-nitrobenzene (3 g, 13.6 mmol) and EtOH (50 mL) was added NaOEt (21% w/w, 50 mL). The mixture stirred for 2 h before concentrating in vacuo. The residue purified by flash chromatography (0-100% EtoAc/Hexane) to afford 62A (3 g, 90%) as an oil. $^1$H NMR (400 MHz, CDCl$_3$) δ ppm 1.49 (t, 3 H) 4.19 (q, 2 H) 7.22 (dd, 2 H) 7.71-7.81 (m, 1 H).

62B: 4-bromo-2-ethoxyaniline

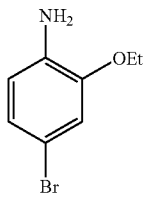

To a refluxing solution of 62A (3.0 g, 12.2 mmol), EtOH (60 mL), water (15 mL) and AcOH (10 mL) was added portion-wise Fe powder (5 g, 89.3 mmol) over 30 min. The mixture was heated for 1 h before cooling to ambient temperature and filtering through celite. The filtrate was concentrated in vacuo to afford 62B (2.5 g, 96%) as an oil. $^1$H NMR (400 MHz, CDCl$_3$) δ ppm 1.42 (t, J=7.03 Hz, 3 H) 4.02 (q, J=6.88 Hz, 2 H) 6.57 (d, J=7.91 Hz, 1 H) 6.85-6.90 (m, 2 H).

62C: 4-bromo-2-ethoxy-1-iodobenzene

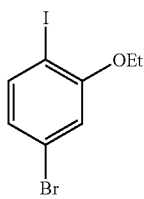

To a solution of 62B (2.5 g, 1.2 mmol) in acetonitrile (30 mL) at 0° C. was added dropwise a solution of iodine (6 g, 2.4 mmol), and t-BuONO (1.44 g, 1.4 mmol) in acetonitrile (100 mL) over 30 min and stirred 1.5 h. The mixture was quenched with aqueous Na$_2$SO$_3$ while maintaining the temperature <10° C. After stirring 1 h the mixture was extracted with hexane (3×100 mL). The combined organics were dried (MgSO$_4$) before concentrating in vacuo and the residue was purified by flash chromatography (0-5% EtOAc/Hexane) to afford 62C (2 g, 53%) as an oil. $^1$H NMR (400 MHz, CDCl$_3$) δ ppm 1.47 (t, J=7.03 Hz, 4 H) 4.06 (q, J=7.03 Hz, 2 H) 6.83 (dd, J=8.35, 1.76 Hz, 1 H) 6.90 (d, J=2.20 Hz, 1 H) 7.59 (d, J=8.35 Hz, 1 H).

62D: 4-bromo-2-ethoxy-1-vinylbenzene

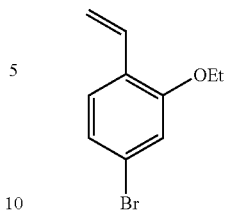

Using a procedure analogous to that used to prepare 30A, 62C (2 g, 6.1 mmol) was reacted with trimethyl(vinyl)silane in a pressure vessel at 160° C. for 1 h and worked up in a manner similar as in 30A to yield 62D (1.4 g, 88%) as an oil. $^1$H NMR (400 MHz, CDCl$_3$) δ ppm 1.44 (t, J=7.03 Hz, 3 H) 4.02 (q, J=6.74 Hz, 2 H) 5.27 (d, J=10.99 Hz, 1 H) 5.74 (d, 1 H) 6.92-7.01 (m, 2 H) 7.04 (d, 1 H) 7.31 (d, J=7.91 Hz, 1 H).

62E: 2-(4-bromo-2-ethoxyphenyl)ethanol

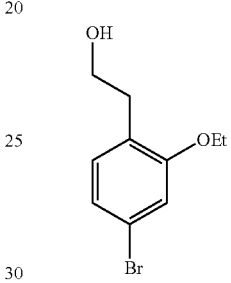

Using a procedure analogous to that used to prepare 30B, 62D (700 mg, 3.3 mmol) was heated in a pressure vessel with 9-BBN at 100° C. for 10 h and worked up as in 30B to yield 62E (620 mg, 82%) as solid. $^1$H NMR (400 MHz, CDCl$_3$) δ ppm 1.41 (t, J=6.95 Hz, 3 H) 2.85 (t, J=6.32 Hz, 2 H) 3.81 (t, J=6.32 Hz, 2 H) 4.02 (q, J=7.07 Hz, 2 H) 6.96 (s, 1 H) 6.99-7.03 (m, 2 H).

62F: 4-bromo-2-ethoxyphenethyl 3-cyanophenylcarbamate

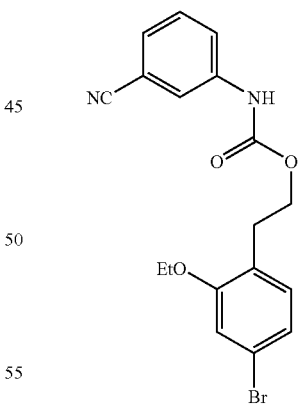

NaH (346 mg, 8.7 mmol, 60% dispersion in oil) was added in one portion to a solution of 3-isocyanatobenzonitrile (567 mmol, 3.9 mmol) and 62E (960 mg, 3.9 mmol) in THF (40 mL) and the cooling bath was removed. After stirring for 2 h at ambient temperature 1.0 N citric acid (50 mL) was added and the mixture was extracted with diethyl ether. The combined organics were washed with brine, dried over Na$_2$SO$_4$ and concentrated in vacuo. The crude residue was purified by flash chromatography (0% to 60% EtOAc in hexanes) to yield 62F (611 mg, 50%) as a pale, yellow solid. MS (ESI) m/z 411.0/413.0 (M+H)$^+$.

62G: 4-(2-(3-cyanophenylcarbamoyloxy)ethyl)-3-ethoxyphenylboronic acid

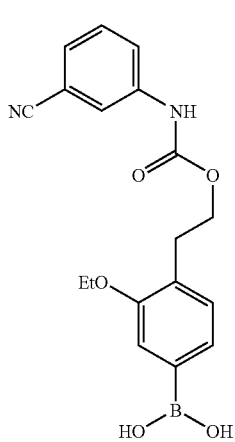

Using a procedure analogous to that used to prepare 6D, 62F (811 mg, 2.1 mmol) was reacted with 5,5',5'-tetramethyl-[2,2']bi[[1,3,2]dioxaborinanyl] to give 62G (400 mg, 54%) as a white solid. MS (ESI) m/z 355.2 (M+H)+.

62H: 2-(3-carbamoylphenylamino)-2-(4-(2-(3-cyanophenylcarbamoyloxy)ethyl)-3-ethoxyphenyl) acetic acid

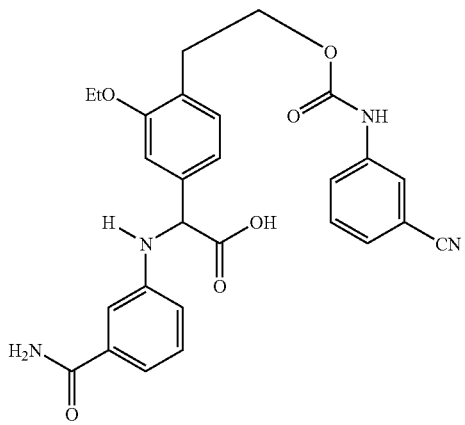

Using a procedure analogous to that used to prepare 2D, 62G (150 mg, 0.423 mmol) was reacted with 3-aminobenzamide and glyoxylic acid monohydrate to afford 62H (170 mg, 80%) as an oil. MS (ESI) m/z 503.2 (M+H)+.

62I: 2-(4-(2-(3-(aminomethyl)phenylcarbamoyloxy)ethyl)-3-ethoxyphenyl)-2-(3-carbamoylphenylamino) acetic acid

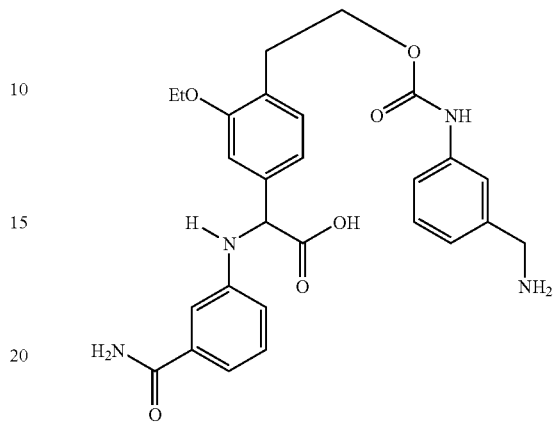

Using a procedure analogous to that used to prepare 6F, 62H (212 mg, 0.42 mmol) was hydrogenated for 18 hrs to give 62I (190 mg, 89%) as an oil. MS (ESI) m/z 507.3 (M+H)+.

Example 62

Using a procedure analogous to that used to prepare Example 28, 62I (190 mg, 0.38 mmol) was cyclized with BOP and purified by HPLC to give Example 62 (23 mg, 13%). $^1$H NMR (400 MHz, CD$_3$OD) δ ppm 1.36 (t, J=6.81 Hz, 1.5 H) 1.47 (t, J=6.81 Hz, 1.5 H) 3.09-3.25 (m, 4 H) 3.88-4.28 (m, 4 H) 4.98-5.05 (m, J=4.39 Hz, 1 H) 6.15-6.30 (m, J=13.18 Hz, 1 H) 6.60-6.72 (m, 1 H) 6.82-6.96 (m, 3 H) 6.98-7.29 (m, 7 H). MS (ESI) m/z 489.3 (M+H)+.

Example 63

2-(1-Amino-isoquinolin-6-ylamino)-17-ethoxy-13-oxa-4,11-diaza-tricyclo[14.2.2.1$^{6,10}$]henicosa-1(19),6,8,10(21),16(20),17-hexaene-3,12-dione trifluoroacetic acid salt

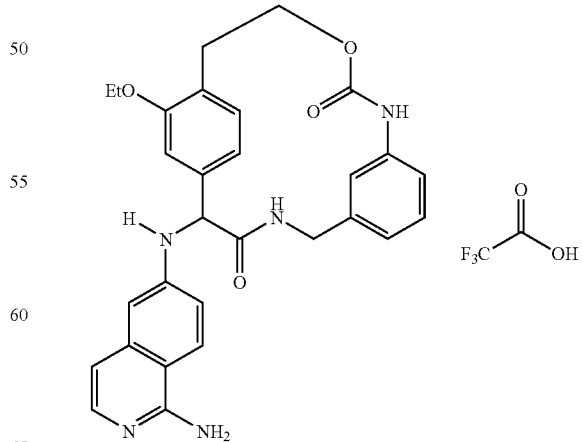

63A: 2-(1-(bis(tert-butoxycarbonyl)amino)isoquino-
lin-6-ylamino)-2-(4-(2-(3-cyanophenylcarbamoy-
loxy)ethyl)-3-ethoxyphenyl)acetic acid

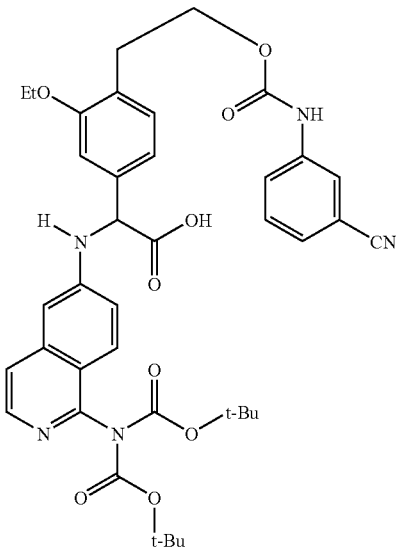

Using a procedure analogous to that used to prepare 2D, 62G (250 mg, 0.0706 mmol) was reacted with Intermediate 1 and glyoxylic acid monohydrate to afford 63A (329 mg, 64%) as a solid. MS (ESI) m/z 726.4 (M+H)$^+$.

63B: 2-(4-(2-(3-(aminomethyl)phenylcarbamoyloxy)
ethyl)-3-ethoxyphenyl)-2-(1-(bis(tert-butoxycarbo-
nyl)amino)isoquinolin-6-ylamino)acetic acid

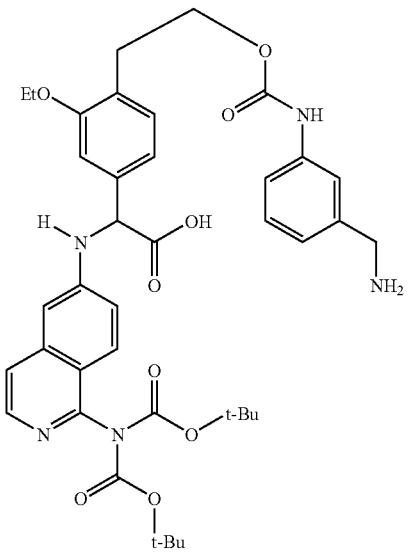

Using a procedure analogous to that used to prepare 6F, 63A (329 mg, 0.45 mmol) was hydrogenated for 18 h to give 63B (300 mg, 91%) as an oil. MS (ESI) m/z 731.4 (M+H)$^+$.

Example 63

Using a procedure analogous to that used to prepare Example 28, 63B (300 mg, 0.41 mmol) was cyclized with BOP, deprotected with trifluoroacetic acid, and purified by HPLC to give Example 63 (35 mg, 17%). $^1$H NMR (400 MHz, CD$_3$OD) δ ppm 1.34 (t, J=7.03 Hz, 1.5 H) 1.50 (t, J=7.03 Hz, 1.5 H) 2.92-3.00 (m, 1 H) 3.13-3.26(m, 1 H) 3.89-4.18(m, 3 H) 4.19-4.34(m, 1 H) 5.10-5.19(m, 1 H) 6.22 (m, 1 H) 6.59-6.94 (m, 4 H) 7.02-7.35 (m, 6 H) 7.98-8.12 (m, 1 H). MS (ESI) m/z 512.3 (M+H)$^+$.

Example 64

3-((2R,5R)-5,17-Dimethyl-3,12-dioxo-13-oxa-4,11-
diaza-tricyclo[14.2.2.1$^{6,10}$]henicosa-1(19),6,8,10
(21),16(20),17-hexaen-2-ylamino)-benzamide

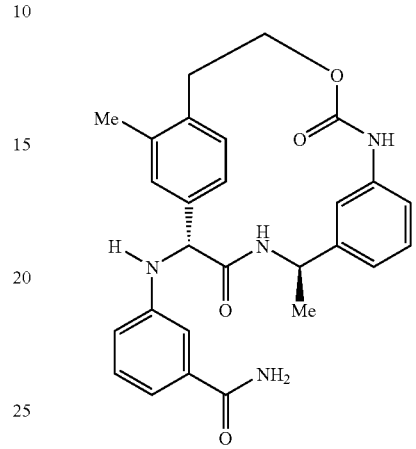

64A: (R)-benzyl 1-(3-nitrophenyl)ethylcarbamate

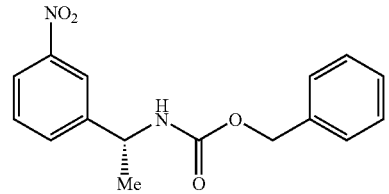

To a solution of benzyl 2,5-dioxopyrrolidin-1-yl carbonate (4.95 g, 19.9 mmol) and TEA (10 mL) in DCM (50 mL) was added a solution of (R)-1-(3-nitrophenyl)ethanamine (3 g, 18 mmol) in DMF (10 mL). The mixture was stirred 2 h and quenched with water (50 mL). The organic layer was separated and dried (MgSO$_4$) before concentrating in vacuo. The residue was purified by flash chromatography (0-35% EtoAc/Hexane) to afford 64A (5 g, 93%) as an oil. $^1$H NMR (400 MHz, CDCl$_3$) δ ppm 1.50 (d, J=6.59 Hz, 3 H) 4.87-4.98 (m, 1 H) 5.00-5.15 (m, 2 H) 7.34 (s, 5 H) 7.49 (t, J=7.69 Hz, 1 H) 7.64 (d, J=7.03 Hz, 1 H) 8.11 (d, J=7.91 Hz, 1 H) 8.17 (s, 1 H).

64B: (R)-benzyl 1-(3-aminophenyl)ethylcarbamate

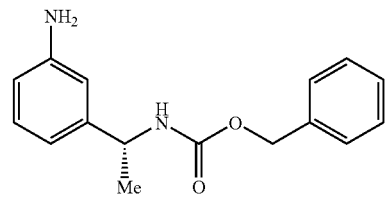

To a refluxing solution of 64A (5 g, 16.7 mmol), EtOH (100 mL), water (30 mL) and AcOH (15 mL) was added portionwise Fe powder (5 g, 89 mmol) over 30 min. The mixture was heated for 1 h. before cooling to ambient temperature. and filtering through celite. The filtrate was concentrated in vacuo to afford 64B (2.7 g, 61%) as an oil. MS (ESI) m/z 271.2 (M+H)$^+$.

64C: (R)-((4-bromo-2-methylnhenyl)ethyl) 3-(1-(benzyloxycarbonylamino)ethyl)phenylcarbamate

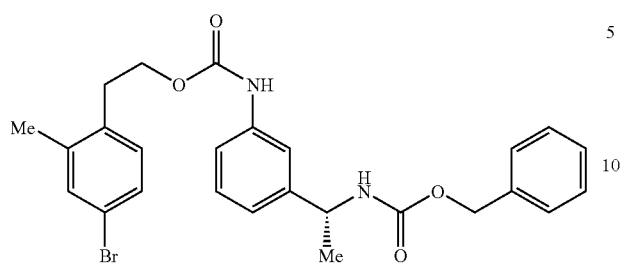

Using a procedure analogous to that used to prepare 34D, 64B (2.7 g, 10 mmol) was reacted with 30B to give 64C (1.8 g, 72%) as an oil. MS (ESI) m/z 513.2 (M+H)$^+$.

64D: (R)-4-(2-(3-(1-(benzyloxycarbonylamino)ethyl)phenylcarbamoyloxy)ethyl)-3-methylphenylboronic acid

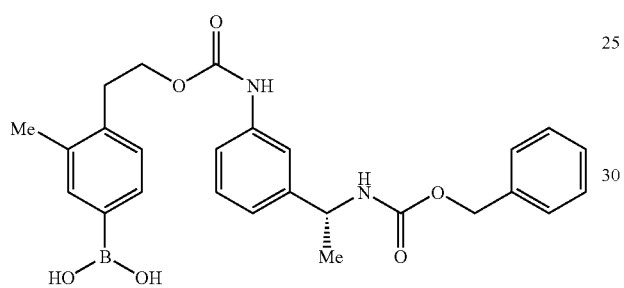

Using a procedure analogous to that used to prepare 6D, 64C (1 g, 1.96 mmol) was reacted with 5,5',5'-tetramethyl-[2,2']bi[[1,3,2]dioxaborinanyl] to give 64D (175 mg, 19%) as a solid. MS (ESI) m/z 475.3 (M+H)$^+$.

64E: 2-(4-(2-(3-((R)-1-(benzyloxycarbonylamino)ethyl)phenylcarbamoyloxy)ethyl)-3-methylphenyl)-2-(3-carbamoylphenylamino)acetic acid

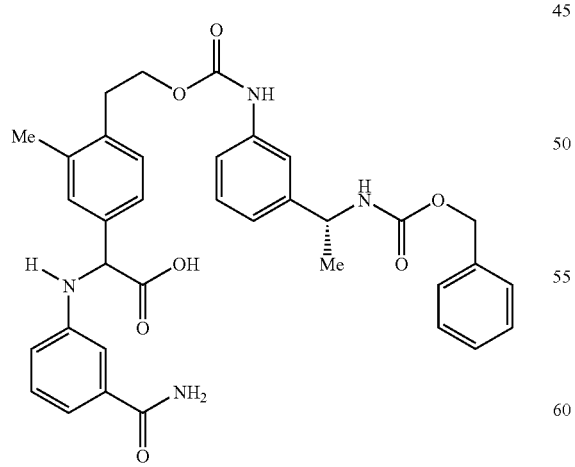

Using a procedure analogous to that used to prepare 2D, 64D (175 mg, 0.37 mmol) was reacted with 3-aminobenzamide and glyoxylic acid monohydrate to afford 64E (175 mg, 70%) as an oil. MS (ESI) m/z 625.3 (M+H)$^+$.

64F: 2-(4-(2-(3-((R)-1-aminoethyl)phenylcarbamoyloxy)ethyl)-3-methylphenyl)-2-(3-carbamoylphenylamino)acetic acid

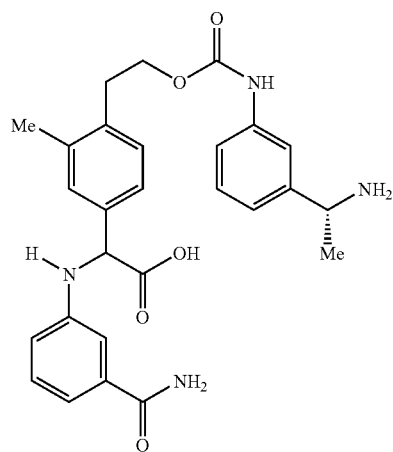

Using a procedure analogous to that used to prepare 6F, 64E (175 mg, 0.28 mmol) was hydrogenated for 18 h to give 64F (116 mg, 85%) as an oil. MS (ESI) m/z 491.1 (M+H)$^+$.

Example 64

Using a procedure analogous to that used to prepare Example 28, 64F (116 mg, 0.24 mmol) was cyclized with BOP and purified by HPLC to give Example 64 (7.39 mg, 13%). MS (ESI) m/z 473.3 (M+H)$^+$. $^1$H NMR (400 MHz, MeOD-d$_4$) δ ppm 2.86 (t, J=5.93 Hz, 3 H) 3.05 (s, 3 H) 4.03 (d, J=15.82 Hz, 1 H) 4.63 (d, 1 H) 5.09 (s, 1 H) 6.82 (d, J=6.59 Hz, 2 H) 6.88-6.94 (m, 1 H) 7.16-7.24 (m, 4 H) 7.27 (d, 2 H) 7.31 (d, J=7.47 Hz, 1 H) 7.46 (d, J=8.35 Hz, 1 H) 7.57 (d, J=7.91 Hz, 1 H).

Example 65

(R)-2-(1-Amino-isoquinolin-6-ylamino)-5,17-dimethyl-13-oxa-4,11-diaza-tricyclo[14.2.2.1$^{6,10}$]henicosa-1(19),6,8,10(21),16(20),17-hexaene-3,12-dione trifluoroacetic acid salt

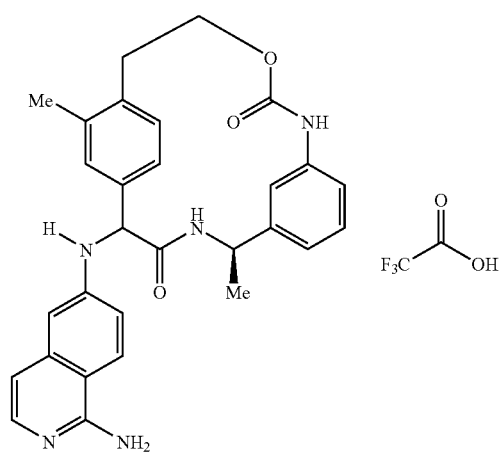

65A: 2-(4-(2-(3-((R)-1-(benzyloxycarbonylamino) ethyl)phenylcarbamoyloxy)ethyl)-3-methylphenyl)-2-(1-(bis(tert-butoxycarbonyl)amino)isoquinolin-6-ylamino)acetic acid

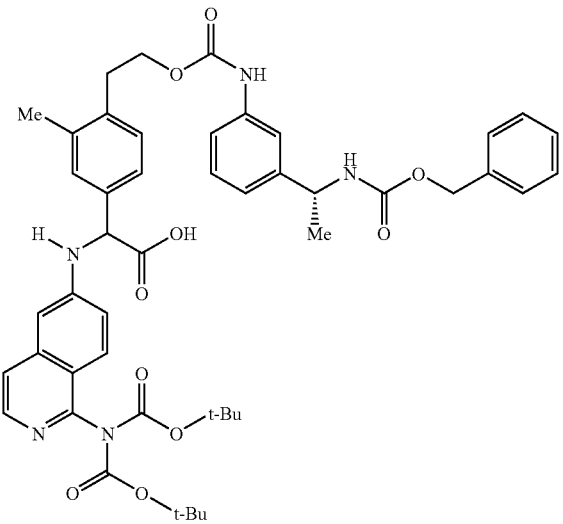

Using a procedure analogous to that used to prepare 2D, 64D (175 mg, 0.37 mmol) was reacted with Intermediate 1 and glyoxylic acid monohydrate to afford 65A (300 mg, 95%) as an oil. MS (ESI) m/z 848.5 (M+H)$^+$.

65B: 2-(4-(2-(3-((R)-1-aminoethyl)phenylcarbamoyloxy)ethyl)-3-methylphenyl)-2-(1-(bis(tert-butoxycarbonyl)amino)isoquinolin-6-ylamino)acetic acid

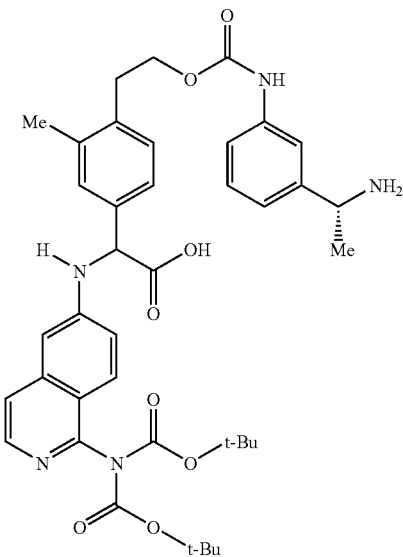

Using a procedure analogous to that used to prepare 6F, 65A (300 mg, 0.35 mmol) was hydrogenated for 18 h to give 65B (220 mg, 88%) as an oil. MS (ESI) m/z 714.2 (M+H)$^+$.

Example 65

Using a procedure analogous to that used to prepare Example 28, 65B (220 mg, 0.31 mmol) was cyclized with BOP, deprotected with trifluoroacetic acid, and purified by HPLC to give Example 65 (6.1 mg, 4%). MS (ESI) m/z 496.2 (M+H)$^+$.

Example 66

14-(1-Amino-isoquinolin-6-ylamino)-2-oxa-5,12-diaza-tricyclo[13.2.2.1$^{6,10}$]icosa-1(18),6(20),7,9,15(19),16-hexaene-4,13-dione trifluoroacetic acid salt

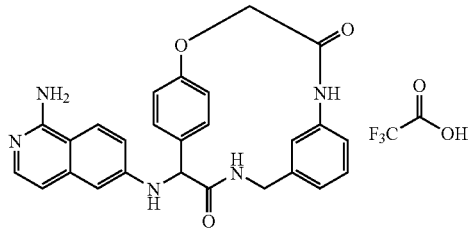

66A: (3-Amino-benzyl)-carbamic acid benzyl ester

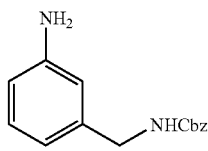

To a solution of 3-aminobenzylamine (610 mg, 5 mmol) and TEA (1.01 g, 10 mmol) in 10 mL of THF at 0° C., was added benzyl chloroformate (936 mg, 5.5 mmol) dropwise. The mixture was stirred at rt for 30 min. The reaction was quenched with water and extracted with EtOAc (3×20 mL). The organic layer was washed with brine, dried (Na$_2$SO$_4$) and concentrated. Purification via flash chromatography (0 to 50% EtOAc in hexanes) gives 66A (911 mg, 71%). MS (ESI) m/z 257.3 (M+H)$^+$.

66B: 3-[2-(4-Bromo-phenoxy)-acetylamino]-benzyl}-carbamic acid benzyl ester

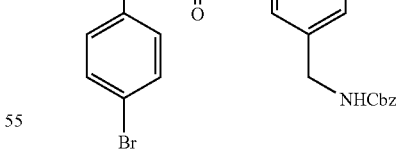

A mixture of 3-bromo phenyoxy acetic acid (222 mg, 0.96 mmol), 66A (246 mg, 0.96 mmol), EDCI (250 mg, 1.3 mmol), HOAt (30 mg, 0.22 mmol), and DIEA (0.5 mL, 3 mmol) in THF (4 mL) was stirred at rt for 16 h. The reaction was quenched with water, extracted with EtOAc (3×20 mL). The organic layer was washed with brine, dried (Na$_2$SO$_4$) and concentrated. Purification via flash chromatography (0-50% EtOAc in hexanes) gives 66B. (398 mg, 88%). MS (ESI) m/z 469.1 (M+H)$^+$.

66C: 4-(2-(3-((benzyloxycarbonylamino)methyl)phenylamino)-2-oxoethoxy)phenylboronic acid

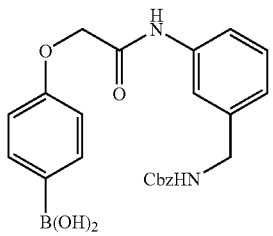

A sealed tube was charged with 66B (235 mg, 0.5 mmol), 5,5,5',5'-Tetramethyl-[2,2']bi[[1,3,2]dioxaborinanyl] (135 mg, 0.6 mmol), potassium acetate (98 mg, 1.25 mmol), and DMSO (2 mL). The resulting orange suspension was deoxygenated by sparging with nitrogen gas. Dichloro[1,1'-bis(diphenylphosphino)ferrocene]palladium(II) dichloromethane adduct (30 mg, 0.041 mmol) was added, and the tube was sealed and heated at 80° C. for 3 h. The reaction was quenched with water, then extracted with EtOAc (3×20 mL). The organic layer washed with brine, dried ($Na_2SO_4$), filtered through a pad of silica gel and concentrated. The residue was purified via reverse phase HPLC to give 66C (157 mg, 72%). MS (ESI) m/z 435.4(M+H)$^+$.

66D: 2-(4-(2-(3-((benzyloxycarbonylamino)methyl)phenylamino)-2-oxoethoxy)phenyl)-2-(1-(bis(tert-butoxycarbonyl)amino)isoquinolin-6-ylamino)acetic acid

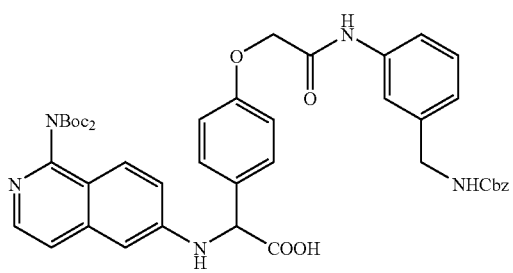

A solution of 66C (127 mg, 0.29 mmol), Intermediate 1 (116 mg, 0.32 mmol), and glyoxylic acid monohydrate (33 mg, 0.35 mmol) in $CH_3CN$ (4 mL)/DMF (0.5 mL) was heated at 65° C. for 16 h in a sealed tube. This mixture was concentrated, then purified by flash chromatography (0 to 10% MeOH in DCM) to give 66D (152 mg, 68% yield) as a yellow solid. MS (ESI) m/z 806.6(M+H)$^+$.

66E: 2-(4-(2-(3-(aminomethyl)phenylamino)-2-oxoethoxy)phenyl)-2-(1-(bis(tert-butoxycarbonyl)amino)isoquinolin-6-ylamino)acetic acid

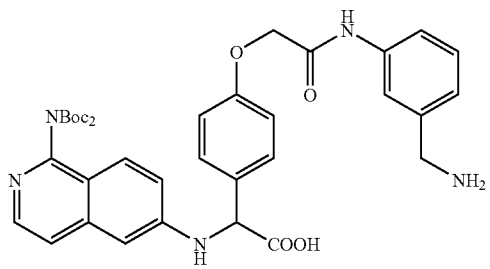

To a solution of 66D (152 mg) in 10 mL MeOH, was added 10% Pd/C (ca. 20 mg). The mixture was hydrogenated at 5 psi for 20 min. The reaction mixture was filtered, concentrated and purified by flash chromatography (0 to 25% MeOH in DCM) to give 66E (85 mg, 68%). MS (ESI) m/z 672.4(M+H)$^+$.

66F: 14-(1-(bis(tert-butoxycarbonyl)amino)isoquinolin-6-ylamino)-2-oxa-5,12-diaza-tricyclo[13.2.2.1$^{6,10}$]icosa-1(18),6(20),7,9,15(19),16-hexaene-4,13-dione

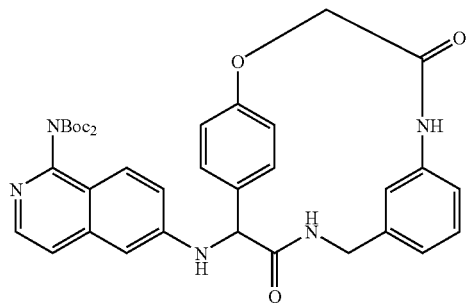

A solution of 66D (55 mg, 0.082 mmol) in 10 mL DMF was added to a solution of PyBOP (88 mg, 0.17 mmol), DMAP (49 mg, 0.4 mmol), and TEA (40 mg, 0.4 mmol) in $CH_2Cl_2$ (30 mL) dropwise through syringe pump over 3 h. The solution was stirred at rt for 16 h. The solution washed with 1M $H_3PO_4$, sat $NaHCO_3$ and brine, dried ($Na_2SO_4$) and concentrated. The crude product was purified by flash chromatography (0 to 80% EtOAc in hexanes) to give 66F (8.5 mg, 16%). MS (ESI) m/z 654.8 (M+H)$^+$.

Example 66

To a solution of 66F (8.5 mg, 0.013 mmol) in 1 mL $CH_2Cl_2$, was added TFA (1 mL). The solution was stirred at rt for 1 h, then concentrated. Purification by reversed phase HPLC afforded 5 mg (85%) of Example 66. MS (ESI) m/z 454.5 (M+H)$^+$. $^1$H NMR (400 MHz, $CD_3OD$) δ ppm 3.78-4.01 (m, 2 H) 4.66 (dd, J=15.94, 8.79 Hz, 2 H) 4.80-4.88 (m, 1 H) 5.06 (s, 1 H) 6.68 (d, J=2.20 Hz, 1 H) 6.78 (d, J=7.15 Hz, 1 H) 6.89-7.05 (m, 3 H) 7.12 (t, J=7.70 Hz, 1 H) 7.18 (dd, J=9.34, 2.20 Hz, 1 H) 7.22 (d, J=7.15 Hz, 1 H) 7.38 (dd, J=8.79, 2.20 Hz, 1H) 7.61 (dd, J=8.52, 2.47 Hz, 1 H) 8.00 (d, J=9.34 Hz, 1 H) 8.30 (s, 1 H)

Example 67

2-(1-Amino-isoquinolin-6-ylamino)-14-oxa-4,11-diaza-tricyclo[14.2.2.1$^{6,10}$]henicosa-1(19),6,8,10(21),16(20),17-hexaene-3,12-dione trifluoroacetic acid salt

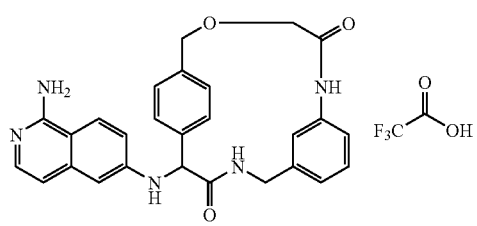

67A: (4-Bromo-benzyloxy)-acetic acid

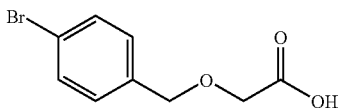

To a flask containing NaH (1 g, 25 mmol) in dry THF (25 mL) at 0° C., was added a solution of 4-bromobenzyl alcohol (2.11 g, 11.3 mmol) in dry THF (10 mL). The solution was stirred at 0° C. for 1 h, then a solution of bromoacetic acid (1 g, 7.14 mmol) in dry THF (10 mL) was added. The solution was refluxed for 3 h, then cooled. A solution of MeOH (1 mL) in water (100 mL) was added, and mixture was extracted with EtOAc (2×20 mL). The water layer was acidified by 1N HCl to pH=2, then extracted with EtOAc (2×20 mL). The combined organic layer was washed with brine, dried ($Na_2SO_4$) and concentrated to give 67A. (1.66 g, 95%). MS (ESI) m/z 169.0 $(M-OCH_2CO_2H)^+$.

67B: benzyl 3-(2-(4-bromobenzyloxy)acetamido)benzylcarbamate

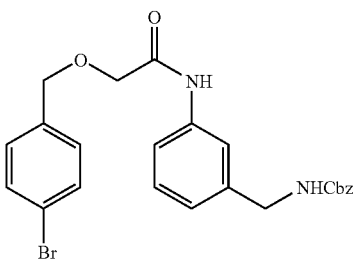

To a solution of 67A (245 mg, 1 mmol) and 66A (268 mg, 1.05 mmol) in DMF (4 mL), was added EDCI (288 mg, 1.5 mmol), HOAt (14 mg, 0.1 mmol) and DIEA (0.54 mL, 3 mmol). The mixture was stirred rt for 16 h, then was quenched with water and extracted with EtOAc (3×20 mL). The organic layer washed by brine, dried ($Na_2SO_4$) and concentrated. Purification via flash chromatography (0-40% EtOAc in hexanes) gave 67B (300 mg, 62%). MS (ESI) m/z 483.3 $(M+H)^+$.

67C: 4-((2-(3-((benzyloxycarbonylamino)methyl)phenylamino)-2-oxoethoxy)methyl)phenylboronic acid

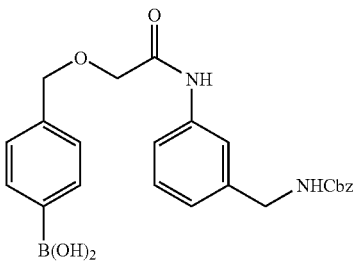

67C (172 mg, 80%) was obtained from 67B (233 mg, 0.48 mmol) using a procedure similar to that used in the preparation of 66C. MS (ESI) m/z 430.2 $(M-H_2O)^+$.

67D: 2-(4-((2-(3-((benzyloxycarbonylamino)methyl)phenylamino)-2-oxoethoxy)methyl)phenyl)-2-(1-(bis(tert-butoxycarbonyl)amino)isoquinolin-6-ylamino)acetic acid

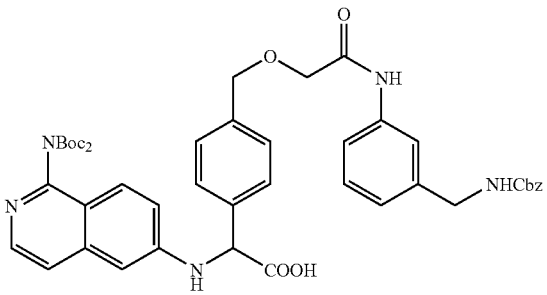

67D (116 mg, 43%) was obtained from 67C (150 mg, 0.33 mmol) using a procedure similar to that used in the preparation of 66D. MS (ESI) m/z 820.9 $(M+H)^+$.

67E: 2-(4-((2-(3-(aminomethyl)phenylamino)-2-oxoethoxy)methyl)phenyl)-2-(1-(bis(tert-butoxycarbonyl)amino)isoquinolin-6-ylamino)acetic acid

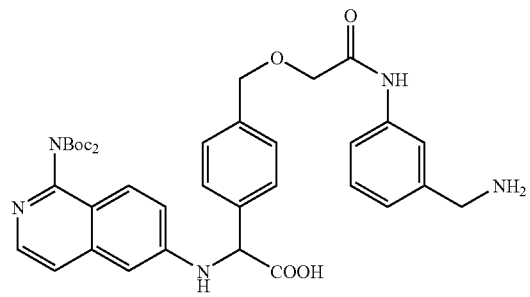

67E (79 mg, 82%) was obtained from 67D (116 mg, 0.14 mmol) using a procedure similar to that used in the preparation of 66E. MS (ESI) m/z 686.8 $(M+H)^+$.

67F: 2-(1-(bis(tert-butoxycarbonyl)amino)isoquinolin-6-ylamino)-14-oxa-4,11-diaza-tricyclo[14.2.2.1$^{6,10}$]henicosa-1(19),6,8,10(21),16(20),17-hexaene-3,12-dione

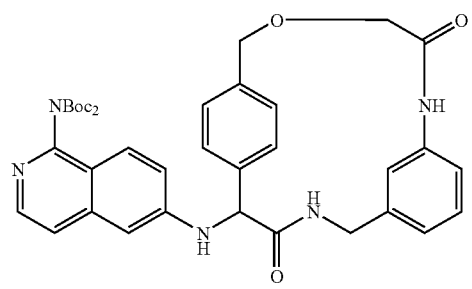

67F (40 mg, 53%) was obtained from 67E (79 mg, 0.115 mmol) using a procedure similar to that used in the preparation of 66F. MS (ESI) m/z 668.4 $(M+H)^+$.

Example 67

Example 67 (20 mg, 79%) was obtained from 67F (40 mg, 0.06 mmol) using a procedure similar to that used in the preparation of Example 66. MS (ESI) m/z 468.3 $(M+H)^+$. $^1$H NMR (400 MHz, $CD_3OD$) δ ppm 4.03 (d, J=16.26 Hz, 1 H) 4.24 (s, 2 H) 4.61-4.81 (m, 3 H) 5.25 (s, 1 H) 5.36 (s, 1 H) 6.71

(d, J=2.20 Hz, 1 H) 6.84 (d, J=7.03 Hz, 1 H) 6.97 (d, J=7.03 Hz, 1 H) 7.16-7.23 (m, 2 H) 7.24 (d, J=2.64 Hz, 1 H) 7.31 (d, J=7.03 Hz, 1 H) 7.42-7.47 (m, 1 H) 7.48-7.53 (m, 1 H) 7.57-7.62 (m, 1 H) 7.81 (dd, J=7.69, 1.98 Hz, 1 H) 8.07 (d, J=9.23 Hz, 1H)

Example 68

14-(1-Amino-isoquinolin-6-ylamino)-5,5-dioxo-5λ$^6$-thia-4,12-diaza-tricyclo[13.2.2.1$^{6,10}$]icosa-1(18),6(20),7,9,15(19),16-hexaen-13-one trifluoroacetic acid salt

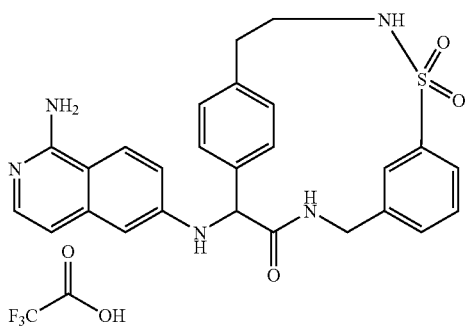

68A: N-(4-bromophenethyl)-3-cyanobenzenesulfonamide

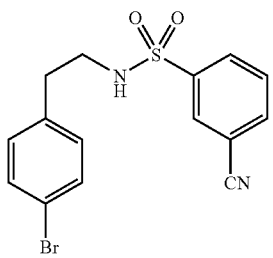

To a solution of 2-(4-bromophenyl)ethanamine (600 mg, 3.13 mmol) and TEA (800 mg, 8 mmol) in THF (10 mL), was added a solution of 3-cyano-benzenesulfonyl chloride (580 mg, 2.88 mmol) in THF (10 mL) at 0° C. The mixture was stirred at rt for 2 h, quenched with water, and extracted with EtOAc (3×20 mL). The organic layer washed with brine, dried (Na$_2$SO$_4$) and concentrated. Purification via flash chromatography (0-50% EtOAc in hexanes) gives 68A (708 mg, 71%). MS (ESI) m/z 365.3 (M+H)$^+$.

68B: 4-(2-(3-cyanophenylsulfonamido)ethyl)phenylboronic acid

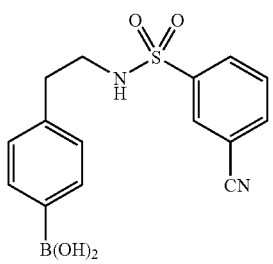

68B (256 mg, 78%) was obtained from 68A (365 mg, 1 mmol) using a procedure similar to that used in the preparation of 66C. $^1$H NMR (400 MHz, CD$_3$OD) δ ppm 2.73 (t, J=7.03 Hz, 2 H) 3.16 (t, J=7.25 Hz, 2 H) 6.99-7.24 (m, 2 H) 7.48 (d, J=7.47 Hz, 1 H) 7.59 (t, J=7.91 Hz, 1 H) 7.67 (q, J=7.91 Hz, 1H) 7.91 (d, J=8.35 Hz, 1 H) 8.02 (d, J=8.35 Hz, 1 H) 8.06 (s, 1 H)

68C: 2-(1-(bis(tert-butoxycarbonyl)amino)isoquinolin-6-ylamino)-2-(4-(2-(3-cyanophenylsulfonamido)ethyl)phenyl)acetic acid

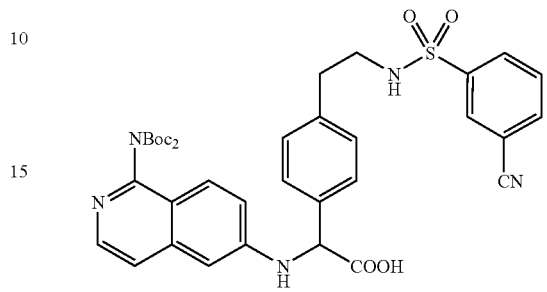

68C (300 mg, 56%) was obtained from 68B (250 mg, 0.76 mmol) using a procedure similar to that used in the preparation of 66D. MS (ESI) m/z 702.3 (M+H)$^+$.

68D: 2-(4-(2-(3-(aminomethyl)phenylsulfonamido)ethyl)phenyl)-2-(1-(bis(tert-butoxycarbonyl)amino)isoquinolin-6-ylamino)acetic acid

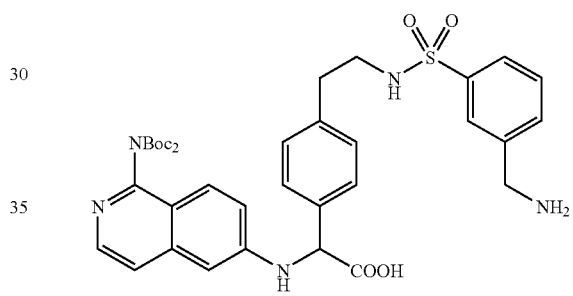

To a solution of 68C (160 mg) in 10 mL MeOH, was added Pd/C (50 mg). The mixture was hydrogenated at 60 psi for 60 min. The mixture was filtered, concentrated and purified by flash chromatography (0 to 15% MeOH in DCM) to give 68D (108 mg, 66%). MS (ESI) m/z 706.3(M+H)$^+$.

68E: 14-(1-(bis(tert-butoxycarbonyl)amino)isoquinolin-6-ylamino)-5,5-dioxo-5λ$^6$-thia-4,12-diaza-tricyclo[13.2.2.1$^{6,10}$]icosa-1(18),6(20),7,9,15(19),16-hexaen-13-one

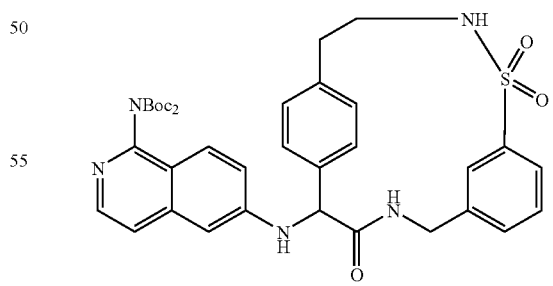

68E (18 mg, 32%) was obtained from 68D (58 mg, 0.082 mmol) using a procedure similar to that used in the preparation of 66F. MS (ESI) m/z 688.9 (M+H)$^+$.

Example 68

Example 68 (14 mg, 91%) was obtained from 68E (18 mg, 0.026 mmol) using a procedure similar to that used in the preparation of Example 66. MS (ESI) m/z 488.3 (M+H)⁺. ¹H NMR (400 MHz, CD₃OD) δ ppm 2.62-2.77 (m, 2H) 3.10-3.24 (m, 1 H) 3.33-3.44 (m, 1 H) 3.90 (dd, J=14.29, 4.40 Hz, 1 H) 4.61 (dd, J=14.29, 8.24 Hz, 1 H) 5.06 (s, 1 H) 6.70 (s, 1 H) 6.80-6.87 (m, 2 H) 6.92-6.98 (m, 1 H) 7.17 (d, J=6.05 Hz, 1 H) 7.21 (dd, J=9.34, 2.20 Hz, 1 H) 7.29 (d, J=7.15 Hz, 1 H) 7.34 (t, J=7.70 Hz, 1 H) 7.46 (d, J=7.70 Hz, 1 H) 7.49 (d, J=7.70 Hz, 1 H) 7.66 (d, J=7.70 Hz, 1 H) 8.06 (d, J=9.34 Hz, 1 H) 8.13 (dd, J=8.24, 4.40 Hz, 1 H)

Example 69

2-(1-Amino-isoquinolin-6-ylamino)-11,11-dioxo-11λ⁶-thia-4,12-diaza-tricyclo[14.2.2.1⁶,¹⁰]henicosa-1(19),6,8,10(21),16(20),17-hexaen-3-one trifluoroacetic acid salt

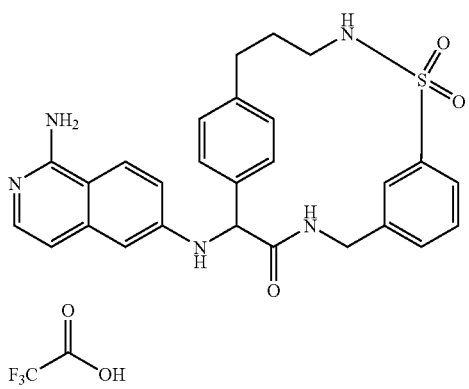

69A: N-(3-(4-bromophenyl)propyl)-3-cyanobenzenesulfonamide

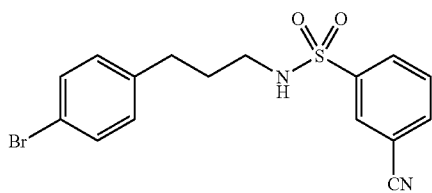

69A (228 mg, 67%) was obtained from 3-(4-bromophenyl)propan-1-amine (630 mg, 3.31 mmol) using a procedure similar to that used in the preparation of 68A. MS (ESI) m/z 365.2 (M+H)⁺.

69B: 4-(3-(3-cyanophenylsulfonamido)propyl)phenylboronic acid

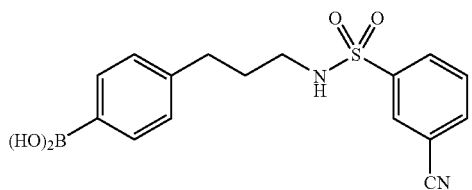

69B (160 mg, 80%) was obtained from 69A (221 mg, 0.58 mmol) using a procedure similar to that used in the preparation of 66C. MS (ESI) m/z 345.2 (M+H)⁺.

69C: 2-(1-(bis(tert-butoxycarbonyl)amino)isoquinolin-6-ylamino)-2-(4-(3-(3-cyanophenylsulfonamido)propyl)phenyl)acetic acid

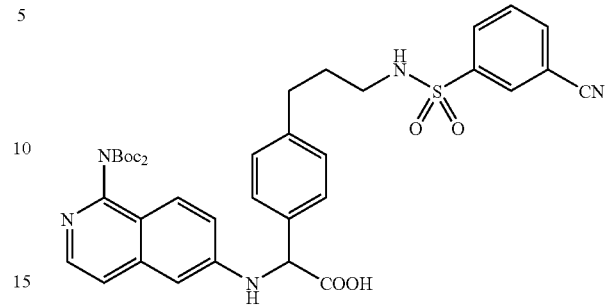

69C (200 mg, 61%) was obtained from 69B (159 mg, 0.46 mmol) using a procedure similar to that used in the preparation of 66D. MS (ESI) m/z 716.5 (M+H)⁺.

69D: 2-(4-(3-(3-(aminomethyl)phenylsulfonamido)propyl)phenyl)-2-(1-(bis(tert-butoxycarbonyl)amino)isoquinolin-6-ylamino)acetic acid

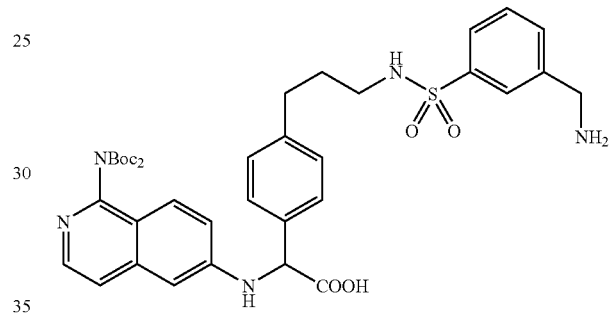

69D (155 mg, 78%) was obtained from 69C (198 mg, 0.28 mmol) using a procedure similar to that used in the preparation of 68D. MS (ESI) m/z 720.6 (M+H)⁺.

69E: 2-(1-(bis(tert-butoxycarbonyl)amino)isoquinolin-6-ylamino)-11,11-dioxo-11λ⁶-thia-4,12-diaza-tricyclo[14.2.2.1⁶,¹⁰]henicosa-1(19),6,8,10(21),16(20),17-hexaen-3-one

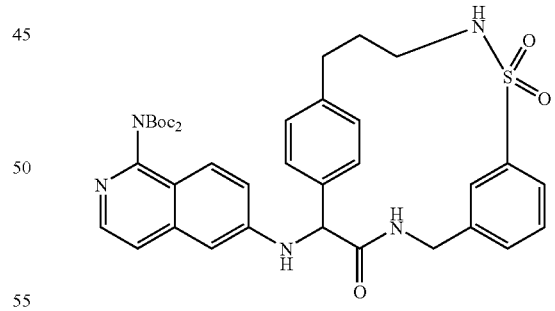

69E (43 mg, 54%) was obtained from 69D (82 mg, 0.114 mmol) using a procedure similar to that used in the preparation of 66F. MS (ESI) m/z 702.4 (M+H)⁺.

Example 69

Example 69 (23 mg, 88%) was obtained from 69E (30 mg, 0.043 mmol) using a procedure similar to that used in the preparation of Example 66. MS (ESI) m/z 502.4 (M+H)⁺. ¹H NMR (400 MHz, DMSO-D₆) δ ppm 1.66-1.91 (m, 2 H) 1.90-2.05 (m, 2 H) 2.68-2.81 (m, 1 H) 3.93 (dd, J=14.94, 4.39 Hz, 1 H) 4.64 (dd, J=14.94, 7.91 Hz, 1 H) 6.65 (s, 1 H) 6.82 (d, J=7.03 Hz, 1 H) 6.94-7.01 (m, 2 H) 7.10 (d, J=7.47 Hz, 1

H) 7.16 (d, J=7.91 Hz, 1 H) 7.34 (s, 1 H) 7.40 (d, J=5.27 Hz, 1 H) 7.42-7.48 (m, 2 H) 7.48-7.58 (m, 3 H) 7.61-7.71 (m, 2 H) 8.15 (d, J=9.23 Hz, 1 H) 8.39 (s, 2 H) 8.68 (dd, J=7.91, 4.39 Hz, 1 H) 12.12-12.36 (m, 1 H)

Example 70

2-(1-Amino-isoquinolin-6-ylamino)-14-ethyl-13-oxa-4,11-diaza-tricyclo[14.2.2.1⁶,¹⁰]henicosa-1(19),6,8,10(21),16(20),17-hexaene-3,12-dione trifluoroacetic acid salt

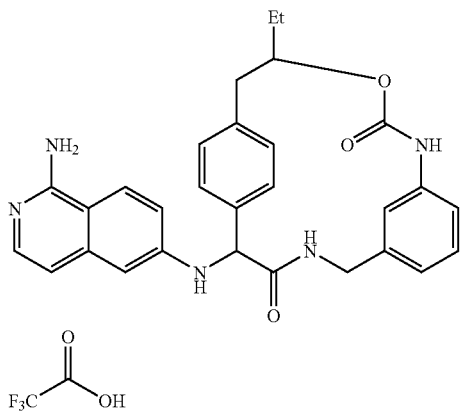

70A:
2-(4-bromophenyl)-N-methoxy-N-methylacetamide

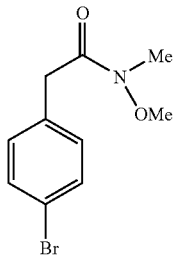

To a round bottom flask containing N-methyl-N-methoxy amine hydrochloride (878 mg, 9 mmol) in CH$_2$Cl$_2$ (6 mL), a solution of ClAlMe$_2$ (9 mL, 1M, 9 mmol) was added at 0° C. dropwise. The solution was stirred at rt for 30 min. A solution of ethyl 4-bromophenylacetate (1.09 g, 4.05 mmol) was added dropwise at 0° C. The solution was stirred at rt for 1 h, quenched with sat. NH$_4$Cl, and extracted with EtOAc (3×20 mL). The organic layer washed with brine, dried (Na$_2$SO$_4$) and concentrated. Purification via flash chromatography (0-50% EtOAc/hexanes) afforded 70A (1.03 g, 80%). MS (ESI) m/z 258.1 (M+H)$^+$.

70B: 1-(4-bromophenyl)butan-2-one

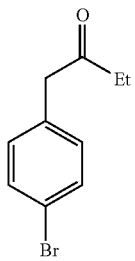

To a round bottom flask contained EtMgCl (10 mL, 2M in THF, 20 mmol) at 0° C., was added a solution of 70A (516 mg, 2 mmol) in 10 mL THF. The solution was stirred at rt for 30 min, then was quenched with sat. NH$_4$Cl and extracted with EtOAc (3×20 mL). The organic layer washed with brine, dried (Na$_2$SO$_4$) and concentrated. Purification via flash chromatography (0-30% EtOAc/hexanes) afforded 70B (288 mg, 65%). MS (ESI) m/z 227.1 (M+H)$^+$.

70C: 1-(4-bromophenyl)butan-2-ol

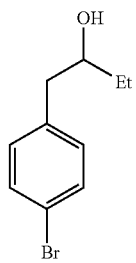

To a solution of 70B (478 mg, 2.1 mmol) in 5 mL MeOH at 0° C., was added NaBH$_4$ (110 mg, 2.98 mmol). The solution was stirred at rt for 30 min, then was diluted with EtOAc and washed with H$_2$O and brine, dried (Na$_2$SO$_4$) and concentrated. Purification via flash chromatography (0-30% EtOAc/hexanes) afforded 70C (460 mg, 96%). MS (ESI) m/z 221.2 (M-OH)$^+$.

70D: 4-(2-hydroxybutyl)phenylboronic acid

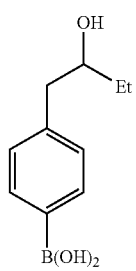

70D (98 mg, 79%) was obtained from 70C (471 mg, 2.06 mmol) using a procedure similar to that used in the preparation of 66C. MS (ESI) m/z 177.3 (M-OTBS)$^+$.

70E: 2-(1-(bis(tert-butoxycarbonyl)amino)isoquinolin-6-ylamino)-2-(4-(2-hydroxybutyl)phenyl)acetic acid

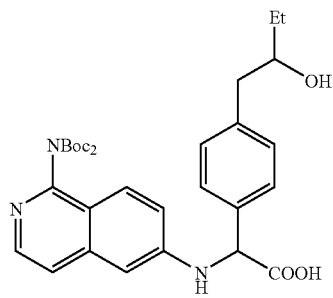

70E (140 mg, 65%) was obtained from 70D (74 mg, 0.38 mmol) using a procedure similar to that used in the preparation of 66D. MS (ESI) m/z 566.6 (M+H)$^+$.

70F: 2-(1-(bis(tert-butoxycarbonyl)amino)isoquinolin-6-ylamino)-2-[4-(2-hydroxy-butyl)-phenyl]-N-(3-nitro-benzyl)-acetamide

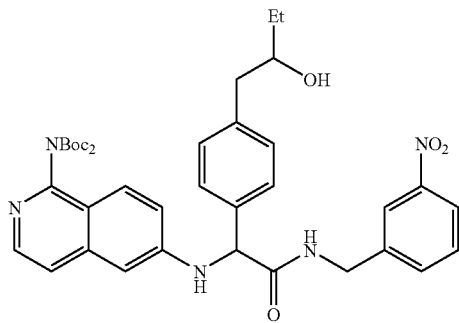

70E (140 mg, 0.25 mmol) was mixed with 3-cyanobenzylamine hydrochloride (57 mg, 0.3 mmol), PyBOP (156 mg, 0.3 mmol), TEA (76 mg, 0.75 mmol) in DMF (3 mL) and stirred at rt for 16 h. The mixture was diluted with H$_2$O and extracted with EtOAc (3×20 mL). The organic layer washed with brine, dried (Na$_2$SO$_4$) and concentrated. Purification via flash chromatography (0-80% EtOAc/hexanes) afforded 70F (180 mg, 63%). MS (ESI) m/z 700.8 (M+H)$^+$.

70G: N-(3-Amino-benzyl)-2-(1-(bis(tert-butoxycarbonyl)amino)isoquinolin-6-ylamino)-2-[4-(2-hydroxy-butyl)-phenyl]-acetamide

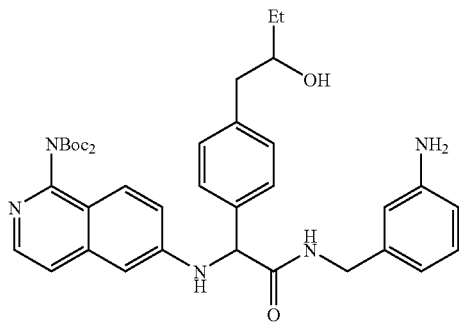

To a solution of 70F (110 mg in 10 mL MeOH, 0.16 mmol) was added 10% Pd/C (20 mg). The mixture was hydrogenated at 40 psi for 3 h, then filtered and concentrated to give 70G (107 mg, 100%). MS (ESI) m/z 670.7 (M+H)$^+$.

70H: 2-(1-(bis(tert-butoxycarbonyl)amino)isoquinolin-6-ylamino)-14-ethyl-13-oxa-4,11-diaza-tricyclo[14.2.2.1$^{6,10}$]henicosa-1(19),6,8,10(21),16(20),17-hexaene-3,12-dione

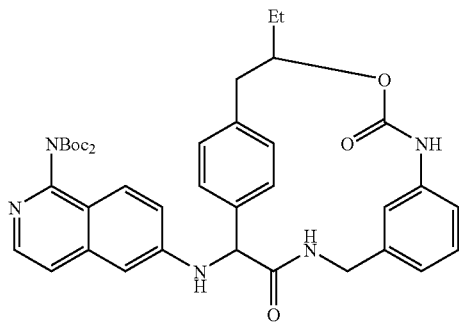

To a solution of 70G (77 mg, 0.115 mmol) in 20 mL CH$_3$CN, was added a solution of COCl$_2$ (20% in toluene, 0.07 mL, 0.13 mmol) at 0° C. The solution was stirred at rt for 30 min, then was bubbled with Ar for 5 min. This solution was added dropwise via a syringe pump over 4 h into a solution of TEA (110 mg, 1 mmol) in 20 mL CH$_3$CN at 65° C. The solution was stirred at rt for 16 h, then concentrated. Purification via reversed phase preparative HPLC afforded 70H (15 mg, 19%). (ESI) m/z 696.5 (M+H)$^+$.

Example 70

Example 70 (3.0 mg, 28%) was obtained from 70H (15 mg, 0.022 mmol) using a procedure similar to that used in the preparation of Example 66. MS (ESI) m/z 496.3 (M+H)$^+$. $^1$H NMR (400 MHz, CD$_3$OD) δ ppm 0.88-1.15 (m, 3H) 1.63-1.90 (m, 2 H) 2.54-2.75 (m, 1 H) 2.92-3.10 (m, 1 H) 3.82-4.74 (m, 1 H) 4.92-5.11 (m, 2 H) 5.09-5.31 (m, 1 H) 6.16 (d, J=29.88 Hz, 1 H) 6.58-6.84 (m, 2 H) 6.83-6.98 (m, 2 H) 7.08-7.41 (m, 5 H) 7.45-7.71 (m, 2 H) 8.06 (t, J=9.67 Hz, 1 H)

Examples 71 and 72

2-(1-Amino-isoquinolin-6-ylamino)-14-ethyl-13-oxa-4,11-diaza-tricyclo[14.2.2.1$^{6,10}$]henicosa-1(19),6,8,10(21),16(20),17-hexaene-3,12-dione trifluoroacetic acid salt, diastereomers 1 and 2, respectively

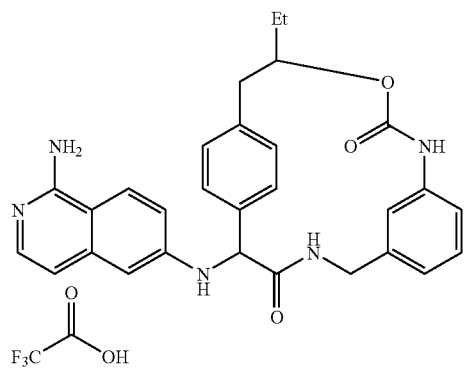

71A and 72A, diastereomers 1 and 2, respectively: 2-(1-(bis(tert-butoxycarbonyl)amino)isoquinolin-6-ylamino)-14-ethyl-13-oxa-4,11-diaza-tricyclo[14.2.2.1$^{6,10}$]henicosa-1(19),6,8,10(21),16(20),17-hexaene-3,12-dione

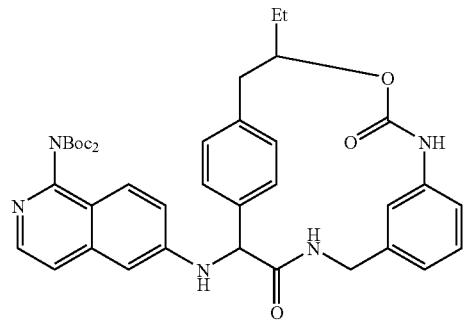

Purification of 70H (5 mg) via flash chromatography (0 to 40% EtOAc/hexanes) afforded 71A (1.5 mg), followed by 72A. MS (ESI) m/z 696.5 (M+H)$^+$, for each intermediate.

Example 71

Example 71 (0.90 mg) was obtained from 71A (1.5 mg, 0.022 mmol) using a procedure similar to that used in the preparation of Example 66. MS (ESI) m/z 496.3 (M+H)⁺. ¹H NMR (400 MHz, CD₃OD) δ ppm 0.88-1.41 (m, 3 H) 1.63-1.88 (m, 2 H) 2.58-2.72 (m, 1 H) 2.94-3.19 (m, 1 H) 3.81 (d, J=15.39 Hz, 1 H) 4.91-5.08 (m, 2 H) 5.15 (s, 1 H) 6.20 (s, 1 H) 6.64 (s, 1 H) 6.72 (d, J=8.24 Hz, 1 H) 6.79 (d, J=7.15 Hz, 1 H) 6.92 (d, J=7.15 Hz, 1 H) 7.15 (t, J=7.97 Hz, 1 H) 7.20 (d, J=7.70 Hz, 1 H) 7.24 (d, J=9.34 Hz, 1 H) 7.29 (d, J=7.15 Hz, 1 H) 7.37 (d, J=8.25 Hz, 1 H) 7.50 (dd, J=10.99, 8.24 Hz, 2 H) 8.07 (d, J=9.34 Hz, 1 H)

Example 72

Example 72 (1.98 mg) was obtained from 72A (2.5 mg, 0.022 mmol) using a procedure similar to that used in the preparation of Example 66. MS (ESI) m/z 496.3 (M+H)⁺. ¹H NMR (400 MHz, CD₃OD) δ ppm 0.96-1.39 (m, 3 H) 1.63-1.86 (m, 2 H) 2.56-2.72 (m, 1 H) 2.98-3.10 (m, 1 H) 4.13 (dd, J=16.49, 4.95 Hz, 1 H) 4.67 (dd, J=16.49, 7.15 Hz, 1 H) 4.98-5.12 (m, 1 H) 5.20 (s, 1 H) 6.09-6.23 (m, 1 H) 6.63-6.70 (m, 1 H) 6.71-6.76 (m, 1 H) 6.85-6.94 (m, 2 H) 7.08-7.23 (m, 3 H) 7.25-7.35 (m, 2 H) 7.43-7.53 (m, 1 H) 7.62-7.70 (m, 1 H) 8.06 (t, J=9.89 Hz, 1 H)

Example 73

2-(1-Amino-isoquinolin-6-ylamino)-15-methyl-13-oxa-4,11-diaza-tricyclo[14.2.2.1⁶,¹⁰]henicosa-1(19),6,8,10(21),16(20),17-hexaene-3,12-dione trifluoroacetic acid salt

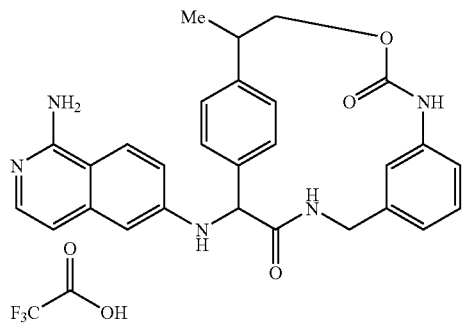

73A: ethyl 2-(4-bromophenyl)propanoate

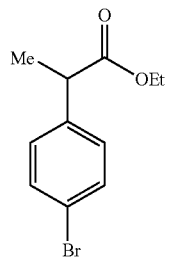

To a solution of LDA (8.66 mL, 2M in heptane/THF/ethylbenzene, 17.3 mmol) in 30 mL THF at −78° C., was added a solution of ethyl 4-bromophenylacetate (4.00 g, 16.5 mmol) in 20 mL THF. The mixture was stirred at −78° C. for 30 min, then a solution of iodomethane (10.7 mL, 2M in methyl tert-butyl ether, 21.5 mmol) was added. The mixture was stirred for 10 min at −78° C., then was removed from the cooling bath and stirred for 30 min. The reaction was quenched with sat. NH₄Cl, then diluted with EtOAc. The organic phase washed with water, sat. Na₂SO₃ and brine, dried (Na₂SO₄) and concentrated. The crude product was purified by flash chromatography (0 to 10% EtOAc/hexanes gradient) to afford 3.07 g of 73A as a colorless oil. MS (ESI) m/z 257.1, 259.1 (M+H)⁺.

73B: 2-(4-bromophenyl)propan-1-ol

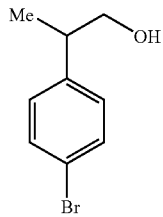

To a solution of 73A (3.06 g, 11.9 mmol) in 50 mL CH₂Cl₂ at −78° C., was added a solution of diisobutylaluminum hydride (35.7 mL, 35.7 mmol, 1M in hexanes). The mixture was removed from the cooling bath, stirred 1 h, then recooled to −50° C. and quenched with EtOAc (2 mL). The reaction mixture was diluted with H₂O, then extracted with EtOAc (3×). The combined organic extract washed with brine, dried (Na₂SO₄), filtered through a 1" pad of SiO₂, then concentrated to afford 2.34 g of 73B as a colorless oil. MS (ESI) m/z 197.1 (M-OH)⁺.

73C: (2-(4-bromophenyl)propoxy)(tert-butyl)dimethylsilane

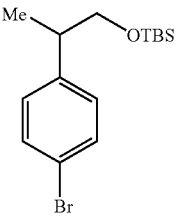

To a solution of 73B (2.34 g, 10.9 mmol) in 30 mL DMF, was added imidazole (1.11 g, 16.3 mmol) and tert-butyldimethylsilyl chloride (1.97 g, 13.1 mmol). The mixture was stirred at rt for 3 h, then was diluted with hexanes. The organic phase washed with H₂O (2×) and brine, dried (Na₂SO₄) and concentrated. The product was purified by flash chromatography (0 to 10% EtOAc/hexanes gradient) to afford 2.00 g of 73C as a colorless oil. MS (ESI) m/z 197.1 (M-OTBS)⁺.

73D: 4-(1-(tert-butyldimethylsilyloxy)propan-2-yl)phenylboronic acid

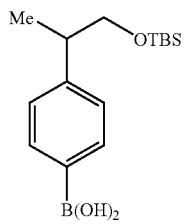

To a solution of 73C (100 mg in 2 mL dry THF, 0.3 mmol) at −78° C. was added n-BuLi (1.6 M, 0.2 mL, 0.32 mmol), followed by B(OMe)₃ (0.1 mL, 0.9 mmol). The solution was stirred at −78° C. for 2 h. 1N HCl (4 mL) was added, and stirred 30 min. The mixture was extracted with EtOAc (3×20 mL). The organic layer washed by brine, dried (Na₂SO₄). Purification through ISCO (0-80% EtOAc in hexanes) gives 73D (37 mg, 40%). ¹H NMR (400 MHz, Chloroform-d) δ ppm −0.03 (d, J=3.52 Hz, 6 H) 0.84-0.89 (m, 9 H) 1.33 (d, J=7.03 Hz, 3H) 2.92-3.06 (m, 1 H) 3.62-3.79 (m, 2 H) 7.36 (d, J=7.91 Hz, 2 H) 8.16 (d, J=7.91 Hz, 2 H)

73E: 2-(1-(bis(tert-butoxycarbonyl)amino)isoquinolin-6-ylamino)-2-(4-(1-hydroxypropan-2-yl)phenyl)acetic acid

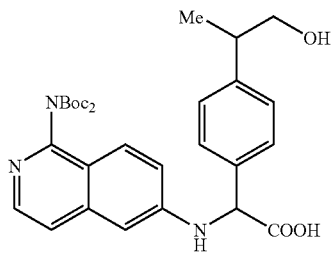

73E (39 mg, 57%) was obtained from 73D (37 mg, 0.126 mmol) using a procedure similar to that used in the preparation of 66D. MS (ESI) m/z 552.5 (M+H)⁺.

73F: 2-(1-(bis(tert-butoxycarbonyl)amino)isoquinolin-6-ylamino)-2-(4-(1-hydroxypropan-2-yl)phenyl)-N-(3-nitrobenzyl)acetamide

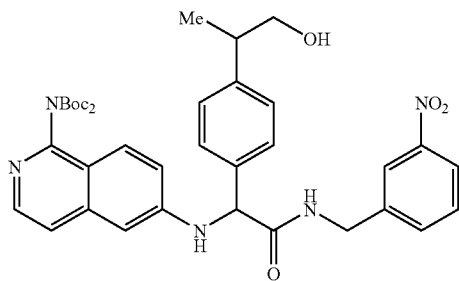

73F (32 mg, 99%) was obtained from 73E (26 mg, 0.047 mmol) using a procedure similar to that used in the preparation of 70F. MS (ESI) m/z 686.5 (M+H)⁺.

73G: N-(3-aminobenzyl)-2-(1-(bis(tert-butoxycarbonyl)amino)isoquinolin-6-ylamino)-2-(4-(1-hydroxypropan-2-yl)phenyl)acetamide

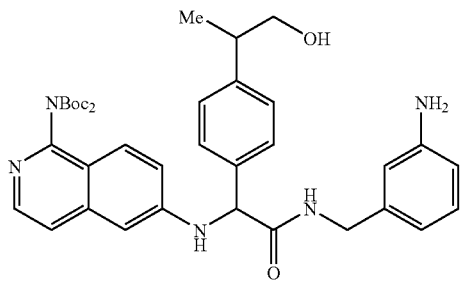

73G (23 mg, 80%) was obtained from 73F (30 mg, 0.044 mmol) using a procedure similar to that used in the preparation of 70G. MS (ESI) m/z 656.5 (M+H)⁺.

73H: 2-(1-(bis(tert-butoxycarbonyl)amino)isoquinolin-6-ylamino)-15-methyl-13-oxa-4,11-diaza-tricyclo[14.2.2.1$^{6,10}$]henicosa-1(19),6,8,10(21),16(20),17-hexaene-3,12-dione

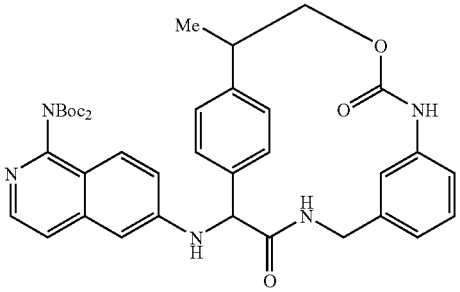

73H (12 mg, 50%) was obtained from 73G (23 mg, 0.035 mmol) using a procedure similar to that used in the preparation of 70H. MS (ESI) m/z 682.5 (M+H)⁺.

Example 73

Example 73 (7 mg, 82%) was obtained from 73H (12 mg, 0.018 mmol) using a procedure similar to that used in the preparation of Example 66. MS (ESI) m/z 482.4. ¹H NMR (400 MHz, CD₃OD) δ ppm 1.20-1.44 (m, 3 H) 3.02-3.18 (m, 1 H) 3.93-4.19 (m, 2 H) 4.24-4.70 (m, 2 H) 5.18 (d, J=15.94 Hz, 1 H) 6.15 (d, J=30.23 Hz, 1 H) 6.62-6.74 (m, 2 H) 6.85 (t, J=7.42 Hz, 1 H) 6.90 (d, J=7.15 Hz, 1 H) 7.13 (t, J=7.70 Hz, 1 H) 7.16-7.21 (m, 1 H) 7.30 (d, J=6.05 Hz, 2 H) 7.38 (d, J=8.25 Hz, 1 H) 7.48 (dd, J=12.09, 8.25 Hz, 1 H) 7.61 (dd, J=57.99, 7.97 Hz, 1 H) 8.06 (dd, J=9.34, 4.95 Hz, 1 H)

Example 74

2-(1-Amino-isoquinolin-6-ylamino)-15,15-dimethyl-13-oxa-4,11-diaza-tricyclo[14.2.2.1$^{6,10}$]henicosa-1(19),6,8,10(21),16(20),17-hexaene-3,12-dione trifluoroacetic acid salt

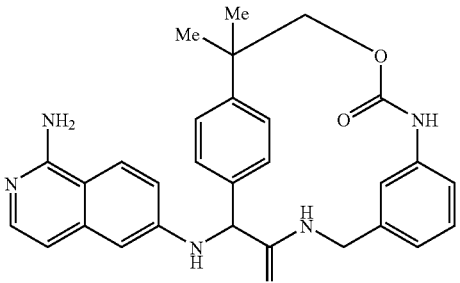

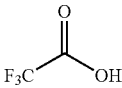

74A: 2-(4-bromophenyl)-2-methylpropan-1-ol

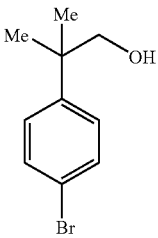

According to the procedure for the preparation of 73B, methyl 2-(4-bromophenyl)-2-methylpropanoate (2.15 g, 8.36 mmol) afforded 1.93 g of 74A as a colorless oil. MS (ESI) m/z 211.1 (M-OH)⁺.

74B: (2-(4-bromophenyl)-2-methylpropoxy)(tert-butyl)dimethylsilane

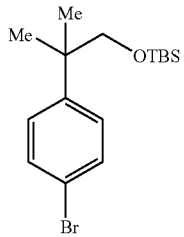

According to the procedure for the preparation of 73C, 74A (1.93 g, 8.42 mmol) afforded 3.04 g of 74B as a colorless oil. MS (ESI) m/z 211.1 (M-OTBS)⁺.

74C: 4-(1-(tert-butyldimethylsilyloxy)-2-methylpropan-2-yl)phenylboronic acid

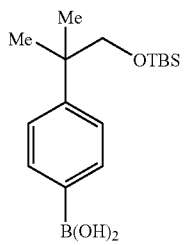

74C (58 mg, 13%) was obtained from 74B (512 mg, 1.49 mmol) using a procedure similar to that used in the preparation of 73D. ¹H NMR (400 MHz, Chloroform-d) δ ppm −0.05-0.02 (m, 6 H) 0.87 (d, J=3.52 Hz, 9 H) 1.36 (d, J=3.08 Hz, 6 H) 3.61 (d, J=3.08 Hz, 2 H) 7.53 (dd, J=8.13, 2.86 Hz, 2 H) 8.17 (dd, J=7.91, 3.08 Hz, 2 H)

74D: 2-(1-(bis(tert-butoxycarbonyl)amino)isoquinolin-6-ylamino)-2-(4-(1-hydroxy-2-methylpropan-2-yl)phenyl)acetic acid

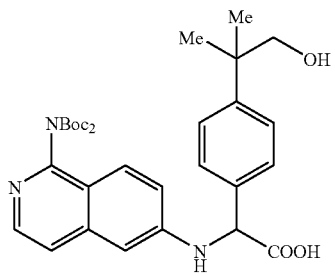

74D (59 mg, 56%) was obtained from 74C (58 mg, 0.188 mmol) using a procedure similar to that used in the preparation of 66D. MS (ESI) m/z 566.6 (M+H)⁺.

74E: 2-(1-(bis(tert-butoxycarbonyl)amino)isoquinolin-6-ylamino)-2-(4-(1-hydroxy-2-methylpropan-2-yl)phenyl)-N-(3-nitrobenzyl)acetamide

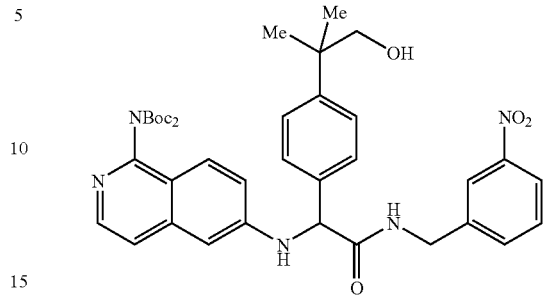

74E (35 mg, 51%) was obtained from 74D (58 mg, 0.104 mmol) using a procedure similar to that used in the preparation of 70F. MS (ESI) m/z 700.3 (M+H)⁺.

74F: N-(3-aminobenzyl)-2-(1-(bis(tert-butoxycarbonyl)amino)isoquinolin-6-ylamino)-2-(4-(1-hydroxy-2-methylpropan-2-yl)phenyl)acetamide

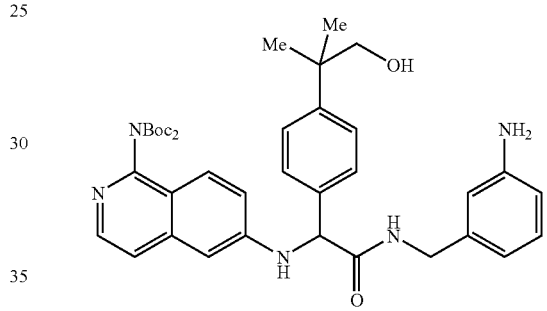

74F (28 mg, 95%) was obtained from 74E (32 mg, 0.046 mmol) using a procedure similar to that used in the preparation of 70G. MS (ESI) m/z 670.7 (M+H)⁺.

74G: 2-(1-(bis(tert-butoxycarbonyl)amino)isoquinolin-6-ylamino)-15,15-dimethyl-13-oxa-4,11-diazatricyclo[14.2.2.1$^{6,10}$]henicosa-1(19),6,8,10(21),16(20),17-hexaene-3,12-dione

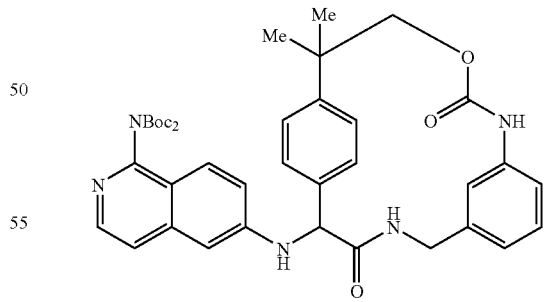

74G was obtained from 74F (27 mg, 0.04 mmol) using a procedure similar to that used in the preparation of 70H. MS (ESI) m/z 696.6 (M+H)⁺.

Example 74

Example 74 (9.5 mg) was obtained from 74G using a procedure similar to that used in the preparation of Example 66. MS (ESI) m/z 496.5 (M+H)+. 1H NMR (400 MHz, CD3OD) δ ppm 1.43 (d, J=8.35 Hz, 6 H) 3.90-4.55 (m, 2 H) 4.71-4.99 (m, 2 H) 5.19 (s, 1 H) 6.12 (s, 1 H) 6.64-6.73 (m, 2 H) 6.83 (d, J=7.03 Hz, 1 H) 6.89 (d, J=7.91 Hz, 1 H) 7.13 (t, J=7.69 Hz, 1 H) 7.19 (dd, J=9.23, 2.20 Hz, 1 H) 7.29 (d, J=7.47 Hz, 1 H) 7.36-7.46 (m, 2 H) 7.53-7.66 (m, 2 H) 8.05 (d, J=9.23 Hz, 1 H)

Example 75

2-(1-Amino-isoquinolin-6-ylamino)-15-ethyl-13-oxa-4,11-diaza-tricyclo[14.2.2.1^{6,10}]henicosa-1(19),6,8,10(21),16(20),17-hexaene-3,12-dione trifluoroacetic acid salt

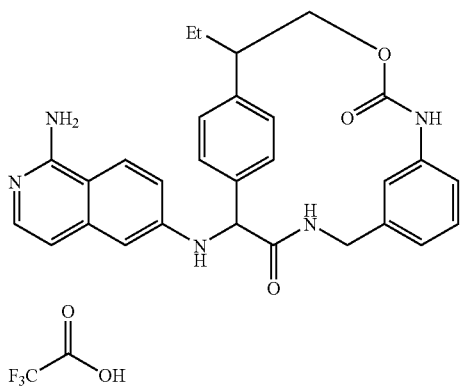

75A: ethyl 2-(4-bromophenyl)butanoate

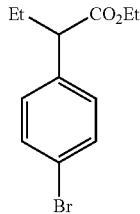

To a solution of ethyl 2-(4-bromophenyl)acetate (972 mg, 4 mmol) in 10 mL dry THF at −78° C. was added LDA (2 M, 2 mL, 4 mmol). The solution was warmed to rt and stirred 2 h, then was recooled to −78° C. EtI (0.52 mL) was added, then the reaction was stirred rt for 16 h. The reaction was quenched with sat. NH4Cl, then extracted with EtOAc (3×20 mL). The organic layer washed with brine, then dried (Na2SO4). Purification via flash chromatography (0-20% EtOAc in hexanes) gives 75A (228 mg, 21%). MS (ESI) m/z 271.0 (M+H)+.

75B: 2-(4-bromophenyl)butanoic acid

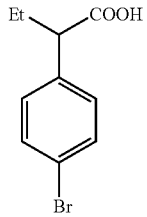

To a solution of 75A (228 mg, 0.85 mmol) in 3 mL THF, was added aq. LiOH (1M, 2 mL, 2 mmol), and the reaction was stirred at rt for 16 h. Water (20 mL) was added, then the mixture was acidified with 1N HCl (pH=2) and extracted with EtOAc (3×20 mL). The organic layer washed with brine, dried (Na2SO4) and concentrated to afford 75B (150 mg, 73%). MS (ESI) m/z 243.0 (M+H)+.

75C: 2-(4-bromophenyl)butan-1-ol

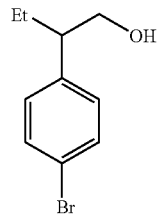

To a solution of 75B (96 mg, 0.4 mmol) in 3 mL THF was added BH3 (2M in THF, 0.5 mL, 1 mmol). The solution was stirred at rt for 16 h. EtOAc (20 mL) was added, and the organic phase washed with 1M H3PO4, sat. NaHCO3 and brine, dried (Na2SO4), and concentrated. Purification via flash chromatography (0-30% EtOAc in hexanes) gives 75C (86 mg, 96%). MS (ESI) m/z 211.2(M−H2O)+.

75D: 4-(1-hydroxybutan-2-yl)phenylboronic acid

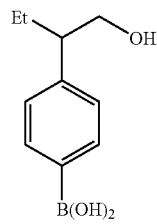

75D (74 mg, 68%) was obtained from 75C (128 mg, 0.56 mmol) using a procedure similar to that used in the preparation of 66C. 1H NMR (400 MHz, CD3OD) δ ppm 0.79 (t, J=7.25 Hz, 3 H) 1.50-1.63 (m, 1 H) 1.79-1.91 (m, 1 H) 2.56-2.68 (m, 1 H) 3.66 (d, J=7.03 Hz, 2 H) 7.20 (d, J=7.91 Hz, 2 H) 7.55 (d, J=7.91 Hz, 2 H)

75E: 2-(1-(bis(tert-butoxycarbonyl)amino)isoquinolin-6-ylamino)-2-(4-(1-hydroxybutan-2-yl)phenyl)acetic acid

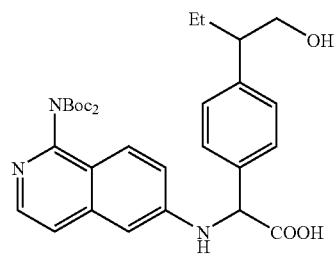

75E (94 mg, 44%) was obtained from 75D (74 mg, 0.38 mmol) using a procedure similar to that used in the preparation of 66D. MS (ESI) m/z 566.6(M+H)+.

75F: 2-(1-(bis(tert-butoxycarbonyl)amino)isoquinolin-6-ylamino)-2-(4-(1-hydroxybutan-2-yl)phenyl)-N-(3-nitrobenzyl)acetamide

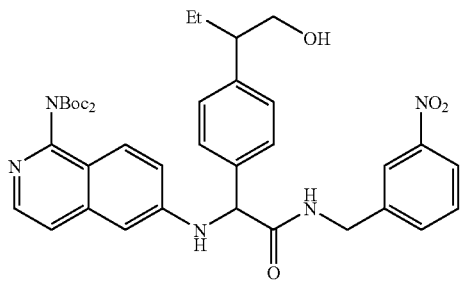

75F (60 mg, 51%) was obtained from 75E (94 mg, 0.17 mmol) using a procedure similar to that used in the preparation of 70F. MS (ESI) m/z 700.8 (M+H)$^+$.

75G: N-(3-aminobenzyl)-2-(1-(bis(tert-butoxycarbonyl)amino)isoquinolin-6-ylamino)-2-(4-(1-hydroxybutan-2-yl)phenyl)acetamide

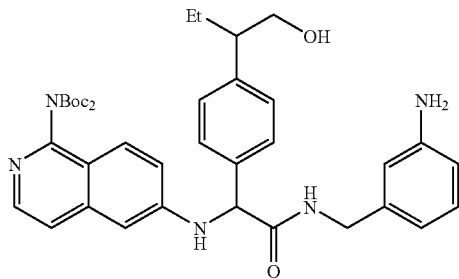

75G (57 mg, 99%) was obtained from 75F (60 mg, 0.086 mmol) using a procedure similar to that used in the preparation of 70G. MS (ESI) m/z 670.7 (M+H)$^+$.

75H: 2-(1-(bis(tert-butoxycarbonyl)amino)isoquinolin-6-ylamino)-15-ethyl-13-oxa-4,11-diaza-tricyclo[14.2.2.1$^{6,10}$]henicosa-1(19),6,8,10(21),16(20),17-hexaene-3,12-dione

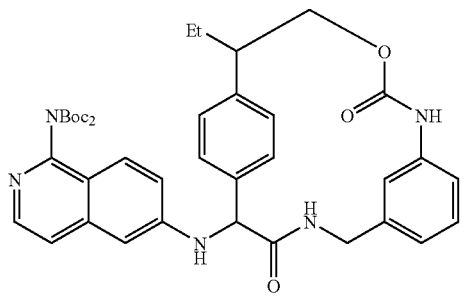

75H (25 mg, 42%) was obtained from 75G (57 mg, 0.085 mmol) using a procedure similar to that used in the preparation of 70H. MS (ESI) m/z 696.6 (M+H)$^+$.

Example 75

Example 75 (17 mg, 94%) was obtained from 75H (25 mg, 0.035 mmol) using a procedure similar to that used in the preparation of Example 66. MS (ESI) m/z 496.6 (M+H)$^+$. $^1$H NMR (400 MHz, CD$_3$OD) δ ppm 0.80-0.95 (m, 3H) 1.64-1.92 (m, 2H) 2.73-2.96 (m, 1 H) 3.96-4.45 (m, 2 H) 4.62-4.86 (m, 2 H) 5.18 (d, J=19.33 Hz, 1 H) 6.15 (d, J=36.91 Hz, 1 H) 6.63-6.74 (m, 2 H) 6.84 (dd, J=7.03, 3.52 Hz, 1 H) 6.89 (d, J=7.47 Hz, 1 H) 7.09-7.40 (m, 5 H) 7.48 (t, J=10.11 Hz, 1 H) 7.52-7.73 (m, 1 H) 8.06 (dd, J=9.23, 5.27 Hz, 1 H).

Example 76

(R)-2-(1-Amino-isoquinolin-6-ylamino)-15-methyl-13-oxa-4,11-diaza-tricyclo[14.2.2.1$^{6,10}$]henicosa-1(19),6,8,10(21),16(20),17-hexaene-3,12-dione trifluoroacetic acid salt

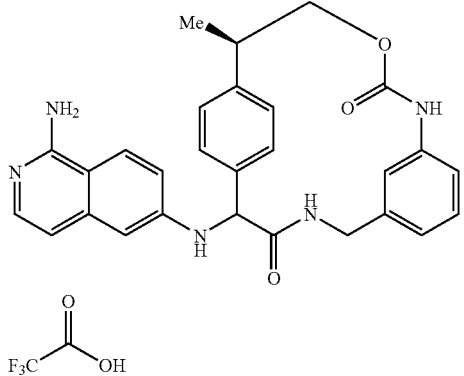

76A: (R)-4-benzyl-3-(2-(4-bromophenyl)acetyl)oxazolidin-2-one

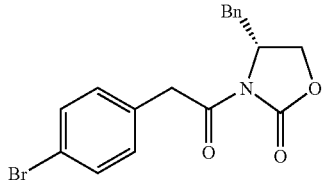

To a round bottom flask contained (R)-4-benzyl-2-oxazolidinone (800 mg, 4.51 mmol) in THF (10 mL), n-BuLi (2.83 mL, 1.6M, 4.52 mmol) was added at –78° C., dropwise. The solution was stirred at –78° C. for 10 min. A solution of 2-(4-bromophenyl)acetyl chloride (1.0 g, 4.28 mmol) in 10 mL THF was added. The solution was stirred –78° C. for 30 min, and rt for 3 h, and then was quenched with sat. NH$_4$Cl and extracted with EtOAc (3×20 mL). The organic layer washed with brine, dried (Na$_2$SO$_4$), and concentrated. Purification via flash chromatography (0-30% EtOAc in hexanes) gives 76A (1.29 g, 80%). MS (ESI) m/z 374.1 (M+H)$^+$.

76B: (R)-4-benzyl-3-((R)-2-(4-bromophenyl)propanoyl)oxazolidin-2-one

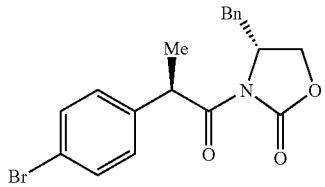

To a solution of 76A (380 mg, 1.01 mmol) in THF (5 mL) at –78° C., was added NaHMDS (1.3 mL, 1.0M, 1.3 mmol), dropwise. The solution was stirred at –78° C. for 3 h. A solution of MeI (0.62 mL, 10 mmol) in 2 mL THF was added. The solution was stirred –78° C. for 3 h, and –40° C. for 1 h.

The reaction was quenched with sat. NH₄Cl and extracted with EtOAc (3×20 mL). The organic layer washed with brine, dried (Na₂SO₄), and concentrated. Purification via flash chromatography (0-30% EtOAc in hexanes) gives 76B (70 mg, 18%). MS (ESI) m/z 388.3 (M+H)⁺.

76C: (R)-2-(4-bromophenyl)propanoic acid

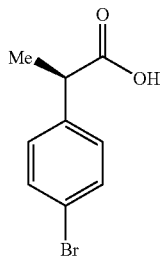

To a solution of 76B (209 mg, 0.54 mmol) in THF (5 mL) at 0° C., was added H₂O₂ (0.33 mL, 50%, 5.4 mmol) dropwise, followed by aq. LiOH (1.1 mL, 1.0 M, 1.1 mmol). The solution was stirred at rt for 2 h. Aq. Na₂SO₃ (1M, 20 mL) was added and stirred rt for 30 min. The aqueous phase was extracted with CH₂Cl₂ (2×10 mL), acidified to pH=2 with 1N HCl, and extracted with EtOAc (3×20 mL). The organic layer washed with brine, dried (Na₂SO₄) and concentrated to give 76C (110 mg, 90%). MS (ESI) m/z 229.0 (M+H)⁺.

76D: (R)-2-(4-bromophenyl)propan-1-ol

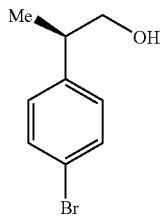

To a solution of 76C (95 mg, 0.42 mmol) in THF (3 mL) at 0° C., was added BH₃ (1M in THF, 0.4 mL, 4 mmol). The mixture was stirred rt for 16 h. EtOAc (20 mL) was added, and the organic phase washed with 1M H₃PO₄, sat. NaHCO₃ and brine, dried (Na₂SO₄), and concentrated to give 76D (90 mg, 100%). MS (ESI) m/z 197.0 (M−H₂O+H)⁺.

76E: (R)-2-(4-boronophenyl)propanoic acid

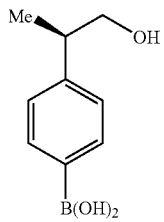

76E (77 mg, 97%) was obtained from 76D (95 mg, 0.44 mmol) using a procedure similar to that used in the preparation of 66C. MS (ESI) m/z 163.1 (M−H₂O+H)⁺.

76F: 2-(1-(bis(tert-butoxycarbonyl)amino)isoquinolin-6-ylamino)-2-(4-((R)-1-hydroxypropan-2-yl)phenyl)acetic acid

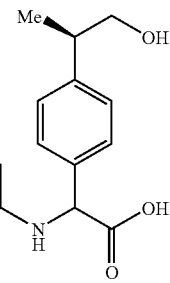

76F (200 mg, 87%) was obtained from 76E (77 mg, 0.43 mmol) using a procedure similar to that used in the preparation of 66D. MS (ESI) m/z 552.3 (M+H)⁺.

76G: 2-(1-(bis(tert-butoxycarbonyl)amino)isoquinolin-6-ylamino)-2-(4-((R)-1-hydroxypropan-2-yl)phenyl)-N-(3-nitrobenzyl)acetamide

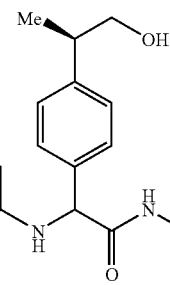

76G (172 mg, 87%) was obtained from 76F (190 mg, 0.34 mmol) using a procedure similar to that used in the preparation of 70F. MS (ESI) m/z 686.4 (M+H)⁺.

76H: N-(3-aminobenzyl)-2-(1-(bis(tert-butoxycarbonyl)amino)isoquinolin-6-ylamino)-2-(4-((R)-1-hydroxypropan-2-yl)phenyl)acetamide

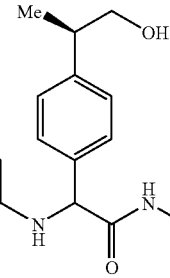

76H (145 mg, 88%) was obtained from 76G (172 mg, 0.25 mmol) using a procedure similar to that used in the preparation of 70G. MS (ESI) m/z 656.4 (M+H)⁺.

76I: (R)-2-(1-(bis(tert-butoxycarbonyl)amino)iso-quinolin-6-ylamino)-15-methyl-13-oxa-4,11-diaza-tricyclo[14.2.2.1^{6,10}]henicosa-1(19),6,8,10(21),16(20),17-hexaene-3,12-dione

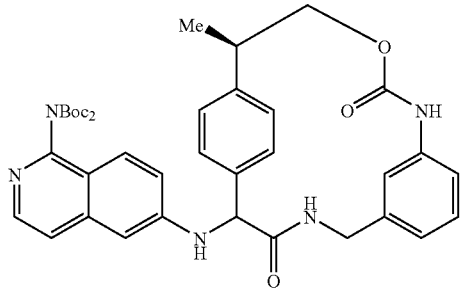

76I (20 mg, 24%) was obtained from 76H (80 mg, 0.122 mmol) using a procedure similar to that used in the preparation of 70H. MS (ESI) m/z 682.6 (M+H)+.

Example 76

Example 76 (13.2 mg, 98%) was obtained from 76I (19 mg, 0.028 mmol) using a procedure similar to that used in the preparation of Example 70. MS (ESI) m/z 482.3 (M+H)+. 1H NMR (400 MHz, CD3OD) δ ppm 1.24-1.45 (m, 3H) 3.01-3.19 (m, 1 H) 3.92-4.15 (m, 2 H) 4.25-4.86 (m, 2 H) 5.18 (d, J=14.94 Hz, 1 H) 6.15 (d, J=29.00 Hz, 1 H) 6.62-6.74 (m, 2 H) 6.82 (t, J=7.47 Hz, 1 H) 6.89 (d, J=7.91 Hz, 1 H) 7.07-7.23 (m, 3 H) 7.25-7.34 (m, 2 H) 7.35-7.73 (m, 2 H) 8.05 (dd, J=9.23, 4.83 Hz, 1 H).

Examples 77 and 78

2-(1-Amino-isoquinolin-6-ylamino)-14-methyl-13-oxa-4,11-diaza-tricyclo[14.2.2.1^{6,10}]henicosa-1(19),6,8,10(21),16(20),17-hexaene-3,12-dione trifluoroacetic acid salt, diastereomers 1 and 2, respectively

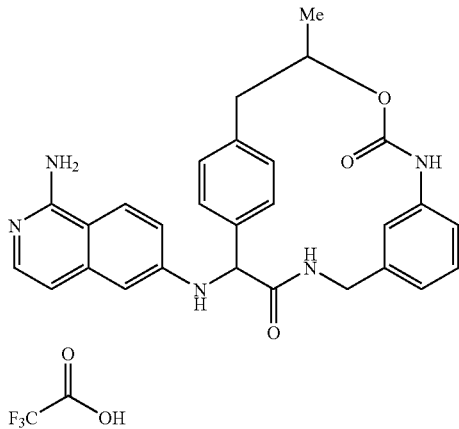

77A: 1-(4-bromophenyl)propan-2-ol

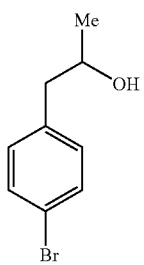

To a solution of 4-bromophenylacetone (5.00 g, 23.5 mmol) in ethanol (100 mL) at 0° C., was added sodium borohydride (976 mg, 25.8 mmol) portionwise over 5 min. The mixture was stirred at rt for 15 h, then quenched with 5% citric acid. The volatile solvent was removed in vacuo. The mixture was diluted with water, the pH was adjusted to 4.5 with 1N HCl, then aqueous phase was extracted with CH2Cl2 (3×). The combined organic washed with brine, dried (Na2SO4), filtered through a pad of SiO2 (eluted with 10% EtOAc/CH2Cl2) and concentrated to afford 4.90 g of 77A as a colorless oil. MS (ESI) m/z 197.1 (M-OH)+.

77B: (1-(4-bromophenyl)propan-2-yloxy)(tert-butyl)dimethylsilane

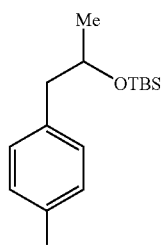

According to the procedure for the preparation of 73C, 77A (4.90 g, 22.8 mmol) afforded 6.51 g (87%) of 77B as a colorless oil. MS (ESI) m/z 197.1 (M-OTBS)+.

77C: 4-(2-(tert-butyldimethylsilyloxy)propyl)phenylboronic acid

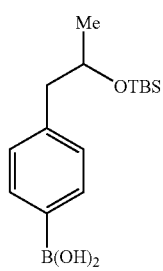

According to the procedure for the preparation of 73D, 77B (2.14 g, 6.50 mmol) afforded 1.04 g (54%) of 77C as a colorless solid. MS (ESI) m/z 295.2 (M+H)+.

77D: 2-(1-(bis(tert-butoxycarbonyl)amino)isoquinolin-6-ylamino)-2-(4-(2-(tert-butyldimethylsilyloxy)propyl)phenyl)acetic acid

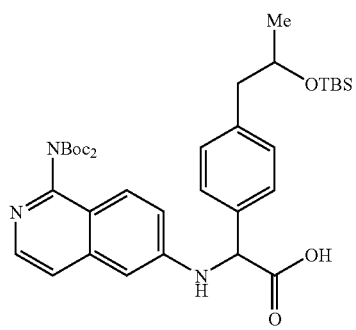

According to the procedure for the preparation of 66D, 77C (200 mg, 0.68 mmol) afforded 295 mg (65%) of 77D as an off-white solid. MS (ESI) m/z 666.4(M+H)+.

77E: 2-(1-(bis(tert-butoxycarbonyl)amino)isoquinolin-6-ylamino)-2-(4-(2-(tert-butyldimethylsilyloxy)propyl)phenyl)-N-(3-nitrobenzyl)acetamide

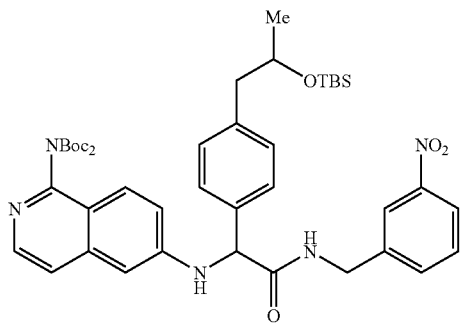

According to the procedure for the preparation of 70F, 77D (150 mg, 0.225 mmol) afforded 172 mg (96%) of 77E as a brown glass. MS (ESI) m/z 800.5 (M+H)$^+$.

77F: 2-(1-(bis(tert-butoxycarbonyl)amino)isoquinolin-6-ylamino)-2-(4-(2-hydroxypropyl)phenyl)-N-(3-nitrobenzyl)acetamide

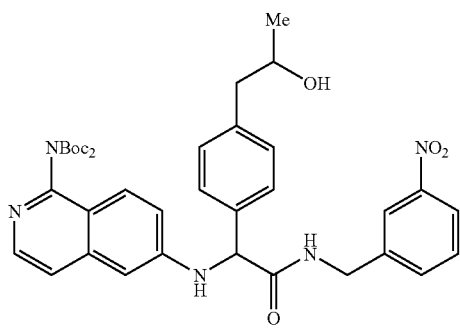

To a solution of 77E (172 mg, 0.215 mmol) in 3 mL THF, was added a solution of TBAF (1M in THF, 1 mL, 1 mmol). The mixture was stirred at 35° C. for 17 h, then concentrated. The residue was dissolved in EtOAc, washed with water (2×) and brine, dried (Na$_2$SO$_4$) and concentrated. Purification by flash chromatography (0 to 100% EtOAc/hexanes) afforded 38 mg (26%) of 77F as a yellow glass. MS (ESI) m/z 686.4 (M+H)$^+$.

77G: N-(3-aminobenzyl)-2-(1-(bis(tert-butoxycarbonyl)amino)isoquinolin-6-ylamino)-2-(4-(2-hydroxypropyl)phenyl)acetamide

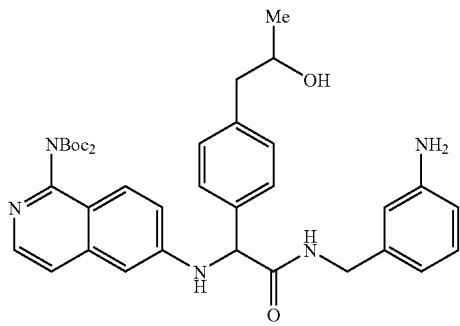

According to the procedure for the preparation of 70G, 77F (38 mg, 0.055 mmol) afforded 29 mg (80%) of 77G as a white solid. MS (ESI) m/z 656.5 (M+H)$^+$.

77H and 77I: 2-(1-(bis(tert-butoxycarbonyl)amino)isoquinolin-6-ylamino)-14-methyl-13-oxa-4,11-diaza-tricyclo[14.2.2.1$^{6,10}$]henicosa-1(19),6,8,10(21),16(20),17-hexaene-3,12-dione, diastereomers 1 and 2, respectively

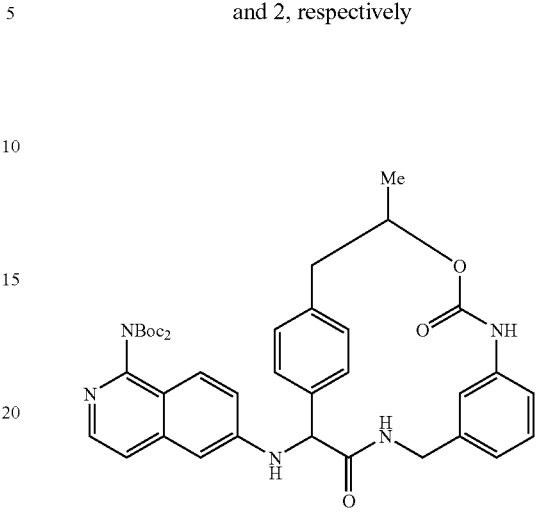

According to the procedure for the preparation of 70H, 77G (29 mg, 0.055 mmol) afforded after flash chromatography (0 to 100% EtOAc/hexanes) 6.8 mg (23%) of 77H as a colorless residue, followed by 9.0 mg (30%) of 77I as an orange solid. MS (ESI) m/z 656.5 (M+H)$^+$ for each diastereomer.

Example 77

According to the procedure for the preparation of Example 66, 77H (6.8 mg) afforded 5.2 mg of Example 77 as a white solid. MS (ESI) m/z 482.4 (M+H)$^+$; $^1$H NMR (400 MHz, CD$_3$OD) d ppm 8.58 (d, J=8.35 Hz, 1 H) 8.08 (d, J=9.23 Hz, 1 H) 7.50 (t, J=8.57 Hz, 2 H) 7.37 (d, J=7.91 Hz, 1 H) 7.29 (d, J=7.03 Hz, 1 H) 7.25 (d, J=10.55 Hz, 1 H) 7.20 (d, J=7.91 Hz, 1 H) 7.14 (t, J=7.91 Hz, 1 H) 6.91 (d, J=7.47 Hz, 1 H) 6.79 (d, J=7.03 Hz, 1 H) 6.71 (d, J=7.91 Hz, 1 H) 6.64 (s, 1 H) 6.21 (s, 1 H) 5.18-5.27 (m, 1 H) 5.15 (s, 1 H) 4.91-4.99 (m, 1 H) 3.86-3.94 (m, 1 H) 2.99 (d, J=11.86 Hz, 1 H) 2.64 (dd, J=13.18, 11.42 Hz, 1 H) 1.40 (d, J=6.59 Hz, 3 H).

Example 78

According to the procedure for the preparation of Example 66, 77I (9.0 mg) afforded 5.2 mg of Example 78 as a white solid. MS (ESI) m/z 482.4 (M+H)$^+$; $^1$H NMR (400 MHz, CD$_3$OD) d ppm 8.77 (t, J=6.15 Hz, 1 H) 8.05 (d, J=9.23 Hz, 1 H) 7.65 (dd, J=7.69, 1.54 Hz, 1 H) 7.48 (dd, J=7.69, 1.10 Hz, 1H) 7.32 (d, J=7.03 Hz, 1 H) 7.28 (dd, J=8.13, 1.54 Hz, 1 H) 7.15-7.19 (m, 2 H) 7.13 (t, J=7.69 Hz, 1 H) 6.88 (t, J=6.15 Hz, 2 H) 6.73 (d, J=1.76 Hz, 1 H) 6.66 (d, J=7.91 Hz, 1 H) 6.14 (s, 1 H) 5.25-5.34 (m, J=17.41, 6.12, 6.12, 2.86 Hz, 1 H) 5.20 (s, 1H) 4.67 (dd, J=16.48, 6.81 Hz, 1 H) 4.13 (dd, J=16.48, 5.05 Hz, 1 H) 3.04 (dd, J=13.40, 1.98 Hz, 1 H) 2.65 (dd, J=13.18, 11.42 Hz, 1 H) 1.41 (d, J=6.59 Hz, 3 H).

Example 79

14-(1-Amino-isoquinolin-6-ylamino)-17,18-dimethyl-9-(ethylsulfonyl)-2-oxa-5,12-diaza-tricyclo[13.2.2.1^{6,10}]icosa-1(18),6(20),7,9,15(19),16-hexaene-4,13-dione trifluoroacetic acid salt

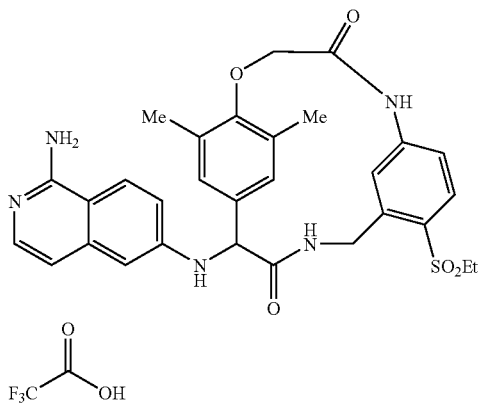

79A: 2-(4-bromo-2,6-dimethylphenoxy)acetic acid

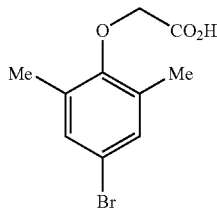

To a suspension of sodium hydride (60%, 437 mg, 10.9 mmol) in THF (10 mL) at rt, was added a solution of 4-bromo-2,6-dimethylphenol (1.00 g, 4.97 mmol) in THF (10 mL), over 5 min. The reddish suspension was stirred at rt for 10 min, then a solution of bromoacetic acid (691 mg, 4.97 mmol) in 5 mL THF was added. The suspension was stirred at rt for 20 h. The volatile solvent was evaporated in vacuo, then the mixture was diluted with 20 mL H$_2$O. The pH was adjusted to 7 with 1N HCl, then the aqueous phase was extracted with Et$_2$O (2×). The aqueous phase was acidified to pH=2 with 1N HCl, then was extracted with EtOAc (2×). The combined organic extract washed with brine, dried (Na$_2$SO$_4$) and concentrated to afford 1.10 g (85%) of 79A as a colorless solid. MS (ESI) m/z 259.0 (M+H)$^+$.

79B: benzyl 5-(2-(4-bromo-2,6-dimethylphenoxy)acetamido)-2-(ethylsulfonyl)benzylcarbamate

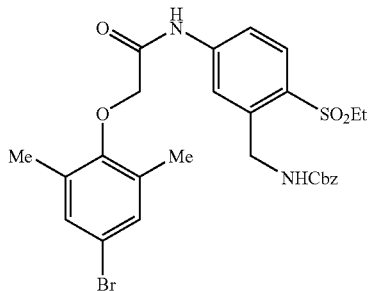

To a solution of 79A (100 mg, 0.386 mmol) and 28A (148 mg, 0.386 mmol) in 2 mL pyridine at −15° C., was added POCl$_3$ (0.040 mL, 0.425 mmol), dropwise. The mixture was stirred at this temperature for 20 min, then was quenched with water. The mixture was diluted with EtOAc, washed with water (2×), 1N HCl, water, sat. NaHCO$_3$ and brine, dried (Na$_2$SO$_4$) and concentrated. The crude product was purified by flash chromatography to afford 222 mg (98%) of 79B as a colorless oil. MS (ESI) m/z 589.2 (M+H)$^+$.

79C: 4-(2-(3-((benzyloxycarbonylamino)methyl)-4-(ethylsulfonyl)phenylamino)-2-oxoethoxy)-3,5-dimethylphenylboronic acid

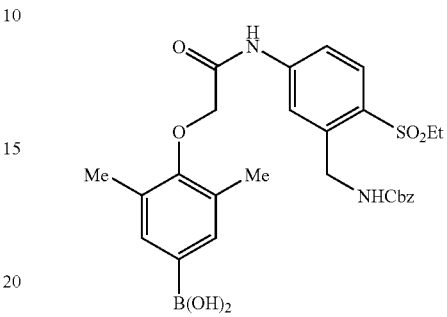

According to the procedure for the preparation of 66C, 79B (375 mg, 0.636 mmol) afforded following reversed phase preparative HPLC 302 mg (86%) of 79C as a colorless solid. MS (ESI) m/z 555.3 (M+H)$^+$.

79D: 2-(4-(2-(3-((benzyloxycarbonylamino)methyl)-4-(ethylsulfonyl)phenylamino)-2-oxoethoxy)-3,5-dimethylphenyl)-2-(1-(bis(tert-butoxycarbonyl)amino)isoquinolin-6-ylamino)acetic acid

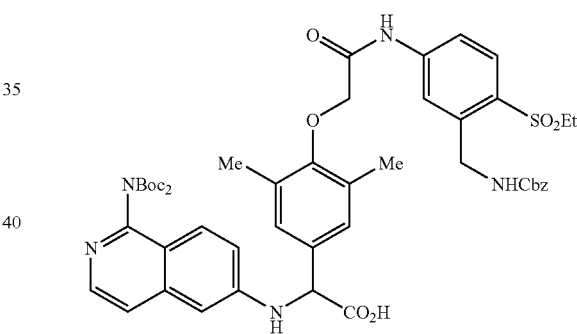

According to the procedure for the preparation of 66D, 79C (150 mg, 0.271 mmol) afforded 205 mg (82%) of 79D as an orange solid. MS (ESI) m/z 926.5 (M+H)$^+$.

79E: 2-(4-(2-(3-(aminomethyl)-4-(ethylsulfonyl)phenylamino)-2-oxoethoxy)-3,5-dimethylphenyl)-2-(1-(bis(tert-butoxycarbonyl)amino)isoquinolin-6-ylamino)acetic acid

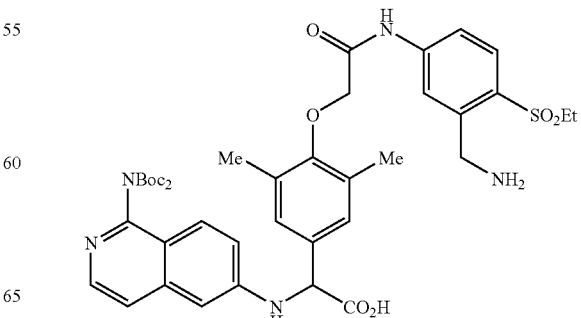

To a solution of 79D (190 mg, 0.205 mmol) in 5 mL methanol, was added 10% Pd—C (30 mg). The reaction was evacuated and flushed with $H_2$ (3×), then stirred under an atmosphere of $H_2$ for 1 h. The reaction was filtered and concentrated to afford 151 mg (93%) of 79E as an orange solid. MS (ESI) m/z 926.5 (M+H)$^+$.

Example 79

To a solution of PyBOP (197 mg, 0.379 mmol), DMAP (116 mg, 0.95 mmol) and TEA (0.132 mL, 0.95 mmol) in $CH_2Cl_2$ (50 mL) at rt, was added a solution of 79E in 5 mL DMF over 4 h via a syringe pump. The mixture was stirred for at rt for 15 h, then was concentrated. The material was diluted with EtOAc, washed with water (2×), sat. $NaHCO_3$ and brine, dried ($Na_2SO_4$) and concentrated. The residue was treated with 5 mL TFA. The mixture was stirred for 5 min, then concentrated. Purification by preparative HPLC afforded 6.5 mg of Example 79 as a yellow solid. MS (ESI) m/z 574.3 (M+H)$^+$; $^1$H NMR (400 MHz, $CD_3OD$) d ppm 8.68-8.74 (m, 1 H) 8.09 (d, J=9.34 Hz, 1 H) 7.82 (d, J=8.79 Hz, 1 H) 7.38 (s, 1 H) 7.32 (d, J=7.15 Hz, 1 H) 7.24-7.23 (m, 1 H) 7.22 (t, J=2.20 Hz, 1 H) 6.98 (s, 1 H) 6.88 (d, J=7.15 Hz, 1 H) 6.74 (d, J=2.20 Hz, 1 H) 5.81 (d, J=1.85 Hz, 1 H) 5.11 (s, 1 H) 5.05 (dd, J=16.49, 7.15 Hz, 1 H) 4.62-4.71 (m, 2 H) 4.29 (dd, J=17.04, 4.95 Hz, 1 H) 3.37-3.32 (m, 2 H) 2.40 (s, 3 H) 2.19 (s, 3 H) 1.24 (t, J=7.15 Hz, 3 H).

Example 80

14-Acetyl-2-(1-amino-isoquinolin-6-ylamino)-4,11,14-triaza-tricyclo[14.2.2.1$^{6,10}$]henicosa-1(19),6,8,10(21),16(20),17-hexaene-3,12-dione trifluoroacetic acid salt

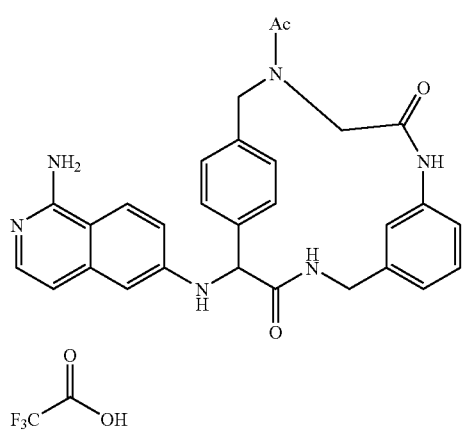

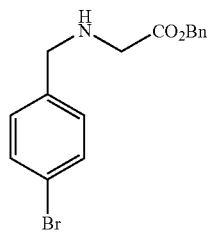

80A: benzyl 2-(4-bromobenzylamino)acetate

To a suspension of glycine benzyl ester hydrochloride (2.02 g, 10.0 mmol) and 4-bromobenzaldehyde (1.85 g, 10.0 mmol) in 50 mL DCE, was added acetic acid (2.9 mL, 50 mmol) and TEA (1.4 mL, 10.0 mmol) to give a clear solution. Sodium triacetoxyborohydride (4.24 g, 20.0 mmol) was added. The suspension was stirred at rt for 17 h. The mixture was neutralized with sat. $NaHCO_3$ and extracted with $CH_2Cl_2$ (3×). The combined organic extract washed with brine, dried ($Na_2SO_4$) and concentrated. The crude product was purified via flash chromatography (0 to 100% EtOAc in hexanes) to afford 80A (2.13 g, 64%). MS (ESI) m/z 334.0 (M+H)$^+$.

80B: benzyl 2-(N-(4-bromobenzyl)acetamido)acetate

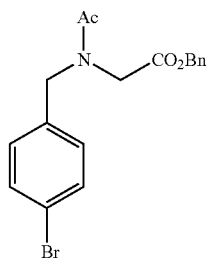

To a solution of 80A (500 mg, 1.50 mmol) in 5 mL $CH_2Cl_2$, were added TEA (0.229 mL, 1.65 mmol) and acetic anhydride (0.156 mL, 1.65 mmol). The mixture was stirred at rt for 2 h, then concentrated. The crude product was purified via flash chromatography (0 to 100% EtOAc in hexanes) to afford 80B (560 mg, 99%). MS (ESI) m/z 376.0 (M+H)$^+$.

80C: 4-((N-(2-(benzyloxy)-2-oxoethyl)acetamido)methyl)phenylboronic acid

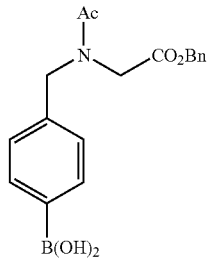

80C (140 mg, 82%) was obtained from 80B (188 mg, 0.5 mmol) using a procedure similar to that used in the preparation of 66C. MS (ESI) m/z 342.2 (M+H)$^+$.

80D: 2-(4-((N-(2-(benzyloxy)-2-oxoethyl)acetamido)methyl)phenyl)-2-(1-(bis(tert-butoxycarbonyl)amino)isoquinolin-6-ylamino)acetic acid

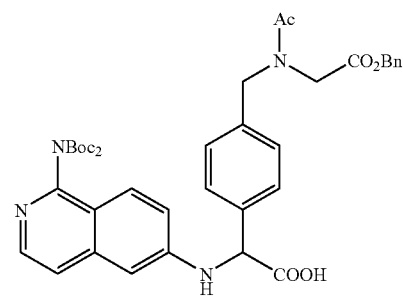

80D (80 mg, 65%) was obtained from 80C (140 mg, 0.38 mmol) using a procedure similar to that used in the preparation of 66D. MS (ESI) m/z 713.2 (M+H)$^+$.

80E: benzyl benzyl 2-(N-(4-(1-(1-(bis(tert-butoxycarbonyl)amino)isoquinolin-6-ylamino)-2-(3-nitrobenzylamino)-2-oxoethyl)benzyl)acetamido)acetate

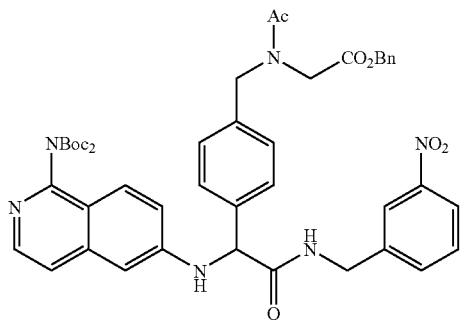

80D (280 mg, 0.39 mmol) was mixed with 3-cyanobenzylamine hydrochloride (116 mg, 0.61 mmol), PyBOP (277 mg, 0.53 mmol), and TEA (202 mg, 2 mmol) in DMF (3 mL) and stirred at rt for 16 h. The mixture was diluted with H$_2$O and extracted with EtOAc (3×20 mL). The organic layer washed with brine, dried (Na$_2$SO$_4$) and concentrated. Purification via flash chromatography (0-80% EtOAc/hexanes) afforded 80E (150 mg, 45%). MS (ESI) m/z 847.5 (M+H)$^+$.

80F: 2-(N-(4-(2-(3-aminobenzylamino)-1-(1-(bis(tert-butoxycarbonyl)amino)isoquinolin-6-ylamino)-2-oxoethyl)benzyl)acetamido)acetic acid

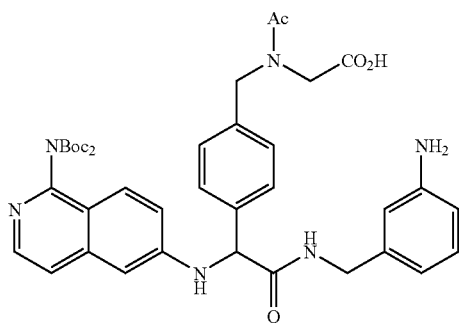

To a solution of 80E (148 mg, 0.18 mmol) in 10 mL MeOH, was added 10% Pd/C (20 mg). The mixture was hydrogenated at 40 psi for 3 h, then filtered and concentrated to give 80F (115 mg, 100%). MS (ESI) m/z 727.7 (M+H)$^+$.

80G: 14-Acetyl-2-(1-(bis(tert-butoxycarbonyl)amino)isoquinolin-6-ylamino)-4,11,14-triaza-tricyclo[14.2.2.1$^{6,10}$]henicosa-1(19),6,8,10(21),16(20),17-hexaene-3,12-dione

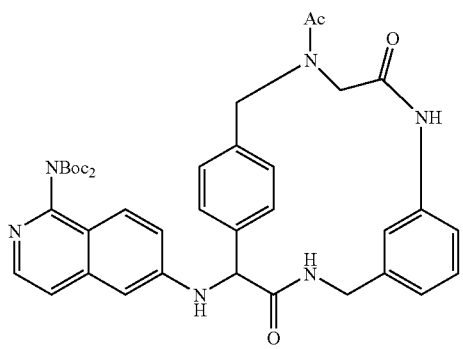

To a solution of BOP (30 mg, 0.065), TEA (0.07 mL, 0.5 mmol) in 40 mL of CH$_2$Cl$_2$, was added a solution of 80F (40 mg, 0.055 mmol) in DMF (8 mL) via a syringe pump over 6 h. The mixture was stirred r.t over night, then was quenched with sat. NH$_4$Cl and extracted with EtOAc (3×20 mL). The organic layer was washed with brine, dried (Na$_2$SO$_4$) and concentrated. Purification via flash chromatography (0-10% MeOH/CH$_2$Cl$_2$) afforded 80G (21 mg, 54%). MS (ESI) m/z 709.5 (M+H)$^+$.

Example 80

To a solution of 80G (15 mg, 0.021 mmol) in 1 mL CH$_2$Cl$_2$, was added TFA (1 mL). The solution was stirred at rt for 1 h, then concentrated. Purification by reversed phase HPLC afforded 4 mg (38%) of Example 80. MS (ESI) m/z 509.1 (M+H)$^+$. $^1$H NMR (400 MHz, CD$_3$OD) δ ppm 2.43-2.90 (m, 3 H) 3.95-4.24(m, 3 H) 4.34-4.57 (m, 1 H) 4.69-4.85 (m, 1 H) 5.15-5.26 (m, 2 H) 5.76-5.88 (m, 1 H) 6.69 (s, H) 6.80-6.89 (m, 2 H) 6.97 (t, J=8.35 Hz, 1 H) 7.17-7.24 (m, 2 H) 7.27-7.46 (m, 3 H) 7.53 (t, J=6.81 Hz, 1 H) 7.65-7.78 (m, 1 H) 8.06 (d, J=9.23 Hz, 1 H).

Example 81

2-(1-Amino-isoquinolin-6-ylamino)-4,11,14-triaza-tricyclo[14.2.2.1$^{6,10}$]henicosa-1(19),6,8,10(21),16(20),17-hexaene-3,12-dione

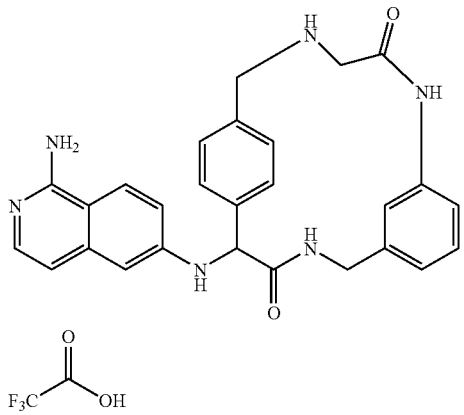

81A: benzyl 2-((4-bromobenzyl)(tert-butoxycarbonyl)amino)acetate

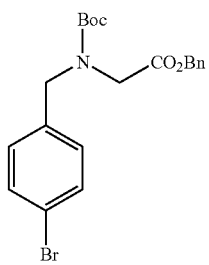

To a solution of 80A (500 mg, 1.50 mmol) in 5 mL CH$_2$Cl$_2$, were added TEA (0.229 mL, 1.65 mmol) and Boc$_2$O (360 mg, 1.65 mmol). The mixture was stirred at rt for 2 h, then additional Boc$_2$O (50 mg) was added. The mixture was stirred an additional 30 min, then was concentrated. The crude product was purified via flash chromatography (0 to 40% EtOAc in hexanes) to afford 81A (599 mg, 92%). MS (ESI) m/z 434.1 (M+H)$^+$.

81B: 2-((4-bromobenzyl)(tert-butoxycarbonyl) amino)acetic acid

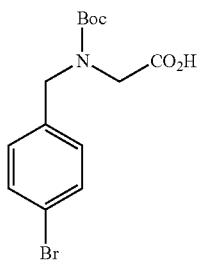

To a solution of 81A (325 mg, 0.75 mmol) in THF (5 mL) was added LiOH (0.5 mL, 3 mmol). The mixture was stirred rt over night, then concentrated. Water (20 mL) was added to the residue, and the organic phase washed with $CH_2Cl_2$ (2×20 mL). The aqueous layer was acidified with 1N HCl, and was extracted with EtOAc (2×20 mL). The combined organic layer washed with brine, dried ($Na_2SO_4$) and concentrated to give 81B (262 mg, 100%). $^1$H NMR (400 MHz, $CD_3OD$) δ ppm 1.36-1.51 (m, 9 H) 3.76-3.99 (m, 2 H) 4.44 (d, J=5.71 Hz, 2 H) 7.18 (d, J=8.35 Hz, 2 H) 7.41-7.49 (m, 2 H).

81C: {[3-(Benzyloxycarbonylamino-methyl)-phenyl-carbamoyl]-methyl}-(4-bromo-benzyl)-carbamic acid tert-butyl ester

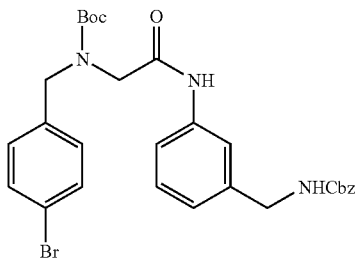

81C (226 mg, 97%) was obtained from 81B (139 mg, 0.40 mmol) using a procedure similar to that used in the preparation of 67B. MS (ESI) m/z 582.3 (M+H)$^+$.

81D: 4-(((2-(3-((benzyloxycarbonylamino)methyl) phenylamino)-2-oxoethyl)(tert-butoxycarbonyl) amino)methyl)phenylboronic acid

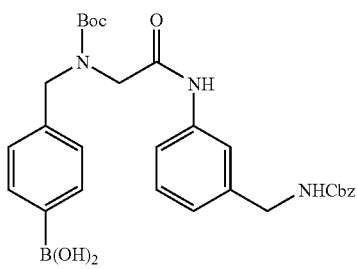

81D (161 mg, 78%) was obtained from 81C (221 mg, 0.38 mmol) using a procedure similar to that used in the preparation of 66C. MS (ESI) m/z 548.5 (M+H)$^+$.

81E: 2-(4-(((2-(3-((benzyloxycarbonylamino)methyl)phenylamino)-2-oxoethyl)(tert-butoxycarbonyl) amino)methyl)phenyl)-2-(1-(bis(tert-butoxycarbonyl)amino)isoquinolin-6-ylamino)acetic acid

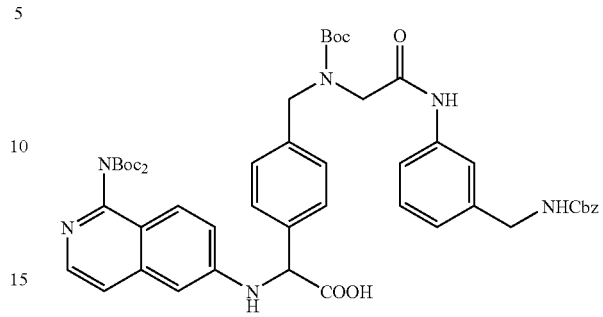

81E (102 mg, 40%) was obtained from 81D (152 mg, 0.28 mmol) using a procedure similar to that used in the preparation of 66D. MS (ESI) m/z 919.5 (M+H)$^+$.

81F: 2-(4-(((2-(3-(aminomethyl)phenylamino)-2-oxoethyl)(tert-butoxycarbonyl)amino)methyl)phenyl)-2-(1-(bis(tert-butoxycarbonyl)amino)isoquinolin-6-ylamino)acetic acid

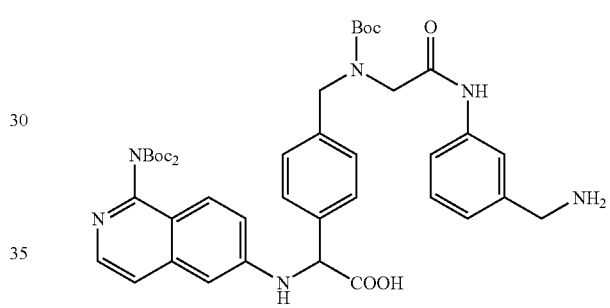

81F (30 mg, 39%) was obtained from 81E (90 mg, 0.1 mmol) using a procedure similar to that used in the preparation of 66E. MS (ESI) m/z 745.8 (M+H)$^+$.

81G: 2-(1-Amino-isoquinolin-6-ylamino)-3,12-di-oxo-4,11,14-triaza-tricyclo[14.2.2.1$^{6,10}$]henicosa-1 (19),6,8,10(21),16(20),17-hexaene-14-carboxylic acid tert-butyl ester

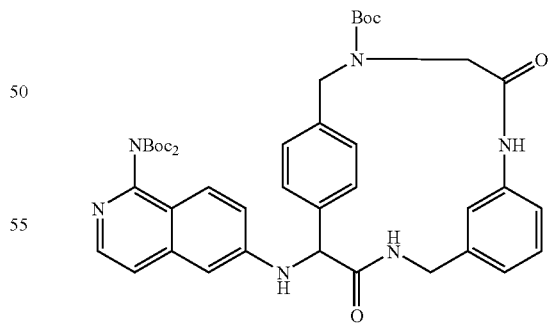

81G (14 mg, 73%) was obtained from 81F (19 mg, 0.024 mmol) using a procedure similar to that used in the preparation of 66F. MS (ESI) m/z 767.6 (M+H)$^+$.

Example 81

Example 81 (3.6 mg, 79%) was obtained from 81G (40 mg, 0.02 mmol) using a procedure similar to that used in the preparation of Example 66. MS (ESI) m/z 467.2. $^1$H NMR (400 MHz, CD$_3$OD) δ ppm 3.90-3.96 (m, 1 H) 4.05-4.14 (m, 3 H) 4.20 (d, J=13.18 Hz, 1 H) 4.43 (d, J=13.18 Hz, 1 H) 4.76 (dd, J=16.48, 7.25 Hz, 1 H) 5.28 (s, 1 H) 6.07 (s, 1 H) 6.68 (d, J=1.76 Hz, 1 H) 6.75 (d, J=8.79 Hz, 1 H) 6.83 (d, J=7.03 Hz, 1 H) 7.03 (d, J=7.47 Hz, 1 H) 7.19-7.24 (m, 2 H) 7.31 (d, J=7.03 Hz, 1 H) 7.49-7.53 (m, 2 H) 7.83 (d, J=7.91 Hz, 1 H) 8.07 (d, J=9.23 Hz, 1 H).

Utility

The compounds of the present invention are inhibitors of factor VIIa and are useful as anticoagulants for the prevention or treatment of thromboembolic disorders in mammals. In general, a thromboembolic disorder is a circulatory disease caused by blood clots (i.e., diseases involving fibrin formation, platelet activation, and/or platelet aggregation). The term "thromboembolic disorders (or conditions)" as used herein includes arterial or venous cardiovascular or cerebrovascular thromboembolic disorders, and thromboembolic disorders in the chambers of the heart. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary and cerebral arterial thrombosis, cerebral embolism, kidney embolisms, pulmonary embolisms, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, and vessel grafts. The procedures include, but are not limited to: cardiopulmonary bypass, percutaneous coronary intervention, and hemodialysis.

It is noted that thrombosis includes vessel occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant or antithrombotic effect of compounds of the present invention is believed to be due to inhibition of coagulation factor VIIa.

The term "thrombosis", as used herein, refers to formation or presence of a thrombus (pl. thrombi); clotting within a blood vessel which may cause ischemia or infarction of tissues supplied by the vessel. The term "embolism", as used herein, refers to sudden blocking of an artery by a clot or foreign material which has been brought to its site of lodgment by the blood current. The term "thromboembolism", as used herein, refers to obstruction of a blood vessel with thrombotic material carried by the blood stream from the site of origin to plug another vessel. The term "stroke", as used herein, refers to embolic stroke or atherothrombotic stroke arising from occlusive thrombosis in the carotid communis, carotid interna, or intracerebral arteries.

The effectiveness of compounds of the present invention as inhibitors of the coagulation factors VIIa, IXa, Xa, XIa, plasma kallikrein or thrombin, can be determined using a relevant purified serine protease, respectively, and an appropriate synthetic substrate. The rate of hydrolysis of the chromogenic substrate by the relevant serine protease was measured both in the absence and presence of compounds of the present invention. Hydrolysis of the substrate resulted in the release of para-nitroaniline (pNA), which was monitored spectrophotometrically by measuring the increase in absorbance at 405 nM, or the release of aminomethylcoumarin (AMC), which was monitored spectrofluorometrically by measuring the increase in emission at 460 nM with excitation at 380 nM. A decrease in the rate of absorbance change at 405 nM in the presence of inhibitor is indicative of enzyme inhibition. Such methods are known to one skilled in the art. The results of this assay are expressed as inhibitory constant, $K_i$.

Factor VIIa determinations were made in 0.005 M calcium chloride, 0.15 M sodium chloride, 0.05 M HEPES buffer containing 0.5% PEG 8000 at a pH of 7.4. Determinations were made using purified human Factor VIIa (Haematologic Technologies) or recombinant human Factor VIIa (Novo Nordisk) at a final assay concentration of 2-5 nM, recombinant soluble tissue factor at a concentration of 18-35 nM and the synthetic substrate H-D-11e-Pro-Arg-pNA (S-2288; Chromogenix or BMPM-2; AnaSpec) at a concentration of 0.001 M. In general, preferred compounds of the present invention, such as the particular compounds disclosed in the above examples, have been identified to be active and exhibit $K_i$'s of equal to or less than 15 µM in the Factor VIIa assay, thereby demonstrating the utility of the compounds of the present invention as especially effective inhibitors of coagulation Factor VIIa, and thus, as inhibitors of the coagulation cascade and as anticoagulants for the prevention or treatment of thromboembolic disorders in mammals. More preferred compounds have $K_i$'s of equal to or less than 5 µM, preferably equal to or less than 1 µM, more preferably equal to or less than 0.5 µM, even more preferably equal to or less than 0.1 µM.

Factor IXa determinations were made in 0.005 M calcium chloride, 0.1 M sodium chloride, 0.05 M TRIS base and 0.5% PEG 8000 at a pH of 7.4. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Phe-Gly-Arg-AMC; CenterChem) at a concentration of 0.0004-0.0005 M. In general, compounds tested in the Factor IXa assay are considered to be active if they exhibit a $K_i$ of equal to or less than 15 µM.

Factor Xa determinations were made in 0.1 M sodium phosphate buffer at a pH of 7.4 containing 0.2 M sodium chloride and 0.5% PEG 8000. Determinations were made using purified human Factor Xa (Haematologic Technologies) at a final assay concentration of 150-1000 µM and the synthetic substrate S-2222 (Bz-Ile-Glu(gamma-OMe, 50%)-Gly-Arg-pNA; Chromogenix) at a concentration of 0.0002-0.0003 M. In general, compounds tested in the Factor Xa assay are considered to be active if they exhibit a $K_i$ of equal to or less than 15 µM.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 µM (Haematologic Technologies) and the synthetic substrate S-2366 (pyroGlu-Pro-Arg-pNA; Chromogenix) at a concentration of 0.0002-0.00025 M. In general, compounds tested in the Factor XIa assay are considered to be active if they exhibit a $K_i$ of equal to or less than 15 µM.

Plasma kallikrein determinations were made in 0.1 M sodium phosphate buffer at a pH of 7.4 containing 0.2 M sodium chloride and 0.5% PEG 8000. Determinations were made using purified human kallikrein (Enzyme Research Laboratories) at a final assay concentration of 200 µM and the synthetic substrate S-2302 (H-(D)-Pro-Phe-Arg-pNA; Chromogenix) at a concentration of 0.00008-0.0004 M. The Km value used for calculation of Ki was 0.00005 to 0.00007 M. In general, compounds tested in the plasma kallikrein assay are considered to be active if they exhibit a $K_i$ of equal to or less than 15 µM.

Thrombin determinations were made in 0.1 M sodium phosphate buffer at a pH of 7.4 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; Chromogenix) at a concentration of 0.0002 M. In general, compounds tested in the thrombin assay are considered to be active if they exhibit a $K_i$ of equal to or less than 15 µM.

The selectivity of a compound may be evaluated by taking the ratio of the $K_i$ value for a given protease with the $K_i$ value for the protease of interest (i.e., selectivity for FVIIa versus protease P=$K_i$ for protease P/$K_i$ for FVIIa). Compounds with selectivity ratios >20 are considered selective. Compounds with selectivity ratios >100 are preferred, and compounds with selectivity ratios >500 are more preferred.

The Michaelis constant, $K_m$, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance change vs time) were measured. The following relationship was used to calculate $K_i$ values:

$(v_o-v_s)/v_s = I/(K_i(1+S/K_m))$ for a competitive inhibitor with one binding site; or $v_s/v_o = A+((B-A)/1+((IC_{50}/(I)^n)))$ and $K_i = IC_{50}/(1+S/K_m)$ for a competitive inhibitor where:
$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme: inhibitor complex;
S is the concentration of substrate; and
$K_m$ is the Michaelis constant for the substrate.

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

In Vivo Electrically-Induced Carotid Artery Thrombosis (ECAT) Model:

The rabbit ECAT model, described by Wong et al. (*J Pharmacol Exp Ther* 2000, 295, 212-218), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to the initiation of thrombosis. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

In Vivo Rabbit Arterio-venous (AV) Shunt Thrombosis Model:

The rabbit AV shunt model, described by Wong et al. (Wong, P. C. et al. *J Pharmacol Exp Ther* 2000, 292, 351-357), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by a nonlinear least square regression program using the Hill sigmoid $E_{max}$ equation (DeltaGraph; SPSS Inc., Chicago, Ill.).

The compounds of the present invention can be administered alone or in combination with one or more additional therapeutic agents. These other agents include, but are not limited to, other anticoagulant or coagulation inhibitory agents, anti-platelet or platelet inhibitory agents, or thrombolytic or fibrinolytic agents.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Other anticoagulant agents (or coagulation inhibitory agents) that may be used in combination with the compounds of this invention include warfarin, heparin (either unfractionated heparin or any commercially available low molecular weight heparin, for example LOVANOX™), synthetic pentasaccharide, direct acting thrombin inhibitors including hirudin and argatroban, as well as other factor VIIa inhibitors, factor IXa inhibitors, factor Xa inhibitors (e.g., Arixtra™, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granular-content secretion of platelets. Such agents include, but are not limited to, the various known non-steroidal anti-inflammatory drugs (NSAIDS) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDS, aspirin (acetylsalicylic acid or ASA), and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR1) antagonists (e.g., SCH-530348, SCH-203099, SCH-529153 and SCH-205831), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the puringergic receptors $P_2Y_1$ and $P_2Y_{12}$, with $P_2Y_{12}$ being even more preferred. Preferred $P_2Y_{12}$ receptor antagonists include ticlopidine and clopidogrel, prasugrel, and AZD-6140, and pharmaceutically acceptable salts or prodrugs thereof. Clopidogrel is an even more preferred agent. Ticlopidine and clopidogrel are also preferred compounds since they are known to be more gentle than aspirin on the gastrointestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K$^+$ channel openers such as $I_{Ach}$ inhibitors, and $I_{Kur}$ inhibitors (e.g., compounds such as those disclosed in WO01/40231).

Examples of suitable antihypertensive agents for use in combination with the compounds of the present invention include alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, spironolactone); renin inhibitors; angiotensin-converting enzyme (ACE) inhibitors (e.g., captopril, lisinopril, fosinopril, enalapril, ceranopril, cilazopril, delapril, pentopril, quinapril, ramipril, lisinopril), angiotensin AT-1 receptor antagonists (e.g., irbestatin, losartan, valsartan); ET-A receptor antagonists (e.g., sitaxsentan, atrsentan and compounds disclosed in U.S. Pat. Nos. 5,612,359 and 6,043,265); Dual ET-A/AT-1 antagonist (e.g., compounds disclosed in WO 00/01389); neutral endopeptidase (NEP) inhibitors; vasopepsidase inhibitors (dual ACE/NEP inhibitors, e.g., omapatrilat gemopatrilat, nitrates) and β-blockers (for example propanolol, nadolo, or carvedilol).

Examples of suitable cardiac glycosides for use in combination with the compounds of the present invention include digitalis and ouabain.

Examples of suitable mineralocorticoid receptor antagonists for use in combination with the compounds of the present invention include sprionolactone and eplirinone.

Examples of suitable anti-diabetic agents for use in combination with the compounds of the present invention include: biguamides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguamide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DPP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-obesity agents for use in combination with the compounds of the present invention include orlistat, aP2 inhibitors (such as those disclosed in WO00/59506), and cannabinoid receptor CB1 antagonists (e.g., rimonabant, AVE-1625, SR-147778, and CP-945598).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Cholesterol/lipid lowering agents for use in combination with the compounds of the present invention include HMG-CoA reductase inhibitors (lovastatin, simvastatin, pravastatin, fluvastatin, atorvsatatin, rosuvastatin, and other statins), sequestrants (cholestyramine and colestipol), nicotonic acid, fenofibric acid derivatives (gemfibrozil, clofibrat, fenofibrate and benzafibrate), and probucol.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of plasma kallikrein, thrombin, factor VIIa, IXa, Xa and/or XIa. Such compounds may be provided in a commercial kit, for example, for use in pharmaceutical research involving plasma kallikrein, thrombin, factor VIIa, IXa, Xa and/or XIa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving plasma kallikrein, thrombin, factor VIIa, IXa, Xa, and/or XIa. For example, the presence of plasma kallikrein, thrombin, factor VIIa, IXa, Xa and/or XIa in an unknown sample could be determined by addition of the relevant chromogenic substrate, for example, S2288 for factor VIIa, to a series of solutions containing test sample and optionally one of the compounds of the present invention. If production of pNA is observed in the solutions containing test sample, but not in the presence of a compound of the present invention, then one would conclude factor VIIa was present.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 0.1 to 20 mg/kg/day. Intravenously, the most preferred doses will range from about 0.1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolyic agent when administered alone may be reduced by about 70-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

What is claimed is:

1. A compound of Formula (I):

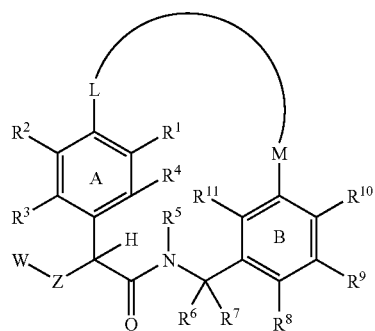

(I)

or a stereoisomer, a tautomer, or a pharmaceutically acceptable salt thereof, wherein:

ring A is phenyl;
ring B is phenyl;
for the definitions of M and L, as they are written from left to right, the atom connectivity is in the order (ring A)-L-M-(ring B);
M is —CONH—, —SO$_2$NH—, —NHCO—, or —NHSO$_2$—;
when M is —CONH—, L is selected from —C(R$^{12}$R$^{13}$)C(R$^{12}$R$^{13}$)—, —XC(R$^{12}$R$^{13}$)—, —C(R$^{12}$R$^{13}$)Y—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)XC(R$^{12}$R$^{13}$)—, —C(R$^{12}$R$^{13}$)C(R$^{12}$R$^{13}$)Y—, —XC(R$^{12}$R$^{13}$)Y—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)C(R$^{12}$R$^{13}$)—, —C(R$^{12}$R$^{13}$)XC(R$^{12}$R$^{13}$)—, —C(R$^{12}$R$^{13}$)C(R$^{12}$R$^{13}$)XC(R$^{12}$R$^{13}$)—, —C(R$^{12}$R$^{13}$)C(R$^{12}$R$^{13}$)C(R$^{12}$R$^{13}$)Y—, —XC(R$^{12}$R$^{13}$)C(R$^{12}$R$^{13}$)Y—, —XC(R$^{12}$R$^{13}$)XC(R$^{12}$R$^{13}$)—, and —C(R$^{12}$R$^{13}$)XC(R$^{12}$R$^{13}$)Y—;
when M is —SO$_2$NH—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)C(R$^{12}$R$^{13}$)—, —C(R$^{12}$R$^{13}$)XC(R$^{12}$R$^{13}$)C(R$^{12}$R$^{13}$)—, —C(R$^{12}$R$^{13}$)XC(R$^{12}$R$^{13}$)—, —C(R$^{12}$R$^{13}$)C(R$^{12}$R$^{13}$)Y—, —C(R$^{12}$R$^{13}$)C(R$^{12}$R$^{13}$)XC(R$^{12}$R$^{13}$)—, —C(R$^{12}$R$^{13}$)C(R$^{12}$R$^{13}$)C(R$^{12}$R$^{13}$)Y—, —XC(R$^{12}$R$^{13}$)C(R$^{12}$R$^{13}$)Y——XC(R$^{12}$R$^{13}$)XC(R$^{12}$R$^{13}$)—, and —C(R$^{12}$R$^{13}$)XC(R$^{12}$R$^{13}$)Y—;
when M is —NHCO—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)C(R$^{12}$R$^{13}$)—, —XC(R$^{12}$R$^{13}$)C(R$^{12}$R$^{13}$)C(R$^{12}$R$^{13}$)—, and —C(R$^{12}$R$^{13}$)XC(R$^{12}$R$^{13}$)C(R$^{12}$R$^{13}$)—;
when M is —NHSO$_2$—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)C(R$^{12}$R$^{13}$)—, and —C(R$^{12}$R$^{13}$)XC(R$^{12}$R$^{13}$)C(R$^{12}$R$^{13}$)—;
W is substituted with 0-2 R$^{14}$ and is selected from:

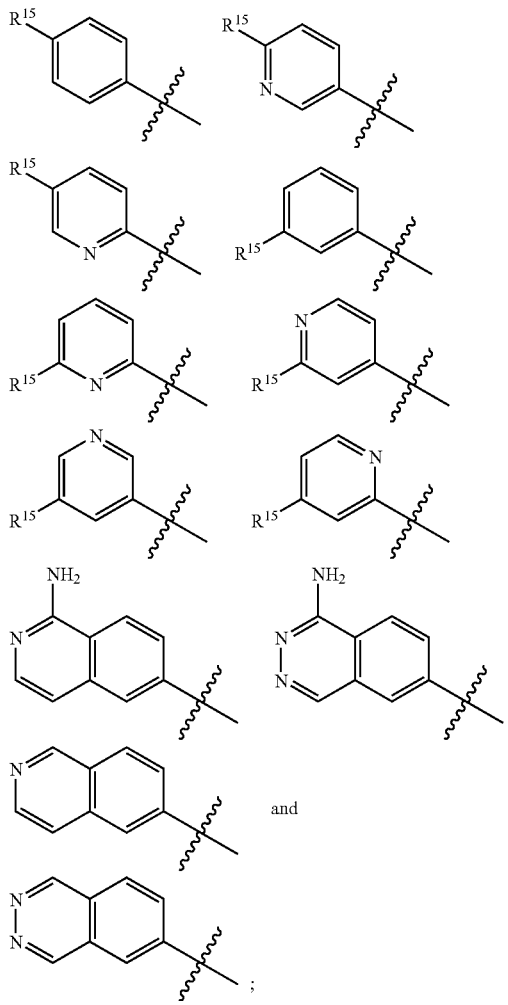

X is O, S(O)$_p$, or NR$^{16}$;
Y is O or NR$^{16a}$;
Z is NH, O or S;
R$^1$ is H, F, Cl, Br, I, C$_{1-4}$ alkyl substituted with 0-1 OH, C$_{1-4}$ fluoroalkyl, C$_{2-4}$ alkenyl, C$_{2-4}$ alkynyl, C$_{1-4}$ alkoxy, C$_{1-4}$ alkylthio, or C$_{3-6}$ cycloalkyl;
R$^2$ is H, F, Cl, Br, I, —(CH$_2$)$_s$OR$^a$, —(CH$_2$)$_s$SR$^b$, —(CH$_2$)$_s$CF$_3$, —(CH$_2$)$_s$OCF$_3$, —(CH$_2$)$_s$OCHF$_2$, —(CH$_2$)$_s$OCH$_2$F, —(CH$_2$)$_s$CN, —(CH$_2$)$_s$NO$_2$, —(CH$_2$)$_s$NR$^c$R$^d$, —(CH$_2$)$_s$C(O)R$^a$, —(CH$_2$)$_s$CO$_2$R$^a$, —(CH$_2$)$_s$NR$^c$C(O) R$^a$, —(CH$_2$)$_s$C(O)NR$^c$R$^d$, —(CH$_2$)$_s$NR$^c$C(O)OR$^b$, —(CH$_2$)$_s$OC(O)OR$^b$, —(CH$_2$)$_s$NR$^c$C(O)NR$^c$R$^d$, —(CH$_2$)$_s$OC(O)NR$^c$R$^d$, —(CH$_2$)$_s$SO$_2$NR$^c$R$^d$, —(CH$_2$)$_s$NR$^c$SO$_2$NR$^c$R$^d$, —(CH$_2$)$_s$NR$^c$SO$_2$R$^b$, —(CH$_2$)$_s$NR$^c$SO$_2$CF$_3$, —(CH$_2$)$_s$SO$_2$CF$_3$, —(CH$_2$)$_s$S(O)$_2$R$^b$, C$_{1-6}$ alkyl substituted with 0-2 R$^e$, C$_{1-4}$ fluoroalkyl, C$_{2-4}$ alkenyl substituted with 0-2 R$^e$, C$_{2-4}$ alkynyl substituted with 0-2 R$^e$, —(CH$_2$)$_s$C$_{3-6}$ carbocycle substituted with 0-2 R$^f$, —(CH$_2$)$_s$-(5- to 6-membered heterocycle), —(CH$_2$)$_s$—NR$^c$(5- to 6-membered heterocycle), or —(CH$_2$)$_s$—O-(5- to 6-membered heterocycle); wherein said heterocycle comprises carbon atoms and 1-3 heteroatoms selected from N, NR$^c$, O, and S(O)$_p$ and is substituted with 0-2 R$^g$;

R$^3$ is H, F, Cl, Br, I, —(CH$_2$)$_s$OR$^a$, —(CH$_2$)$_s$SR$^b$, —(CH$_2$)$_s$CF$_3$, —(CH$_2$)$_s$OCF$_3$, —(CH$_2$)$_s$OCHF$_2$, —(CH$_2$)$_s$OCH$_2$F, —(CH$_2$)$_s$CN, —(CH$_2$)$_s$NO$_2$, —(CH$_2$)$_s$NR$^c$R$^d$, —(CH$_2$)$_s$C(O)R$^a$, —(CH$_2$)$_s$CO$_2$R$^a$, —(CH$_2$)$_s$NR$^c$C(O)R$^a$, —(CH$_2$)$_s$C(O)NR$^c$R$^d$, —(CH$_2$)$_s$NR$^c$C(O)OR$^b$, —(CH$_2$)$_s$OC(O)OR$^b$, —(CH$_2$)$_s$NR$^c$C(O)NR$^c$R$^d$, —(CH$_2$)$_s$OC(O)NR$^c$R$^d$, —(CH$_2$)$_s$SO$_2$NR$^c$R$^d$, —(CH$_2$)$_s$NR$^c$SO$_2$NR$^c$R$^d$, —(CH$_2$)$_s$NR$^c$SO$_2$R$^b$, —(CH$_2$)$_s$NR$^c$SO$_2$CF$_3$, —(CH$_2$)$_s$SO$_2$CF$_3$, —(CH$_2$)$_s$S(O)$_2$R$^b$, —O(CH$_2$)$_n$CO$_2$R$^a$, —(CH$_2$)$_s$SO$_2$NHCOR$^b$, —(CH$_2$)$_s$CONHSO$_2$R$^b$, C$_{1-6}$ alkyl substituted with 0-2 R$^e$, C$_{1-4}$ fluoroalkyl, C$_{2-4}$ alkenyl substituted with 0-2 R$^e$, C$_{2-4}$ alkynyl substituted with 0-2 R$^e$, —O(benzyl substituted with CO$_2$R$^a$), —(CH$_2$)$_s$tetrazolyl, —(CH$_2$)$_s$—C$_{3-6}$ carbocycle substituted with 0-2 R$^{f1}$, —(CH$_2$)$_s$-(5- to 6-membered heterocycle), —(CH$_2$)$_s$—NR$^c$-(5- to 6-membered heterocycle), or —(CH$_2$)$_s$—O-(5- to 6-membered heterocycle); wherein said heterocycle comprises carbon atoms and 1-3 heteroatoms selected from N, NR$^c$, O, and S(O)$_p$ and is substituted with 0-2 R$^{g1}$;

R$^4$ is H, F, Cl, Br, I, or C$_{1-4}$ alkyl;

R$^5$ is H, C$_{1-4}$ alkyl, —CH$_2$CO$_2$R$^a$, —CH$_2$C(O)NR$^c$R$^d$, —CH$_2$CH$_2$CO$_2$R$^a$, —CH$_2$CH$_2$C(O)NR$^c$R$^d$, —CH$_2$CH$_2$OR$^a$, or —CH$_2$CH$_2$OR$^a$;

R$^6$ is H, —CH$_2$OR$^a$, —CH$_2$CH$_2$OR$^a$, CN, C$_{1-4}$ alkyl, —CO$_2$R$^a$, —C(O)NR$^c$R$^d$, —CH$_2$CO$_2$R$^a$, or —CH$_2$C(O)NR$^c$R$^d$;

R$^7$ is H or C$_{1-6}$ alkyl;

R$^8$ is H, F, Cl, Br, CN, CH$_2$F, CHF$_2$, —(CH$_2$)$_s$CF$_3$, —(CH$_2$)$_s$OCF$_3$, —(CH$_2$)$_s$SCF$_3$, —(CH$_2$)$_s$OCHF$_2$, —(CH$_2$)$_s$OCH$_2$F, —(CH$_2$)$_s$CN, —(CH$_2$)$_s$NO$_2$, C$_{1-6}$ alkyl, C$_{2-6}$ alkenyl, C$_{2-6}$ alkynyl, —(CH$_2$)$_n$—OR$^a$, —(CH$_2$)$_n$—SR$^b$, —(CH$_2$)$_n$—NR$^c$R$^d$, —(CH$_2$)$_s$C(O)R$^a$, —(CH$_2$)$_s$CO$_2$R$^a$, —(CH$_2$)$_s$NR$^c$C(O)R$^a$, —(CH$_2$)$_s$CONR$^c$R$^d$, —(CH$_2$)$_s$SO$_2$R$^b$, —(CH$_2$)$_s$SO$_2$NR$^c$R$^d$, —(CH$_2$)$_s$NR$^c$C(O)OR$^b$, —(CH$_2$)$_s$OC(O)OR$^b$, —(CH$_2$)$_s$NR$^c$C(O)NR$^c$R$^d$, —(CH$_2$)$_s$OC(O)NR$^c$R$^d$, —(CH$_2$)$_s$NR$^c$SO$_2$NR$^c$R$^d$, —(CH$_2$)$_s$NR$^c$SO$_2$R$^b$, —(CH$_2$)$_s$NR$^c$SO$_2$CF$_3$, —(CH$_2$)$_s$SO$_2$CF$_3$, —O(CH$_2$)$_n$CO$_2$R$^a$, —(CH$_2$)$_s$SO$_2$NHCOR$^b$, —(CH$_2$)$_s$CONHSO$_2$R$^b$, —O(benzyl substituted with CO$_2$R$^a$), —(CH$_2$)$_s$tetrazolyl, C$_{1-6}$ alkyl substituted with 0-2 R$^e$, C$_{1-4}$ fluoroalkyl, C$_{2-4}$ alkenyl substituted with 0-2 R$^e$, C$_{2-4}$ alkynyl substituted with 0-2 R$^e$, —(CH$_2$)$_s$—C$_{3-6}$ carbocycle substituted with 0-2 R$^{f1}$, or —(CH$_2$)$_n$-5- to 10-membered heterocycle comprising: carbon atoms and 1-4 heteroatoms selected from N, NR$^c$, O, and S(O)$_p$, wherein said phenyl and heterocycle are substituted with 0-3 R$^{g1}$;

R$^9$, R$^{10}$, and R$^{11}$ are, independently at each occurrence, H, F, Cl, Br, I, C$_{1-4}$ alkyl, or C$_{1-4}$ alkoxy;

R$^{12}$ and R$^{13}$ are, independently at each occurrence, H, F, Cl, OR$^a$, SR$^b$, CF$_3$, OCF$_3$, OCHF$_2$, OCH$_2$F, CN, NO$_2$, —NR$^c$R$^d$, —C(O)R$^a$, —CO$_2$R$^a$, —NR$^c$C(O)R$^a$, —C(O)NR$^c$R$^d$, —NR$^c$C(O)OR$^b$, —NR$^c$C(O)NR$^c$R$^d$, —OC(O)NR$^c$R$^d$, —OC(O)OR$^a$, —SO$_2$NR$^c$R$^d$, —NR$^c$SO$_2$NR$^c$R$^d$, —NR$^c$SO$_2$R$^b$, —NR$^c$SO$_2$CF$_3$, —SO$_2$CF$_3$, —S(O)$_2$R$^b$, or C$_{1-6}$ alkyl substituted with 0-2 R$^e$;

alternately, two R$^{12}$ or R$^{13}$ on the same carbon atom can be replaced with oxo;

optionally, two R$^{12}$ or R$^{13}$ on adjacent carbon atoms in L may be replaced with a double or triple bond between the two carbon atoms;

R$^{14}$ is, independently at each occurrence, CN, F, Cl, Br, I, OH, N(R$^{17}$R$^{17}$), C$_{1-3}$ alkyl, or C$_{1-3}$ alkoxy;

R$^{15}$ is, independently at each occurrence, H, —C(=NH)NH$_2$, N(R$^{17}$R$^{17}$), —C(R$^{17}$R$^{17}$)N(R$^{17}$R$^{17}$), —CON(R$^{17}$R$^{17}$), CN, F, Cl, Br, I, OH, C$_{1-3}$ alkyl, or C$_{1-3}$ alkoxy;

R$^{16}$ is, independently at each occurrence, H or C$_{1-6}$ alkyl;

R$^{16a}$ is, independently at each occurrence, H or C$_{1-6}$ alkyl;

R$^{17}$ is, independently at each occurrence, H or Me;

R$^a$ is, independently at each occurrence, H, C$_{1-4}$ alkyl, C$_{3-6}$ cycloalkyl, phenyl, or benzyl; wherein said alkyl and cycloalkyl are optionally substituted with 0-2 R$^e$, and said phenyl and benzyl are optionally substituted with 0-2 R$^f$;

R$^b$ is, independently at each occurrence, C$_{1-4}$ alkyl, C$_{3-6}$ cycloalkyl, phenyl, or benzyl; wherein said alkyl and cycloalkyl are optionally substituted with 0-2 R$^e$, and said phenyl and benzyl are optionally substituted with 0-2 R$^f$;

R$^c$ and R$^d$ are, independently at each occurrence, H, C$_{1-4}$ alkyl, C$_{3-6}$ cycloalkyl, phenyl, or benzyl;

R$^e$ is, independently at each occurrence, F, CF$_3$, OH, or C$_{1-3}$ alkoxy;

R$^f$ is, independently at each occurrence, F, Cl, Br, CF$_3$, OH, C$_{1-3}$ alkyl, or C$_{1-3}$ alkoxy;

R$^{f1}$ is, independently at each occurrence, R$^f$, —CO$_2$R$^a$, —C(O)NR$^c$R$^d$, —CONHSO$_2$R$^b$, or —CH$_2$CONHSO$_2$R$^b$;

R$^g$ is, independently at each occurrence, =O, F, Cl, Br, CF$_3$, OH, C$_{1-3}$ alkyl, or C$_{1-3}$ alkoxy;

R$^{g1}$ is, independently at each occurrence, R$^g$, —CO$_2$R$^a$, —C(O)NR$^c$R$^d$, —CONHSO$_2$R$^b$, or —CH$_2$CONHSO$_2$R$^b$;

n, at each occurrence, is selected from 0, 1, 2, 3, and 4;

p, at each occurrence, is selected from 0, 1, and 2;

q, at each occurrence is selected from 2 or 3;

r, at each occurrence is selected from 1, 2, or 3; and s, at each occurrence, is selected from 0, 1, and 2.

2. A compound according to claim 1, wherein the compound is of Formula (I), a stereoisomer, a tautomer, or a pharmaceutically acceptable salt thereof, wherein:

M is —CONH—, —SO$_2$NH—, —NHCO—, or —NHSO$_2$—;

when M is —CONH—, L is selected from —C(R$^{12}$R$^{13}$)C(R$^{12}$R$^{13}$)—, —XC(R$^{12}$R$^{13}$)—, —C(R$^{12}$R$^{13}$)Y—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)XC(R$^{12}$R$^{13}$)—, —C(R$^{12}$R$^{13}$)C(R$^{12}$R$^{13}$)Y—, —XC(R$^{12}$R$^{13}$)Y—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)C(R$^{12}$R$^{13}$)—, —C(R$^{12}$R$^{13}$)XC(R$^{12}$R$^{13}$)C(R$^{12}$R$^{13}$)—, —C(R$^{12}$R$^{13}$)C(R$^{12}$R$^{13}$)XC(R$^{12}$R$^{13}$)—, —C(R$^{12}$R$^{13}$)C(R$^{12}$R$^{13}$)C(R$^{12}$R$^{13}$)Y—, and —XC(R$^{12}$R$^{13}$)C(R$^{12}$R$^{13}$)Y—;

when M is —SO$_2$NH—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)C(R$^{12}$R$^{13}$)C(R$^{12}$R$^{13}$)C(R$^{12}$R$^{13}$)—, —XC(R$^{12}$R$^{13}$)C(R$^{12}$R$^{13}$)C(R$^{12}$R$^{13}$)—, and —C(R$^{12}$R$^{13}$)XC(R$^{12}$R$^{13}$)C(R$^{12}$R$^{13}$)—;

when M is —NHCO—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)C(R$^{12}$R$^{13}$)C(R$^{12}$R$^{13}$)C(R$^{12}$R$^{13}$)—, —XC(R$^{12}$R$^{13}$)C(R$^{12}$R$^{13}$)C(R$^{12}$R$^{13}$)—, and —C(R$^{12}$R$^{13}$)XC(R$^{12}$R$^{13}$)C(R$^{12}$R$^{13}$)—;

when M is —NHSO$_2$—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)C(R$^{12}$R$^{13}$)C(R$^{12}$R$^{13}$)C(R$^{12}$R$^{13}$)—, —XC(R$^{12}$R$^{13}$)C(R$^{12}$R$^{13}$)C(R$^{12}$R$^{13}$)—, and —C(R$^{12}$R$^{13}$)XC(R$^{12}$R$^{13}$)C(R$^{12}$R$^{13}$)—;

X is O, S, or NR$^{16}$;

Z is NH or O;

R$^2$ is H, F, Cl, Br, I, OR$^a$, SR$^b$, CF$_3$, OCF$_3$, OCHF$_2$, OCH$_2$F, CN, NO$_2$, —NR$^c$R$^d$, —C(O)R$^a$, —CO$_2$R$^a$, —NR$^c$C(O)R$^a$, —C(O)NR$^c$R$^d$, —NR$^c$C(O)OR$^b$, —NR$^c$C(O)NR$^c$R$^d$, —OC(O)NR$^c$R$^d$, —SO$_2$NR$^c$R$^d$, —NR$^c$SO$_2$NR$^c$R$^d$, —NR$^c$SO$_2$R$^b$, —NR$^c$SO$_2$CF$_3$, —SO$_2$CF$_3$, —S(O)$_2$R$^b$, C$_{1-6}$ alkyl substituted with 0-2 R$^e$, C$_{2-4}$ alkenyl substituted with 0-2 R$^e$, C$_{2-4}$ alkynyl substituted with 0-2 R$^e$, C$_{3-6}$ carbocycle substituted with 0-2 R$^f$, —(CH$_2$)$_s$-(5- to 6-membered heterocycle), —NR$^c$-(5- to 6-membered heterocycle), or —O-(5- to 6-membered heterocycle); wherein said heterocycle comprises carbon atoms and 1-3 heteroatoms selected from N, NR$^c$, O, and S(O)$_p$ and is substituted with 0-2 R$^g$;

R$^3$ is H, F, Cl, Br, I, OR$^a$, SR$^b$, CF$_3$, OCF$_3$, OCHF$_2$, OCH$_2$F, CN, NO$_2$, —NR$^c$R$^d$, —C(O)R$^a$, —CO$_2$R$^a$, —NR$^c$C(O)R$^a$, —C(O)NR$^c$R$^d$, —NR$^c$C(O)OR$^b$, —NR$^c$C(O)NR$^c$R$^d$, —OC(O)NR$^c$R$^d$, —SO$_2$NR$^c$R$^d$, —NR$^c$SO$_2$NR$^c$R$^d$, —NR$^c$SO$_2$R$^b$, —NR$^c$SO$_2$CF$_3$, —SO$_2$CF$_3$, —S(O)$_2$R$^b$, —O(CH$_2$)$_n$CO$_2$R$^a$, —SO$_2$NHCOR$^b$, —CONHSO$_2$R$^b$, C$_{1-6}$ alkyl substituted with 0-2 R$^e$, C$_{2-4}$ alkenyl substituted with 0-2 R$^e$, C$_{2-4}$ alkynyl substituted with 0-2 R$^e$, —O(benzyl substituted with CO$_2$R$^a$), or tetrazolyl;

R$^8$ is, H, F, Cl, Br, CN, CH$_2$F, CHF$_2$, CF$_3$, OCF$_3$, SCF$_3$, NO$_2$, C$_{1-6}$ alkyl, C$_{2-6}$ alkenyl, C$_{2-6}$ alkynyl, —(CH$_2$)$_n$—OR$^a$, —(CH$_2$)$_n$—SR$^b$, —(CH$_2$)$_n$—NR$^c$R$^d$, —CONR$^c$R$^d$, —SO$_2$R$^b$, —SO$_2$NR$^c$R$^d$, —(CH$_2$)$_n$-phenyl, or —(CH$_2$)$_n$-5- to 10-membered heterocycle comprising: carbon atoms and 1-4 heteroatoms selected from N, O, and S(O)$_p$, wherein said phenyl and heterocycle are substituted with 0-3 R$^g$;

R$^9$ is H, F, Cl, Br, I, C$_{1-4}$ alkyl, or C$_{1-4}$ alkoxy; and

R$^{10}$ and R$^{11}$ are, independently at each occurrence, H, F, Cl, Br, I, or C$_{1-4}$ alikyl.

3. A compound according to claim 1, wherein the compound is of Formula (I), a stereoisomer, a tautomer, or a pharmaceutically acceptable salt thereof wherein:

M is —CONH—, —SO$_2$NH—, —NHCO—, or —NHSO$_2$—;

when M is —CONH—, L is selected from —C(R$^{12}$R$^{13}$)C(R$^{12}$R$^{13}$)—, —XC(R$^{12}$R$^{13}$)—, —C(R$^{12}$R$^{13}$)Y—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)XC(R$^{12}$R$^{13}$)—, XC(R$^{12}$R$^{13}$)Y—, and —C(R$^{12}$R$^{13}$)C(R$^{12}$R$^{13}$)Y—;

when M is —SO$_2$NH—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)C(R$^{12}$R$^{13}$)C(R$^{12}$R$^{13}$)C(R$^{12}$R$^{13}$)—, —XC(R$^{12}$R$^{13}$)C(R$^{12}$R$^{13}$)C(R$^{12}$R$^{13}$)—, and —C(R$^{12}$R$^{13}$)XC(R$^{12}$R$^{13}$)C(R$^{12}$R$^{13}$)—;

when M is —NHCO—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)C(R$^{12}$R$^{13}$)C(R$^{12}$R$^{13}$)C(R$^{12}$R$^{13}$)—, —XC(R$^{12}$R$^{13}$)C(R$^{12}$R$^{13}$)C(R$^{12}$R$^{13}$)—, and —C(R$^{12}$R$^{13}$)XC(R$^{12}$R$^{13}$)C(R$^{12}$R$^{13}$)—;

when M is —NHSO$_2$—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, —XC(R$^{12}$R$^{13}$)C(R$^{12}$R$^{13}$)—, —C(R$^{12}$R$^{13}$)C(R$^{12}$R$^{13}$)C(R$^{12}$R$^{13}$)C(R$^{12}$R$^{13}$)—, —XC(R$^{12}$R$^{13}$)C(R$^{12}$R$^{13}$)C(R$^{12}$R$^{13}$)—, and —C(R$^{12}$R$^{13}$)XC(R$^{12}$R$^{13}$)C(R$^{12}$R$^{13}$)—;

Z is NH or O;

R$^4$ is H or F;

R$^{10}$ and R$^{11}$ are H; and

R$^{15}$ is, independently at each occurrence, —C(=NH)NH$_2$, N(R$^{17}$R$^{17}$), —C(R$^{17}$R$^{17}$)N(R$^{17}$R$^{17}$), —CON(R$^{17}$R$^{17}$), or OH.

4. A compound according to claim 1, wherein the compound is of Formula (I), or a stereoisomer, a tautomer, or a pharmaceutically acceptable salt thereof, wherein:

ring A is phenyl;

ring B is phenyl;

M is —CONH— or —NHSO$_2$—;

when M is —CONH—, L is selected from —C(R$^{12}$R$^{13}$)C(R$^{12}$R$^{13}$)—, —XC(R$^{12}$R$^{13}$)—, —C(R$^{12}$R$^{13}$)Y—, —C(R$^{12}$R$^{13}$)C(R$^{12}$R$^{13}$)C(R$^{12}$R$^{13}$)—, —C(R$^{12}$R$^{13}$)XC(R$^{12}$R$^{13}$)—, and —C(R$^{12}$R$^{13}$)C(R$^{12}$R$^{13}$)Y—;

when M is —NHSO$_2$—, L is selected from —C(R$^{12}$R$^{13}$)C(R$^{12}$R$^{13}$)—, —C(R$^{12}$R$^{13}$)C(R$^{12}$R$^{13}$)C(R$^{12}$R$^{13}$)—, and —XC(R$^{12}$R$^{13}$)C(R$^{12}$R$^{13}$)—;

W is substituted with 0-2 R$^{14}$ and is selected from:

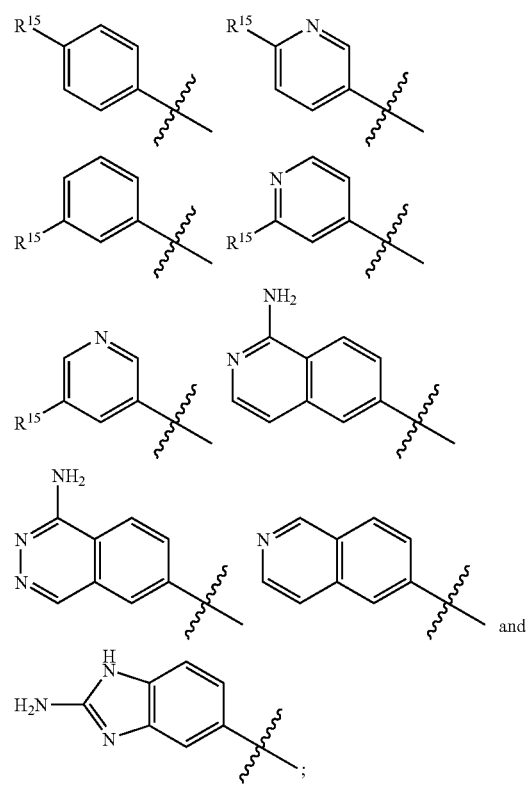

Z is NH;

R$^1$ is H, Cl, Br, methyl, ethyl, 1-hydroxyethyl, propyl, isopropyl, vinyl, allyl, 2-propenyl, ethynyl, 1-propynyl, methoxy, ethoxy, cyclopropyl, cyclobutyl, or cyclopentyl;

R$^4$ is H;

R$^5$ is H, C$_{1-4}$ alkyl, —CH$_2$CO$_2$R$^a$, —CH$_2$C(O)NR$^c$R$^d$, —CH$_2$CH$_2$CO$_2$R$^a$, —CH$_2$CH$_2$C(O)NR$^c$R$^d$, —CH$_2$CH$_2$OR$^a$, or —CH$_2$CH$_2$CH$_2$OR$^a$;

R$^6$ is H, —CH$_2$OR$^a$, —CH$_2$CH$_2$OR$^a$, CN, C$_{1-4}$ alkyl, —CO$_2$R$^a$, —C(O)NR$^c$R$^d$, —CH$_2$CO$_2$R$^a$, or —CH$_2$C(O)NR$^c$R$^d$;

R$^7$ is H;

$R^{10}$ and $R^{11}$ are H; and
$R^{15}$ is, independently at each occurrence, —C(=NH)NH$_2$, N($R^{17}R^{17}$), —C($R^{17}R^{17}$)N($R^{17}R^{17}$), or —CONH$_2$.

5. A compound according to claim 1, wherein the compound is of Formula (I), or a stereoisomer, a tautomer, or a pharmaceutically acceptable salt thereof, wherein:
ring A is phenyl;
ring B is phenyl;
M is —CONH—;
L is selected from —C($R^{12}R^{13}$)C($R^{12}R^{13}$)—, —XC($R^{12}R^{13}$)—, —C($R^{12}R^{13}$)Y—, —C($R^{12}R^{13}$)C($R^{12}R^{13}$)C($R^{12}R^{13}$)—, —C($R^{12}R^{13}$)XC($R^{12}R^{13}$)—, and —C($R^{12}R^{13}$)C($R^{12}R^{13}$)Y—;
W is substituted with 0-2 $R^{14}$ and is selected from:

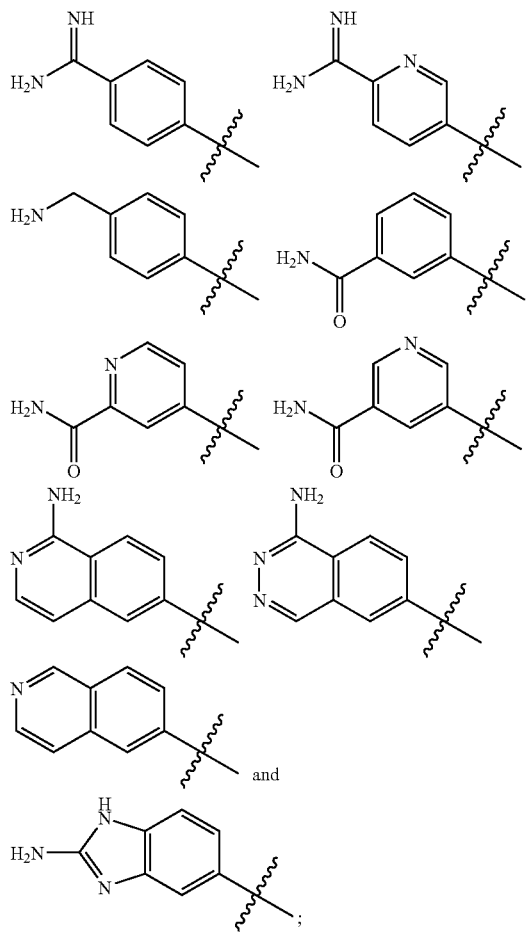

Z is NH;
$R^1$ is H, Cl, Br, methyl, ethyl, vinyl, 2-propenyl, allyl, ethynyl, 1-propynyl, methoxy, ethoxy, or cyclopropyl;
$R^4$ is H;
$R^5$ is H, $C_{1-4}$ alkyl, —CH$_2$CO$_2R^a$, —CH$_2$C(O)NR$^c$R$^d$, —CH$_2$CH$_2$CO$_2R^a$, —CH$_2$CH$_2$C(O)NR$^c$R$^d$, —CH$_2$CH$_2$OR$^a$, or —CH$_2$CH$_2$CH$_2$OR$^a$;
$R^6$ is H, —CH$_2$OR$^a$, —CH$_2$CH$_2$OR$^a$, CN, $C_{1-4}$ alkyl, —CO$_2R^a$, —C(O)NR$^c$R$^d$, —CH$_2$CO$_2R^a$, or —CH$_2$C(O)NR$^c$R$^d$;
$R^7$ is H;
$R^8$ is H, $C_{1-6}$ alkyl, OR$^a$, —CONR$^c$R$^d$, —SO$_2R^b$, —SO$_2$NR$^c$R$^d$, phenyl, or 5- to 6-membered heterocycle comprising: carbon atoms and 1-3 heteroatoms selected from N, O, and S(O)$_p$, wherein said phenyl and heterocycle are substituted with 0-3 R$^g$;

$R^9$, $R^{10}$, and $R^{11}$ are H; and
$R^{14}$ is, independently at each occurrence, F, Cl, methyl, ethyl, hydroxyl, or methoxy.

6. A compound according to claim 1, wherein the compound is of Formula (I), or a stereoisomer, a tautomer, or a pharmaceutically acceptable salt thereof, wherein:
ring A is phenyl;
ring B is phenyl;
M is —CONH—;
L is selected from —C($R^{12}R^{13}$)C($R^{12}R^{13}$)C($R^{12}R^{13}$)—, —C($R^{12}R^{13}$)NR$^{16}$C($R^{12}R^{13}$)—, —C($R^{12}R^{13}$)C($R^{12}R^{13}$)Y—, C($R^{12}R^{13}$)C($R^{12}R^{13}$)—, —OC($R^{12}R^{13}$)—, or —C($R^{12}R^{13}$)Y—;
W is selected from:

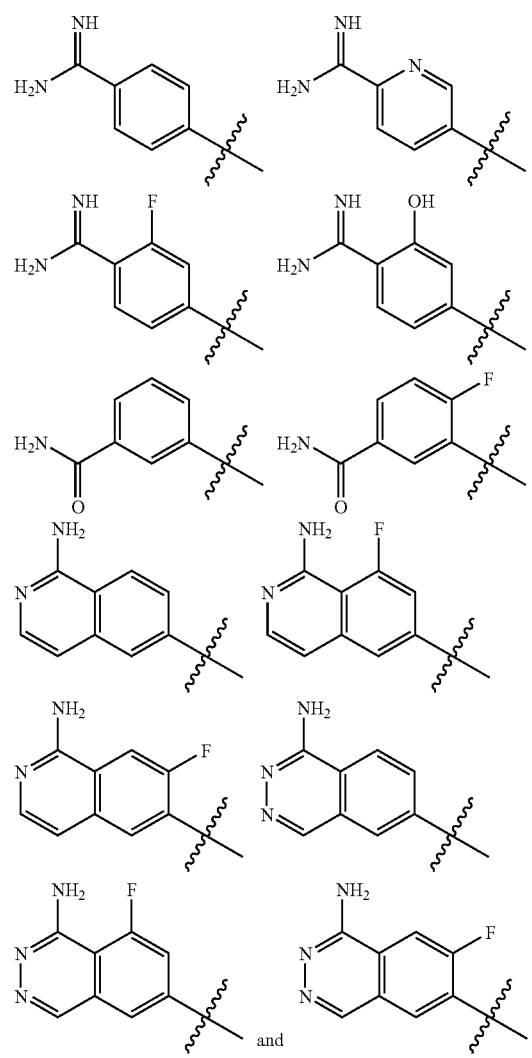

Y is O or NMe,
Z is NH;
$R^1$ is H, Cl, Br, methyl, ethyl, vinyl, 2-propenyl, ethynyl, methoxy, or ethoxy;
$R^2$ is H, F, Cl, Br, —OR$^a$, —SR$^b$, —CF$_3$, —OCF$_3$, —OCHF$_2$, —OCH$_2$F, CN, NO$_2$, —NR$^c$R$^d$, —C(O)R$^a$, —CO$_2R^a$, —NR$^c$C(O)R$^a$, —C(O)NR$^c$R$^d$, —NR$^c$C(O)OR$^b$, —OC(O)OR$^b$, —NR$^c$C(O)NR$^c$R$^d$, —OC(O)NR$^c$R$^d$, —SO$_2R^b$, —NR$^c$SO$_2$NR$^c$R$^d$, —NR$^c$SO$_2R^b$, —S(O)$_2R^b$, $C_{1-6}$ alkyl substituted with 0-2 R$^e$, $C_{1-4}$ fluoroalkyl, $C_{2-4}$ alkenyl substituted with 0-2 R$^e$, C$_{2-4}$ alkynyl substituted with 0-2 R$^e$, —C$_{3-6}$ carbocycle substituted with 0-2 R$^f$, -(5- to 6-membered heterocycle), —NR$^c$-(5- to 6-membered heterocycle), or —O-(5- to 6-membered heterocycle); wherein said heterocycle comprises carbon atoms and 1-3 heteroatoms selected from N, NR$^c$, O, and S(O)$_p$ and is substituted with 0-2 R$^g$;

R$^3$ is H, F, Cl, Me, OCH$_2$CO$_2$H;

R$^4$ is H;

R$^5$ is H, C$_{1-4}$ alkyl, —CH$_2$CO$_2$R$^a$, or —CH$_2$C(O)NR$^c$R$^d$;

R$^6$ is H, C$_{1-4}$ alkyl, —CO$_2$R$^a$, —C(O)NR$^c$R$^d$, —CH$_2$CO$_2$R$^a$, or —CH$_2$C(O)NR$^c$R$^d$;

R$^7$ is H;

R$^8$ is —CONR$^c$R$^d$, —SO$_2$R$^b$, —SO$_2$NR$^c$R$^d$, or 4-morpholino;

R$^9$, R$^{10}$, and R$^{11}$ are H;

R$^{12}$ and R$^{13}$ are, independently at each occurrence, H, methyl, ethyl, propyl, isopropyl, cyclopropyl, t-butyl, methoxy, ethoxy, propoxy, isopropoxy, or cyclopropoxy, with the proviso that no more than two of R$^{12}$ and R$^{13}$ in L are other than H; and R$^{16}$ is H, C$_{1-4}$ alkyl, —C(O)R$^a$, —C(O)NR$^c$R$^d$, —C(O)OR$^b$, or —S(O)$_2$R$^b$.

7. A compound according to claim 6, wherein the compound is of Formula (I), or a stereoisomer, a tautomer, or a pharmaceutically acceptable salt thereof, wherein:

M is —CONH—;

L is selected from —C(R$^{12}$R$^{13}$)C(R$^{12}$R$^{13}$)CH$_2$—, —C(R$^{12}$R$^{13}$)C(R$^{12}$R$^{13}$)O—, —C(R$^{12}$R$^{13}$)C(R$^{12}$R$^{13}$)NMe-, —C(R$^{12}$R$^{13}$)N(C=OCH$_3$)CH$_2$—, —C(R$^{12}$R$^{13}$)NHCH$_2$—, —C(R$^{12}$R$^{13}$)CH$_2$—, and —OCH$_2$—;

W is selected from:

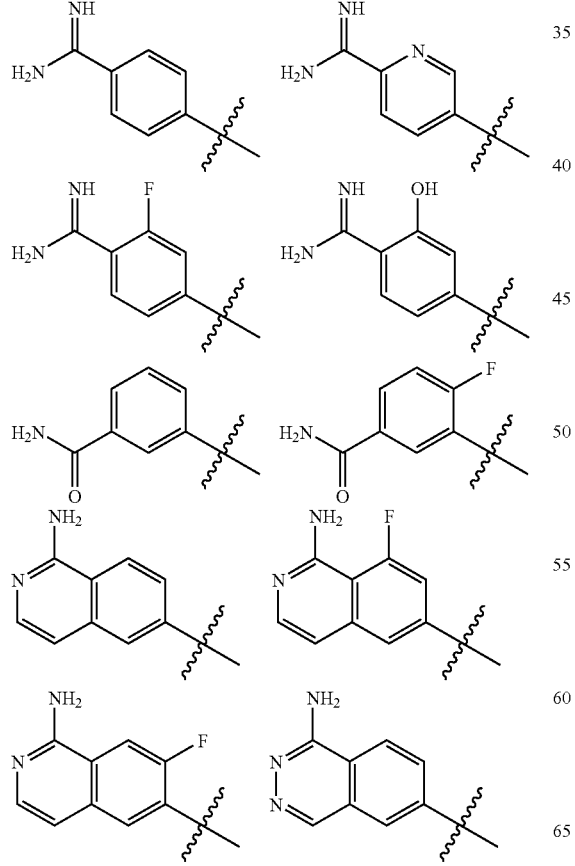

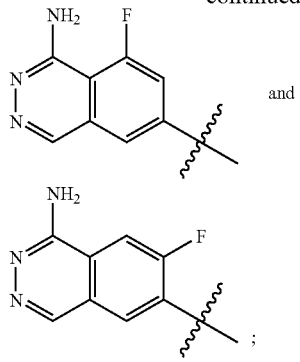

R$^1$ is H, Cl, Br, methyl, ethyl, methoxy, or ethoxy;
R$^2$ is H, Cl, Br, methyl, ethyl, methoxy, or ethoxy;
R$^3$ is H;
R$^4$ is H;
R$^5$ is H, methyl, ethyl, or —CH$_2$CO$_2$H;
R$^6$ is H, methyl, ethyl, —CO$_2$H or —CH$_2$CO$_2$H;
R$^7$ is H; and
R$^8$ is —CONR$^c$R$^d$ or —SO$_2$R$^b$.

8. A compound according to claim 1, wherein the compound is of Formula (I), or a stereoisomer, a tautomer, or a pharmaceutically acceptable salt thereof, wherein:

when M is —CONH—; L is selected from —(CH$_2$)$_2$—, —(CH$_2$)$_3$—, —(CH$_2$)$_4$—, —O(CH$_2$)—, —O(CH$_2$)$_2$—, —O(CH$_2$)$_3$—, —(CH$_2$)$_2$O—, —CH(Me)CH$_2$O—, —C(Me)$_2$CH$_2$O—, —CH$_2$CH(Me)O—, —CH(Et)CH$_2$O—, —CH$_2$CH(Et)O—, —CH$_2$OCH$_2$—, —(CH$_2$)$_2$NMe-, —(CH$_2$)$_3$NMe-, —CH$_2$NHCH$_2$—, and —CH$_2$N(Ac)CH$_2$—;

when M is —NHSO$_2$—, L is selected from —(CH$_2$)$_2$— and —(CH$_2$)$_3$—;

W is selected from:

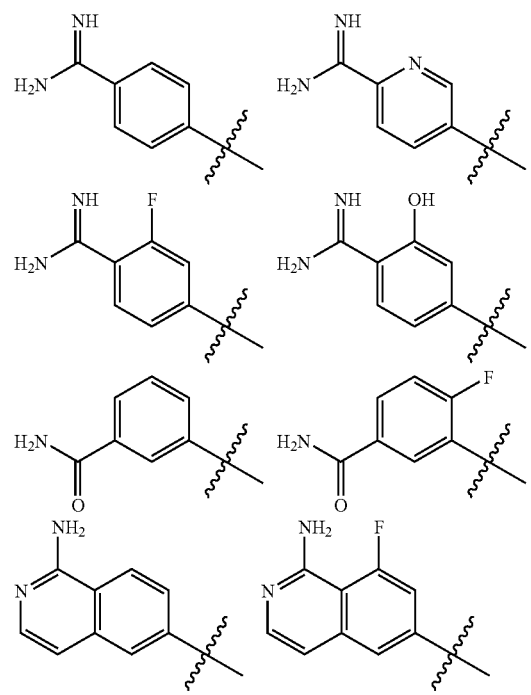

-continued

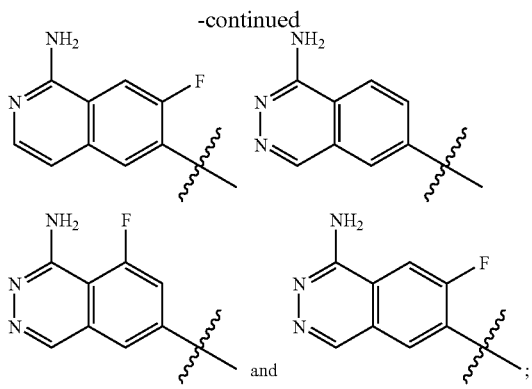

Z is NH;
$R^1$ is H, Cl, Br, $C_{1-4}$ alkyl, or $C_{1-4}$ alkoxy;
$R^2$ is H, Cl, Br, $C_{1-4}$ alkyl, or $C_{1-4}$ alkoxy;
$R^3$ is H;
$R^4$ is H;
$R^5$ is H, $C_{1-4}$ alkyl, —$CH_2CO_2H$, or —$CH_2CO_2Et$;
$R^6$ is H, $C_{1-4}$ alkyl, —$CO_2H$, —$CH_2CO_2H$, or —$CH_2CO_2Et$;
$R^7$ is H;
$R^8$ is H, —$SO_2(C_{1-4}$ alkyl), or —$S(C_{1-4}$ alkyl);
$R^9$ is H; and
$R^{10}$ is H.

9. A compound according to claim 8, wherein the compound is of Formula (I), or a stereoisomer, a tautomer, or a pharmaceutically acceptable salt thereof, wherein:
W is selected from:

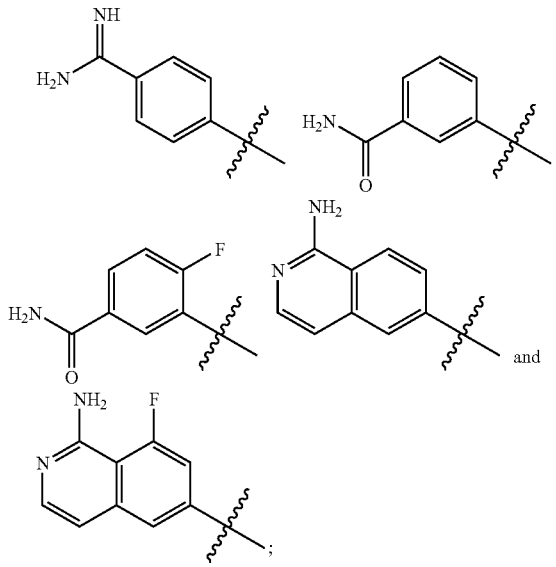

$R^1$ is H, Cl, Br, methyl, ethyl, methoxy, or ethoxy;
$R^2$ is H, Cl, Br, methyl, ethyl, methoxy, or ethoxy;
$R^5$ is H, methyl, ethyl, or —$CH_2CO_2H$;
$R^6$ is H, methyl, ethyl, —$CO_2H$, —$CH_2CO_2H$, or —$CH_2CO_2Et$; and
$R^8$ is H, —$SO_2Et$, —$SO_2(i-Pr)$, —$SO_2(t-Bu)$, or —$S(i-Pr)$.

10. A pharmaceutical composition, comprising: a pharmaceutically acceptable carrier and a compound of claim 1, or a stereoisomer, a tautomer, or a pharmaceutically acceptable salt thereof.

11. A method for treating a thromboembolic disorder, comprising: administering to a patient in need thereof a therapeutically effective amount of a compound of claim 1, or a stereoisomer, a tautomer, or a pharmaceutically acceptable salt thereof.

12. A method according to claim 11, wherein the thromboembolic disorder is selected from the group consisting of arterial cardiovascular thromboembolic disorders, venous cardiovascular thromboembolic disorders, and thromboembolic disorders in the chambers of the heart or in the peripheral circulation.

13. A method according to claim 11, wherein the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

14. A compound selected from the group consisting of:

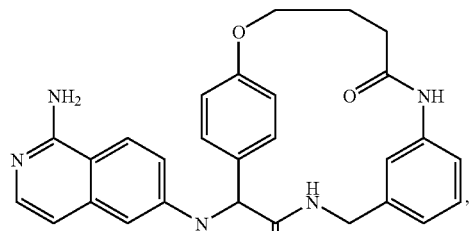

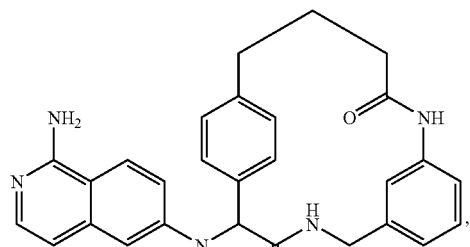

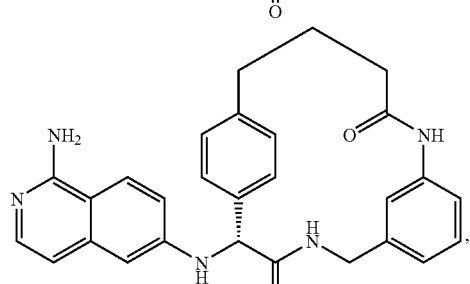

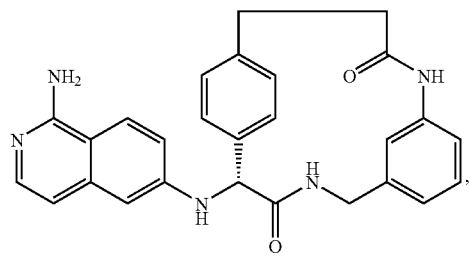

247
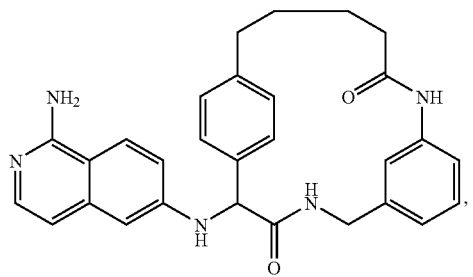
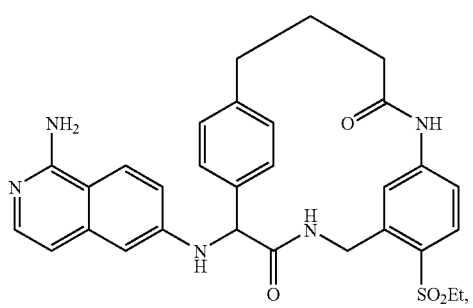
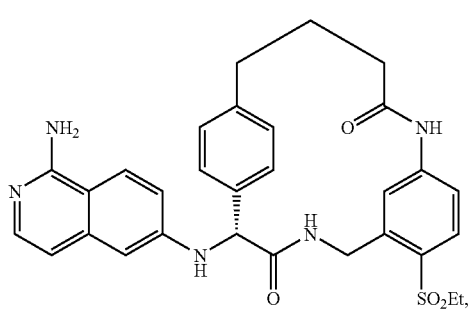
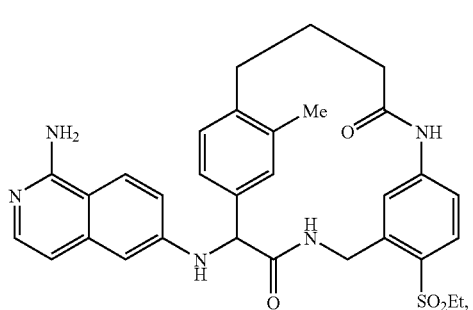
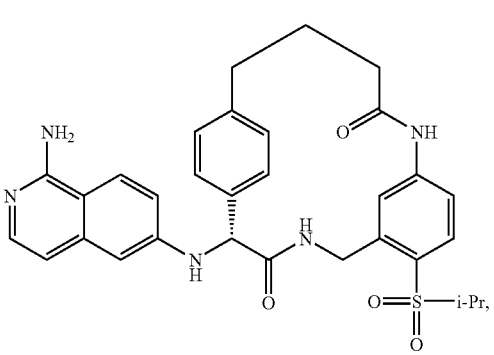
248
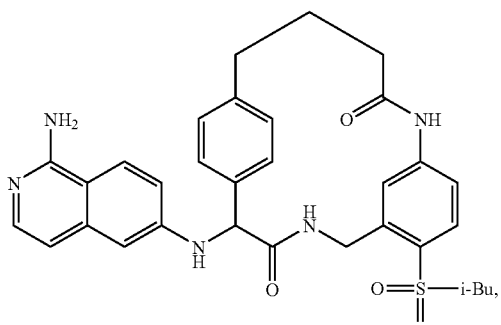
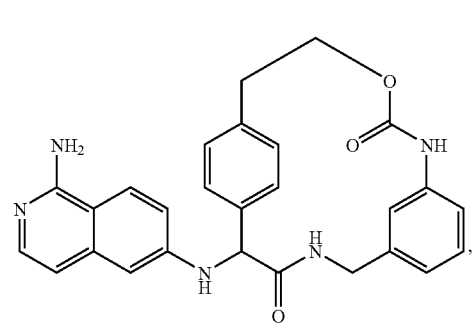
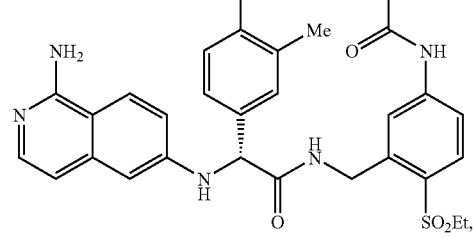
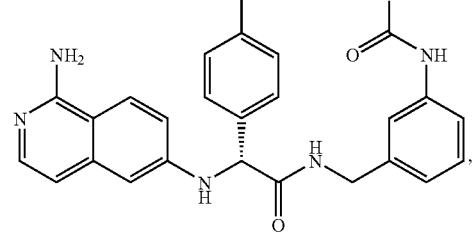
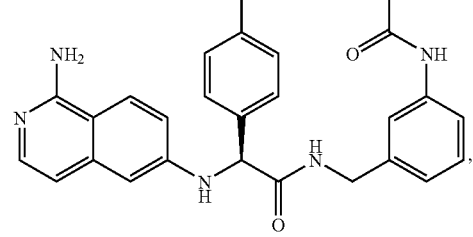

-continued
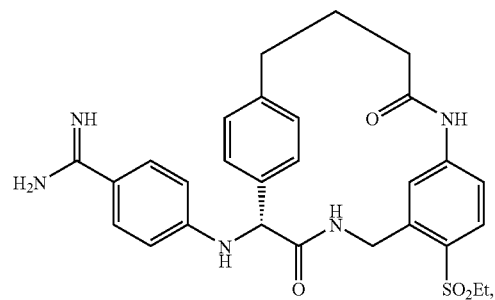
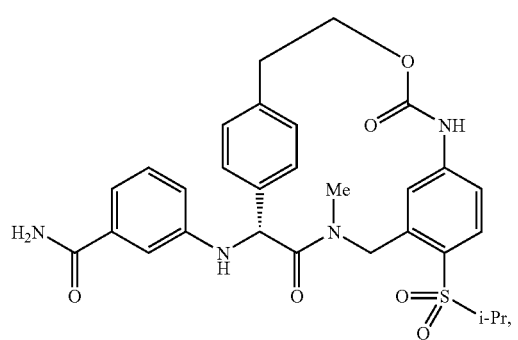
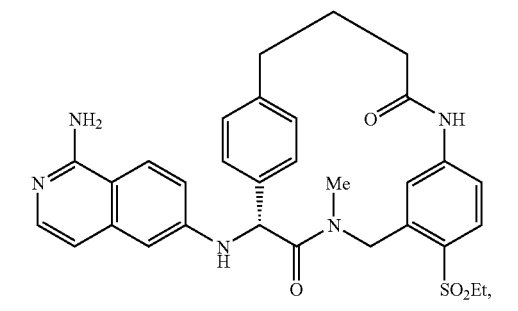
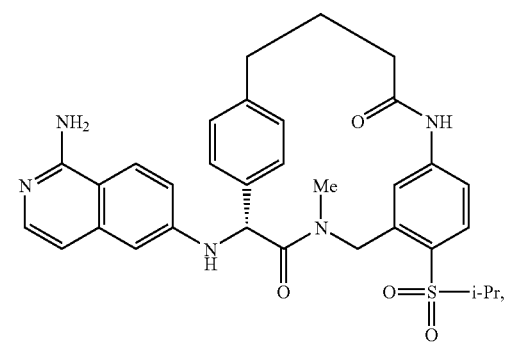
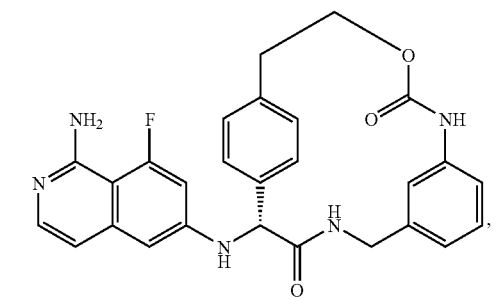
-continued
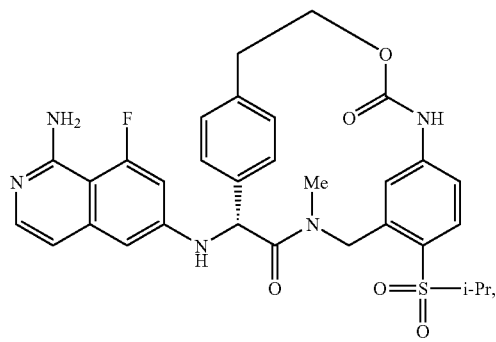
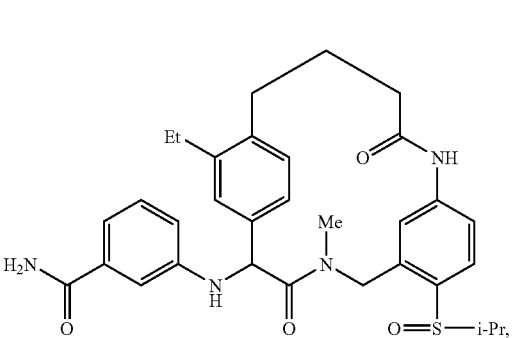
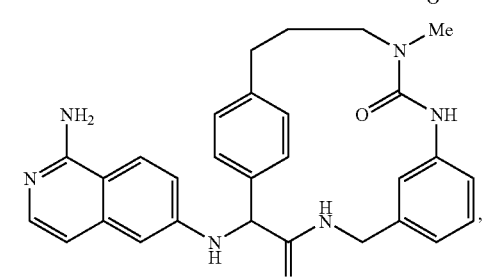
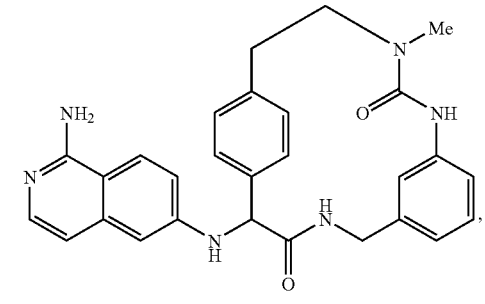
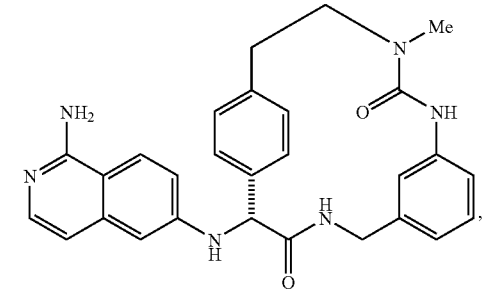

-continued
251
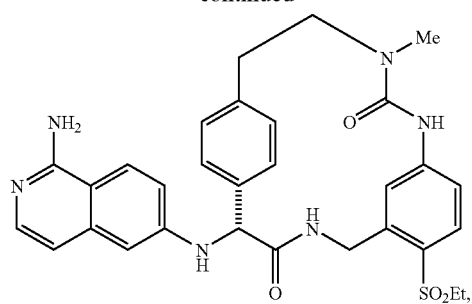
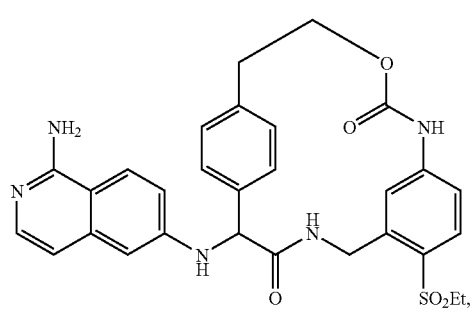
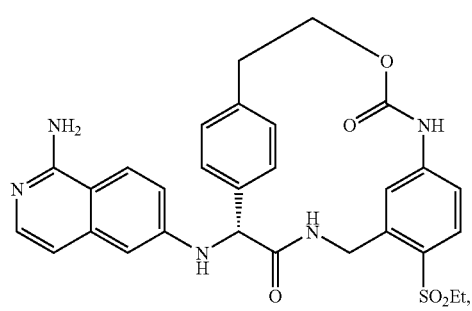
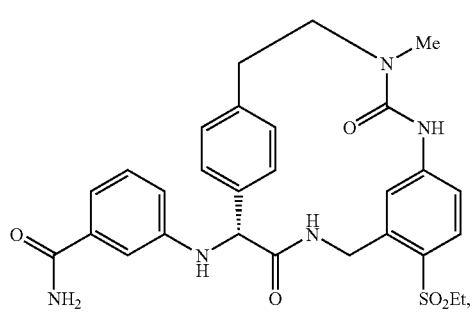
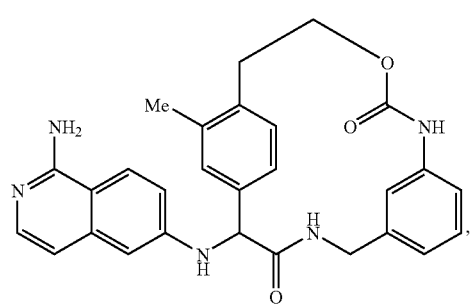
252
-continued
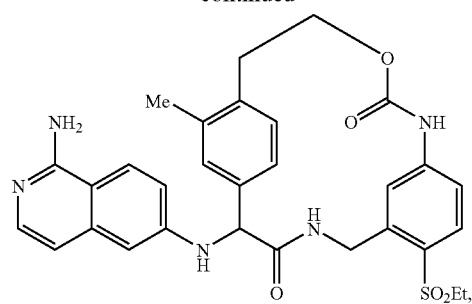
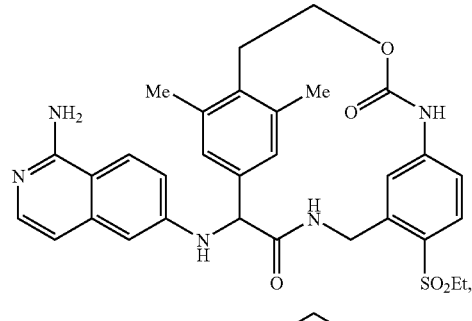
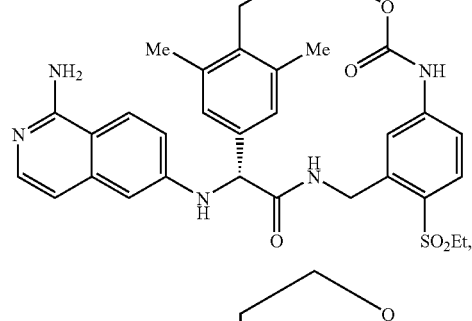
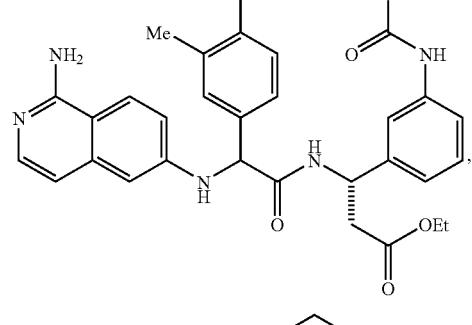
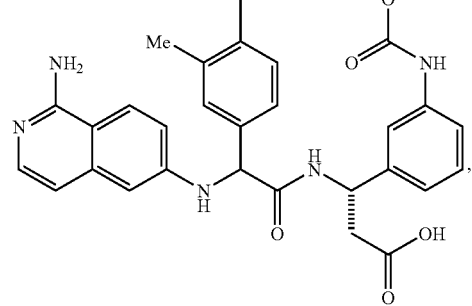

-continued
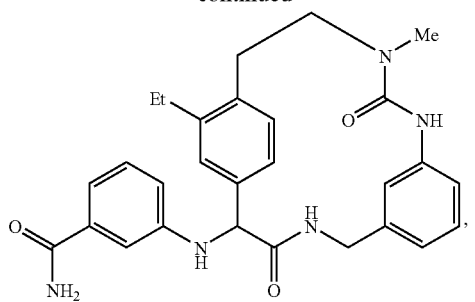
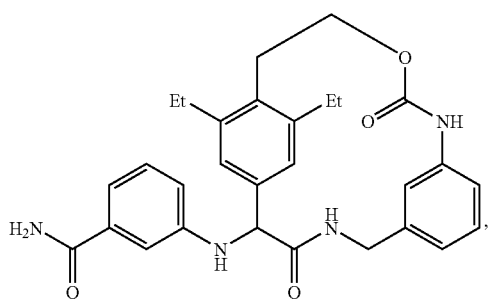
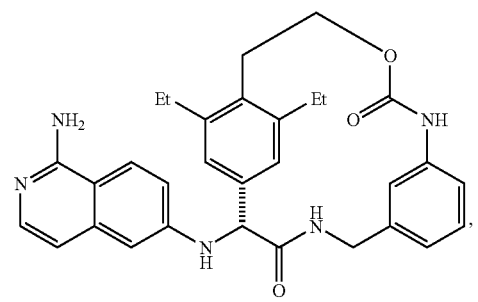
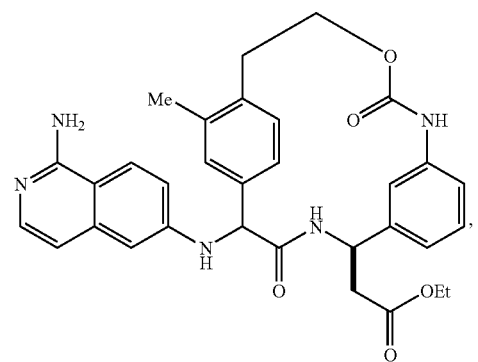
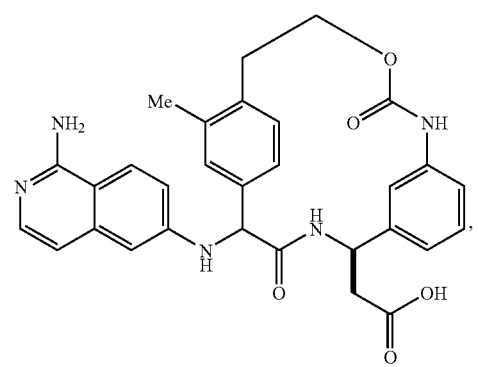
-continued
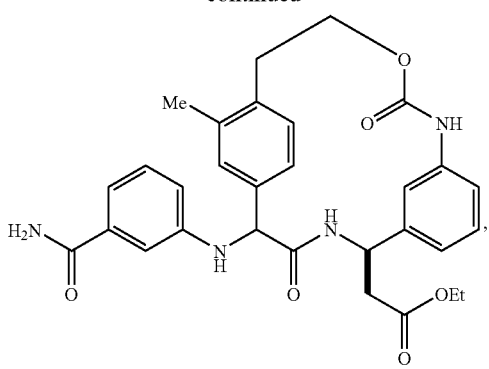
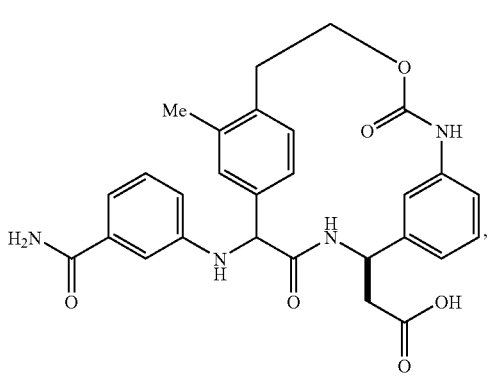
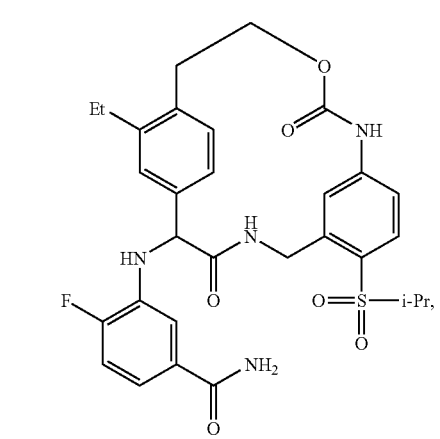
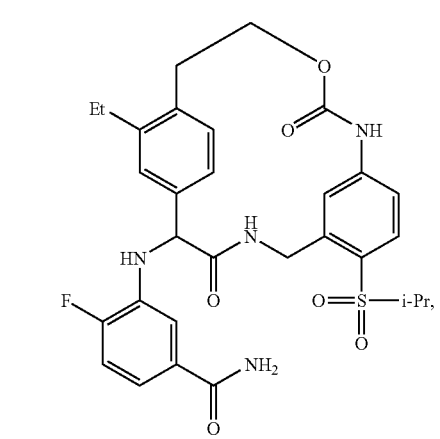
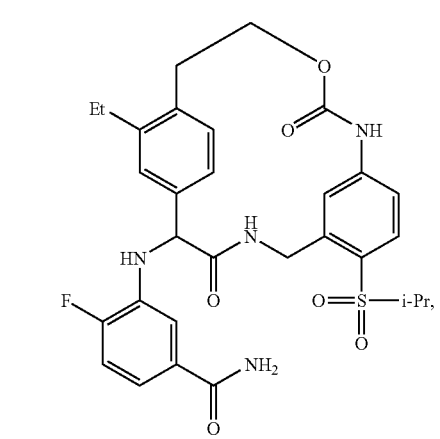

255
-continued
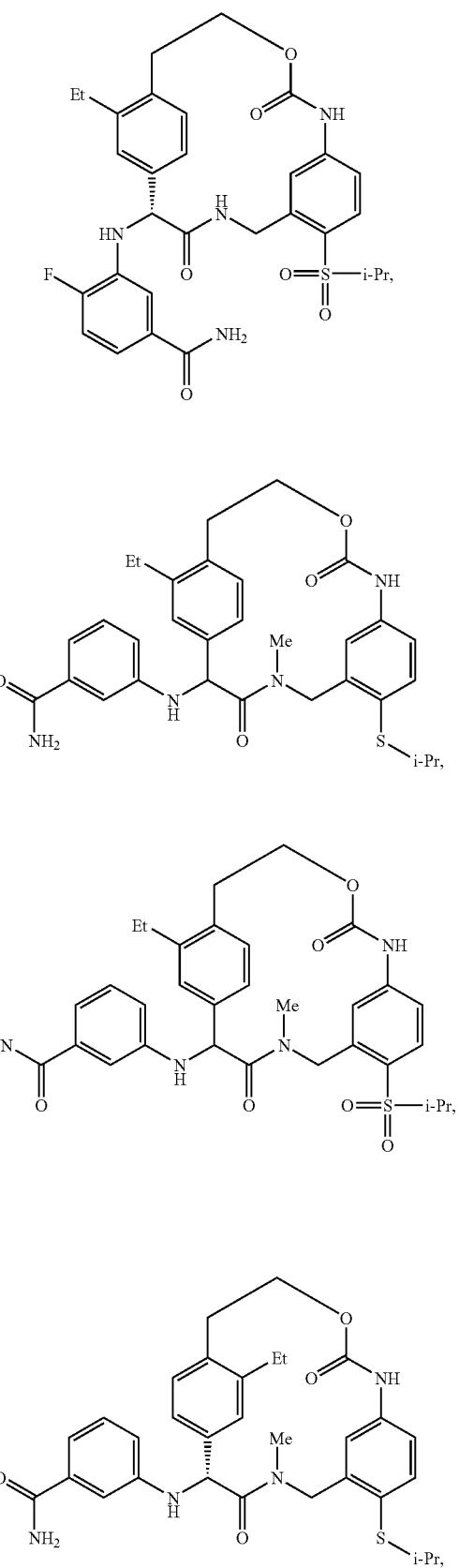
256
-continued
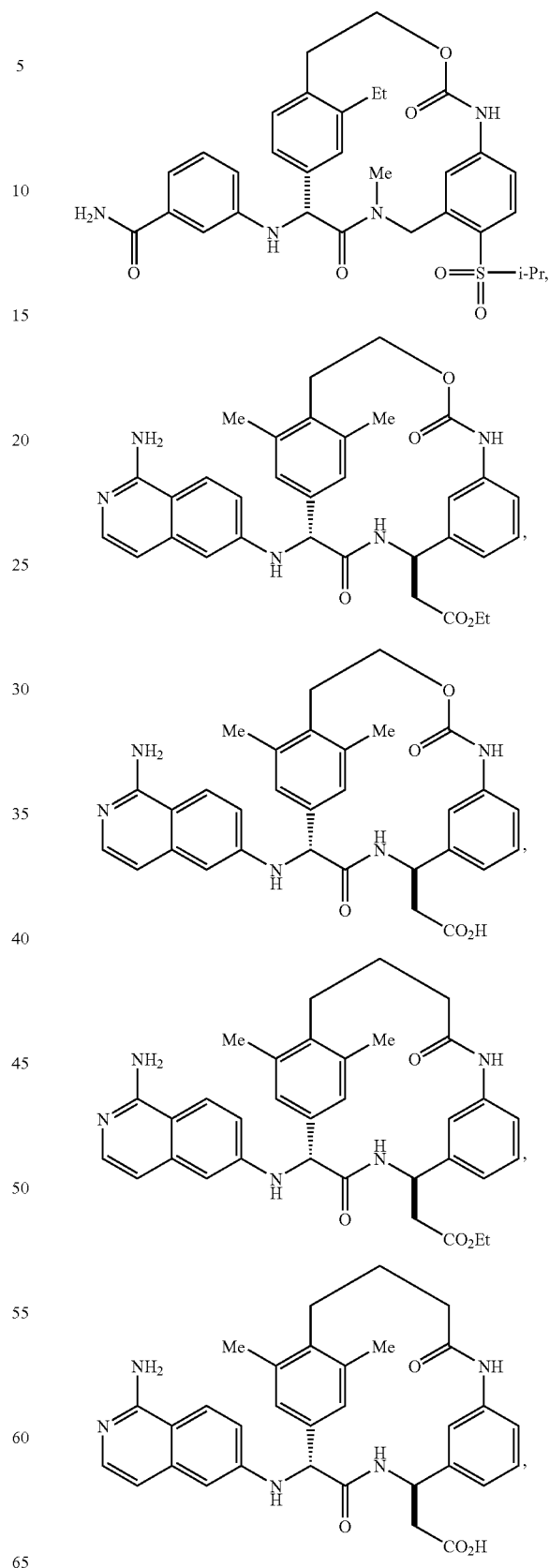

257
-continued
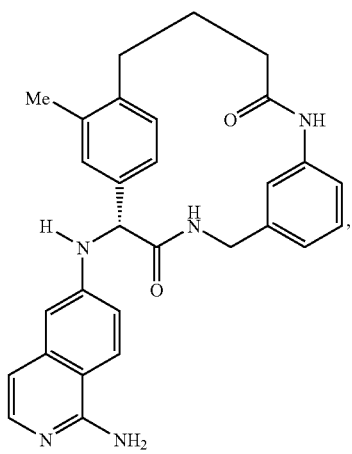
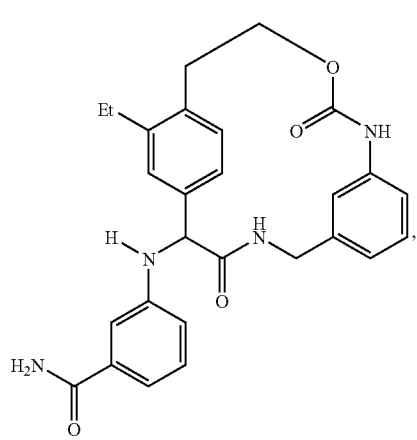
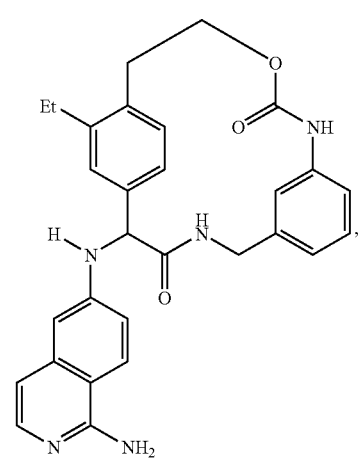
258
-continued
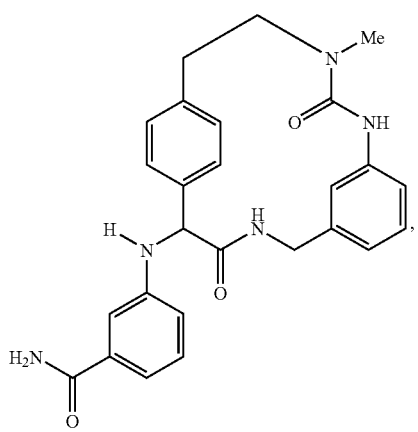
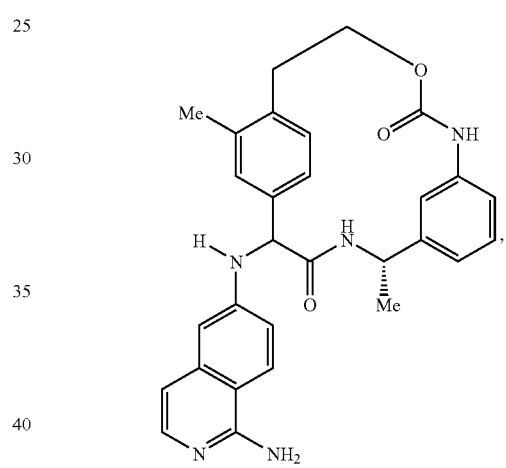
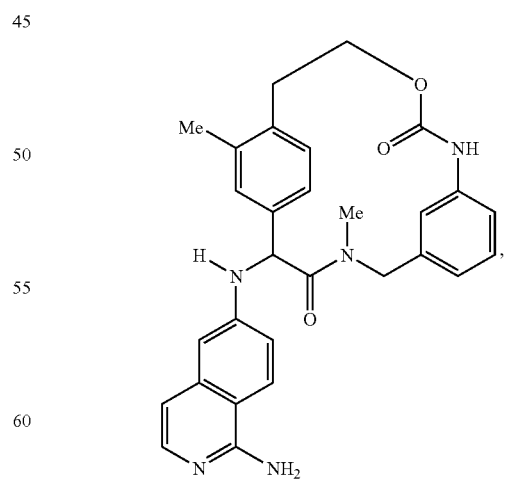

259
-continued
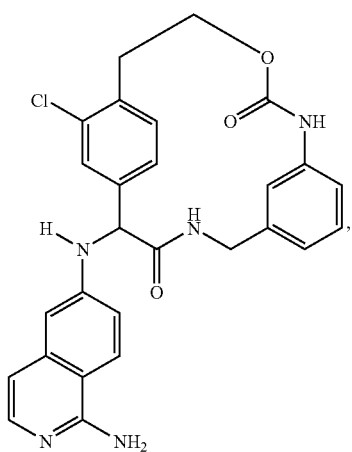
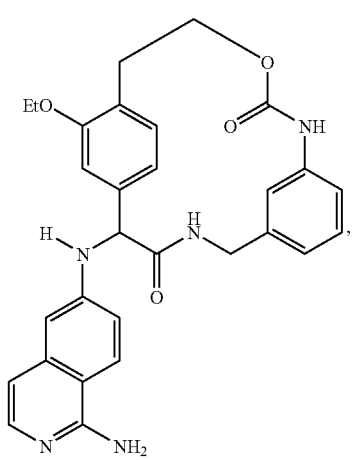
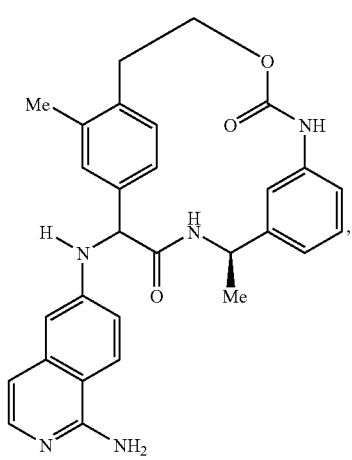
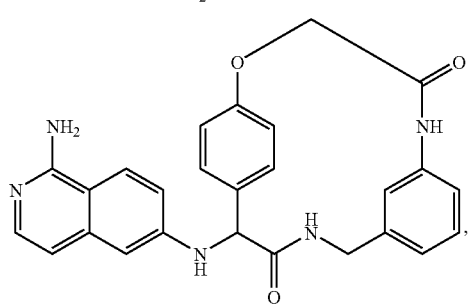
260
-continued
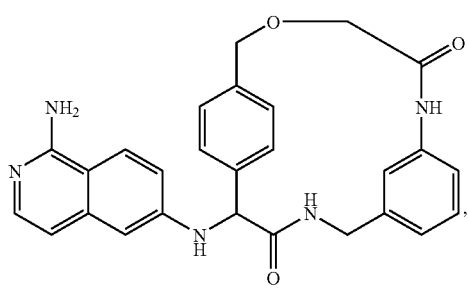
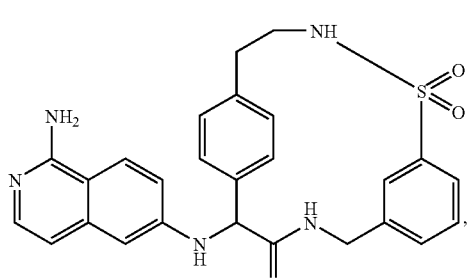
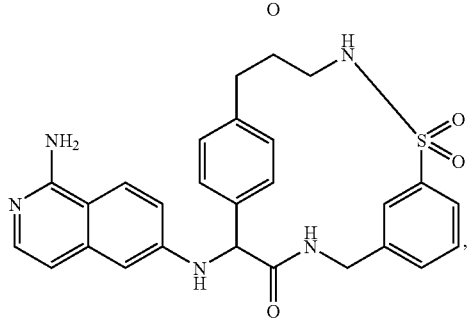
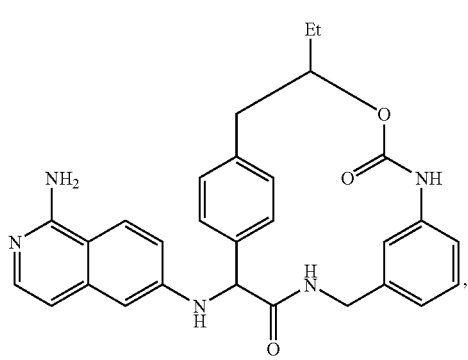
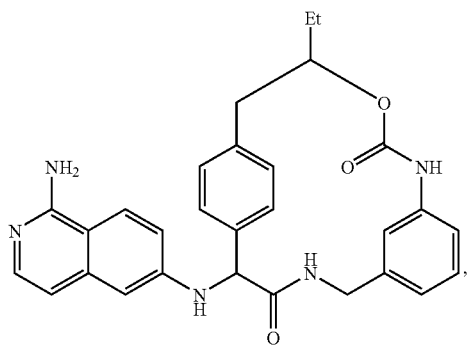

261
-continued
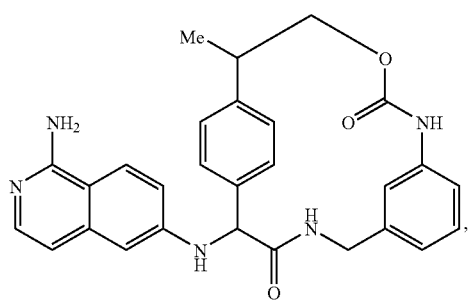
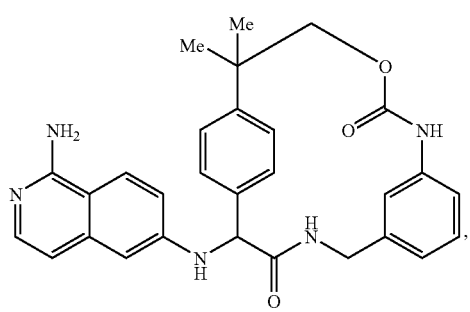
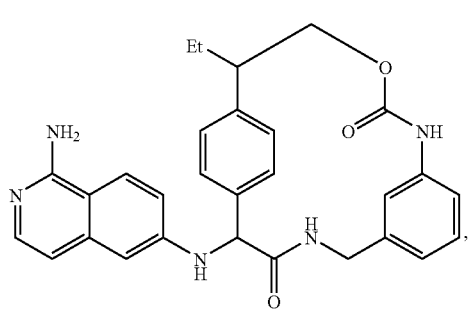
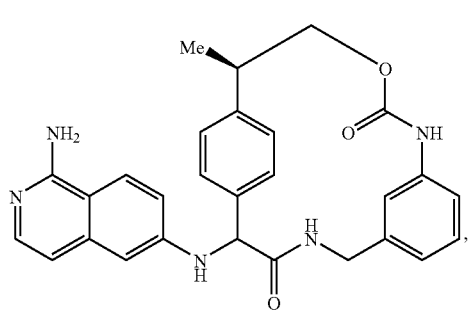
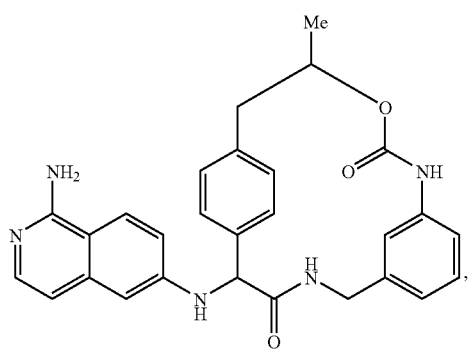
262
-continued
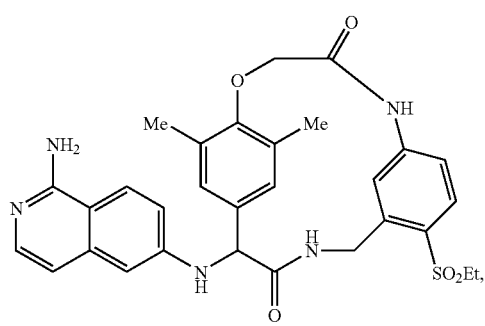
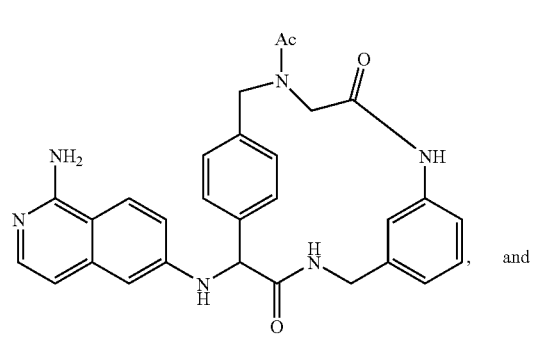, and
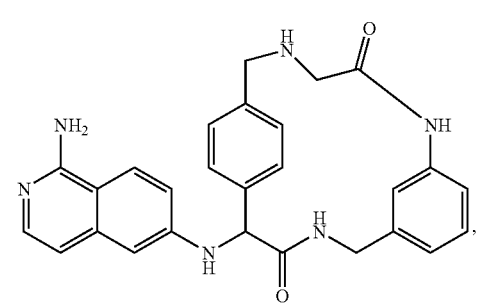
or a stereoisomer, a tautomer, or a pharmaceutically acceptable salt thereof.
15. A compound selected from the group consisting of:
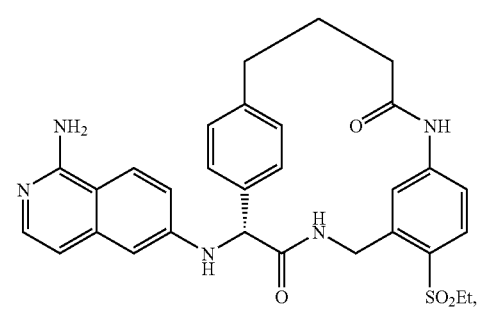

263
-continued
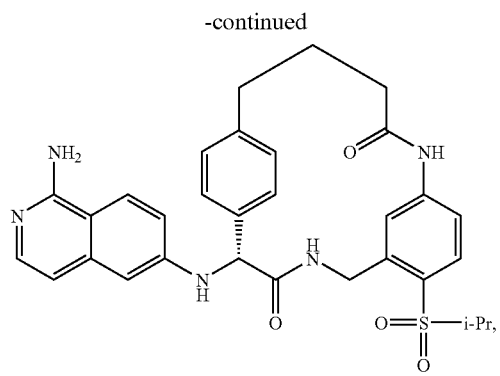
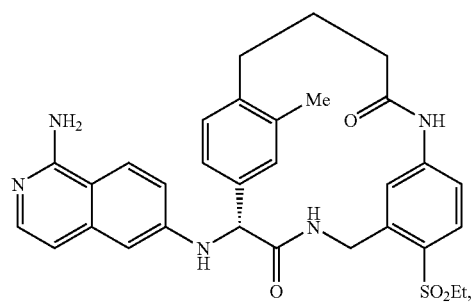
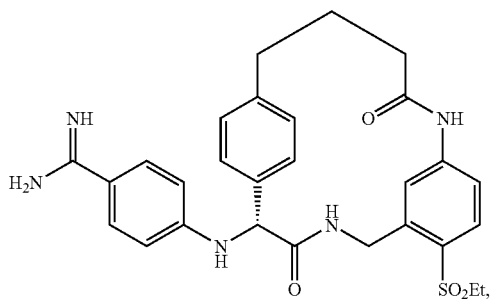
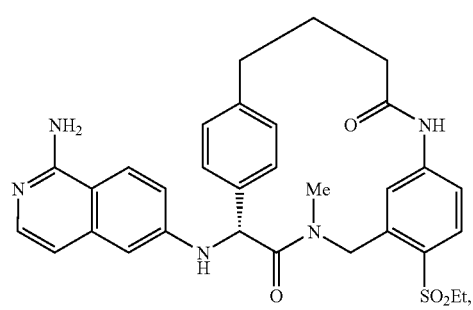
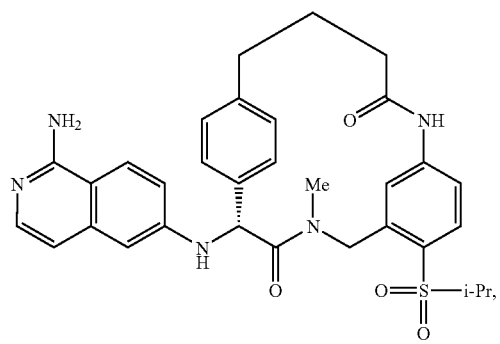
264
-continued
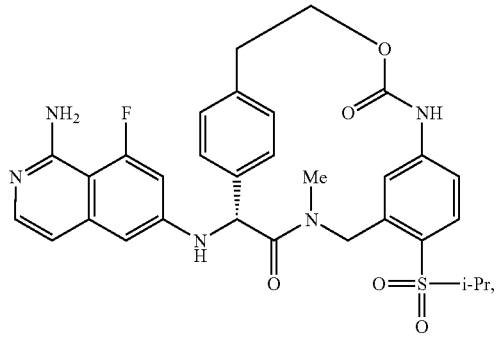
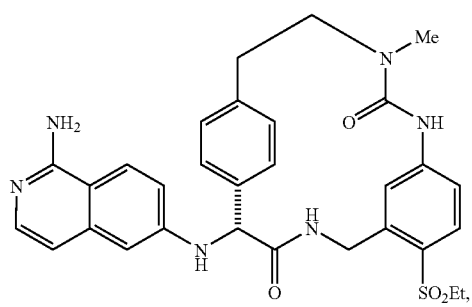
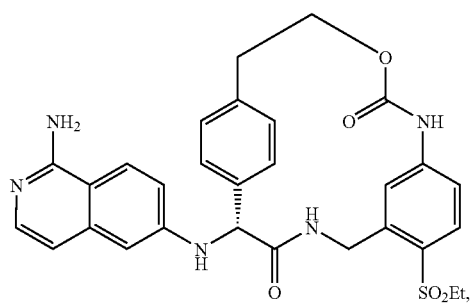
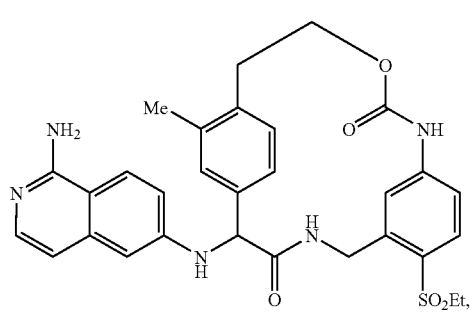
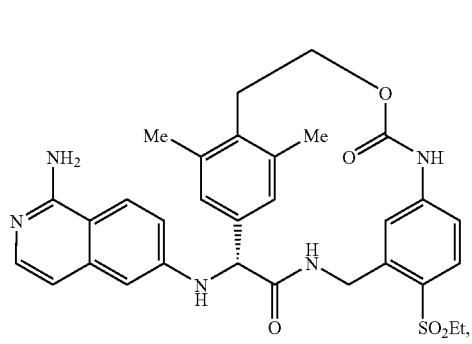

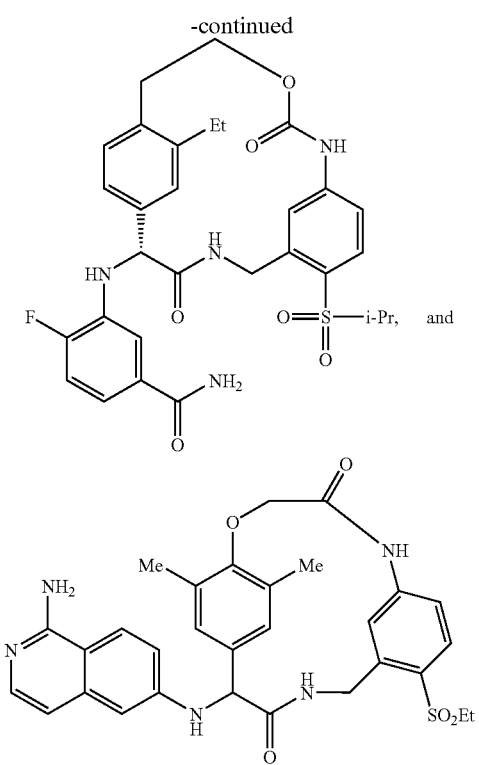

or a stereoisomer, a tautomer, or a pharmaceutically acceptable salt thereof.

16. A pharmaceutical composition, comprising: a pharmaceutically acceptable carrier and a compound of claim 2, or a stereoisomer, a tautomer, or a pharmaceutically acceptable salt thereof.

17. A pharmaceutical composition, comprising: a pharmaceutically acceptable carrier and a compound of claim 3, or a stereoisomer, a tautomer, or a pharmaceutically acceptable salt thereof.

18. A pharmaceutical composition, comprising: a pharmaceutically acceptable carrier and a compound of claim 4, or a stereoisomer, a tautomer, or a pharmaceutically acceptable salt thereof.

19. A pharmaceutical composition, comprising: a pharmaceutically acceptable carrier and a compound of claim 5, or a stereoisomer, a tautomer, or a pharmaceutically acceptable salt thereof.

20. A pharmaceutical composition, comprising: a pharmaceutically acceptable carrier and a compound of claim 6, or a stereoisomer, a tautomer, or a pharmaceutically acceptable salt thereof.

21. A pharmaceutical composition, comprising: a pharmaceutically acceptable carrier and a compound of claim 7, or a stereoisomer, a tautomer, or a pharmaceutically acceptable salt thereof.

22. A pharmaceutical composition, comprising: a pharmaceutically acceptable carrier and a compound of claim 8, or a stereoisomer, a tautomer, or a pharmaceutically acceptable salt thereof.

23. A pharmaceutical composition, comprising: a pharmaceutically acceptable carrier and a compound of claim 9, or a stereoisomer, a tautomer, or a pharmaceutically acceptable salt thereof.

24. A pharmaceutical composition, comprising: a pharmaceutically acceptable carrier and a compound of claim 14, or a stereoisomer, a tautomer, or a pharmaceutically acceptable salt thereof.

25. A pharmaceutical composition, comprising: a pharmaceutically acceptable carrier and a compound of claim 15, or a stereoisomer, a tautomer, or a pharmaceutically acceptable salt thereof.

* * * * *

UNITED STATES PATENT AND TRADEMARK OFFICE
CERTIFICATE OF CORRECTION

PATENT NO.       : 7,592,331 B2                          Page 1 of 2
APPLICATION NO.  : 11/614131
DATED            : September 22, 2009
INVENTOR(S)      : Eldon Scott Priestley et al.

It is certified that error appears in the above-identified patent and that said Letters Patent is hereby corrected as shown below:

Column 239
Line 42, "alikyl." should read -- alkyl. --.

Column 240

Line 45-50, " 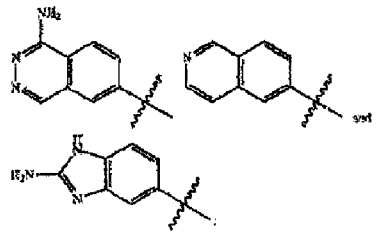 " should read

-- 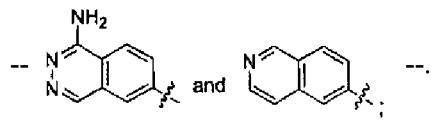 --.

Column 241

Line 40-50, " 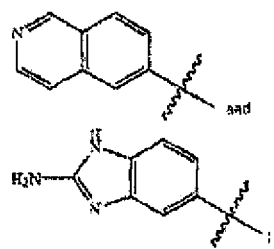 " should read -- and ; --.

Column 242

Line 25-30, after " 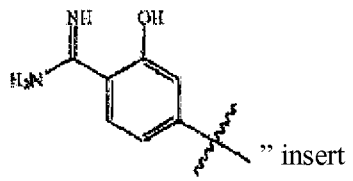 " insert

-- 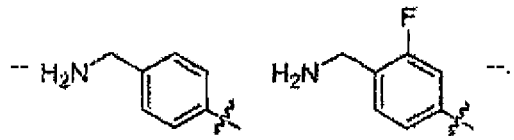 --.

UNITED STATES PATENT AND TRADEMARK OFFICE
CERTIFICATE OF CORRECTION

PATENT NO. : 7,592,331 B2
APPLICATION NO. : 11/614131
DATED : September 22, 2009
INVENTOR(S) : Eldon Scott Priestley et al.

It is certified that error appears in the above-identified patent and that said Letters Patent is hereby corrected as shown below:

Column 242

Line 30-35, after " 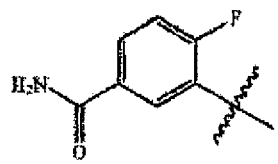 " insert -- 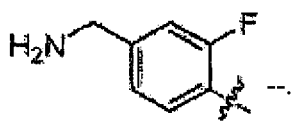 --.

Signed and Sealed this

Twenty-ninth Day of December, 2009

David J. Kappos
*Director of the United States Patent and Trademark Office*